(12) United States Patent
Miccio et al.

(10) Patent No.: US 12,139,720 B2
(45) Date of Patent: *Nov. 12, 2024

(54) RECOMBINANT LENTIVIRAL VECTOR FOR STEM CELL- BASED GENE THERAPY OF SICKLE CELL DISORDER

(71) Applicants: INSTITUT NATIONAL DE LA SANTE ET DE LA RECHERCHE MEDICALE (INSERM), Paris (FR); UNIVERSITE PARIS DESCARTES, Paris (FR); ASSISTANCE PUBLIQUE—HOPITAUX DE PARIS, Paris (FR); IMAGINE—INSTITUT DES MALADIES GENETIQUES NECKER ENFANTS MALADES, Paris (FR)

(72) Inventors: Annarita Miccio, Paris (FR); Vasco Meneghini, Bretigny-sur-Orge (FR)

(73) Assignees: INSTITUT NATIONAL DE LA SANTE ET DE LA RECHERCHE MEDICALE (INSERM), Paris (FR); UNIVERSITE PARIS DESCARTES, Paris (FR); ASSISTANCE PUBLIQUE-HOPITAUX DE PARIS, Paris (FR); IMAGINE—INSTITUT DES MALADIES GENETIQUES NECKER ENFANTS MALADES, Paris (FR)

( * ) Notice: Subject to any disclaimer, the term of this patent is extended or adjusted under 35 U.S.C. 154(b) by 877 days.

This patent is subject to a terminal disclaimer.

(21) Appl. No.: 16/618,226

(22) PCT Filed: Jun. 1, 2018

(86) PCT No.: PCT/EP2018/064531
§ 371 (c)(1),
(2) Date: Nov. 29, 2019

(87) PCT Pub. No.: WO2018/220210
PCT Pub. Date: Dec. 6, 2018

(65) Prior Publication Data
US 2020/0190536 A1    Jun. 18, 2020

(30) Foreign Application Priority Data
Jun. 2, 2017  (EP) .................................... 17305647

(51) Int. Cl.
| C12N 15/00 | (2006.01) |
| A61K 38/42 | (2006.01) |
| C12N 5/074 | (2010.01) |
| C12N 9/22  | (2006.01) |
| C12N 15/86 | (2006.01) |

(52) U.S. Cl.
CPC .............. *C12N 15/86* (2013.01); *A61K 38/42* (2013.01); *C12N 5/0607* (2013.01); *C12N 9/22* (2013.01); *C12N 2310/20* (2017.05); *C12N 2740/15043* (2013.01); *C12N 2830/40* (2013.01); *C12N 2830/48* (2013.01)

(58) Field of Classification Search
CPC ........ C12N 15/86; C12N 5/0607; C12N 9/22; C12N 2310/20; C12N 2740/15043; C12N 2830/40; C12N 2830/48; A61K 38/42
See application file for complete search history.

(56) References Cited

U.S. PATENT DOCUMENTS

| 2016/0201089 A1* | 7/2016 | Gersbach ................. C12N 9/96 |
| | | 435/320.1 |
| 2018/0171297 A1* | 6/2018 | Bauer ....................... A61P 7/06 |
| 2018/0223313 A1* | 8/2018 | Uchida .......... C12Y 502/01008 |
| 2020/0157515 A1* | 5/2020 | Gori ..................... A61K 38/465 |
| 2021/0254061 A1* | 8/2021 | Gori ..................... C12N 15/113 |
| 2022/0073951 A1* | 3/2022 | Gori ......................... C12N 9/22 |

FOREIGN PATENT DOCUMENTS

| WO | WO-2013126794 A1 * | 8/2013 | ........... A61K 38/465 |
| WO | WO-2014043131 A1 * | 3/2014 | ........ A61K 48/0066 |
| WO | 2016037138 A1 | 3/2016 | |
| WO | WO-2017059241 A1 * | 4/2017 | ........... C07K 14/155 |
| WO | WO-2018035388 A1 * | 2/2018 | ........... A61K 9/1271 |

OTHER PUBLICATIONS

The Canver Dissertation; Harvard University, Feb. 2016. (Year: 2016).*
Hoban et al "CRISPR/Cas9-Mediated Correction of the Sickle Mutation in Human CD34+ cells", Molecular Therapy, vol. 24, No. 9; Sep. 1, 2016; IDS reference). (Year: 2016).*
Negre et al (Human Gene Therapy, vol. 27, No. 2, published online Jan. 22, 2016). (Year: 2016).*
Drakopoulou, "Review Article, The Ongoing Challenge of Hematopoietic Stem Cell-Based Gene Therapy for β-Thalassemia," Stem Cells International, vol. 2011. (Year: 2011).*
Finotti et al in "Recent trends in the gene therapy of β-thalassemia" (Journal of Blood Medicine: 2015: vol. 6, pp. 69-85). (Year: 2015).*
Lattanzi et al Molecular Therapy vol. 27, No. 1, Jan. 2019, pp. 137-150. (Year: 2019).*
Levasseur et al The JBC vol. 279, Jun. 25, 2004, pp. 27518-27524). (Year: 2004).*
Cavazzana et al Molecular Therapy vol. 25, No. 5, May 2017, pp. 1142-1154. (Year: 2017).*

(Continued)

*Primary Examiner* — Catherine S Hibbert
(74) *Attorney, Agent, or Firm* — MH2 TECHNOLOGY LAW GROUP, LLP

(57) ABSTRACT

This invention relates to recombinant lentiviral vectors, compositions thereof, the use of the vectors or the compositions thereof, kits of parts comprising said vectors or compositions thereof and a catalytically active Cas9 or Cpf1 protein, methods for modifying the genome of a hematopoietic stem/progenitor cell (HSPC), and the HSPC obtainable by such methods.

22 Claims, 37 Drawing Sheets

Specification includes a Sequence Listing.

(56) References Cited

OTHER PUBLICATIONS

Ramadier et al Molecular Therapy vol. 30, No. 1, Jan. 2022, pp. 145-163. (Year: 2022).*
Metais et al "Genome editing of HBG1 and HBG2 to induce fetal hemoglobin" Blood Advances, Nov. 12, 2019, vol. 3, No. 21, pp. 3379-3392. (Year: 2019).*
Graslund et al, "Exploring strategies for the design of artificial transcription factors: targeting sites proximal to known regulatory regions for the induction of gamma-globin expression and the treatment of sickle cell disease," J Biol Chem 280, 2005, 3707-3714. (Year: 2005).*
Cottle et al in "Treating Hemoglobinopathies Using Gene Correction Approaches: Promises And Challenges" (Hum Genet 2016 Sep. 2017 vol. 139, No. 9: pp. 993-1010). (Year: 2016).*
Lidonnici et al in "Gene therapy and gene editing strategies for hemoglobinopathies" (Blood Cells, Molecules and Diseases 2018 pp. 87-101, published online Jan. 3, 2018). (Year: 2018).*
Zuccato et al A combined approach for beta-thalassemia based on gene therapy-mediated adult hemoglobin (HbA) production and fetal hemoglobin (HbF) induction, Ann. Hematol. vol. 91 2012, pp. 1201-1213). (Year: 2012).*
Loucari in "Isoform-specific disruption of the BCL11A transcription factor induces γ-globin but delays erythroid differentiation" (Molecular Therapy, suppl. Supplement 125.5: 172. American Society of Gene and Cell Therapy. (Abstract May 2017)). (Year: 2017).*
Loucari et al "Rapid and Sensitive Assessment of Globin Chains for Gene and Cell Therapy of Hemoglobinopathies" (Human Gene Therapy, vol. 29 No. 1, published online Jan. 11, 2018.) (Year: 2018).*
Masuda et al ("Transcription factors LRF and BCL11A independently repress expression of fetal hemoglobin" Science vol. 351 No. 6270, Jan. 15, 2016). (Year: 2016).*
Masuda et al 2016 Science Supplemental Material (Year: 2016).*
Cavazzana et al., "Gene Therapy for β-Hemoglobinopathies", Molecular Therapy, vol. 25, No. 5 (2017) pp. 1142-1154.
Hoban et al., "CRISPR/Cas9-mediated Correction of the Sickle Mutation in human CD34+ cells", Supplmentary Information (short title: CRISPR/CAS9 Correction of Sickle Mutation in CD34+), pp. 1-12.
Hoban et al., "CRISPR/Cas9-Mediated Correction of the Sickle Mutation in human CD34+ Cells", Molecular Therapy, vol. 24, No. 9 (2016) pp. 1561-1569.
Negre et al., "Gene Therapy of the β-Hemoglobinopathies by Lentiviral Transfer of the βA(T87Q)-Globin Gene", Human Gene Therapy, vol. 27, No. 2 (2016) pp. 148-165.
International Search Report issued in corresponding International Application No. PCT/EP2018/064531 on Oct. 25, 2018, pp. 1-5.
Traxler et al., "A genome-editing strategy to treat β-hemoglobinopathies that recapitulates a mutation associated with a benign genetic condition," Nature Medicine, 2016, vol. 22, No. 9, pp. 987-990.
Wilber et al., "Therapeutic levels of fetal hemoglobin in erythroid progeny of β-thalassemic CD34+ cells after lentiviral vector-mediated gene transfer," Blood, 2011, vol. 117, No. 10, pp. 2817-2826.

* cited by examiner

FIGURE 1
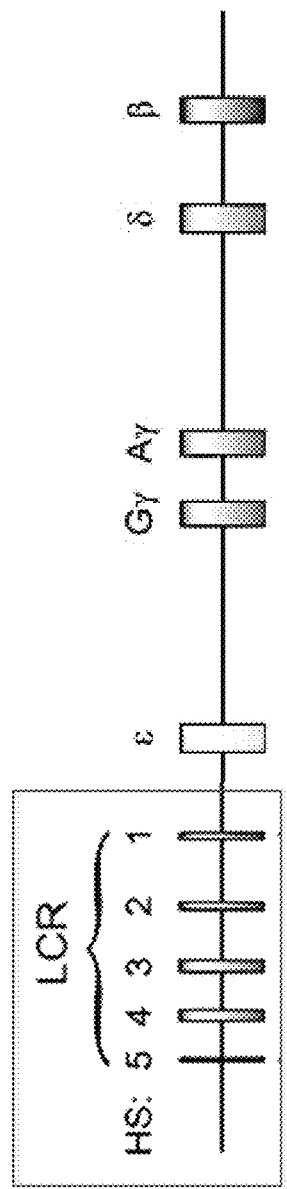
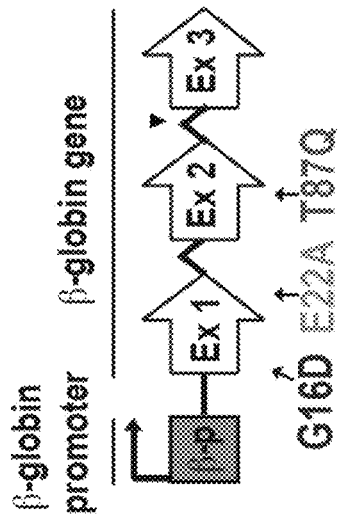

C

FIGURE 2
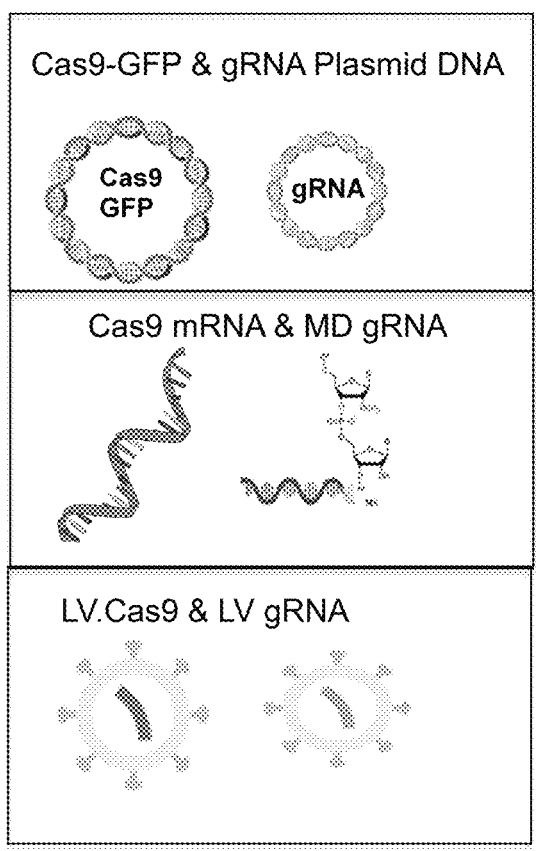
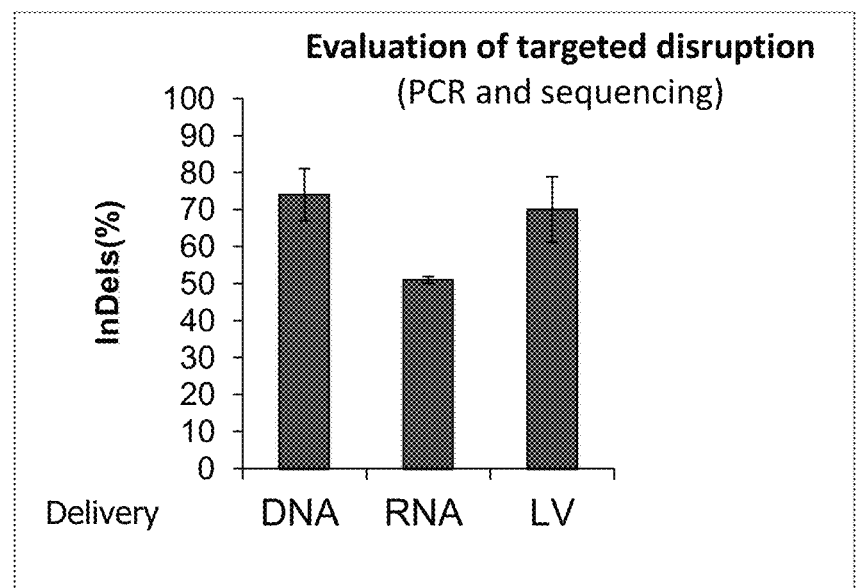

FIGURE 4

A. SELECTION OF CODING DNA SEQUENCE (E.G. HBB EXON 1) OF TARGET GENE IN UCSC GENOME BROWSER USING HUMAN GRCh37/hg19 GENOME ASSEMBLY

B. DOWNLOAD THE GENOMIC DNA SEQUENCE OF THE SELECTED TARGET REGION (E.G. HBB EXON 1)

*(CONT-1)*

| POSITION/ STRAND | GUIDE SEQUENCE + PAM RESTRICTION ENZYMES | SPECIFICITY SCORE | PREDICTED EFFICIENCY | | | | | | | | OUT-OF-FRAME | OFF-TARGETS FOR 0-1-2-3-4 MISMATCHES +NEXT TO PAM | GENOME BROWSER LINKS TO MATCHES SORTED BY OFF-TARGET SCORE ☐ EXAMS ONLY ☐ CHR11 ONLY |
|---|---|---|---|---|---|---|---|---|---|---|---|---|---|
| | | | FUSI | CHARI | XU | DOENCH | WANG | MOR-MATEOS | HOUSDEN | PROX GC | | | |
| 76 / FW | GTAACGGCAGACTTCTCCTC AGG PCR PRIMERS | 76 | 53 | 58 | 0.1 | 41 | 63 | 58 | 6 | + | 62 | 0-0-1-8-76 0-0-0-2-3 85 OFF-TARGETS | 2:INTERGENIC:RNU6-239P-RNU6-121P 3:INTERGENIC:RP11-416O18.1-RP11-416O18.2 3:INTERGENIC:AC022431.2-AC008940.1 SHOW ALL... |
| 45 / REV | GTCTGCCGTTACTGCCCTGT GGG PCR PRIMERS | 72 | 41 | 39 | -0.4 | 2 | 42 | 45 | 5 | + | 60 | 0-0-1-9-66 0-0-1-1-2 76 OFF-TARGETS | 2:INTERGENIC:MTND3P4-ARL2BPP7 3:INTRON:ARID1B 3:INTERGENIC:RP11-320A16.1-RP11-326A19.2 SHOW ALL... |

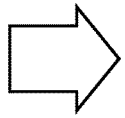

D. SELECT THE gRNAs WITH:
- THE HIGHEST SPECIFICITY SCORE
- THE HIGHEST PREDICTED EFFICIENCY
- THE HIGHEST OUT-OF-FRAME SCORE
- NO OFF-TARGETS WITH MISMATCHES ≤2

*FIGURE 4*
*(CONT-2)*

FIGURE 6
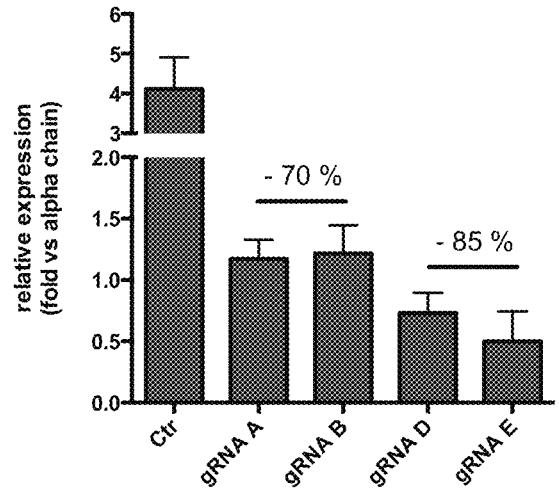
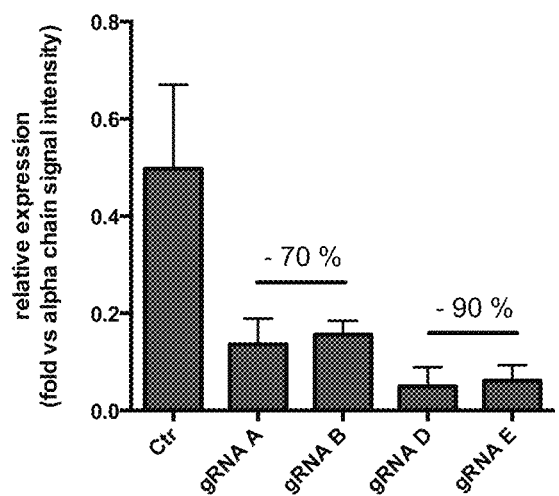

Beta AS1 (T87Q) (not modified) – SEQ ID NO: 1
TTAGTGATACTTGTGGGCCAGGGCATTAGCCACACCAGCCACCACTTTCTGATAGGCA
GCCTGCACTGGTGGGGTGAATTCTTTGCCAAAGTGATGGGCCAGCACACAGACCAGCA
CGTTGCCCAGGAGCTGTGGGAGGAAGATAAGAGGTATGAACATGATTAGCAAAAGGGC
CTAGCTTGGACTCAGAATAATCCAGCCTTATCCCAACCATAAAATAAAAGCAGAATGGT
AGCTGGATTGTAGCTGCTATTAGCAATATGAAACCTCTTACATCAGTTACAATTTATATG
CAGAAATACCCTGTTACTTCTCCCCTTCCTATGACATGAACTTAACCATAGAAAAGAAGG
GGAAAGAAAACATCAAGGGTCCCATAGACTCACCCTGAAGTTCTCAGGATCCACGTGC
AGCTTGTCACAGTGCAGCTCACTCAGCTGGGCAAAGGTGCCCTTGAGGTTGTCCAGGT
GAGCCAGGCCATCACTAAAGGCACCGAGCACTTTCTTGCCATGAGCCTTCACCTTAGG
GTTGCCCATAACAGCATCAGGAGTGGACAGATCCCCAAAGGACTCAAAGAACCTCTGG
GTCCAAGGGTAGACCACCAGCAGCCTAAGGGTGGGAAAATAGACCAATAGGCAGAGA
GAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCA
ACTTCATCCACGTTCACCTTGCCCCACAGGGCAGTAACGGCAGACTTCTCCTCAGGAG
TCAGGTGCACCA

Beta AS1 (T87Q) (modified to avoid targeting by gRNA D) – SEQ ID NO: 7
TTAGTGATACTTGTGGGCCAGGGCATTAGCCACACCAGCCACCACTTTCTGATAGGCA
GCCTGCACTGGTGGGGTGAATTCTTTGCCAAAGTGATGGGCCAGCACACAGACCAGCA
CGTTGCCCAGGAGCTGTGGGAGGAAGATAAGAGGTATGAACATGATTAGCAAAAGGGC
CTAGCTTGGACTCAGAATAATCCAGCCTTATCCCAACCATAAAATAAAAGCAGAATGGT
AGCTGGATTGTAGCTGCTATTAGCAATATGAAACCTCTTACATCAGTTACAATTTATATG
CAGAAATACCCTGTTACTTCTCCCCTTCCTATGACATGAACTTAACCATAGAAAAGAAGG
GGAAAGAAAACATCAAGGGTCCCATAGACTCACCCTGAAGTTCTCAGGATCCACGTGC
AGCTTGTCACAGTGCAGCTCACTCAGCTGGGCAAAGGTGCCCTTGAGGTTGTCCAGGT
GAGCCAGGCCATCACTAAAGGCACCGAGCACTTTCTTGCCATGAGCCTTCACCTTAGG
GTTGCCCATAACAGCATCAGGAGTGGACAGATCCCCAAAGGACTCAAAGAACCTCTGG
GTCCAAGGGTAGACCACCAGCAGCCTAAGGGTGGGAAAATAGACCAATAGGCAGAGA
GAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCA
ACTTCATCCACGTTCACCTTGCCCCAGAGGCGGTGACGGCGGACTTCTCCTCAGGAG
TCAGGTGCACCAT

Beta AS3 (not modified) – SEQ ID NO: 2
TTAGTGATACTTGTGGGCCAGGGCATTAGCCACACCAGCCACCACTTTCTGATAGGCA
GCCTGCACTGGTGGGGTGAATTCTTTGCCAAAGTGATGGGCCAGCACACAGACCAGCA
CGTTGCCCAGGAGCTGTGGGAGGAAGATAAGAGGTATGAACATGATTAGCAAAAGGGC
CTAGCTTGGACTCAGAATAATCCAGCCTTATCCCAACCATAAAATAAAAGCAGAATGGT
AGCTGGATTGTAGCTGCTATTAGCAATATGAAACCTCTTACATCAGTTACAATTTATATG
CAGAAATACCCTGTTACTTCTCCCCTTCCTATGACATGAACTTAACCATAGAAAAGAAGG
GGAAAGAAAACATCAAGGGTCCCATAGACTCACCCTGAAGTTCTCAGGATCCACGTGC
AGCTTGTCACAGTGCAGCTCACTCAGCTGGGCAAAGGTGCCCTTGAGGTTGTCCAGGT
GAGCCAGGCCATCACTAAAGGCACCGAGCACTTTCTTGCCATGAGCCTTCACCTTAGG
GTTGCCCATAACAGCATCAGGAGTGGACAGATCCCCAAAGGACTCAAAGAACCTCTGG
GTCCAAGGGTAGACCACCAGCAGCCTAAGGGTGGGAAAATAGACCAATAGGCAGAGA
GAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCA
ACGGCATCCACGTTCACCTTGTCCCACAGGGCAGTAACGGCAGACTTCTCCTCAGGAG
TCAGGTGCACCAT

FIGURE 14 (continuation)

Beta AS3 (modified to avoid targeting by gRNA D) – SEQ ID NO: 8
TTAGTGATACTTGTGGGCCAGGGCATTAGCCACACCAGCCACCACTTTCTGATAGGCA
GCCTGCACTGGTGGGGTGAATTCTTTGCCAAAGTGATGGGCCAGCACACAGACCAGCA
CGTTGCCCAGGAGCTGTGGGAGGAAGATAAGAGGTATGAACATGATTAGCAAAAGGGC
CTAGCTTGGACTCAGAATAATCCAGCCTTATCCCAACCATAAAATAAAAGCAGAATGGT
AGCTGGATTGTAGCTGCTATTAGCAATATGAAACCTCTTACATCAGTTACAATTTATATG
CAGAAATACCCTGTTACTTCTCCCCTTCCTATGACATGAACTTAACCATAGAAAGAAGG
GGAAAGAAAACATCAAGGGTCCCATAGACTCACCCTGAAGTTCTCAGGATCCACGTGC
AGCTTGTCACAGTGCAGCTCACTCAGCTGGGCAAAGGTGCCCTTGAGGTTGTCCAGGT
GAGCCAGGCCATCACTAAAGGCACCGAGCACTTTCTTGCCATGAGCCTTCACCTTAGG
GTTGCCCATAACAGCATCAGGAGTGGACAGATCCCCAAAGGACTCAAAGAACCTCTGG
GTCCAAGGGTAGACCACCAGCAGCCTAAGGGTGGGAAAATAGACCAATAGGCAGAGA
GAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCA
ACGGCATCCACGTTCACCTTGTCCCAAGAGCGGTACAGCGGACTTCTCCTCAGGAG
TCAGGTGCACCAT

Gamma-beta hybrid – SEQ ID NO: 3
TCAGTGGTATCTGGAGGACAGGGCACTGGCCACTGCAGTCACCATCTTCTGCC
AGGAAGCCTGCACCTCAGGGGTGAATTCTTTGCCGAAATGGATTGCCAAAACG
GTCACCAGCACATTTCCCAGGAGCTGTGGGAGGAAGATAAGAGGTATGAACAT
GATTAGCAAAAGGGCCTAGCTTGGACTCAGAATAATCCAGCCTTATCCCAACC
ATAAAATAAAAGCAGAATGGTAGCTGGATTGTAGCTGCTATTAGCAATATGAAA
CCTCTTACATCAGTTACAATTTATATGCAGAAATACCCTGTTACTTCTCCCCTTC
CTATGACATGAACTTAACCATAGAAAGAAGGGGAAAGAAAACATCAAGGGTC
CCATAGACTCACGGGTCCCATAGACTCACCTTGAAGTTCTCAGGATCCACATG
CAGCTTGTCACAGTGCAGTTCACTCAGCTGGGCAAAGGTGCCCTTGAGATCAT
CCAGGTGCTTTGTGGCATCTCCCAAGGAAGTCAGCACCTTCTTGCCATGTGCC
TTGACTTTGGGGTTGCCCATGATGGCAGAGGCAGAGGACAGGTTGCCAAAGC
TGTCAAAGAACCTCTGGGTCCATGGGTAGACAACCAGGAGCCTAAGGGTGGG
AAAATAGACCAATAGGCAGAGAGAGTCAGTGCCTATCAGAAACCCAAGAGTCT
TCTCTGTCTCCACATGCCCAGTTTCTATTGGTCTCCTTAAACCTGTCTTGTAAC
CTTGATACCAACCTTCCCAGGGTTTCTCCTCCAGCATCTTCCACATTCACCTTG
CCCCACAGGCTTGTGATAGTAGCCTTGTCCTCCTCTGTGAAATGACCCAT

Gamma-beta hybrid AS2 (G16D and D22A) – SEQ ID NO: 4
TCAGTGGTATCTGGAGGACAGGGCACTGGCCACTGCAGTCACCATCTTCTGCC
AGGAAGCCTGCACCTCAGGGGTGAATTCTTTGCCGAAATGGATTGCCAAAACG
GTCACCAGCACATTTCCCAGGAGCTGTGGGAGGAAGATAAGAGGTATGAACAT
GATTAGCAAAAGGGCCTAGCTTGGACTCAGAATAATCCAGCCTTATCCCAACC
ATAAAATAAAAGCAGAATGGTAGCTGGATTGTAGCTGCTATTAGCAATATGAAA
CCTCTTACATCAGTTACAATTTATATGCAGAAATACCCTGTTACTTCTCCCCTTC
CTATGACATGAACTTAACCATAGAAAGAAGGGGAAAGAAAACATCAAGGGTC
CCATAGACTCACGGGTCCCATAGACTCACCTTGAAGTTCTCAGGATCCACATG
CAGCTTGTCACAGTGCAGTTCACTCAGCTGGGCAAAGGTGCCCTTGAGATCAT
CCAGGTGCTTTGTGGCATCTCCCAAGGAAGTCAGCACCTTCTTGCCATGTGCC
TTGACTTTGGGGTTGCCCATGATGGCAGAGGCAGAGGACAGGTTGCCAAAGC
TGTCAAAGAACCTCTGGGTCCATGGGTAGACAACCAGGAGCCTAAGGGTGGG
AAAATAGACCAATAGGCAGAGAGAGTCAGTGCCTATCAGAAACCCAAGAGTCT
TCTCTGTCTCCACATGCCCAGTTTCTATTGGTCTCCTTAAACCTGTCTTGTAAC
CTTGATACCAACCTTCCCAGGGTTTCTCCTCCAGCGGCTTCCACATTCACCTTG
TCCCACAGGCTTGTGATAGTAGCCTTGTCCTCCTCTGTGAAATGACCCAT

FIGURE 14 (continuation)

Delta-beta hybrid – SEQ ID NO: 5
TCAATGGTACTTGTGAGCCAGGGCATTAGCCACACCAGCCACCACCTTCTGAT
AGGCAGCCTGCATTTGTGGGGTGAATTCCTTGCCAAAGTTGCGGGCCAGCAC
ACACACCAGCACATTGCCCAAGAGCTGTGGGAGGAAGATAAGAGGTATGAACA
TGATTAGCAAAAGGGCCTAGCTTGGACTCAGAATAATCCAGCCTTATCCCAAC
CATAAAATAAAAGCAGAATGGTAGCTGGATTGTAGCTGCTATTAGCAATATGAA
ACCTCTTACATCAGTTACAATTTATATGCAGAAATACCCTGTTACTTCTCCCCTT
CCTATGACATGAACTTAACCATAGAAAAGAAGGGGAAAGAAAACATCAAGGGT
CCCATAGACTCACCCTGAAGTTCTCAGGATCCACGTGCAGCTTGTCACAGTGC
AGCTCACTCAGCTGAGAAAAAGTGCCCTTGAGGTTGTCCAGGTGAGCCAGGC
CATCACTAAAGGCACCTAGCACCTTCTTGCCATGAGCCTTCACCTTAGGGTTG
CCCATAACAGCATCAGGAGAGGACAGATCCCCAAAGGACTCAAAGAACCTCTG
GGTCCAAGGGTAGACCACCAGTAATCTAAGGGTGGGAAAATAGACCAATAGGC
AGAGAGAGTCAGTGCCTATCAGAAACCCAAGAGTCTTCTCTGTCTCCACATGC
CCAGTTTCTATTGGTCTCCTTAAACCTGTCTTGTAACCTTGATACCAACCTGCC
CAGGGCCTCACCACCAACTGCATCCACGTTCACTTTGCCCCACAGGGCATTGA
CAGCAGTCTTCTCCTCAGGAGTCAGATGCACCAT

Delta-beta hybrid AS1 (G16D) – SEQ ID NO: 6
TCAATGGTACTTGTGAGCCAGGGCATTAGCCACACCAGCCACCACCTTCTGAT
AGGCAGCCTGCATTTGTGGGGTGAATTCCTTGCCAAAGTTGCGGGCCAGCAC
ACACACCAGCACATTGCCCAAGAGCTGTGGGAGGAAGATAAGAGGTATGAACA
TGATTAGCAAAAGGGCCTAGCTTGGACTCAGAATAATCCAGCCTTATCCCAAC
CATAAAATAAAAGCAGAATGGTAGCTGGATTGTAGCTGCTATTAGCAATATGAA
ACCTCTTACATCAGTTACAATTTATATGCAGAAATACCCTGTTACTTCTCCCCTT
CCTATGACATGAACTTAACCATAGAAAAGAAGGGGAAAGAAAACATCAAGGGT
CCCATAGACTCACGGGTCCCATAGACTCACCCTGAAGTTCTCAGGATCCACGT
GCAGCTTGTCACAGTGCAGCTCACTCAGCTGAGAAAAAGTGCCCTTGAGGTTG
TCCAGGTGAGCCAGGCCATCACTAAAGGCACCTAGCACCTTCTTGCCATGAGC
CTTCACCTTAGGGTTGCCCATAACAGCATCAGGAGAGGACAGATCCCCAAAGG
ACTCAAAGAACCTCTGGGTCCAAGGGTAGACCACCAGTAATCTAAGGGTGGGA
AAATAGACCAATAGGCAGAGAGAGTCAGTGCCTATCAGAAACCCAAGAGTCTT
CTCTGTCTCCACATGCCCAGTTTCTATTGGTCTCCTTAAACCTGTCTTGTAACC
TTGATACCAACCTGCCCAGGGCCTCACCACCAACTGCATCCACGTTCACTTTG
TCCCACAGGGCATTGACAGCAGTCTTCTCCTCAGGAGTCAGATGCACCAT The gRNA D target site is underlined. The nucleotides changes in the Beta AS3 and Beta AS1 transgenes are highlighted in green.

A

FIGURE 21A (continuation)
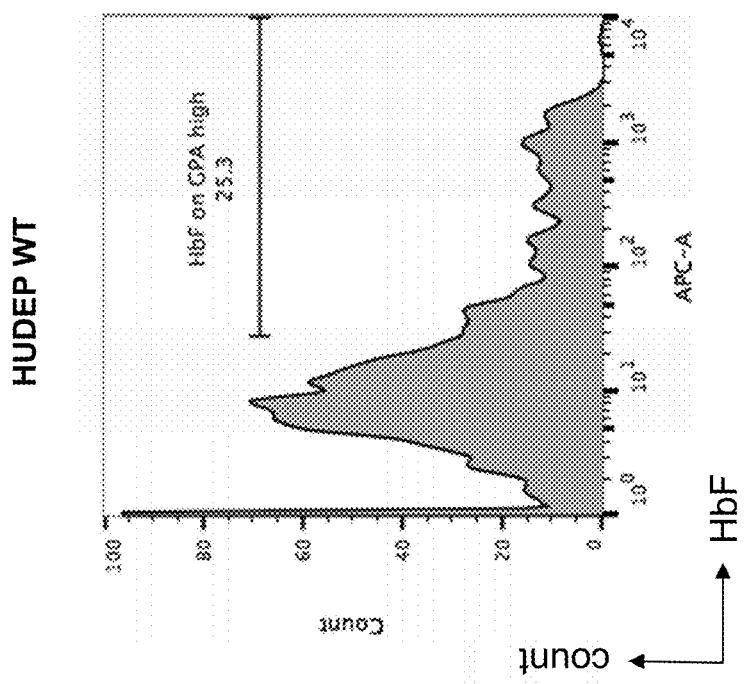

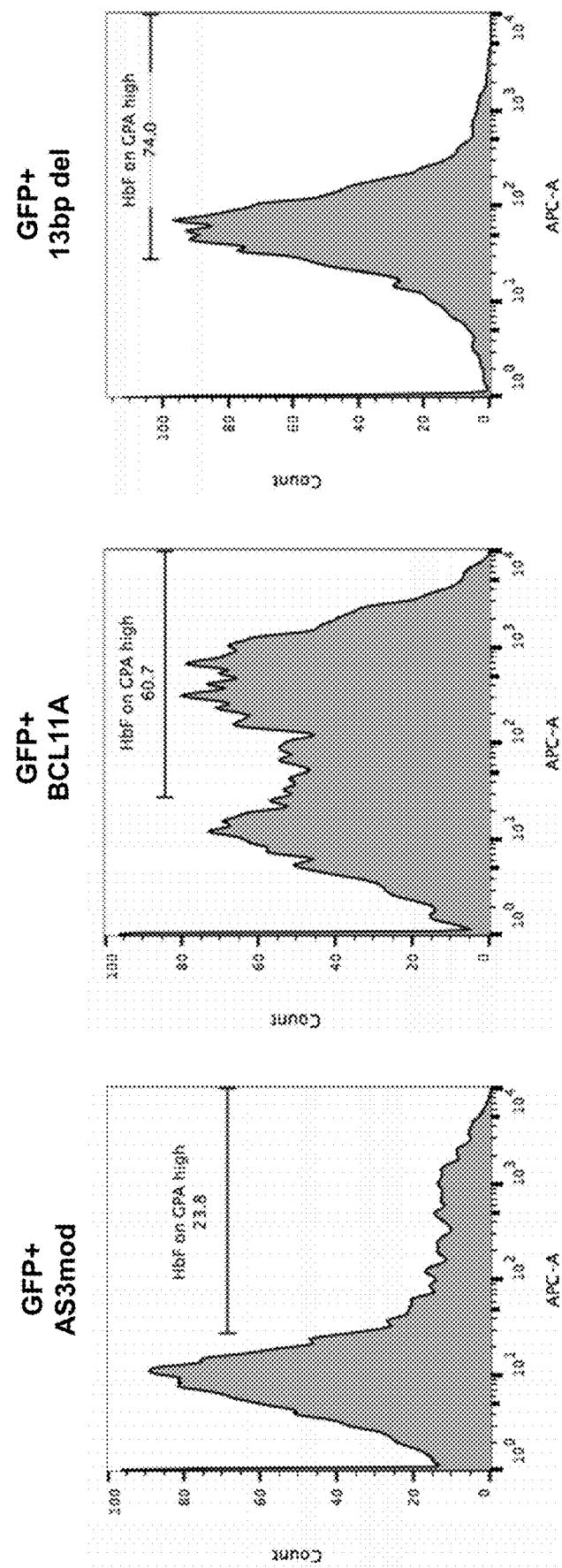
FIGURE 21A (continuation)

RECOMBINANT LENTIVIRAL VECTOR FOR STEM CELL-BASED GENE THERAPY OF SICKLE CELL DISORDER

CROSS-REFERENCE TO RELATED APPLICATIONS

This application is a U.S. National Stage Application of International Application No. PCT/EP2018/064531, filed on Jun. 1, 2018, which claims priority to European Patent Application No. 17305647.4, filed on Jun. 2, 2017, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 18 Sep. 2024, is named 0061_0011_SUB-STITUTE_ST.25 and is 124,257 bytes in size.

BACKGROUND OF THE INVENTION

Sickle cell disease (SCD) is amongst the most common inherited blood disorders. The disease is caused by a single amino acid substitution of a polar glutamic acid with a nonpolar valine residue in the beta-globin chain. At low oxygen tensions, this residue interacts with a hydrophobic pocket (aa 85-88) on the surface of a second Hb tetramer, thus leading to the polymerization of sickle hemoglobin (HbS) and formation of sickle Red Blood Cells (RBC). This can cause occlusions of small blood vessels, leading to impaired oxygen delivery to tissues, pain crises, respiratory complications, and organ damage, often associated with a high mortality rate. SCD represents an increasing health problem in Mediterranean, American and Asian countries. In particular, SCD has become one of the most common genetic diseases in France (birth prevalence of 1:2,400).

Currently, the main treatment involves symptomatic care and transfusion of RBC as clinically necessary. However, the use of regular transfusion therapy can lead to significant side effects, such as iron overload, which can even occur when the strictest iron-chelation regimens are used.

The clinical course of SCD is also improved in the presence of elevated expression of the fetal gamma-globin genes. Indeed, in SCD, fetal gamma-globin can exert a potent anti-sickling effect decreasing the incidence of vaso-occlusions. Therefore, the expectation is that pharmacological treatments that increase gamma-globin expression would benefit SCD patients. However, pharmacological treatments are not equally effective for all patients and are associated with considerable toxicity. There are clinical data showing that high expression of delta globin results in mild disease phenotype in SCD patients The only definitive cure for SCD is allogeneic hematopoietic stem/precursor cell (HSPC) transplantation, which is, however, available to a small proportion (<30%) of the patients with an HLA-compatible donor.

Therefore, new approaches remain highly desired because such treatments are not equally effective for all patients, are associated with considerable toxicity and do not represent a definitive treatment.

Autologous transplantation of genetically corrected HSPC is considered an attractive therapeutic option, for example it is an alternative for patients lacking a compatible donor. Transplantation of autologous genetically corrected HSPC is currently based on the use of lentiviral vectors expressing a mutated beta-globin gene with anti-sickling properties and showed a partial correction of the SCD phenotype in human RBC (Romero et al., J Clin Invest, 2013, 23(8):3317-30). Lentivirus vectors (LVs) expressing the human beta-globin gene have been successfully used in preclinical murine models and in human thalassemic cells (Imren et al., Proc Natl Acad Sci USA, 2002, 99(22):14380-5; Miccio et al., Proc Natl Acad Sci USA, 2008, 105(30): 10547-52; Miccio et al., PLoS One, 2011, 6(12):e27955; Puthenveetil et al., Blood, 2004, 104(12):3445-53). Therapeutic approaches based on the use of gamma-globin expressing LVs have also been proposed, leading to the improvement of the murine SCD phenotype (Perumbeti et al., Blood, 2009, 114(6):1174-85). Early clinical data indicate that the expression of an anti-sickling beta-globin molecule harboring an aminoacid derived from the gamma-globin chain in erythrocytes provides some degree of clinical benefit in beta-thalassemic patients and in a SCD patient (Ribeil J A, abstract n.2311, 58$^{th}$ annual meeting ASH, 2016) (Ribeil et al. N Engl J Med, 2017, 376(9):848-55).

However, to achieve the functional correction of a high number of SCD RBC, it is mandatory to find new gene therapy approaches. Indeed, despite the undeniable progress in the gene therapy field, the treatment of SCD requires further key improvements to achieve the functional correction of a high number of SCD RBC in order to cure SCD.

The applicant now proposes a new approach to achieve these therapeutic goals through a novel gene therapy/genome editing combined strategy based on a high-titer lentiviral vector carrying: (i) the anti-sickling globin transgene under the control of the endogenous beta-globin promoter and LCR enhancers; (ii) a gRNA targeting the endogenous HBB (beta-hemoglobin) gene or gRNA resulting in an inhibition of the repression of gamma globins. LV transduction of a large proportion of patient hematopoietic stem cells (HSC) followed by transient Cas9 delivery will permanently alter the endogenous sickle HBB gene, ensuring meanwhile the expression of globin transgene in genome-edited cells.

SUMMARY OF THE INVENTION

The inventors propose here new recombinant lentiviral vectors and processes for autologous gene therapy that are particularly efficient and easy to practice for both incorporating a therapeutic DNA into a patient's cell and to knock out an altered gene in said patient's cells.

The invention relates to a recombinant lentiviral vector comprising in its genome:
  (i) a nucleotide sequence encoding a protein that has a therapeutic effect, said protein being selected from the group consisting of gamma-globin, beta-globin, delta-globin and variants thereof; and
  (ii) a nucleotide sequence encoding a guide RNA (gRNA) that comprises a spacer adapted to bind to a target nucleotide sequence, said target nucleotide sequence is
    a) within the coding sequence or within a transcribed non-coding sequence of a target gene, said target gene is selected from beta-globin gene and BCL11A gene, or
    b) within the promoter region of a target gene, said target gene is gamma-globin gene.

The invention also relates to a composition comprising a vector according to the invention or a plurality of vectors according to the invention.

The invention also relates to a kit of parts comprising:
  a vector of the invention or a composition of the invention; and
  a catalytically active Cas9 or Cpf1 protein or a nucleotide sequence encoding a catalytically active Cas9 or Cpf1 protein.

The invention also relates to the use of a recombinant lentiviral vector of the invention or a composition of the invention or a kit of the invention for introducing into a hematopoietic stem/progenitor cell (HSPC):
  (i) the nucleotide sequence encoding a protein that has a therapeutic effect, said protein being selected from the group consisting of gamma-globin, beta-globin, delta-globin and variants thereof; and
  (ii) the nucleotide sequence encoding a guide RNA (gRNA) that comprises a spacer adapted to bind to a target nucleotide sequence, said target nucleotide sequence is
    a. within the coding sequence or within a transcribed non-coding sequence of a target gene, said target gene is selected from beta-globin gene and BCL11A gene, or
    b. within the promoter region of a target gene, said target gene is gamma-globin gene.

The invention also relates to a method for modifying the genome of hematopoietic stem/progenitor cells (HSPC), in vitro or ex vivo, comprising the steps of:
  a) contacting a HSPC with a recombinant lentiviral vector of the invention or a composition of the invention to obtain a transduced HSPC, wherein the lentiviral vector is integrated into the genome of said HSPC; and
  b) introducing into the transduced HSPC a catalytically active Cas9 or Cpf1 protein or a nucleotide sequence encoding a catalytically active Cas9 or Cpf1 protein, said catalytically active Cas9 or Cpf1 protein disrupts the expression and/or the function of the target gene when introduced or expressed into the transduced HSPC.

The invention also relates to a method for preparing a genetically modified hematopoietic stem/progenitor cell (HSPC), in vitro or ex vivo, comprising the steps of:
  a) contacting a HSPC with a recombinant lentiviral vector of the invention or a composition of the invention to obtain a transduced HSPC, wherein the lentiviral vector is integrated into the genome of said HSPC; and
  b) introducing into the transduced HSPC a catalytically active Cas9 or Cpf1 protein or a nucleotide sequence encoding a catalytically active Cas9 or Cpf1 protein, said catalytically active Cas9 or Cpf1 protein disrupts the expression and/or the function of the target gene when introduced or expressed into the transduced HSPC.

The invention also relates to a genetically modified HSPC obtainable by the methods of the invention.

DETAILED DESCRIPTION OF THE INVENTION

Recombinant Vector

The invention relates to a recombinant lentiviral vector comprising in its genome:
  (i) a nucleotide sequence encoding a protein that has a therapeutic effect, said protein being selected from the group consisting of gamma-globin, beta-globin, delta-globin and variants thereof; and
  (ii) a nucleotide sequence encoding a guide RNA (gRNA) that comprises a spacer adapted to bind to a target nucleotide sequence, said target nucleotide sequence is:
    a. within the coding sequence or within a transcribed non-coding sequence of a target gene, said target gene is selected from beta-globin gene and BCL11A gene, or
    b. within the promoter region of a target gene, said target gene is gamma-globin gene.

In some embodiments, said target nucleotide sequence is within a coding sequence or within a non-coding sequence implied in the expression of BCL11A gene, such as erythroid-specific BCL11A intronic enhancer.

Lentiviruses are used as a vector or delivery system for the transfer of nucleotide sequences to a cell. The transfer can occur in vitro, ex vivo or in vivo. When used in this fashion, the lentiviruses are typically called "lentiviral vectors".

The lentiviral vector according to the invention is a virus particle that contains a lentivirus-derived viral genome, lacks self-renewal ability, and has the ability to introduce a nucleotide sequence into a cell. The recombinant lentiviral vector of the invention is therefore a "recombinant lentiviral integrative vector".

The lentiviral vector may be derived from complex retroviruses such as the human immunodeficiency virus (HIV). In the present invention, lentiviral vectors derived from any strain and subtype can be used. The lentiviral vector may be based on a human or primate lentivirus, such as HIV, or a non-human lentivirus such as feline immunodeficiency virus, simian immunodeficiency virus or equine infectious anemia virus (EIAV). In a preferred embodiment, the lentiviral vector is a HIV-based vector and especially a HIV-1-based vector.

"Recombinant" is used consistently with its usage in the art to refer to a nucleotide sequence that comprises portions that do not naturally occur together as part of a single sequence or that have been rearranged relative to a naturally occurring sequence. A recombinant nucleotide sequence (or transgene) is created by a process that involves the human intervention and/or is generated from a nucleic acid that was created by human intervention (e.g., by one or more cycles of replication, amplification, transcription, etc.). A recombinant virus is one that comprises a recombinant nucleotide sequence. A recombinant cell is one that comprises in its genome a recombinant nucleotide sequence. Thus, a "recombinant lentiviral vector" according to the invention refers to a lentiviral vector comprising in its genome a recombinant nucleotide sequence (or transgene).

The recombinant lentiviral vector "genome", as used herein, accordingly contains, apart from the so-called recombinant nucleotide sequences placed under control of proper regulatory sequences for its expression, the sequences of the original lentivirus genome which are non-coding regions of said genome, and are necessary to provide recognition signals for DNA or RNA synthesis and processing (mini-viral genome). These sequences are cis-acting sequences necessary for packaging, reverse transcription and transcription and furthermore they contain a functional sequence favoring nuclear import in cells and accordingly transgenes transfer efficiency in said cells, which element is described as a DNA Flap element.

The lentiviral vector can be based on any suitable lentivirus which is able to deliver genetic information to a hematopoietic stem/progenitor cell (HSPC), in particular a human HSPC.

In the lentiviral vector of the present invention, the recombinant nucleotide sequences encode (i) a protein that has a therapeutic effect, said protein being selected from the group consisting of gamma-globin, beta-globin, delta-globin and variants thereof, and (ii) a gRNA that comprises a spacer adapted to bind to a target nucleotide sequence, said target nucleotide sequence is:
  a. within the coding sequence or within a transcribed non-coding sequence of a target gene, said target gene is selected from beta-globin gene and BCL11A gene, or
  b. within the promoter region of a target gene, said target gene is gamma-globin gene.

The official symbols of beta-like globin genes are: HBB (beta-globin gene), HBD (delta-globin gene), HBG1 and HBG2 (gamma-globin genes), HBA1 and HBA2 (alpha-globin genes). The Greek symbols (e.g. α, β, γ and δ) and the corresponding denomination (e.g. alpha, beta, gamma, and delta) are used independently in the present description. Furthermore, the beta-like globin genes/mRNA/proteins are independently used in italic or not in the present description (e.g. HBB gene or HBB gene; HBB mRNA and HBB mRNA and HBB protein or HBB protein).

The term "gamma-globin target gene" means HBG1, HBG2 or both HBG1 and HGB2.

The terms "protein that has a therapeutic effect" means a protein that provides an effect which is judged to be desirable and beneficial to a patient, in particular a patient with a sickle cell disease (SCD). Examples of a protein that has a therapeutic effect in the present invention may be the functional protein of a protein that has become dysfunctional due to a sickle cell disease (SCD). Thus, in one embodiment, the term "protein that has a therapeutic effect" refers to a protein that does not induce a sickle cell disease (SCD), and which is effective to provide therapeutic benefits to a patient, in particular a patient with a sickle cell disease (SCD). The protein that has a therapeutic effect may be a wild-type (WT) protein appropriate for a patient with a sickle cell disease (SCD) to be treated, or it may be a mutant form of the WT protein (i.e. a variant of the WT protein) appropriate for a patient to be treated. In another embodiment the terms "protein that has a therapeutic effect" refer to a protein that may be incorporated within hemoglobin tetramers and does not allow the hemoglobin tetramer polymerization in which SCD originates.

For example, a globin (e.g. a beta-like globin) that has a therapeutic effect refers to a globin protein that does not produce a hemoglobinopathy phenotype, and which is effective to provide therapeutic benefits to a patient defective for said globin. A globin that has a therapeutic effect may be a wild-type globin appropriate for a patient to be treated, or variant thereof, preferably a variant which provides for superior properties, for example superior anti-sickling properties.

All the globin variants are encoded by a transgene containing the introns of the beta-globin gene, the gamma-globin gene and/or the delta-globin gene, preferably the intron of the beta-globin gene, as contained in the GLOBE vector (Miccio et al., Proc Natl Acad Sci USA, 2008, 105(30):10547-52). In some embodiments, the second intron harbors a 600-bp RsaI to SspI deletion.

In some embodiments, the globin variant has one or more mutations that increase the anti-sickling properties of the protein, for example:
  beta-globin comprising one mutation Thr87Gln (i.e. beta-globin wild-type sequence having threonine replaced by glutamine at position 87, named Beta AS1 (T87Q), encoded by SEQ ID NO: 1) (Ribeil J A, abstract n.2311, 58$^{th}$ annual meeting ASH, 2016) (Ribeil et al. N Engl J Med, 2017, 376(9):848-55),
  beta-globin comprising three mutations Gly16Asp, Glu22Ala and Thr87Gln (i.e. beta-globin wild-type sequence having glycine replaced by aspartic acid at position 16; Glutamic acid replaced by alanine at position 22 and threonine replaced by glutamine at position 87, named Beta AS3, encoded by SEQ ID NO: 2) (Romero et al., J Clin Invest, 2013, 23(8):3317-30),
  gamma-globin comprising two mutations Gly16Asp and Glu22Ala (gamma-globin wild-type sequence having glycine replaced by aspartic acid at position 16 and glutamic acid replaced by alanine at position 22, named Gamma-beta hybrid AS2 (G16D and D22A), encoded by SEQ ID NO: 4), or
  delta-globin comprising one mutation Gly16Asp (i.e. delta-globin wild-type sequence having glycine replaced by aspartic acid at position 16, named Delta-beta hybrid AS1 (G16D), encoded by SEQ ID NO: 6).

In a specific embodiment, Gamma-beta hybrid AS2 (G16D and D22A) may be A-Gamma-beta hybrid AS2 (G16D and D22A), i.e. the protein encoded by the genes HBG1, or G-Gamma-beta hybrid AS2 (G16D and D22A), i.e. the protein encoded by the genes HGB2, preferably A-Gamma-beta hybrid AS2 (G16D and D22A).

In a preferred embodiment, the protein that has a therapeutic effect is gamma-globin, beta-globin or a variant thereof, for example a variant having anti-sickling properties. Preferably, the protein that has a therapeutic effect is beta-globin or a variant thereof.

In a specific embodiment, the intended patient is a mammalian being, preferably a human being, regardless of age and gender. In particular, the patient has a sickle cell disease (SCD). Thus, in a specific embodiment, the protein that has a therapeutic effect is selected from the group consisting of human beta-globin, human gamma-globin, human delta-globin and variants thereof, in particular human beta-globin or human gamma-globin, preferably human beta-globin. The variants thereof may be:
  Beta AS1 (T87Q), encoded by SEQ ID NO: 1;
  Beta AS3, encoded by SEQ ID NO: 2;
  Gamma-beta hybrid, encoded by SEQ ID NO: 3;
  Gamma-beta hybrid AS2 (G16D and D22A), encoded by SEQ ID NO: 4;
  Delta-beta hybrid, encoded by SEQ ID NO: 5; or
  Delta-beta hybrid AS1 (G16D), encoded by SEQ ID NO: 6.

In a specific embodiment, beta-globin, gamma-globin, delta-globin and their variants can harbor silent mutations that impair the gRNA binding to the transgene, for example:
  Beta AS1 (T87Q) modified to avoid targeting by gRNA D, encoded by SEQ ID NO: 7; or
  Beta AS3 modified to avoid targeting by gRNA D, encoded by SEQ ID NO: 8.

In some embodiments, the protein that has a therapeutic effect is involved in a sickle cell disease (SCD) when said protein is altered in a patient.

The terms "protein is altered" or "altered protein" means a change (increase or decrease) in the expression levels and/or activity of the protein and/or a structural change in the protein. An altered protein may cause a sickle cell disease (SCD). In particular, for SCD, mutation in beta-globin increases the propensity of hemoglobin tetramers to polymerize. Said "altered protein" is encoded by an "altered gene" (e.g. altered HBB gene).

According to the invention, the gRNA comprises a spacer (said spacer is also called "CRISPR spacer" or "gRNA spacer" in the present description) adapted to bind to a target nucleotide sequence. The terms "target nucleotide sequence" means any endogenous nucleic acid sequence of the genome of a cell, such as, for example a gene or a non-coding sequence within or adjacent to a gene, in which it is desirable to modify it by targeted non-homologous end-joining (NHEJ) or MMEJ (Microhomology-mediated end-joining), in particular to disrupt (e.g. to knock-out) the expression and/or the function of said gene (also called "target gene"). The target nucleotide sequence can be present in a chromosome. In some embodiments, the target nucleotide sequence is within the coding sequence of the target gene or within a transcribed non-coding sequence of the target gene such as, for example, leader sequences, trailer sequence or introns. According to the invention, the target gene is known to be involved in a sickle cell disease (SCD) when said target gene is expressed in a patient. In a specific embodiment, the target gene is betaS-globin gene. The term "betaS-globin gene" means the altered HBB gene in SCD patients. The "betaS-globin gene" comprises a mutation A>T in the seventh codon of the beta-globin gene (in the sixth codon of the beta globin in the old nomenclature).

Generally, the nucleotide sequence encoding the gRNA is designed to encode a gRNA that may disrupt the expression and/or the function of a target gene through the insertion of frameshift mutations in its coding sequence. Thus, the nucleotide sequence encoding the gRNA is designed to encode a gRNA that may disrupt the function and/or the expression of a target protein. This disruption takes place when said gRNA forms a complex with Cas9 or Cpf1 in the transduced cell through the CRISPR/Cas9 system or CRISPR/Cpf1 system respectively (see below).

The gRNA can also be designed to reproduce small deletion detected in Hereditary Persistent of Fetal Hemoglobin (HPFH) patients (e.g. 13 bp small deletion; Traxler E A et al., Nat Med, 2016, 22(9):987-90) within the promoters of HBG1 and HBG2. Accordingly, in a specific embodiment of the present invention, the recombinant lentiviral vector comprises in its genome a nucleotide sequence encoding a guide RNA (gRNA) that comprises a gRNA spacer adapted to generate a mimetic effect to the one of 13 bp small deletion within the promoters of HBG1 and HBG2. In some embodiments, said gRNA spacer is encoded by SEQ ID No: 73 (5'-CTTGTCAAGG CTATTGGTCA-3).

In a specific embodiment of the present invention, the recombinant lentiviral vector comprises in its genome a nucleotide sequence encoding a guide RNA (gRNA) that comprises a gRNA spacer adapted to bind to the wild-type or the altered HBB gene. In some embodiments, the gRNA spacer is encoded by a nucleotide sequence selected from SEQ ID No: 23 to SEQ ID No: 36.

In another specific embodiment of the present invention, the recombinant lentiviral vector comprises in its genome a nucleotide sequence encoding a guide RNA (gRNA) that comprises a gRNA spacer adapted to bind to BCL11A gene. In a specific embodiment, said guide RNA (gRNA) comprises a gRNA spacer adapted to bind the intronic erythroid specific enhancer of BCL11A gene. In some embodiments, the gRNA spacer is encoded by the nucleotide sequence SEQ ID NO: 74) (5'-CACAGGCTCCAGGAAGGGTT-3').

Thus, according to the invention, the recombinant lentiviral vector provides expression of the protein that has a therapeutic effect and of the gRNA into a hematopoietic stem/progenitor cell (HSPC) transduced by said vector (also called "transduced HSPC"). The transduced HSPC therefore expresses a gRNA that may disrupt the gene and, as a consequence, the function and/or expression of a target protein in the transduced HSPC by forming a complex with Cas9 or Cpf1.

The terms "disrupt the function of a target protein" or "target protein is disrupted" or "disrupted target protein" means a decrease in the expression levels and/or activity of the target protein.

The terms "disrupt the function of a target gene" or "target gene is disrupted" or "disrupted target gene" means a decrease in the expression level and/or function of the target gene.

The term "to disrupt" comprises "to knock out". In a specific embodiment, the gRNA disrupts the expression and/or the function of the target gene and therefore the gRNA disrupts the expression and/or the activity of the target protein. In a specific embodiment, the target gene is a gene coding for the betaS-globin (i.e. betaS-globin gene).

In a preferred embodiment, the recombinant lentiviral vector of the invention further comprises the elements 1, 2, 3, 4 and 5 below, or elements 1, 2, 3, 4, 5, and 6 below:
1) An expression cassette encoding the protein that has a therapeutic effect;
2) A self-inactivating (SIN) LTR configuration;
3) A packaging signal;
4) A Rev Responsive Element (RRE) to enhance nuclear export of unspliced recombinant lentiviral vector RNA;
5) A central polypurine tract (cPPT) to enhance nuclear import of recombinant lentiviral vector genomes; and
6) A post-transcriptional regulatory element (PRE) to enhance recombinant lentiviral vector genome stability and to improve recombinant lentiviral vector titers (e.g. WPRE).

An Expression Cassette Encodinq the Protein that has a Therapeutic Effect

As indicated above, in various embodiments the recombinant lentiviral vector described herein comprises an expression cassette encoding the protein that has a therapeutic effect. For example, the expression cassette is a beta-like globin gene (i.e. gamma-globin gene, beta-globin gene or delta-globin gene, or variants thereof) cassette which encodes the protein that has a therapeutic effect. For example, the expression cassette encodes a human globin, for example the expression cassette comprises ~1.95 kb recombinant human gamma-beta hybrid globin gene (i.e. gamma-globin exons and beta-globin introns, where beta-globin intron 2 has a 600-bp RsaI to SspI deletion) under the control of transcriptional control elements (e.g. the human beta-globin gene promoter (e.g., −265 bp/+50 bp)), and a 2.7 kb composite human beta-globin locus control region (e.g., HS2 −1203 bp; HS3 −1213 bp and/or HS4 −954 bp).

The beta-like globin gene (i.e. beta-globin gene, gamma-globin gene, delta-globin gene, or variants thereof) cassette, however, is illustrative and need not be limiting. Using the known cassette described herein, numerous variations will be available to one of skill in the art.

Such variations include, for example, further and/or alternative mutations to the beta-globin to further enhance non-sickling properties (e.g., PAS3 cassette is described by Levasseur (2003) Blood 102: 4312-4319), alterations in the transcriptional control elements (e.g., promoter and/or enhancer such as HS4), variations on the intron size/structure, and the like. In a preferred embodiment, the cassette lacks HS4 (i.e. the recombinant lentiviral vector lacks HS4). The inventors showed that the absence of HS4 increases recombinant lentiviral vector titer and therefore efficiency and efficacy of the recombinant lentiviral vector; and the absence of HS4 does not affect the therapeutic potential of the globin-expressing recombinant lentiviral vectors.

Self Inactivating (SIN) LTR Configuration.

To further improve safety, in various embodiments, the recombinant lentiviral vectors described herein comprise a TAT-independent, self-inactivating (SIN) configuration. Thus, in various embodiments it is desirable to employ in the LVs described herein an LTR region that has reduced promoter activity relative to wild-type LTR. Constructs can be provided that are effectively "self-inactivating" (SIN), which provides a biosafety feature. SIN vectors are ones in which the production of full-length vector RNA in transduced cells is greatly reduced or abolished altogether. This feature minimizes the risk that replication-competent recombinants (RCRs) will emerge. Furthermore, it reduces the risk that cellular coding sequences located adjacent to the recombinant lentiviral vector integration site will be aberrantly expressed. The SIN configurations are well known in the art.

Packaging Signal.

In various embodiments the recombinant lentiviral vectors described herein further comprise a packaging signal. A "packaging signal", "packaging sequence", or "psi sequence" is any nucleic acid sequence sufficient to direct packaging of a nucleic acid whose sequence comprises the packaging signal into a retroviral particle. The term includes naturally occurring packaging sequences and also engineered variants thereof. Packaging signals of a number of different retroviruses, including lentiviruses, are known in the art. In a specific embodiment, the packaging sequence is the naturally occurring packaging sequences.

Rev Responsive Element (RRE).

In certain embodiments, the recombinant lentiviral vectors described herein comprise a Rev Response Element (RRE) to enhance nuclear export of unspliced RNA. RREs are well known to those of skill in the art.

Expression-Stimulating Posttranscriptional Regulatory Element (PRE)

In certain embodiments, the recombinant lentiviral vectors described herein may comprise any of a variety of posttranscriptional regulatory elements (PREs) whose presence within a transcript increases expression of the heterologous nucleic acid (e.g., Gamma-beta hybrid globin gene) at the protein level. PREs may be particularly useful in certain embodiments, especially those that involve lentiviral constructs with poorly efficient promoters.

One type of PRE is an intron positioned within the expression cassette, which can stimulate gene expression. However, introns can be spliced out during the life cycle events of a lentivirus. Hence, if introns are used as PREs they are typically placed in an opposite orientation to the recombinant lentiviral vector genomic transcript. PREs are well known to those of skill in the art.

The recombinant lentiviral vector of the invention is able to provide expression of the gRNA into a hematopoietic stem/progenitor cell (HSPC) transduced by said recombinant lentiviral vector and is able to provide expression of the protein that has a therapeutic effect into an erythroblast derived from the transduced HSPC and/or into a differentiate progeny of the transduced HSPC.

In a specific embodiment, recombinant lentiviral vector is SEQ ID NO: 47, SEQ ID NO: 75 (LV.GLOBE-AS3modified.gRNA-BCL11Aenhancer), SEQ ID NO: 76 (LV.GLOBE-AS3modified.gRNA-13 bp-del) or SEQ ID NO: 94 (LV.GLOBE-AS3modified.gRNAD).

The invention also relates to a composition comprising a recombinant lentiviral vector of the invention or a plurality of recombinant lentiviral vectors of the invention. The recombinant lentiviral vector or a plurality of recombinant lentiviral vectors of the invention can be purified to become substantially pure. The terms "substantially pure" means that the recombinant lentiviral vectors contain substantially no replicable virus other than the recombinant lentiviral vectors. The purification can be achieved using known purification and separation methods such as filtration, centrifugation and column purification. If necessary, the recombinant lentiviral vector or a plurality of recombinant lentiviral vectors of the invention can be prepared as compositions by appropriately combining them with desired pharmaceutically acceptable carriers or vehicles. The term "pharmaceutically acceptable carrier" refers to a material that can be added to the recombinant lentiviral vector or the plurality of recombinant lentiviral vectors of the invention and does not significantly inhibit recombinant lentiviral vector-mediated gene transfer. Specifically, the recombinant lentiviral vector or the plurality of recombinant lentiviral vectors can be appropriately combined with, for example, sterilized water, physiological saline, culture medium, serum, and phosphate buffered saline (PBS). The recombinant lentiviral vector or the plurality of recombinant lentiviral vectors can also be combined with a stabilizer, biocide, etc. Compositions containing a recombinant lentiviral vector or a plurality of recombinant lentiviral vectors of the present invention are useful as reagents or pharmaceuticals. For example, compositions of the present invention can be used as reagents for gene transfer into a cell, preferably for transduction of a hematopoietic stem/progenitor cell (HSPC), in particular a human HSPC.

The invention also relates to a kit of parts comprising:
- a recombinant lentiviral vector of the invention or a composition of the invention; and
- a catalytically active Cas9 or Cpf1 protein or a nucleotide sequence encoding a catalytically active Cas9 or Cpf1 protein.

According to the invention, the terms "catalytically active Cas9 or Cpf1" means either a "wild-type version of Cas9 or Cpf1" or a "catalytically active variant of Cas9 or Cpf1".

According to the invention, a complex gRNA/Cas9 or gRNA/Cpf1 induces the target nucleotide sequence to be removed and/or new ones added through a system called "CRISPR/Cas9 system" or "CRISPR/Cpf1 system". CRISPR means Clustered Regularly Interspaced Short Palindromic Repeats.

The CRISPR/Cas system is a prokaryotic immune system that confers resistance to foreign genetic elements such as those present within plasmids and phages, and provides a form of acquired immunity. CRISPR associated proteins (Cas), e.g. Cas9, use the CRISPR spacers to recognize and cut a target nucleotide sequence. By delivering into a cell the Cas9 and gRNA that comprises a spacer adapted to bind to a target nucleotide sequence, the cell genome can be cut at a desired location, inducing a target nucleotide sequence to be removed and/or new ones added (Mandal et al., Cell Stem Cell, 2014, 15(5):643-52).

According to the invention, said target nucleotide sequence is within the coding sequence of the target gene, within a transcribed non-coding sequence of the target gene. Therefore, the complex gRNA/Cas9 or gRNA/Cpf1 may disrupt (e.g. may induce knock-out of) the target gene.

It is well disclosed in the art that CRISPR/Cas9 system, when utilized for genome editing, may include Cas9, CRISPR RNA (crRNA) and trans-activating crRNA (tracrRNA).
- crRNA comprises the RNA that binds to a target nucleotide sequence, said RNA is along with a tracrRNA (generally in a hairpin loop form);

tracrRNA and crRNA form an active complex, named guide RNA (gRNA). Because eukaryotic systems lack some of the proteins required to process crRNA, the synthetic construct gRNA was created to combine the essential pieces of RNA for Cas9 targeting into a single RNA. Commonly, the gRNA is expressed with the RNA polymerase type III promoter U6 (promoter U6); Cas9 is a nuclease protein whose active form is able to modify DNA. Many variants exist with differing functions (i.e. single strand nicking, double strand break, DNA binding) due to Cas9's DNA site recognition function. In a preferred embodiment of the invention, Cas9 has a double strand break function.

The nucleic acid cleavages caused by Cas9 or Cpf1 are commonly repaired through the distinct mechanisms of homologous recombination or non-homologous end joining (NHEJ). NHEJ is an imperfect repair process that often results in changes to the nucleotide sequence at the site of the cleavage (i.e. the target nucleotide sequence). Repair via non-homologous end joining (NHEJ) often results in small insertions or deletions and can be used for the creation of specific gene knock-outs.

According to the present invention, CRISPR/Cas9 or CRISPR/Cpf1 system modifies the genome of a hematopoietic stem/progenitor cell (HSPC), preferably a human HSPC. Thus, in one aspect of the present invention, CRISPR/Cas9 or CRISPR/Cpf1 system aims to induce knock-out of the target nucleotide sequence in the transduced HSPC, and therefore to disrupt (e.g. to induce knock-out of) the target gene in the transduced HSPC, and therefore to disrupt (e.g. to suppress) the expression and/or the activity of the target protein in transduced HSPC and/or in the differentiated progeny of the transduced HSPC, such as the erythroid progeny of the transduced HSPC.

The invention also relates to the use of a lentiviral recombinant vector of the invention or a composition of the invention for introducing into a hematopoietic stem/progenitor cell (HSPC) (i) the nucleotide sequence encoding a protein that has a therapeutic effect, said protein being selected from the group consisting of beta-globin, gamma-globin, delta-globin and variants thereof, and (ii) the nucleotide sequence encoding a guide RNA (gRNA) that comprises a spacer adapted to bind to a target nucleotide sequence, said target nucleotide sequence is within the coding sequence of a target gene or within a transcribed non-coding sequence of a target gene, said target gene being selected from the group consisting of beta-globin gene and gamma-globin gene.

In some embodiment, the use according to the invention is in vitro or ex vivo. In another embodiment, the use according to the invention is in vivo.

The invention also relates to a method for modifying the genome of a hematopoietic stem/progenitor cell (HSPC), in vitro or ex vivo, comprising the steps of:
a) contacting a HSPC with a recombinant lentiviral vector of the invention or a composition of the invention to obtain a transduced HSPC, wherein the lentiviral vector is integrated into the genome of said HSPC; and
b) introducing into the transduced HSPC a catalytically active Cas9 or Cpf1 protein or a nucleotide sequence encoding a catalytically active Cas9 or Cpf1 protein, said catalytically active Cas9 or Cpf1 protein disrupts the expression and/or the function of the target gene when introduced or expressed into the transduced HSPC.

The invention also relates to a method for preparing a genetically modified hematopoietic stem/progenitor cell (HSPC), in vitro or ex vivo, comprising the steps of:
a) contacting a HSPC with a recombinant lentiviral vector of the invention or a composition of the invention to obtain a transduced HSPC, wherein the lentiviral vector is integrated into the genome of said HSPC; and
b) introducing into the transduced HSPC a catalytically active Cas9 or Cpf1 protein or a nucleotide sequence encoding a catalytically active Cas9 or Cpf1 protein, said catalytically active Cas9 or Cpf1 protein disrupts the expression and/or the function of the target gene when introduced or expressed into the transduced HSPC.

The term "transduction", according to the invention, means the process by which a foreign nucleotide sequence is introduced into the genome of a cell by a recombinant viral vector. According to the invention, a hematopoietic stem/progenitor cell (HSPC) transduced by the recombinant lentiviral vector of the invention, also referred as a "transduced HSPC", encodes (i.e. comprises in its genome) the nucleotide sequence encoding the protein that has a therapeutic effect and the nucleotide sequence encoding a gRNA that comprises a spacer adapted to bind to the target nucleotide sequence. Thus, according to a preferred embodiment, a transduced HSPC expresses the protein that has a therapeutic effect and the gRNA that comprises a spacer adapted to bind to the target nucleotide sequence.

The methods of the invention involve introducing a catalytically active Cas9 or Cpf1 protein (hereafter "Cas9" or "Cpf1") or a nucleotide sequence encoding Cas9 or Cpf1, preferably a RNA encoding Cas9 or Cpf1, into the transduced HSPC. The following paragraphs only refer to "Cas9", however, "Cas9" can be replaced by "Cfp1".

According to the invention, Cas9 can be optimized for the organism in which it is being introduced. Thus, for example, Cas9 polynucleotide sequence derived from the S. pyogenes (Cas9 recognizing the NGG Protospacer adjacent motif (PAM), mutant VQR Cas9 recognizing the NGA PAM, mutant VRER recognizing the NGCG PAM), S. thermophilus, N. meningitidis or S. Aureus codon optimized for use in human cells is set forth in Cong et al., Science, 2013,339 (6121):819-23; Mali et al., Science, 2013,339(61210):823-6; Kleinstiver et al., Nature, 2015,523(7561):481-5; Hou et al., Proc Natl Acad Sci USA, 2013,110(39):11644-9; Ran et al., Nature, 2015,520(7546):186-191.

Cas9 may be directly introduced into the transduced HSPC as a protein or may be synthesized (or expressed) in situ in the cell as a result of the introduction of a nucleotide sequence encoding Cas9, for example a DNA or a RNA encoding Cas9, preferably a RNA encoding Cas9.

Cas9 or a nucleotide sequence encoding Cas9 can be produced outside the cell and then introduced thereto.

Methods for introducing a nucleotide sequence into cells are known in the art and including, as non-limiting examples, stable transduction methods wherein the nucleotide sequence is integrated into the genome of the cell (recombinant viral vector-mediated methods) or transient transfection methods wherein nucleotide sequence is not integrated into the genome of the cell (recombinant non-integrating viral vector-mediated methods, liposomes, microinjection, electroporation, particle bombardment and the like). Said nucleotide sequence may be included in a vector, more particularly a plasmid or a viral vector, in view of being expressed in the cells. In a preferred embodiment, the method for introducing a nucleotide sequence encoding Cas9 into HSPC is a transient transfection method.

In a specific embodiment, the nucleotide sequence encoding Cas9 is a DNA encoding Cas9. In this embodiment, the transient transfection is particularly advantageous because the DNA sequence encoding Cas9 is not integrated into the genome of the HSPC and therefore Cas9 is thus produced transiently in a limited period of time. After the transient production, given that the HSPC does not comprise in its genome a nucleotide sequence encoding Cas9, the cell does not produce Cas9 anymore. This is particularly advantageous when the HSPC is then used as a medicament. Furthermore, the rapid gRNA degradation in absence of Cas9 nuclease will avoid interferon response and apoptosis, improving therefore safety issues.

In another specific embodiment, the nucleotide sequence encoding Cas9 is a RNA encoding Cas9. The RNA also has the advantage of not being integrated into the genome of the HSPC. For example, a RNA encoding Cas9 is introduced by electroporation.

Methods for introducing a protein into cells are known in the art and include as non-limiting examples the use of liposomes, microinjection, electroporation or particle bombardment. For example, Cas9 may be introduced into the HSPC by electroporation.

In a particular embodiment, Cas9 is introduced into the cell as a protein. In this embodiment, Cas9 has the advantage of not being integrated into the genome of the cell and to be rapidly degraded. Cas9 expression can therefore be easily controlled. Furthermore, though reduced as exemplified in the experimental section, the potential risk for off-target activity is even more reduced because of this transient expression of Cas9 endonuclease activity. For example, Cas9 is introduced by electroporation or nanoparticles.

According to the invention, Cas9 may form a complex with the gRNA in the transduced HSPC. Said Cas9/gRNA complex may bind to the target nucleotide sequence and may therefore disrupt the expression or the function of the target gene. In a preferred embodiment, the Cas9/gRNA complex induces a knock-out of the expression or the function of the target gene. In a specific embodiment, the methods of the invention are particularly advantageous because, the only cells that are able to survive after the disruption of the target gene are those that comprise in their genome the nucleotide sequence encoding the protein that has a therapeutic effect and that express said protein that has a therapeutic effect. In this specific embodiment, the protein that has a therapeutic effect is needed by the cell to survive after the disruption of the target gene.

The invention also relates to a genetically modified HSPC obtainable by the methods according the invention and said genetically modified HSPC for use as a medicament.

In another embodiment, the invention relates to a genetically modified HSPC obtainable by the methods according the invention for use in the treatment of sickle cell disease (SCD).

The recombinant lentiviral vectors are particularly useful for the transduction of HSPC, obtained either from the bone marrow, the peripheral blood or the umbilical cord blood. Particularly preferred cells are CD34+ cells.

The invention also relates to a method of treating sickle cell disease (SCD) in a patient comprising the steps of:
 a) obtaining a hematopoietic stem/progenitor cell (HSPC) from the patient;
 b) contacting the HSPC with a recombinant lentiviral vector of any of claims 1 to 4 or a composition of claim 5 to obtain a transduced HSPC;
 c) introducing into the transduced HSPC a catalytically active Cas9 or Cpf1 protein or a nucleotide sequence encoding a catalytically active Cas9 or Cpf1 protein, said catalytically active Cas9 or Cpf1 protein disrupts the expression and/or the function of the target gene when introduced or expressed into the transduced HSPC, to obtain a genetically modified HSPC; and
 d) administrating the genetically modified HSPC to the patient In one embodiment, a human HSPC can be removed from a human, e.g. a human patient, using methods well known to those of skill in the art and modified as noted above. The modified HSPC (i.e. the genetically modified HSPC) is then reintroduced into the same human.

In some embodiments, the administration may be a transplantation or an inoculation, in particular a transplantation or an inoculation in the bone narrow.

According to the invention, when the protein that has a therapeutic effect is a functional version (e.g. the wild-type version) of the target protein, the design of the nucleotide(s) sequence(s) (e.g. the nucleotide sequence encoding the protein that has a therapeutic effect and/or the nucleotide sequence encoding the gRNA) will be easily adapted by the skilled person in order to avoid that the gRNA targets the nucleotide sequence encoding the protein that has a therapeutic effect (codon design). For example, the recombinant lentiviral vector comprises a nucleotide sequence encoding beta-globin (e.g. PAS3 beta-globin cassette, described by Levasseur et al., Blood, 2003,102(13):4312-9 and a nucleotide sequence encoding a gRNA targeting the sickle beta-globin. In this case, to avoid the unwanted disruption of the nucleotide sequence encoding beta-globin (i.e. the beta-globin transgene), the nucleotide sequence encoding beta-globin will be modified introducing silent mutations in the transgene sequence, so that it will not be recognized by the gRNA (see for example SEQ ID NO: 7 and SEQ ID NO: 8, FIG. 14). To this aim, the skilled person commonly uses synonymous codons (coding for the same amino acids), allowing the change of the nucleotide sequence and the production of an identical beta-globin protein. Generally, synonymous codons will be chosen amongst the most frequently used codons in the beta- and alpha-globin genes.

BRIEF DESCRIPTION OF THE DRAWINGS

FIG. 2: Evaluation of genome editing efficiency in hematopoietic cells using the CRISPR-Cas9 system

FIG. 6: Down regulation of beta-globin expression in HUDEP-2

FIG. 14: nucleotide sequences encoding globin variants that have a therapeutic effect according to the invention. The gRNA D target site is underlined. The nucleotides changes in the Beta AS3 (modified to avoid targeting by gRNA D) and Beta AS1 (T87Q) (modified to avoid targeting by gRNA D) transgenes are highlighted in grey/green.

EXAMPLES

Figure 1:
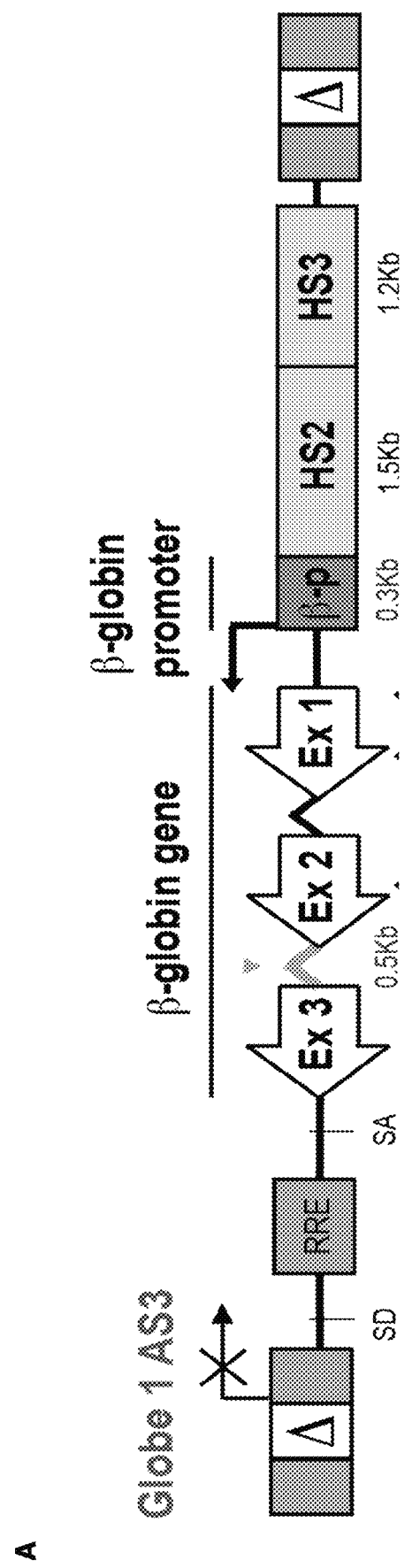
FIG. 1: Construction of a recombinant lentiviral vector encoding a beta-like globin gene
Figure 1:
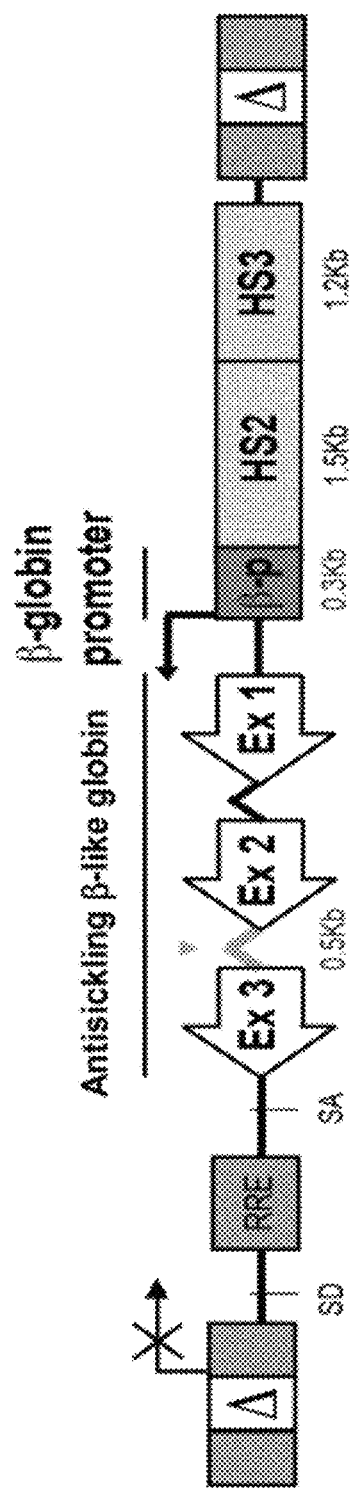

Example 1: Construction of a Recombinant Lentiviral Vector Encoding a Beta-Like Globin Gene A recombinant lentiviral vector able to express at high levels a beta-like globin gene has been produced using the GLOBE lentiviral vector (Miccio et al., Proc Natl Acad Sci USA, 2008, 105(30):10547-52, Roselli et al., EMBO Mol Med, 2010, 2(8):315-28). The GLOBE lentiviral vector in its proviral form contains LTRs deleted of 400 bp in the HIV U3 region (A), rev-responsive element (RRE), splicing donor (SD) and splicing acceptor (SA) sites, human beta-globin gene (exons and introns), beta-globin promoter ($\beta$p), and DNase I-hypersensitive sites HS2 and HS3 from beta-globin LCR (FIGS. 1A and B). The construction of the recombinant lentiviral vector is detailed in FIG. 1C. An anti-sickling transgene (e.g. Beta AS3 (not modified), SEQ ID NO: 2; FIG. 1B) is included in the GLOBE lentiviral vector (FIG. 1C). The exons of the human beta-globin gene are replaced by exons of different anti-sickling transgenes (e.g. selected from SEQ ID NO: 1 to 8) by site-directed mutagenesis.

Example 2: Evaluation of Genome Editing Efficiency in Hematopoietic Cells Using the CRISPR-Cas9 System One million K562 hematopoietic cells were transfected with:
 (i) 4 µg of a Cas9-GFP expressing plasmid (pMJ920, Addgene plasmid #42234) and 0.8 µg of a unrelated gRNA-expressing plasmid (MLM3636, Addgene plasmid #43860),
 (ii) 20 µg of Cas9 mRNA modified with pseudouridine and 5-methylcytidine to reduce immune stimulation (Trilink, #L-6125) and 15 µg of chemically modified gRNAs (MD gRNA, 2' O-Methyl unrelated gRNA, resistant to general base hydrolysis, Trilink); or
 (iii) lentiviral vectors expressing Cas9 (Addgene, #52962) and an unrelated gRNA under the control of the human U6 promoter (FIG. 2A).

The above mentioned gRNAs were unrelated gRNAs, i.e. gRNAs binding regions which are not related to beta-globin gene or gamma-globin gene. In fact, the gRNA targets the gamma-delta intergenic region in the beta-globin locus (e.g. SEQ ID NO: 48).

K562 cells were transfected in a 100 µl volume using Nucleofector I (Lonza), the AMAXA Cell Line Nucleofector Kit V (Lonza, VCA-1003) and the T16 program.

After transfection, K562 cells were maintained in RPMI 1640 medium (Lonza) containing 2 mM glutamine and supplemented with 10% fetal bovine serum (FBS, BioWhittaker, Lonza), HEPES (20 mM, LifeTechnologies), sodium pyruvate (1 mM, LifeTechnologies) and penicillin and streptomycin (100 U/ml each, LifeTechnologies).

One week after transfection, DNA was extracted using PURE LINK Genomic DNA Mini kit (LifeTechnologies) following manufacturer's instructions. The genomic region encompassing the gRNA target site was amplified by PCR and subjected to Sanger sequencing. The genome editing efficiency (% InDels, frequency of small insertions and deletions), evaluated using TIDE (Tracking of In/Dels by Decomposition; (Brinkman et al., Nucleic Acids Res, 2014, 42(22):e168)) was higher than 50% for all the delivery systems (FIG. 2B).

These results showed that the use of DNA, RNA and lentiviral (LV) delivery systems for gRNA and Cas9 leads to a good editing efficiency in K562 hematopoietic cells.

Example 3: Construction and Screening of a gRNA for Beta-Globin Gene Inactivation 1. Selection of gRNAs Targeting the Beta-Globin Gene To reduce the expression of the sickle beta-globin gene (i.e. BetaS-globin gene), we selected 4 publicly available gRNAs targeting the exon 1 of the beta-globin gene (Cradick et al., Nucleic Acids Res, 2013, 41(20):9584-92; Liang et al., Protein Cell, 2015, 6(5):363-72) (gRNA spacer-encoding sequences A, B, D and E, FIG. 3, respectively SEQ ID NO: 23 to 26).

Figure 3:
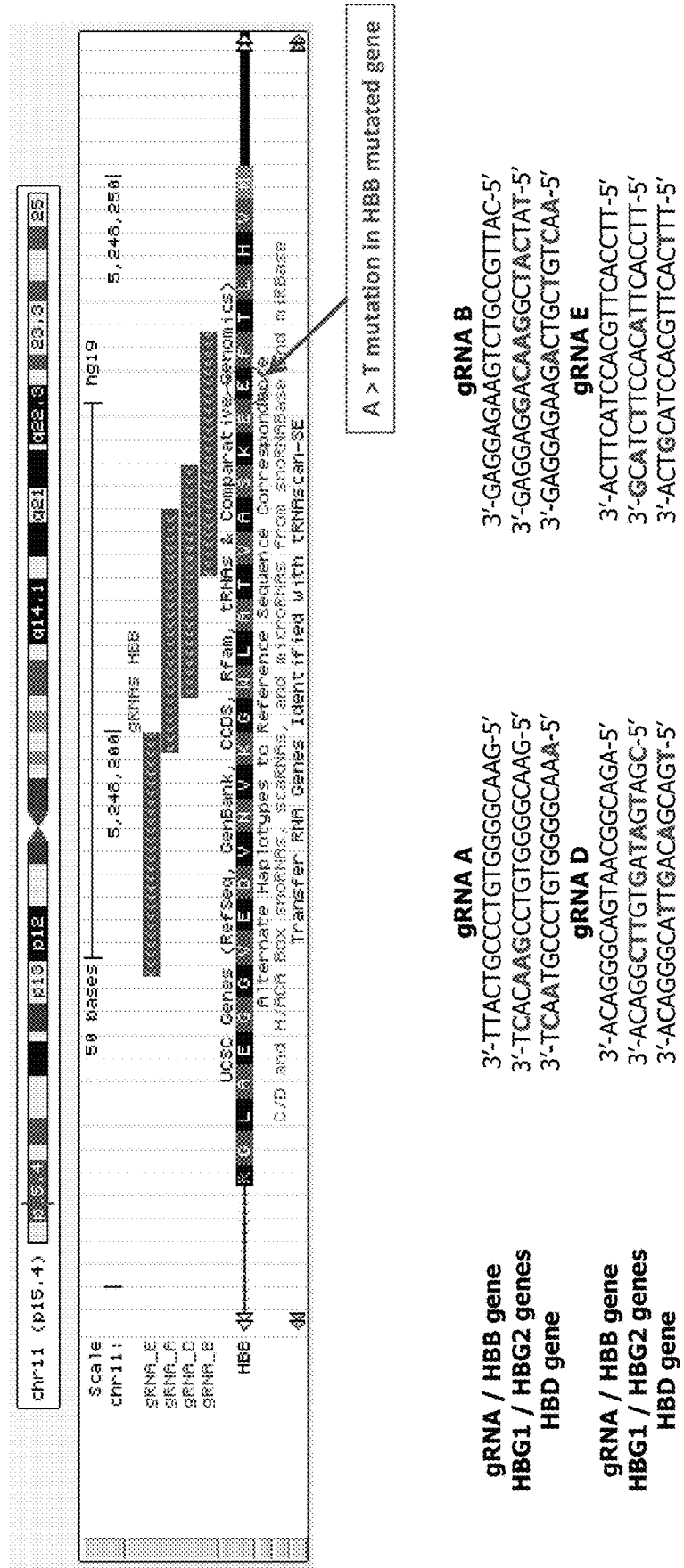
FIG. 3: Construction and screening of a gRNA for beta-globin gene inactivation: design of gRNAs targeting HBB gene. The amino acid sequence is set forth as SEQ ID NO: 95. The primer sequences are set forth as SEQ ID NOS: 49-60 (oriented in the 5' to 3' direction).

Bioinformatic prediction using COSMID (CRISPR Off-target Sites with Mismatches, Insertions, and Deletions; crispr.bme.gatech.edu; Cradick et al, MolTher Nucleic Acids, 2014, 3(12):e214) showed a low number of predicted off-targets, all of them harboring ≥2 mismatches with the delta-globin target sequence (FIG. 3).

Importantly, HBG1/2 genes (coding for gamma-globins) were not included in the list of potential off-targets, the selected gRNAs displaying low similarity with the sequence of gamma-globin genes. Amongst the 4 gRNA spacers, only gRNA spacer E displays less than 3 mismatches with the sequence of exon 1 of the delta-globin gene. Bioinformatic prediction of off-target activity indicates this gene as a potential off-target of gRNA E.

The gRNA-encoding sequences A, B, D and E were cloned in MLM3636 plasmids (MLM3636, Addgene plasmid #43860), generating the following plasmids:
 MLM3636 gRNA A coding for gRNA A
 MLM3636 gRNA B coding for gRNA B
 MLM3636 gRNA D coding for gRNA D
 MLM3636 gRNA E coding for gRNA E For the generation of MLM3636 plasmids carrying the gRNA-encoding sequences A, B, D and E, the following protocol was applied:
a. Annealing RNA Oligos
Oligonucleotide Sequences:

| Oligo Name | Sequence 5' to 3' (*) | SEQ ID NO: |
|---|---|---|
| Oligo FOR-gRNA A | ACACCGCTTGCCCCACAGGGC AGTAAG | 37 |
| Oligo REV-gRNA A | AAAACTTACTGCCCTGTGGGG CAAGCG | 38 |
| Oligo FOR-gRNA B | ACACCGTAACGGCAGACTTCT CCTCG | 39 |
| Oligo REV-gRNA B | AAAACGAGGAGAAGTCTGCCG TTACG | 40 |
| Oligo FOR-gRNA D | ACACCGTCTGCCGTTACTGCC CTGTG | 41 |
| Oligo REV-gRNA D | AAAACACAGGGCAGTAACGGC AGACG | 42 |
| Oligo FOR-gRNA E | ACACCGAAGGTGAACGTGGAT GAAGTG | 43 |
| Oligo REV-gRNA E | AAAACACTTCATCCACGTTCA CCTTCG | 44 |

(*) In bold: nucleotide sequence encoding the gRNA spacer

Preparation of 10× annealing Buffer [400 μl 1M Tris HCl pH8, 200 μl 1M MgCl2, 100 μl 5M NaCl, 20 μl 0.5M EDTA pH8, 280 μl DEPC-water]. Preparation of MIX 1 for gRNA oligo annealing [1 μl 100 μM gRNA oligo FOR, 1 μl 100 μM gRNA oligo REV, 5 μl 10× annealing Buffer, 43 μl DEPC-water]. Annealing reaction in PCR machine with gradient annealing temperature: from 95° C. to 4° C. in 60 minutes, thus decreasing the annealing temperature of −1.5° C. each minute.

b. Digestion of MLM3636 Plasmid

Incubate the digestion mix reaction [x μl (2.5 μg) of MLM3636 plasmid (Addgene plasmid #43860), 5 μl of BSMB I enzyme (50 U), 5 μl of enzyme buffer 10×, (50-x) μl of DEPC-water] over-night at 55° C. Purify from low melting agarose (0.8%) gel the linearized MLM3636 plasmid (size: 2265 bp) with QIAquick Gel Extraction Kit (QIAGEN).

c. Insertion of gRNA within MLM3636 plasmid

Incubation of ligation mix [x μl (10 ng) linearized MLM3636 plasmid, 1.1 μl of annealed gRNA-encoding sequence (diluted 1:10), 5 μl of 2× Ligase Buffer, 1 μl of Ligase (QUICK LIGASE NEB-Biolabs-M22OO), (10-x) μl of DEPC-water] for 15 minutes at room temperature.

d. Transformation of Bacteria and Amplification of Plasmid

Chemical competent E. coli bacteria (One Shot TOP10 Chemically competent E. coli-Invitrogen-C4040) are transformed with 5 μl of ligation products, following manufacture's instruction, and plated in LB AGAR+100 μg/ml Ampicillin over-night at 37° C.

Single-colonies of transformed E. coli bacteria are picked from LB AGAR plate and grown in 3 ml of LB medium+100 μg/ml Ampicillin (inoculation culture) over-night at 37° C. For maxiprep cultures, 0.5 ml of inoculation culture is grown in 250 ml of LB medium+100 μg/ml Ampicillin.

e. Purification of Plasmid DNA

Plasmid DNA is isolated from 250 ml of maxiprep culture of transformed E. coli bacteria by using PureLink HiPure Plasmid DNA Purification Kit (Invitrogen—K2100) applying manufacter's instruction.

2. Selection of gRNAs Targeting β-Globin Gene: Design of Novel gRNAs

Novel gRNAs spacer-encoding sequences (F, G, H, I, J, K, L, M, N and O—respectively SEQ ID NOs: 27 to 36) were designed by using CRISPOR tool (crispor.tefor.net). The genomic DNA sequence of the target region (e.g. exon 1 or exon 2 of HBB gene) was selected (FIG. 4A) using human GRCh37/hg19 genome assembly and downloaded (FIG. 4B) from UCSC Genome Browser (genome-euro.ucsc.edu/index.html). The genomic DNA sequence of the target region was uploaded on crispor.tefor.net and gRNAs associated with a specific PAM (e.g. NGG—Streptococcus Pyogenes or NGA—S. pyogenes mutant VQR) were designed based on the "Homo sapiens—human—UCSC February 2009 (GRCh37/hg19)+SNPs" genome (FIG. 4C). From the list of the resulting gRNAs, we selected the gRNAs with a highest (i) specificity score (cfdSpecScore ≥85), (ii) predicted efficiency (ChariEffScore ≥38) and (iii) out-of-frame score (≥60) and no off-targets with mismatches ≤2 in delta- and gamma-globin genes (FIG. 4D).

3. Cleavage Efficiency of gRNAs A, B, D and E in K562 and HUDEP-2 Erythroid Cell Lines Fetal K562 and adult HUDEP-2 erythroid cells are known to naturally comprise the beta-globin gene in their genome. Therefore, we tested the gRNAs targeting the beta-globin gene in these cell lines.

One million cells were transfected with 4 μg of a Cas9-GFP expressing plasmid (pMJ920, Addgene plasmid #42234) and 0.8 μg of each gRNA-containing plasmid (MLM3636 gRNA A, MLM3636 gRNA B, MLM3636 gRNA D and MLM3636 gRNA E) in a 100 μl volume using Nucleofector I (Lonza). Control cells were treated with 4 μg of a Cas9-GFP expressing plasmid (pMJ920, Addgene plasmid #42234). We used AMAXA Cell Line Nucleofector Kit V (VCA-1003) for K562 and HUDEP-2 (T16 and L-29 programs). After transfection, K562 were maintained in RPMI 1640 medium (Lonza) containing 2 mM glutamine and supplemented with 10% fetal bovine serum (FBS, BioWhittaker, Lonza), HEPES (20 mM, LifeTechnologies), sodium pyruvate (1 mM, LifeTechnologies) and penicillin and streptomycin (100 U/ml each, LifeTechnologies) and HUDEP-2 were maintained as described in Canver et al., Nature, 2015,527(7577):192-7. One week after transfection, DNA was extracted using PURE LINK Genomic DNA Mini kit (LifeTechnologies) following manufacturer's instructions.

Figure 5:
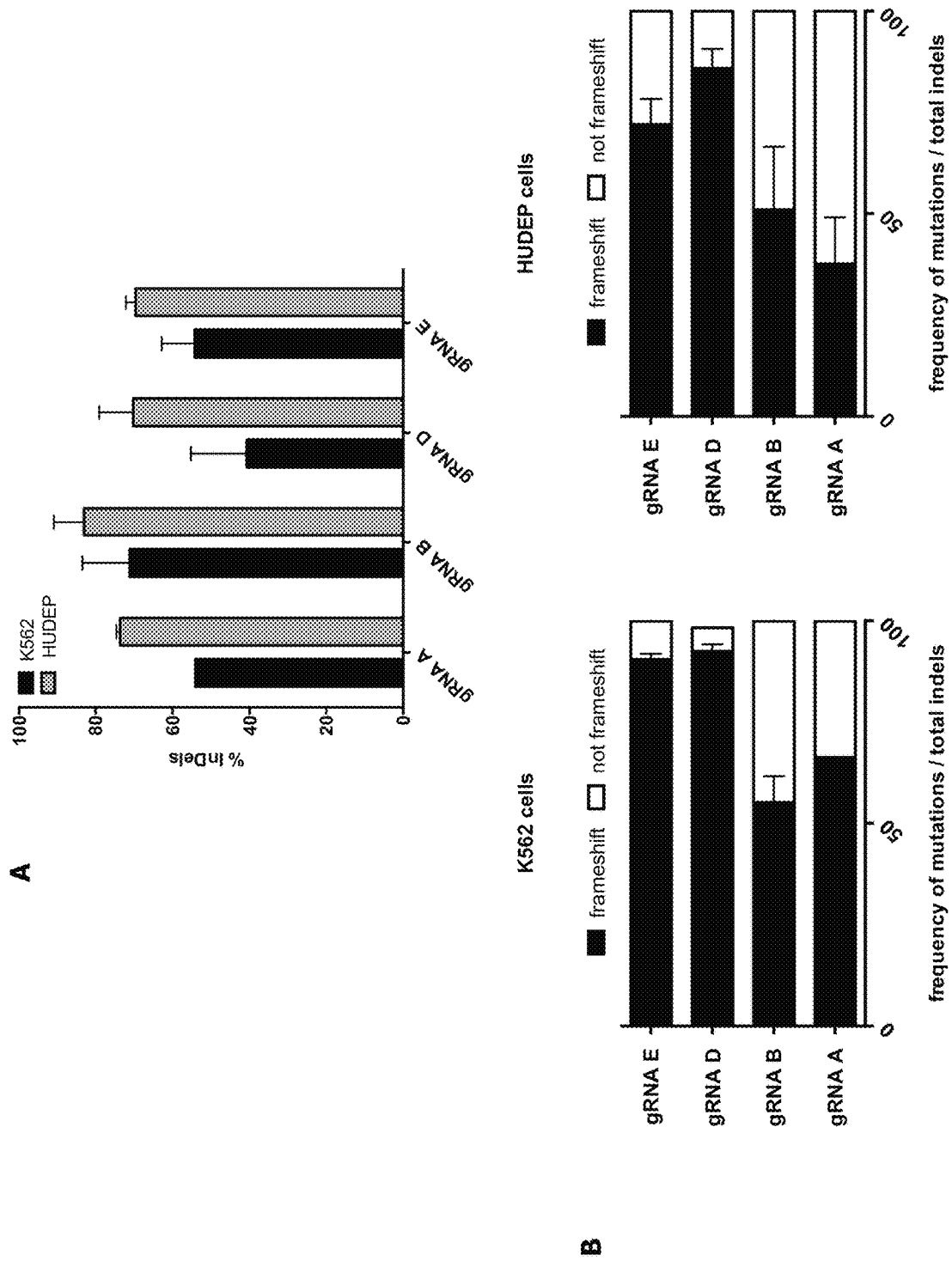
FIG. 5: Cleavage efficiency of gRNAs A, B, D and E in K562 and HUDEP-2 erythroid cell lines

The genomic region of fetal K562 and adult HUDEP-2 erythroid cells encompassing the gRNA target sites was amplified by PCR. PCR was performed using primers HBBex1 F (5'-CAGCATCAGGAGTGGACAGA-3', SEQ ID NO: 9) and HBBex1 R (5'-AGTCAGGGCAGAGC-CATCTA-3', SEQ ID NO: 10). We performed Sanger sequencing and TIDE analysis to evaluate the frequency of InDels and frameshift mutations. All the screened gRNAs (i.e. A, B, D, E) were able to cut at >35% of the genomic loci in transfected K562 and HUDEP-2 cells (FIG. 5A). The cells transfected with gRNA D led to the highest frequency of frameshift mutations, which resulted in the generation of stop-codons in the exon 1 (FIG. 5B). These results showed that gRNA A, B, D and E are particularly efficient to generate frameshift mutations of beta-globin gene in fetal K562 and adult HUDEP-2 erythroid cells resulting in the generation of stop codon in Exon 1.

4. Down-Regulation of Beta-Globin Expression in HUDEP-2

The efficiency of beta-globin knock-down was evaluated in HUDEP2 cells, which express high levels of the beta-globin chain (Kurita et al., PLoS One, 2013, 8(3):e59890). HUDEP-2 cells were transfected with 4 µg of a Cas9-GFP expressing plasmid (pMJ920, Addgene plasmid #42234) and 0.8 µg of each gRNA-containing plasmid (MLM3636 gRNA A, MLM3636 gRNA B, MLM3636 gRNA C and MLM3636 gRNA D), as described above (Example 3). Control cells were treated with 4 µg of a Cas9-GFP expressing plasmid (pMJ920, Addgene plasmid #42234). After one week, total RNA was extracted using RNeasy micro kit (QIAGEN) following manufacturer's instructions. Mature transcripts were reverse-transcribed using SuperScript First-Strand Synthesis System for RT-PCR (Invitrogen) with oligo(dT) primers. qRT-PCR was performed using SYBR green (Applied Biosystems). Primers HBB F (5'-GCAAGGTGAACGTGGATGAAGT-3', SEQ ID NO: 11) and HBB R (5'-TAACAGCATCAGGAGTGGACAGA-3', SEQ ID NO: 12) were used to amplify the beta-globin transcripts. Primers HBA1 F (5'-CGGTCAACTT-CAAGCTCCTAA-3', SEQ ID NO: 13) and HBA1 R (5'-ACAGAAGCCAGGAACTTGTC 3', SEQ ID NO: 14) were used to amplify the alpha-globin transcripts. Beta-globin expression results were normalized to alpha-globin. In parallel, total proteins were extracted in lysis buffer [PBS 1×, 50 mM, TriS-HCl PH 7.4-7.5, 150 mM NaCl, 0.5% DOC, 0.1% SDS, 2 mM EDTA, 1% Triton, protease inhibitor 7× (EDTA-Free Protease Inhibitor Cocktail, Roche) and phosphatase inhibitor 10× (PhosphoSTOP, Roche)], subjected to 3 rounds of sonication (three cycles of 10 pulses, Amplitude 0.7, 0.5 s oscillation) and to 3 freeze/thaw cycles (3 min each). Lysates were centrifuged at 12.000×g for 12 min at 4° C., and supernatants were used for western blot analysis. We measured protein content using the Bradford Protein Assay kit with bovine serum albumin (BSA) as reference standard. After boiling for 5 min in loading buffer (30% glycerol, 5% SDS, 9.25% Dithiothreitol, 1 µl of Bromophenol Blue, Tris-HCl 0.5 M, pH 6.8). samples containing 20-50 g protein were separated using a 15% acrylamide gel SDS-PAGE electrophoresis. The transfer was performed at 250 mA for 2 hour at 4° C. or room temperature (RT). The PDVF membranes were dried and then incubated in blocking solution TBS-Tween 0.1% (Tris-Buffered Saline+Tween 20; TBS-T; Sigma Aldrich) 5% milk over-night at 4° C., and stained for 1-2 hours at RT with primary antibodies diluted in TBS-Tween 5% milk solution. The primary antibodies are specific for beta-globin (dilution 1:200; hemoglobin beta (37-8), sc-21757, Santa Cruz Biotechnology) and alpha-globin (dilution 1:200; hemoglobin alpha (D-16), sc-31110, Santa Cruz Biotechnology). After 3 washes (10 minutes each) in TBS-Tween, antibody staining was revealed using HRP-conjugated anti-mouse (1:5.000; Thermo Scientific) and HRP-conjugated anti-goat (1:5.000; Thermo Scientific) for 1 hour at RT in TBS-T 5% milk solution. Blots were developed with ECL system (Immobilon Western, Millipore) and were exposed to x-ray films (different exposure times according to the intensity of signals). Membranes were stripped for 15' with Stripping Buffer (Thermo Scientific). The bands corresponding to beta-globin were quantified by using ImageJ software and/or Gel Pro software and the values (in pixels) obtained were normalized to those of the alpha-globin bands. Both qRT-PCR (FIG. 6) and Western Blot (FIG. 6) analysis showed a reduction in the beta-globin expression in cells treated with Cas9+gRNAs targeting HBB gene, which was more pronounced in cells electroporated in the presence of the gRNAs allowing the highest frequency of frameshift mutations (gRNA D and E).

These results showed that gRNA A, B, D and E are particularly efficient to disrupt the expression of beta-globin in HUDEP-2 cells.

Figure 7:
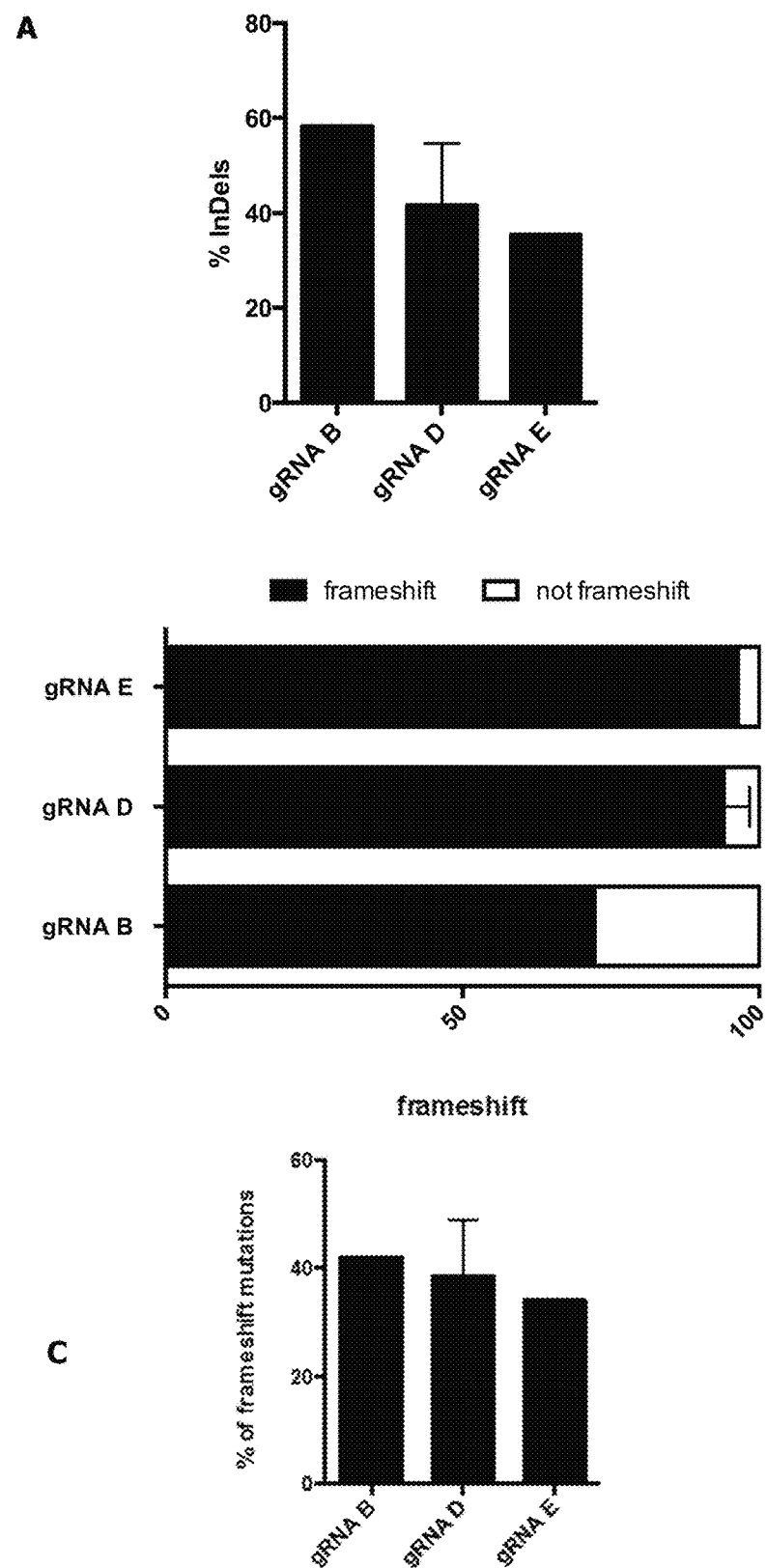
FIG. 7: Cleavage efficiency of selected gRNA (B, D and E) in HSPCs
Figure 7:
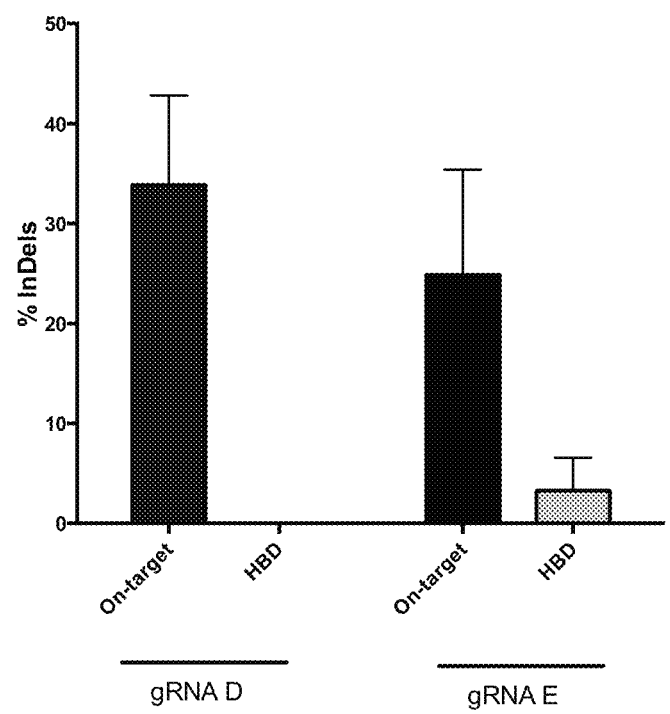

5. Cleavage Efficiency of Selected gRNAs in HSPCs 5.1 Transfection of Primary HSPCs with gRNA B, D and E: Editing Efficiency gRNAs allowing the highest frequency of frameshift mutations (B, D and E) were tested in adult HSPC from a healthy donor. HSPC were cultured in expansion medium: StemSpan SFEM medium (StemCell Technologies), containing 2 mM glutamine, penicillin and streptomycin (100 U/ml each, Gibco, LifeTechnologies), Flt3-Ligand (300 ng/ml, Peprotech), SCF (300 ng/ml, Peprotech), TPO (100 ng/ml, Peprotech) and IL3 (60 ng/ml, Peprotech). 48 hours after thawing, one million cells were transfected with 4 µg of a Cas9-GFP expressing plasmid (pMJ920, Addgene plasmid #42234) and 1.6 µl of each gRNA-containing plasmid (MLM3636 gRNA B, MLM3636 gRNA C and MLM3636 gRNA D) in a 100 µl volume using Nucleofector I (Lonza). Control cells were treated with 4 µg of a Cas9-GFP expressing plasmid (pMJ920, Addgene plasmid #42234). We used AMAXA Human CD34 Cell Nucleofector Kit (VPA-1003) for HSPC (U-08 program). After transfection, HSPC were maintained in the same medium supplemented with Z-VAD-FMK (120 uM, InvivoGen) and StemRegenin 1 (750 uM, Stem Cell Technologies). On day 5 after transfection, DNA was extracted to evaluate the editing efficiency, as described above for K562 and HUDEP-2 cells (Example 3). Genome editing efficiency was higher for gRNA B (FIG. 7A), however the rate of frameshift mutations generated by gRNA B was lower compared to gRNA D and E (FIG. 7B). Overall, gRNA B and D allowed the highest absolute frequency of frameshift mutations (FIG. 7C) in HSPC. However, gRNA D was selected for the following experiments, because it generated non-frameshift mutations at a lower frequency (FIG. 7B) and did not have predicted off-targets in the beta-like globin genes.

These results showed that gRNA B, D and E are particularly efficient to generate frameshift mutations of beta-globin gene in HSPC.

5.2 Transfection of Primary HSPC Cells: Off Target Analysis

To evaluate off-target activity in primary HSPCs, plasmids encoding the selected gRNAs were individually delivered together with a Cas9-GFP-expressing plasmid to cord blood-derived CD34+ HSPCs. Protocol is slightly different from 5.1. Cells were transfected with 4 µg of Cas9-GFP expressing plasmid and 3.2 µg of each gRNA-containing vector using Nucleofector I (Lonza), AMAXA Human CD34 Cell Nucleofector Kit (VPA-1003) and U08 program. Transfection efficiency was verified by flow cytometry analyses 18 hours after electroporation (30-50% of GFP+ Cas9-expressing cells).

TIDE (Tracking of Indels by Decomposition) analysis (Brinkman E K et al., 2014) of the genomic region containing HBB exon 1 and amplified from genomic DNA extracted 4 days after transfection showed that gRNA D and E display a cleavage efficiency of ≈35% and ≈25%, respectively, with a frequency of frameshift mutations of 90-95% for both the gRNAs (not shown). Conversely, gRNA B displays an editing efficiency of ≈60% with a lower frequency of frameshift mutations in comparison with gRNA D and E (not shown). TIDE analysis the genomic region containing HBD exon 1 showed absence of InDels in samples treated with gRNA D, whereas ≈3% of HBD alleles are edited ("off-target") upon treatment with gRNA E (FIG. 7D). This result can be explained by the low number of mismatches (2) between gRNA E sequence and the corresponding off-target in HBD exon 1 (FIG. 3), whereas a higher number of mismatches is observed for gRNA D (4; FIG. 3), which likely decreases the probability of off-target activity in the HBD gene.

6. Down-Regulation of Beta-Globin Expression in HSPC-Derived Erythroid Cells

Figure 8:
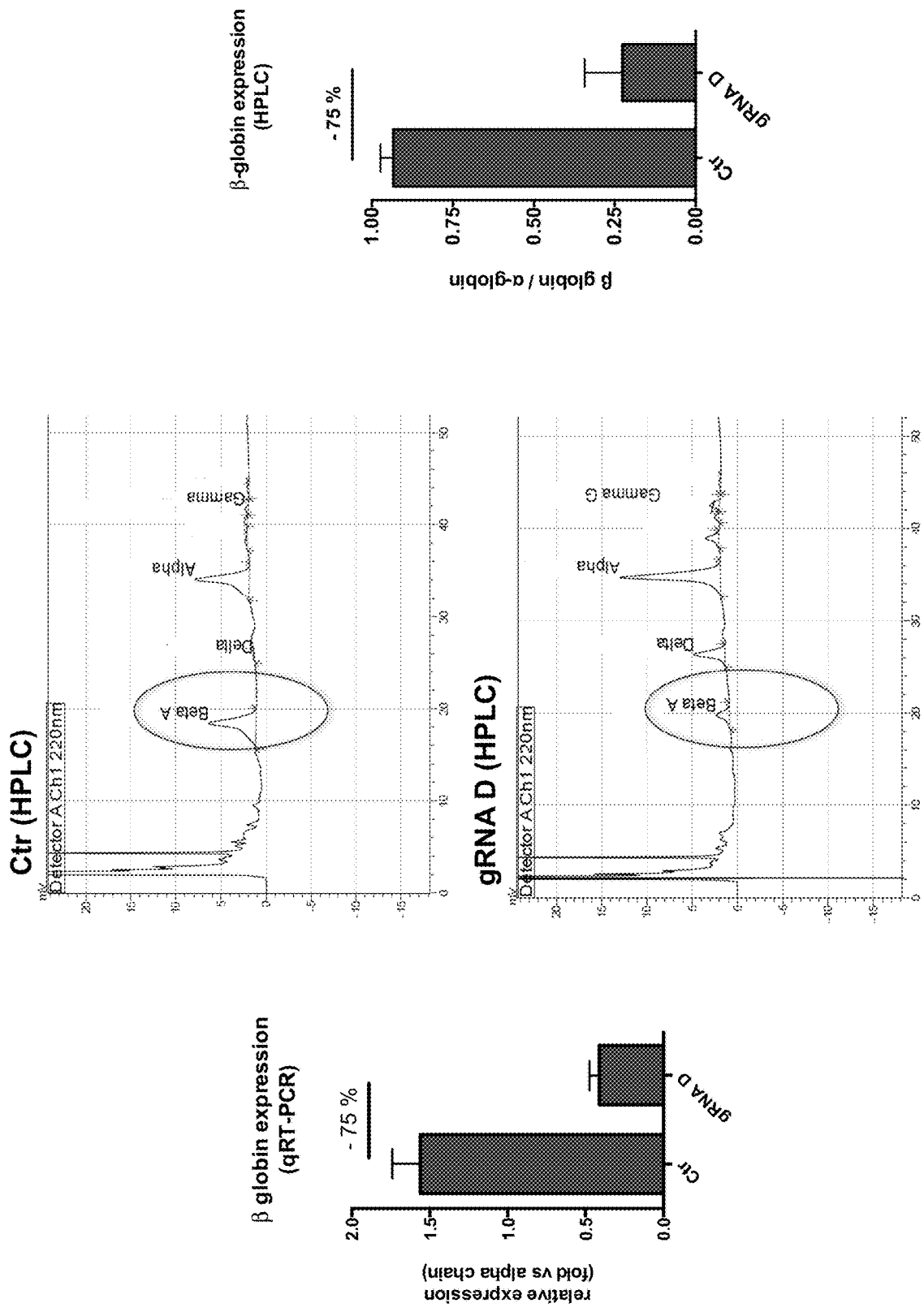
FIG. 8: Down regulation of beta-globin expression in HSPC-derived erythroid cells

Cas9 and gRNA D were delivered by plasmid transfection in adult HSPC derived from a healthy donor (plasmids pMJ920 Cas9-GFP and MLM3636 gRNA D) as described above (Example 5). Control cells were electroporated in the presence of the plasmid pMJ920. One day after, GFP-positive HSPC were sorted by FACS 2 days after transfection, HSPC were differentiated towards the erythroid lineage in liquid culture as previously described (Sankaran, Science, 2008, 322(5909):1839-42). After 11 days, RNA was extracted from mature erythroid cells to evaluate the beta-globin expression levels. Total RNA was extracted using RNeasy micro kit (QIAGEN) following manufacturer's instructions. Mature transcripts were reverse-transcribed using SuperScript First-Strand Synthesis System for RT-PCR (Invitrogen) with oligo(dT) primers. qRT-PCR was performed using SYBR green (Applied Biosystems). Primers HBB F (5'-GCAAGGTGAACGTGGATGAAGT-3', SEQ ID NO: 11) and HBB R (5'-TAACAGCATCAG-GAGTGGACAGA-3', SEQ ID NO: 12) were used to amplify the beta-globin transcripts. Primers HBA1 F (5'-CGGTCAACTTCAAGCTCCTAA-3', SEQ ID NO: 13) and HBA1 R (5'-ACAGAAGCCAGGAACTTGTC 3', SEQ ID NO: 14) were used to amplify the alpha-globin transcripts. Beta-globin expression results were normalized to alpha-globin. In parallel, reverse phase HPLC (RP-HPLC) analysis of globin chains was performed using a NexeraX2 SIL-30AC chromatograph (Shimadzu) and the LC Solution software. Globin chains from in vitro differentiated mature erythroblasts were separated by HPLC using a 250×4.6 mm, 3.6 µm Aeris Widepore column (Phenomenex). Samples were eluted with a gradient mixture of solution A (water/acetonitrile/trifluoroacetic acid, 95:5:0.1) and solution B (water/acetonitrile/trifluoroacetic acid, 5:95:0.1). The absorbance was measured at 220 nm. Both qRT-PCR and RP-HPLC analyses showed a dramatic down-regulation of beta-globin expression in mature erythroblasts electroporated with plasmid MLM3636 gRNA D (FIG. 8).

These results showed that gRNA D is particularly efficient to disrupt the expression of beta-globin in HSPC-derived erythroblasts.

Example 4: Optimization of gRNA Activity

The original gRNA scaffold developed by Cong et al., Science, 2013,339(6121):819-23 was recently optimized by Dang et al., Genome Biol, 2015, 16:280 to increase knock-out efficiency.

The gRNA spacer-encoding sequences B, D and E (respectively SEQ ID NOs: 24, 25 and 26) were cloned in Dang p.hU6 gRNA plasmids (Addgene #53188), generating the following plasmids:
Dang p.hU6 gRNA B coding for gRNA B
Dang p.hU6 gRNA D coding for gRNA D
Dang p.hU6 gRNA E coding for gRNA E For the generation of Dang p.hU6 plasmids (Addgene #53188) carrying gRNA B, D and E, the following protocol was applied:
a. Annealing gRNA Oligos
Oligonucleotide Sequences:

| Oligo Name | Sequence 5' to 3' (*) | SEQ ID No: |
|---|---|---|
| Oligo FOR-Opt_gRNA B | CACCGTAACGGCAGACTTCTCCTC | 15 |
| Oligo REV-Opt_gRNA B | AAACGAGGAGAAGTCTGCCGTTAC | 16 |
| Oligo FOR-Opt_gRNA D | CACCGTCTGCCGTTACTGCCCTGT | 17 |
| Oligo REV-Opt_gRNA D | AAACACAGGGCAGTAACGGCAGAC | 18 |
| Oligo FOR-Opt_gRNA E | CACCGAAGGTGAACGTGGATGAAGT | 19 |
| Oligo REV-Opt_gRNA E | AAACACTTCATCCACGTTCACCTTC | 20 |

(*) In bold: nucleotide sequence encoding the gRNA spacer

Preparation of MIX 1 for gRNA oligo annealing [8 µl 10 µM gRNA oligo FOR-Opt, 8 µl 10 µM gRNA oligo REV-Opt, 2 µl 10×NEB Ligase buffer (Biolabs—M22OO), 2 µl DEPC-water]. Annealing reaction in PCR machine, following this PCR program: from 96° C. 300 seconds, 85° C. 20 seconds, 75° C. 20 seconds, 65° C. 20 seconds, 55° C. 20 seconds, 45° C. 20 seconds, 35° C. 20 seconds, 25° C. 20 seconds b. Digestion of Dang p.hU6 Plasmid Incubate the digestion mix reaction [x µl (20 µg) of Dang p.hU6 plasmid (Addgene #53188), 10 µl of BbsI enzyme (100 U), 10 µl of enzyme buffer 10×, (100-x) µl of DEPC-water] over-night at 37° C. Purify from low melting agarose (0.8%) gel the linearized Dang p.hU6 plasmid (size: 3515 bp) with QIAquick Gel Extraction Kit (QIAGEN).

c. Insertion of gRNA within Dang p.hU6 Plasmid

Incubation of ligation mix [x µl (50 ng) linearized MA128.hU6 plasmid, 1 µl of annealed gRNA oligos, 1 µl of 10× Ligase Buffer, 1 µl of Ligase (QUICK LIGASE NEB—M22OO), (10-x) µl of DEPC-water] for 15 minutes at room temperature.

d. Transformation of Bacteria and Amplification of Plasmid

Chemical competent E. coli bacteria (One Shot TOP10 Chemically competent E. coli—Invitrogen—C4040) are transformed with 5 µl of ligation products, following manu-facter's instruction, and plated in LB AGAR+100 µg/ml Ampicillin over-night at 37° C.

Single-colonies of transformed E. coli bacteria are picked from LB AGAR plate and grown in 3 ml of LB medium+100 µg/ml Ampicillin (inoculation culture) over-night at 37° C. For maxiprep cultures, 0.5 ml of inoculation culture is grown in 250 ml of LB medium+100 µg/ml Ampicillin.

e. Purification of Plasmid DNA

Plasmid DNA is isolated from 250 ml of maxiprep culture of transformed E. coli bacteria by using PureLink HiPure Plasmid DNA Purification Kit (Invitrogen—K2100) applying manufacter's instruction.

Figure 9:
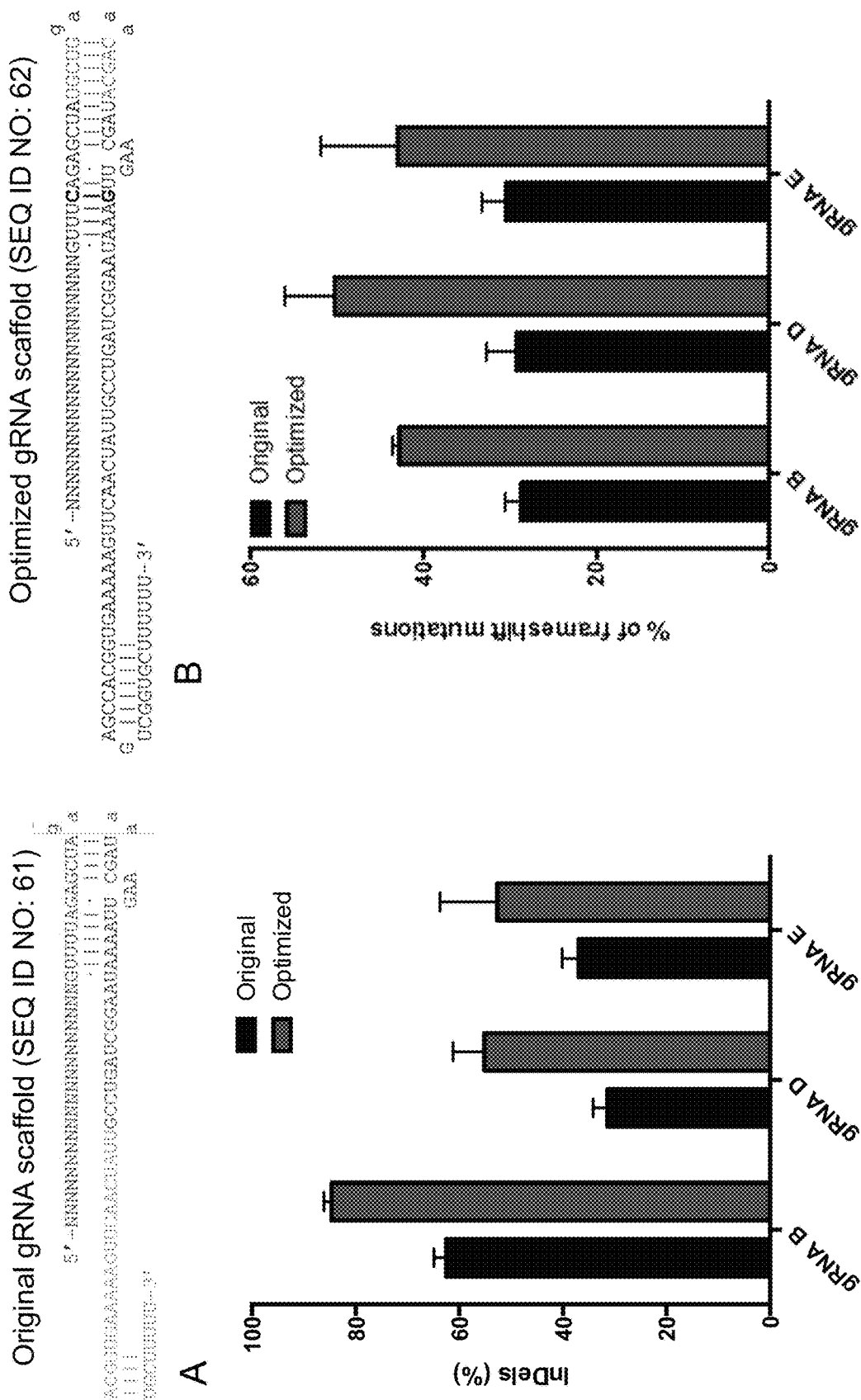
FIG. 9: Optimization of gRNA-mediated disruption of the target site

One million of K562 cells were transfected with 4 µg of a Cas9-GFP expressing plasmid (pMJ920, Addgene plasmid #42234) and 0.8 of each gRNA-containing plasmid (MLM3636 gRNA B, MLM3636 gRNA C and MLM3636 gRNA D, Dang p.hU6 gRNA B, Dang p.hU6 gRNA C and Dang p.hU6 gRNA D) in a 100 µl volume using Nucleofector I (Lonza). Control cells were treated with 4 µg of a Cas9-GFP expressing plasmid (pMJ920, Addgene plasmid #42234). We used AMAXA Cell Line Nucleofector Kit V (VCA-1003) for K562 cells (T16 program). After transfection, K562 were maintained in RPMI 1640 medium (Lonza) containing 2 mM glutamine and supplemented with 10% fetal bovine serum (FBS, BioWhittaker, Lonza), HEPES (20 mM, LifeTechnologies), sodium pyruvate (1 mM, LifeTechnologies) and penicillin and streptomycin (100 U/ml each, LifeTechnologies). One week after transfection, DNA was extracted using PURE LINK Genomic DNA Mini kit (LifeTechnologies) following manufacturer's instructions. All the gRNAs with the optimized structure (Dang p.hU6 gRNA B, Dang p.hU6 gRNA C and Dang p.hU6 gRNA D; Dang et al., Genome Biol, 2015, 16:280) show higher InDels efficiency (FIG. 9A) and frequency of frameshift mutation in HBB gene (FIG. 9B) compared to the corresponding gRNAs with original structure (MLM3636 gRNA B, MLM3636 gRNA C and MLM3636 gRNA D; Cong et al., Science, 2013,339(6121):819-23).

These results showed that the modification of the scaffold in the gRNAs targeting the beta-globin gene (see Example 3) can further increase their frequency of gene disruption.

Figure 10:
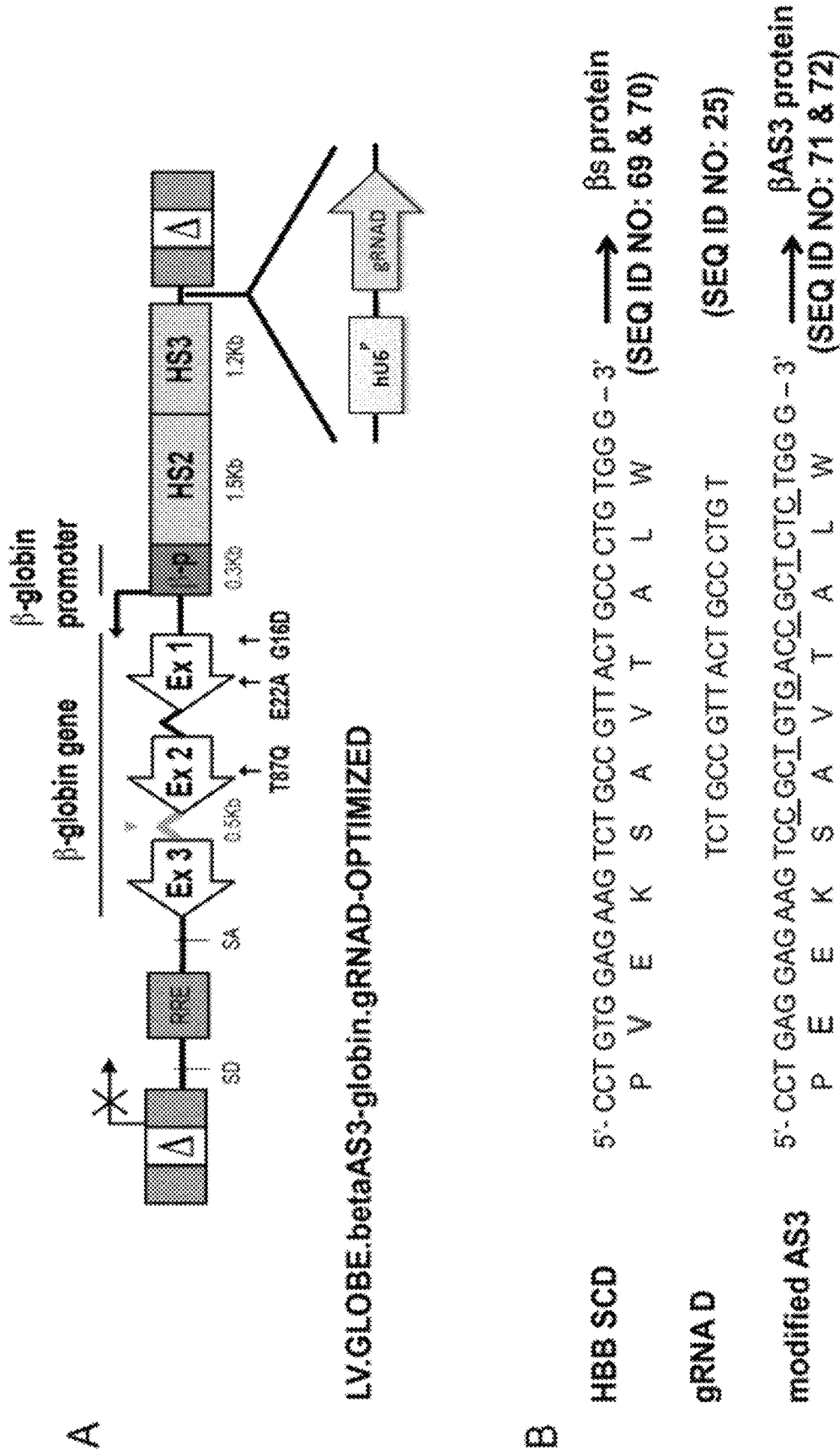
FIG. 10: Construction of a recombinant lentiviral vector according to the invention
Figure 10:
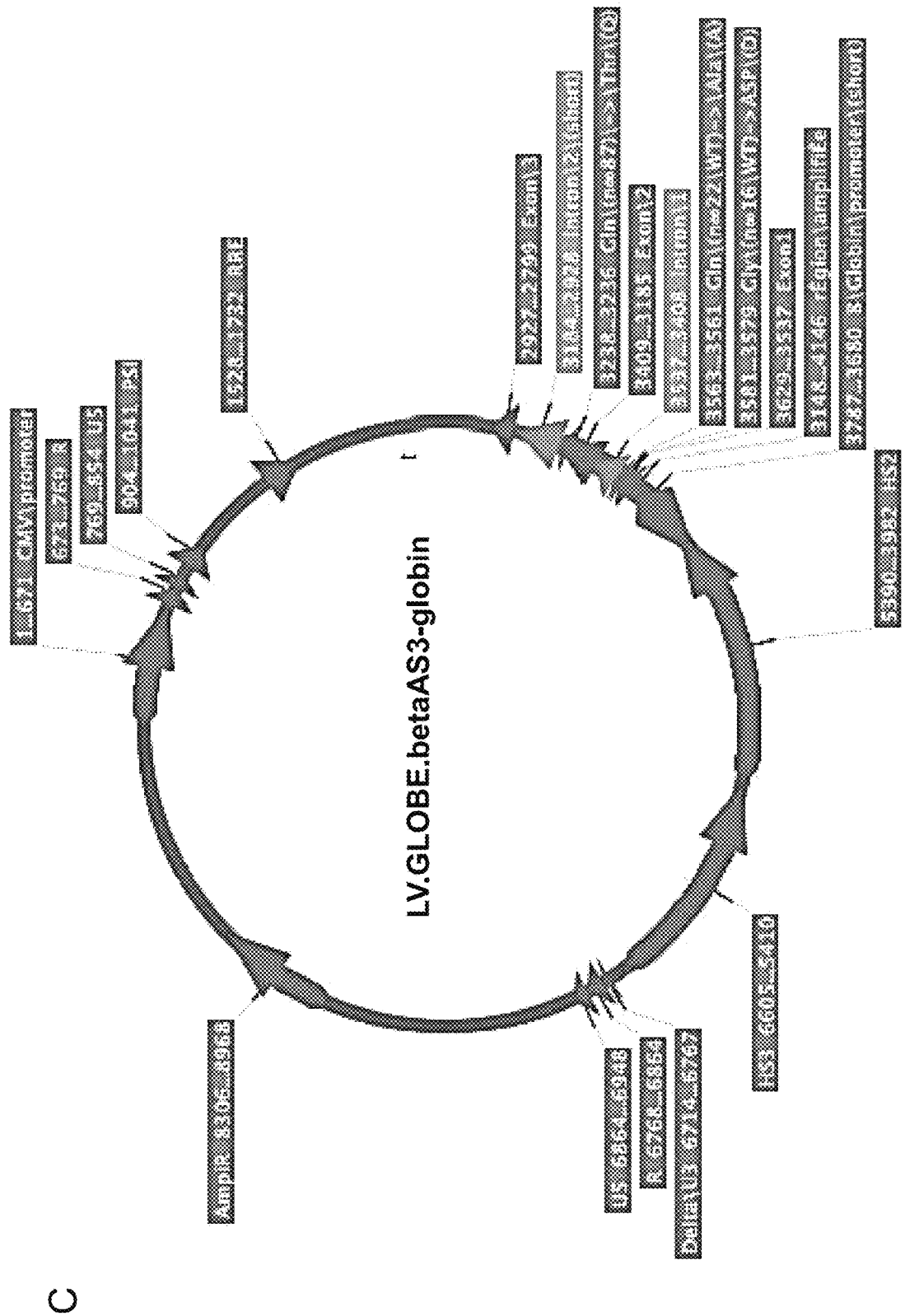
Figure 10:
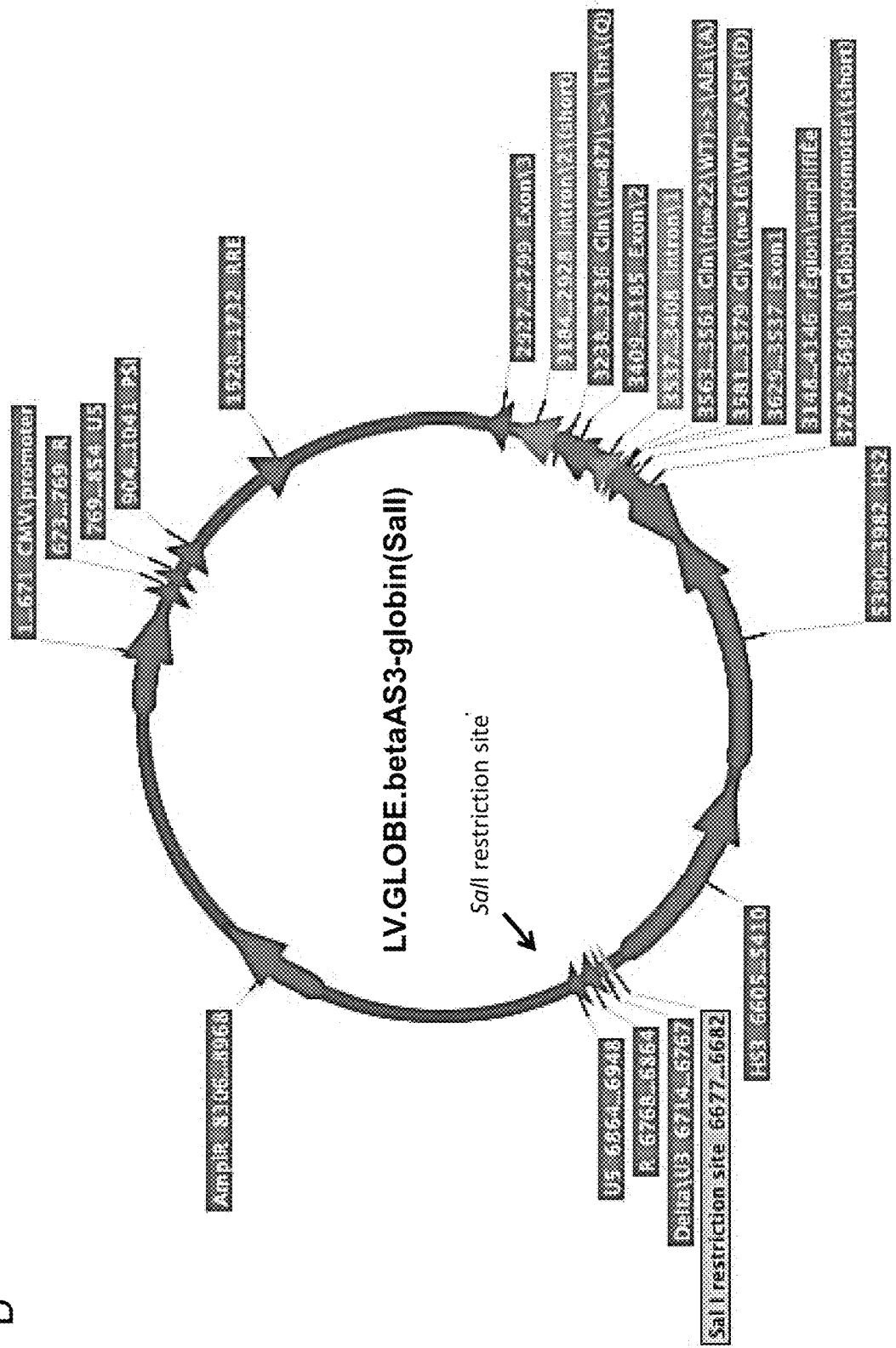
Figure 10:
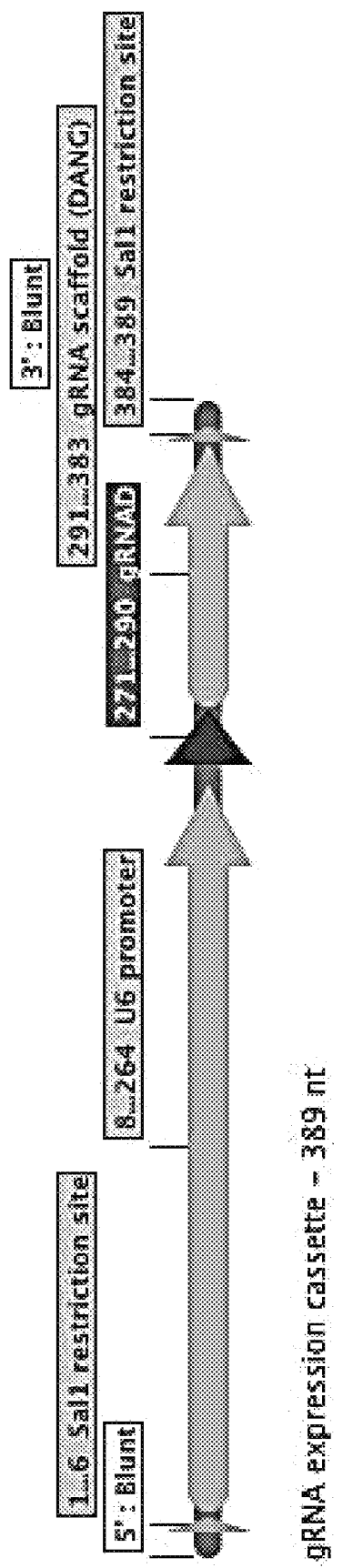
Figure 10:
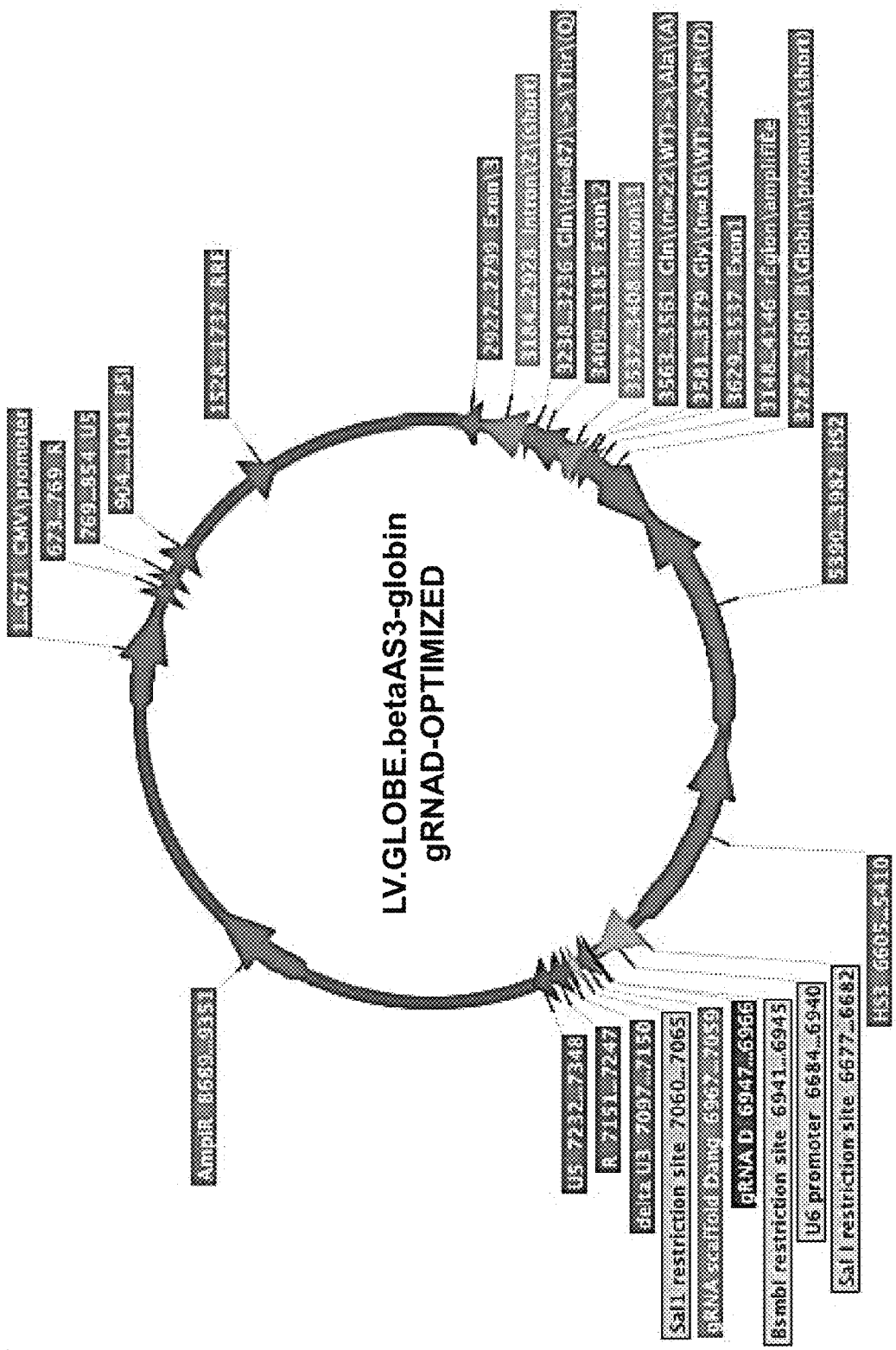

Example 5: Construction of a Recombinant Viral Vector (i.e. Lentivector) According to the Invention The LV.GLOBE.betaAS3-globin.gRNA D-OPTIMIZED lentiviral construct (FIG. 10A, such as SEQ ID NO: 47) carries: (1) an anti-sickling gene (FIG. 10B, e.g. modified Beta AS3 SEQ ID NO: 8) harboring silent mutations (indicated as underscored letters in FIG. 10B) inserted by site-directed mutagenesis in order to impair the gRNA binding to the transgene and the three antisickling mutations [Gly16Asp (G16D), Glu22Ala (E22A) and Thr87Gln (T87Q)] in the exons 1 and 2 (FIG. 10A); (2) a gRNA showing (i) a high efficiency of beta-globin gene disruption; (ii) a high rate of frameshift mutations; (iii) a low off-target activity (e.g. no off-targets in the beta like-globin genes), such as gRNA D (FIG. 10B), under the control of the human U6 promoter (FIG. 10A).

In FIGS. 10C, 10D, 10E and 10F, (A.) the restriction site SalI is inserted between HS3 and DeltaU3 elements of the LV.GLOBE.betaAS3-globin plasmid (FIG. 10C; SEQ ID NO: 45) by site-directed mutagenesis to generate the LV.GLOBE. betaAS3-globin (SalI) plasmid (SEQ ID NO: 46). (B.) A DNA fragment containing the hU6 promoter and the gRNA-encoding sequence (e.g. gRNA D) flanked by SalI restriction sites (called "gRNA expression cassette"; FIG. 10E) is synthesized. (C.) LV.GLOBE. betaAS3-globin (SalI) plasmid (SEQ ID NO: 46) is digested [digestion mix reaction: x µl (20 µg) of LV.GLOBE. betaAS3-globin (SalI) plasmid (SEQ ID NO: 46), 10 µl of SalI enzyme (100 U), 10 µl of enzyme buffer 10×, (100-x) µl of DEPC-water] over-night at 37° C. The linearized LV.GLOBE. betaAS3-globin-globin(SalI) plasmid (size: 10195 bp) is purified by low melting agarose (0.8%) gel using QIAquick Gel Extraction Kit (QIAGEN). In parallel, the gRNA expression cassette is digested [digestion mix reaction: x µl (20 µg) of gRNA expression cassette, 10 µl of SalI enzyme (100 U), 10 µl of enzyme buffer 10×, (100-x) µl of DEPC-water] over-night at 37° C. The linearized gRNA expression cassette (size: 383 bp) is purified by low melting agarose (1.5%) gel using QIAquick Gel Extraction Kit (QIAGEN). (D.) The gRNA expression cassette is inserted within LV.GLOBE. betaAS3-globin -globin(SalI) plasmid through incubation of ligation mix [x µl (50 ng) linearized gRNA expression cassette, γ µl (50 ng) linearized LV.GLOBE. betaAS3-globin-globin(SalI) plasmid, 1 µl of 10× Ligase Buffer, 1 µl of Ligase (QUICK LIGASE NEB-M2200), (10-x-y) µl of DEPC-water] for 15 minutes at room temperature. Chemical competent E. coli bacteria (One Shot TOP10 Chemically competent E. Coli—Invitrogen—C4040) are transformed with 5 µl of ligation products, following manufacter's instruction, and plated in LB AGAR+100 µg/ml Ampicillin over-night at 32° C. Single-colonies of transformed E. coli bacteria are picked from LB AGAR plate and grown in 50 ml of LB medium+100 µg/ml Ampicillin (miniprep cultures) over-night at 32° C. Plasmid DNA is isolated from 10 ml of miniprep culture of transformed E. coli bacteria by using PureLink HiPure Plasmid DNA Purification Kit (Invitrogen—K2100) applying manufacter's instruction. Plasmid DNA will be analyse by Sanger-sequencing to verify that gRNA expression cassette is inserted in the opposite orientation compare to betaAS3-globin expression cassette. Miniprep cultures (10 ml) derived from colonies containing plasmids fitting these criteria are grown in 250 ml of LB medium+100 µg/ml Ampicillin over-night at 32° C. Plasmid DNA is isolated from 250 ml of maxiprep culture of transformed E. coli bacteria by using PureLink HiPure Plasmid DNA Purification Kit (Invitrogen—K2100) applying manufacter's instruction. The isolated plasmid DNA (LV.GLOBE. betaAS3-globin.gRNA D-OPTIMIZED; FIG. 10F, SEQ ID NO: 47) is used as backbone for recombinant lentiviral vector production.

Figure 11:
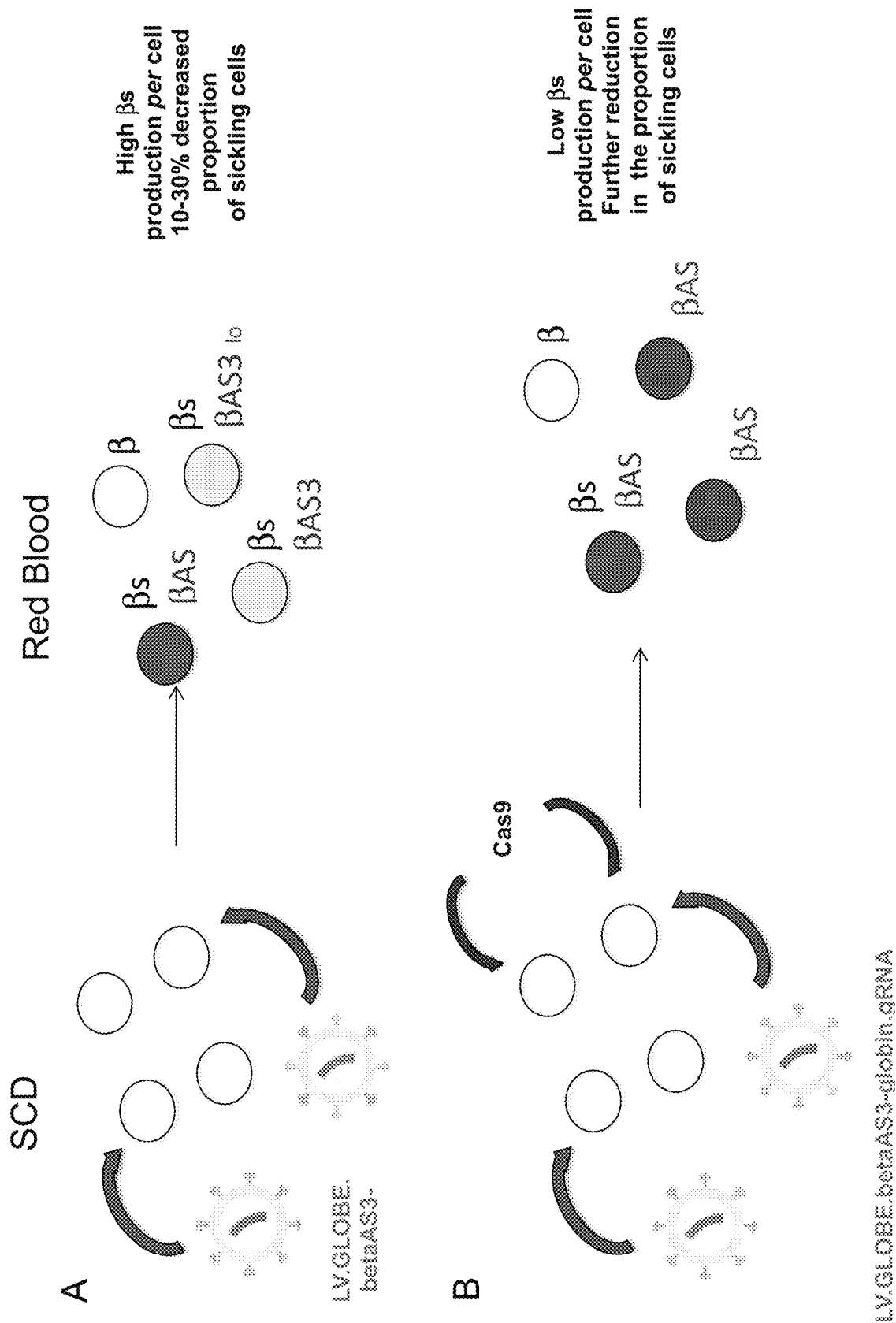
FIG. 11: Transduction of HSPC with a recombinant lentiviral vector according to the invention and introduction of Cas9 into the transduced cell.

Example 6: Transduction of HSPC with a Recombinant Lentiviral Vector According to the Invention and Introduction of Cas9 into the Transduced Cell (A) In the classical gene therapy approach the lentiviral vector expressing an anti-sickling gene (e.g. LV.GLOBE-.beta-globin and LV.AS3 (Romero et al., JCI, 2016)) does not strongly reduce the sickle beta-globin expression in the erythroid progeny of SCD HSPC and allows the correction of only 10% to 30% of mature Red Blood Cells (FIG. 11A).

(B) SCD HSPC are transduced with the gamma-beta hybrid globin and gRNA expressing lentiviral vector (e.g. LV.GLOBE.gamma-beta-globin.gRNA) and Cas9 is delivered transiently. This approach allows the expression of an anti-sickling transgene and the concomitant reduction of the sickle beta-globin levels, which will lead to an increase frequency of corrected Red Blood Cells Importantly, Cas9-mediated disruption of the sickle beta-globin gene will be observed only in transduced SCD cells where the knock out of the sickle beta-globin is compensated by the expression of the anti-sickling gene, thus avoiding an absence of Beta like chain leading to the risk of alpha-chain precipitation, leading to cell death and anemia, as observed in beta-thalassemia (FIG. 11B).

Example 7: Genetic Modification of Patient SCD HSPC In Vitro

SCD CD34+ HSPC are transduced with lentiviral vectors expressing an anti-sickling gene and a gRNA targeting the beta-globin gene (e.g. LV.GLOBE.betaAS3-globin.gRNAD-OPTIMIZED, SEQ ID NO: 47 or LV.GLOBE-AS3modified.gRNAD, SEQ ID NO: 94) or the intronic erythroid-specific BCL11A enhancer (e.g. LV.GLOBE-AS3modified.gRNA-BCL11Aenhancer, SEQ ID NO: 75) or the gamma-globin promoters (e.g. LV.GLOBE-AS3modified.gRNA-13 bp-del, SEQ ID NO: 76) and Cas9 is delivered transiently (DNA-, RNA-, protein- or lentiviral-delivery).

HSPC derived from bone marrow or mobilized peripheral blood of SCD patients are cultured in RetroNectin (20 µg/ml, Takara Shuzo Co.)-coated plates in expansion medium (pre-activation step): StemSpan SFEM medium (StemCell Technologies), containing 2 mM glutamine, penicillin and streptomycin (100 U/ml each, Gibco, LifeTechnologies), Flt3-Ligand (300 ng/ml, Peprotech), SCF (300 ng/ml, Peprotech), TPO (100 ng/ml, Peprotech) and IL3 (60 ng/ml, Peprotech). 24 hours after thawing (day1), 200.000 cells are transduced with LV.GLOBE.betaAS3-globin.gR-NAD-OPTIMIZED (SEQ ID NO: 47) (MOI 20-100) in expansion medium+protein sulfate (4 µg/ml) and plated in RetroNectin (20 µg/ml, Takara Shuzo Co.)-coated 96-well plates. Control cells are transduced with LV.GLOBE.betaAS3-globin. (SalI) (SEQ ID NO: 46) (MOI 20-100) or LV.GLOBE.gRNAD (MOI 20-100) (LV.GLOBE vector carrying gRNA expression cassette without beta AS3 globin transgene). Medium is change 24 hours after transduction (day2) and $1-3*10^6$ cells are transfected with 20 µg of Cas9 mRNA modified with pseudouridine and 5-methylcytidine to reduce immune stimulation (Trilink, #L-6125) in a 100 µl volume using Nucleofector 4D (Lonza). Alternatively, $1-3*10^5$ cells are transfected with 30-180 Cas9 pmol in a 20 µl volume using Nucleofector 4D (Lonza). We use AMAXA Human CD34 Cell Nucleofector Kit (VPA-1003) for HSPC (CA137 program). After transfection, HSPC were maintained in the same medium supplemented with Z-VAD-FMK (120 uM, InvivoGen) and StemRegenin 1 (750 uM, Stem Cell Technologies). The day after (day3), treated HSPC are either in vitro differentiated towards the erythroid lineage using a 3-phase liquid erythroid culture system (Giarratana et al., Blood, 2011, 118(19):5071-9) or plated in a semi-solid medium containing cytokines supporting the growth of erythroid and myeloid hematopoietic progenitors (Clonal progenitor assay; medium GFH4435, Stem Cell Technologies). On day 13 of liquid culture and clonal progenitor assay, samples are collected for DNA extraction to evaluate the editing efficiency, as described above for K562 and HUDEP-2 cells (example 3), and the frequency of transduced cells in bulk (erythroid) and clonal culture by PCR followed by Tracking of In/Dels by Decomposition (Brinkman E K, Chen T, Amendola M, and van Steensel B. Easy quantitative assessment of genome editing by sequence trace decomposition. Nucleic acids research. 2014; 42(22):e168.) also called TIDE analysis (as described in example 3) and qPCR (using primers recognizing specifically the lentiviral vector; Miccio et al., Proc Natl Acad Sci USA, 2008, 105(30):10547-52), respectively.

A genome-wide analysis of Double Strand Breaks using Genome-wide, unbiased identification of DSBs enabled by sequencing, also called GUIDE-seq (Tsai et al., Nat Biotechnol, 2015, 33(2):187-97) is performed to detect and quantify off-target cleavage sites in HSPC and their differentiated progeny (DNA extracted from samples collected at day13 of clonal progenitor assay). LV integration sites in SCD HSPC are analyzed in order to evaluate the potential genotoxic risk of globin-expressing LV vectors. Integration sites are amplified by ligation-mediated PCR, sequenced and mapped to the human genome, as previously described (Romano et al., Sci Rep, 2016, 6:24724). The anti-sickling globin and betaS-globin expression are evaluated by qRT-PCR in samples collected upon 13, 16, 18 and 21 days of liquid culture differentiation. Total RNA is extracted using RNeasy micro kit (QIAGEN) following manufacturer's instructions. Mature transcripts are reverse-transcribed using SuperScript First-Strand Synthesis System for RT-PCR (Invitrogen) with oligo(dT) primers. qRT-PCR was performed using SYBR green (Applied Biosystems). Primers HBB F (5'-GCAAGGTGAACGTGGATGAAGT-3', SEQ ID NO: 11) and HBB R (5'-TAACAGCATCAG-GAGTGGACAGA-3', SEQ ID NO: 12) are used to amplify the beta-globin transcripts and primers HBB-AS3 F (5'-AAGGGCACCTTTGCCCAG-3', SEQ ID NO: 21) and HBB-AS3 R (5'-GCCACCACTTTCTGATAGGCAG-3', SEQ ID NO: 22) are used to amplify the beta AS3 globin transcripts. Primers HBA1 F (5'-CGGTCAACTT-CAAGCTCCTAA-3', SEQ ID NO: 13) and HBA1 R (5'-ACAGAAGCCAGGAACTTGTC 3', SEQ ID NO: 14) are used to amplify the alpha-globin transcripts. Beta-globin expression results are normalized to alpha-globin. In parallel, reverse phase HPLC (RP-HPLC) analysis is performed (as described above in Example 6) in genetically modified HSPC differentiated in vitro into fully mature, enucleated Red Blood Cells (day 21 of liquid culture differentiation). The recovery of functional RBC properties is assessed enucleated Red Blood Cells (day 21 of liquid culture differentiation) by evaluating the reversion of the sickling and the correction of the increased adhesiveness and rigidity of SCD cells, features involved in the pathological occurrence of vaso-occlusive events (Picot et al., Am J Hematol, 2015, 90(4):339-45). Sickling dynamics is evaluated in enucleated Red Blood Cells (day 21 of liquid culture differentiation) exposing the cells to an oxygen-deprived atmosphere (0% $O_2$). Time-course of sickling is monitored in real-time by video microscopy for 1 hour, capturing images every 5 minutes using the AxioObserver Z1 microscope (Zeiss) and a 40× objective.

Figure 12:
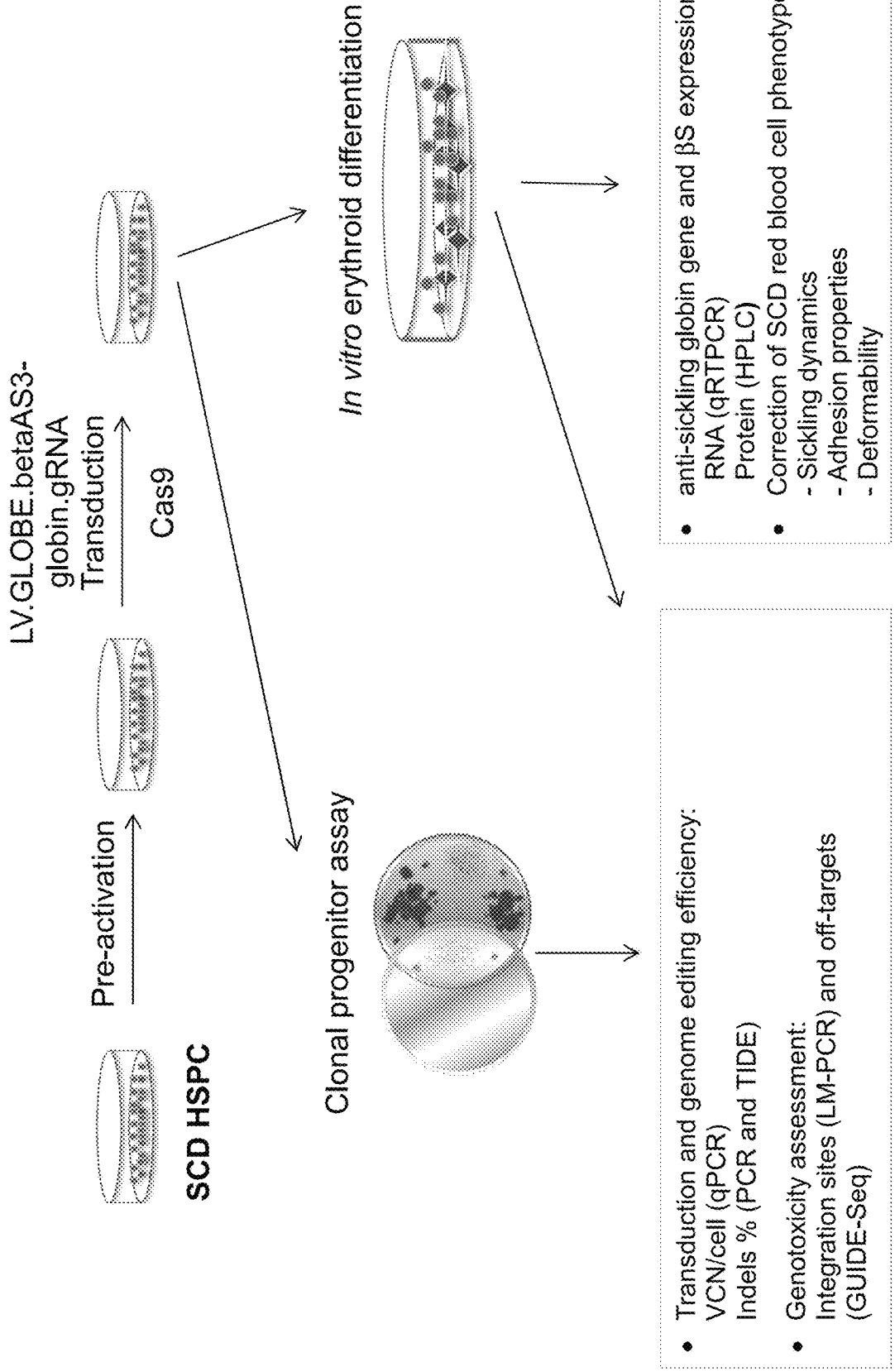
FIG. 12: Genetic modification of patient SCD HSPC in vitro

This process is illustrated in FIG. 12.

Such method is applied mutatis mutandis when using any of lentiral vectors of the invention.

Example 8: Genetic Modification of Patient SCD HSC In Vivo

The engraftment capability of genetically modified patient SCD HSC and the efficacy of the therapeutic approach in Red Blood Cells derived from engrafting SCD HSC are assessed in in vivo mouse experiments. The in vivo frequency of modified HSC and the efficacy of the therapeutic strategy have to be similar to the same parameters measured in vitro in HSPC to exclude any HSC impairment due to our treatment.

HSPC derived from bone marrow or mobilized peripheral blood of SCD patients are cultured in RetroNectin (20 µg/ml, Takara Shuzo Co.)-coated plates in expansion medium (pre-activation step): StemSpan SFEM medium (StemCell Technologies), containing 2 mM glutamine, penicillin and streptomycin (100 U/ml each, Gibco, LifeTechnologies), Flt3-Ligand (300 ng/ml, Peprotech), SCF (300 ng/ml, Peprotech), TPO (100 ng/ml, Peprotech) and IL3 (60 ng/ml, Peprotech). 24 hours after thawing (day1), $1-2*10^6$ cells are transduced with a lentiviral vector expressing an anti-sickling gene and a gRNA targeting the beta-globin gene (e.g. LV.GLOBE.betaAS3-globin.gRNAD-OPTIMIZED, SEQ ID NO: 47 or LV.GLOBE-AS3modified.gRNAD, SEQ ID NO: 94) or a gRNA targeting the intronic erythroid-specific BCL11A enhancer (LV.GLOBE-AS3modified.gRNA-BCL11Aenhancer, SEQ ID NO: 75) or a gRNA targeting the gamma-globin promoters (LV.GLOBE-AS3modified.gRNA-13 bp-del, SEQ ID NO: 76) (MOI 20-100) in expansion medium+protein sulfate (4 µg/ml) and plated in RetroNectin (20 µg/ml, Takara Shuzo Co.)-coated 96-well plates. Control cells are transduced with LV.GLOBE.gamma-beta-globin(SalI) (MOI 20-100) and LV.GLOBE.gRNAD (MOI 20-100) (LV.GLOBE vector carrying gRNA expression cassette without beta AS3 globin transgene). Medium is change 24 hours after transduction (day2) and 1-3*10⁶ cells are transfected with 20 µg of Cas9 mRNA modified with pseudouridine and 5-methylcytidine to reduce immune stimulation (Trilink, #L-6125) in a 100 µl volume using Nucleofector 4D (Lonza). Alternatively, 1-3*10⁵ cells are transfected with 30-180 Cas9 pmol in a 20 µl volume using Nucleofector 4D (Lonza). We use AMAXA Human CD34 Cell Nucleofector Kit (VPA-1003) for HSPC (CA137 program). After transfection, HSPC were maintained in the same medium supplemented with Z-VAD-FMK (120 uM, InvivoGen) and StemRegenin 1 (750 uM, Stem Cell Technologies). The day after (day3), cells are injected (0.5-1*10⁶ cells per mouse) i.v. in 9 to 10-week-old partially myeloablated immunodeficient NSG (NOD SCID GAMMA; NOD.Cg-Prkdc$^{scid}$ 112Il2$^{tm1Wjl}$/SzJ) mice. After 16 weeks, mice are euthanized and bone marrow, thymus and spleen are analyzed for engraftment of human cells by flow cytometry using anti-human CD45 vs. anti-murine CD45 antibodies. The percentage of engrafted human cells is defined as follows: % huCD45+/(% huCD45++% muCD45+). Analysis of the different hematopoietic cell types present was performed by cell-specific staining for human CD34, human CD45, human CD19, human CD33, human CD71, human CD36 and human CD235a. Transduction efficiency and genome editing efficiency is determined in the purified HSPC and lymphoid and myeloid progeny, as described above in example 7.

Human CD34+ HSPC is isolated from bone marrow of engrafted mice using immunomagnetic separation (CD34 MicroBeads kit human; Miltenyi Biotech). The hCD34-positive fraction is cultured in 3-phase liquid erythroid culture system (Giarratana et al., Blood, 2011,118(19):5071-9) or plated in a semi-solid medium containing cytokines supporting the growth of erythroid and myeloid hematopoietic progenitors (Clonal progenitor assay; medium GFH4435, Stem Cell Technologies). Given the low number of erythroid cells obtained in vivo in NSG mice, the expression of the anti-sickling transgene, the down-regulation of sickle beta-globin expression and the functional correction of the SCD phenotype are assessed ex vivo in the erythroid progeny of modified SCID-Repopulating cells, as describe above (example 7).

Figure 13:
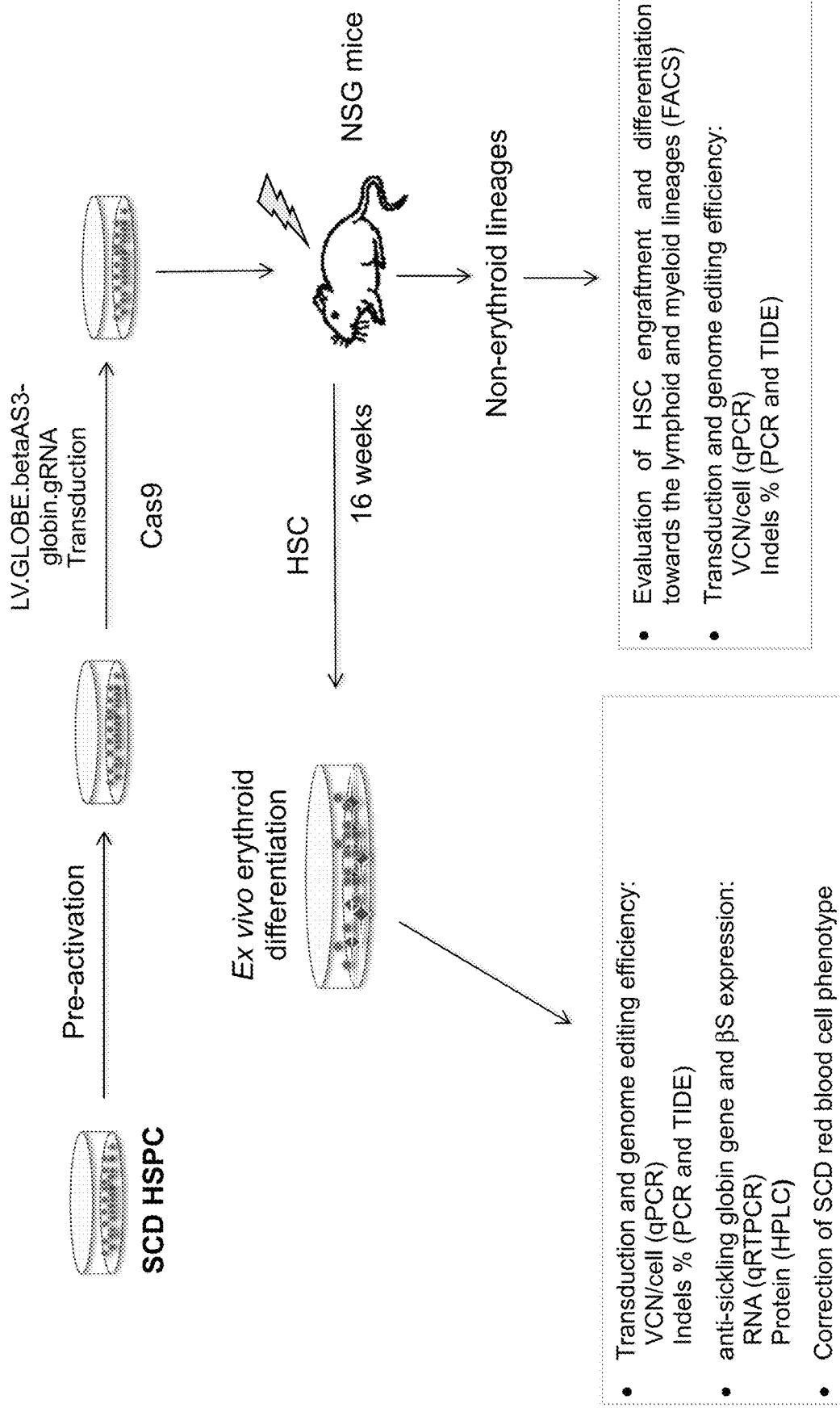
FIG. 13: Genetic modification of patient SCD HSC in vivo

This process is illustrated in FIG. 13.

Example 9: Evaluation of Transgene Expression, Genome Editing Efficiency and (i) Beta-Globin Down-Regulation (gRNA D) or (ii) Gamma-Globin Re-Activation (gRNA-13 bp-Del and gRNA-BCL11Aenhancer)

Protocols
Lentiviral Vectors Used

LV.GLOBE-AS3modified (LV.GLOBE.betaAS3-globin plasmid (SEQ ID NO: 45): lentiviral vector harboring only a Beta-AS3 transgene modified by inserting silent mutations in the sequence of exon 1 targeted by gRNA-D (AS3modified transgene), does not express gRNAD LV.GLOBE-AS3modified.gRNAD (LV.GLOBE-AS3modified.gRNAD, SEQ ID NO: 94): lentiviral vector expressing AS3modified transgene and optimized gRNA D.

LV.GLOBE-AS3modified.gRNA-luciferase (SEQ ID NO: 93): lentiviral vector expressing AS3modified transgene and optimized gRNA targeting the luciferase gene, which is not present in the human genome.

LV.GLOBE-AS3modified.gRNA-BCL11Aenhancer (SEQ ID NO: 75): lentiviral vector expressing AS3modified transgene and optimized BCL11A gRNA (5'-CACAGGCTCCAGGAAGGGTT-3'—SEQ ID NO: 74) targeting the intronic erythroid-specific enhancer of BCL11A gene. To evaluate the editing efficiency of BCL11A gRNA by TIDE the following primers were used:

```
BCL11A-TIDE FORWARD:
                            (SEQ ID NO: 77)
5'-TGGACAGCCCGACAGATGAA-3'

BCL11A-TIDE REVERSE:
                            (SEQ ID NO: 78)
5'-AAAAGCGATACAGGGCTGGC-3'
```

LV.GLOBE-AS3modified.gRNA-13 bp-del (SEQ ID NO: 76): lentiviral vector expressing AS3modified transgene and optimized 13 bp-del gRNA (SEQ ID NO: 71) designed to reproduce the 13 bp small HPFH deletion within the promoters of HBG1 and HBG2 genes. To evaluate the editing efficiency of 13 bp-del gRNA by TIDE the following primers were used:

```
13 bp-del-TIDE FORWARD:
                            (SEQ ID NO: 79)
5'-AAAAACGGCTGACAAAAGAAGTCCTGGTAT-3'

13 bp-del-TIDE REVERSE:
                            (SEQ ID NO: 80)
5'-ATAACCTCAGACGTTCCAGAAGCGAGTGTG-3'
```

Transduction of HUDEP-2 Cells

HUDEP-2 WT cells were transduced at MOI 50 with LVs LV.GLOBE-AS3modified.gRNAD (D, SEQ ID NO: 94), LV.GLOBE-AS3modified.gRNA-BCL11Aenhancer (BCL11A, SEQ ID NO: 75) and LV.GLOBE-AS3modified.gRNA-13 bp-del (13bpdel, SEQ ID NO: 76). Untransduced (UT) samples or cells transduced with LV.GLOBE-AS3modified (AS3, SEQ ID NO: 45) and LV.GLOBE-AS3modified.gRNA-luciferase (Luc) LVs were used as controls.

10 days after transduction, transduced cells were transfected using 4 µg GFP-Cas9 plasmid (pMJ920, Addgene plasmid #42234). After 18 hours plasmid-transfected Cas9-GFP+ cells (29%-45%, not shown) were sorted by FACS.

In parallel, an LVs LV.GLOBE-AS3modified.gRNAD-transduced sample was electroporated using 10 µg (60 pmol) of Cas9-GFP protein by using Nucleofector 4D (CA-137 program), achieving ~90% of GFP+ Cas9-expressing cells (not shown).

Sorted plasmid-transfected and unsorted Cas9-protein-transfected D samples, as well as non-transduced and non-transfected cells (UT) and transduced but non-transfected samples used as controls were then differentiated in mature erythroblasts.

mRNAs Quantification

Figure 15:
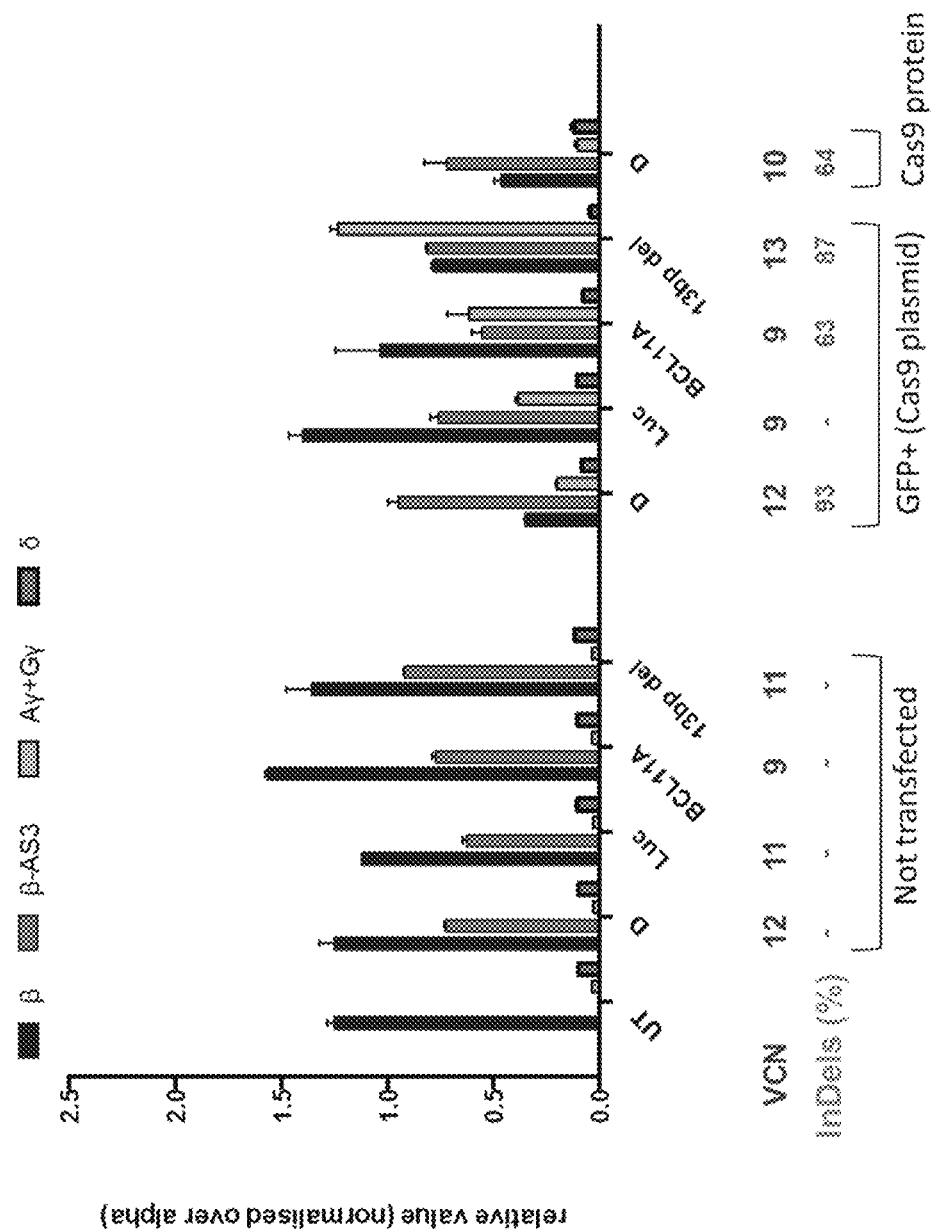
FIG. 15: Assessment of globin mRNAs expression in mature erythroblasts (day 9 of differentiation) derived from control and genetically modified HUDEP-2 cell lines. UT: mature erythroblasts derived from non-transduced and non-transfected HUDEP-2 cells: "normal" level of globin β, δ and γ globin (negative control); VCN: «vector copy number»; Not transfected: mature erythroblasts derived from non-transfected HUDEP-2 cells; GFP+ (Cas9 plasmid): mature erythroblasts derived from HUDEP-2 cells expressing Cas9-GFP fusion protein, selected by FACS upon transfection with GFP-Cas9 plasmid; Cas9 protein: mature erythroblasts derived from HUDEP-2 cells transfected with Cas9-GFP protein without using selection-based strategies; when transduced, cells were treated with a lentiviral vector expressing beta-globin AS3mod transgene and a gRNA selected from: "D" lentiviral vector encoding optimized gRNA D, "luc" lentiviral vector encoding an optimized gRNA targeting the luciferase gene, which is not present in the human genome (negative control), "BCL11A" lentiviral vector encoding an optimized gRNA targeting the intronic erythroid-specific enhancer of BCL11A gene, "13bpdel" lentiviral vector encoding a gRNA designed to reproduce the 13 bp small HPFH deletion within the promoters of HBG1 and HBG2 genes; β: endogenous beta-globin mRNA; β-AS3: AS3 beta-globin transgene mRNA; Aγ+Gγ: gamma-globin mRNA; δ: delta-globin mRNA.

Globin mRNA expression in mature erythroblasts (day 9 of differentiation) is presented in FIG. 15.

Globin expression was evaluated by qRT-PCR in samples collected at day 9 of differentiation. Total RNA was extracted using RNeasy micro kit (QIAGEN) following manufacturer's instructions. Mature transcripts were reverse-transcribed using SuperScript First-Strand Synthesis System for RT-PCR (Invitrogen) with oligo(dT) primers. qRT-PCR was performed using SYBR green (Applied Biosystems).

Primers HBG1+HBG2 FORWARD: 5'-CCTGTCCTCTGCCTCTGCC-3' (SEQ ID NO: 81) and HBG1+HBG2 REVERSE: 5'-GGATTGCCAAAACGGTCAC-3' (SEQ ID NO: 82) were used to amplify the γ-globin transcripts. Primers HBB-AS3 FORWARD 5'-AAGGGCACCTTTGCCCAG-3', (SEQ ID NO: 21) and HBB-AS3 REVERSE 5'-GCCACCACTTTCTGATAGGCAG-3' (SEQ ID NO: 22) were used to amplify exclusively the beta AS3 globin transcripts. Primers HBB FORWARD: 5'-AAGGGCACCTTTGCCACA-3', (SEQ ID NO: 81) and HBB REVERSE: 5'-gccaccactttctgataggcag-3' (SEQ ID NO: 82) were used to amplify the endogenous β-globin transcripts. Primers HBD FORWARD: 5'-CAAGGGCACTTTTTTCTCAG-3' (SEQ ID NO: 85) and HBD REVERSE: 5'-AATTCCTTGCCAAAGTTGC-3' (SEQ ID NO: 86) were used to amplify the δ-globin transcripts. Primers HBA1 F (5'-CGGTCAACTTCAAGCTCCTAA-3', SEQ ID NO: 13) and HBA1 R (5'-ACAGAAGCCAGGAACTTGTC 3', SEQ ID NO: 14) were used to amplify the alpha-globin transcripts. Endogenous beta-globin, AS3 beta-globin, gamma-globin and delta-globin results were normalized to alpha-globin.

BCL11A mRNA expression in undifferentiated (day0) HUDEP WT cells and in differentiated erythroblasts at different days of differentiation (day5, day7 and day9) was evaluated by qRT-PCR (as described above) in samples transduced with LV.GLOBE-AS3modified.gRNA-BCL11Aenhancer with or without transfection with Cas9-GFP plasmids followed by flow cytometry-based selection of GFP+ cells. Time-course analysis of the total BCL11A mRNA isoforms and of the BCL11A isoform XL, mainly involved in the regulation of gamma-globin expression, was performed by using qRT-PCR with the following primers:

```
BCL11A FORWARD:
                              (SEQ ID NO: 87)
5'-AACCCCAGCACTTAAGCAAA-3'

BCL11A REVERSE:
                              (SEQ ID NO: 88)
5'-GGAGGTCATGATCCCCTTCT-3'

BCL11AXL FORWARD:
                              (SEQ ID NO: 89)
5'-ATGCGAGCTGTGCAACTATG-3'

BCL11AXL REVERSE:
                              (SEQ ID NO: 90)
5'-GTAAACGTCCTTCCCCACCT-3'

GAPDH FORWARD:
                              (SEQ ID NO: 91)
5'-CTTCATTGACCTCAACTACATGGTTT-3'

GAPDH REVERSE:
                              (SEQ ID NO: 92)
5'-TGGGATTTCCATTGATGACAAG-3'
```

HPLC Analyses of Globin Chains and Hemoglobin Tetramers

Figure 16:
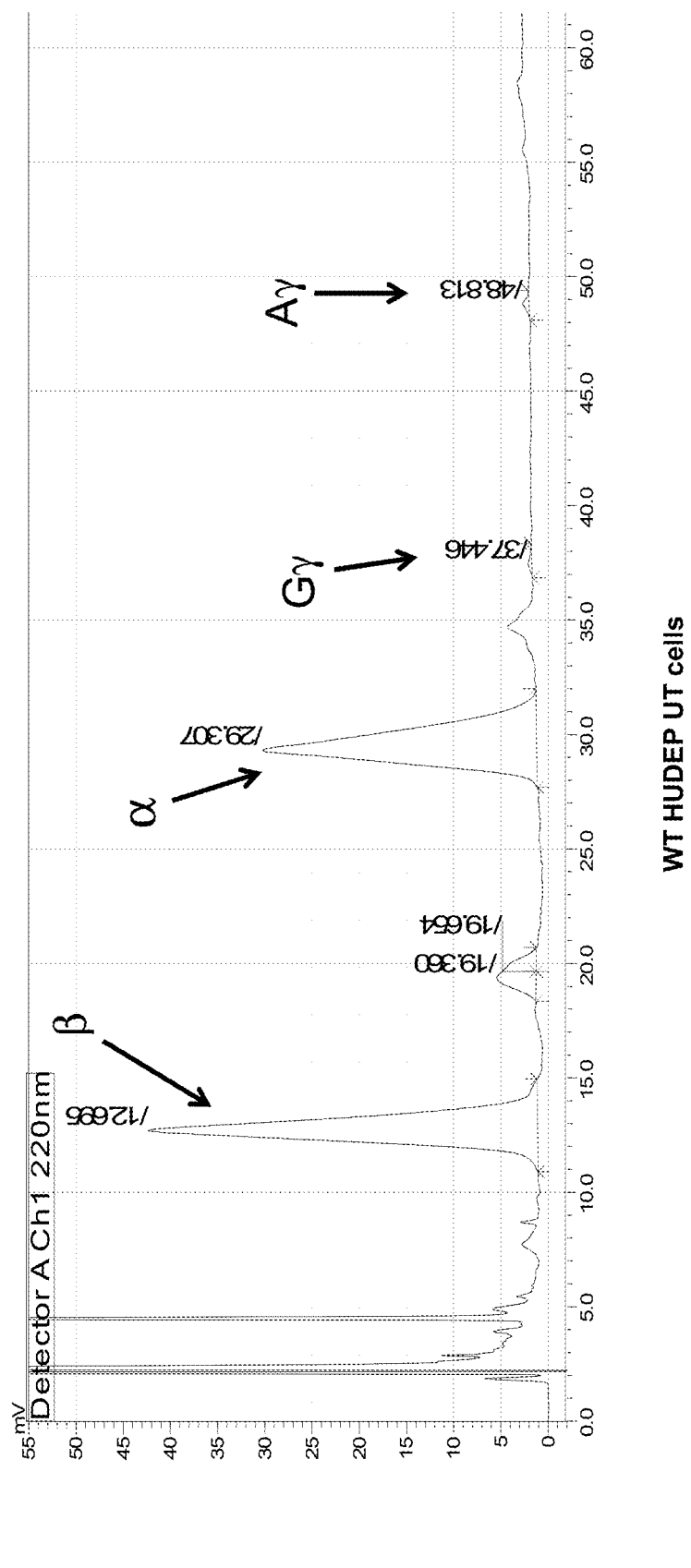
FIG. 16: Reverse phase HPLC profile of single globin chains in mature erythroblasts (day 9 of differentiation) derived from control and genetically modified HUDEP-2 cell lines. (A) mature erythroblasts derived from WT (wild-type) HUDEP-2 UT cells: not transduced and not transfected cells expressing "normal" level of globin β, δ and γ globin (negative control); (B) mature erythroblasts derived from HUDEP-2 cells transduced with LV.GLOBE.AS3mod-beta-globin.gRNA D (lentiviral GLOBE vector encoding the AS3modified beta-globin and the optimized gRNA D) but not transfected with Cas9-GFP plasmid: cells express the AS3modified beta-globin transgene and the endogenous beta-globin chain (no modification of the endogenous HBB gene); (C) mature erythroblasts derived from HUDEP-2 cells transduced cells with the LV.GLOBE.AS3mod-beta-globin.gRNA D (lentiviral GLOBE vector encoding the AS3modified beta-globin and the optimized gRNA D) and transfected with the GFP-Cas9 plasmid: cells express the AS3modified beta-globin transgene but not endogenous beta-globin chain because of the high rate of genome editing in the exon 1 of the endogenous HBB gene.
Figure 16:
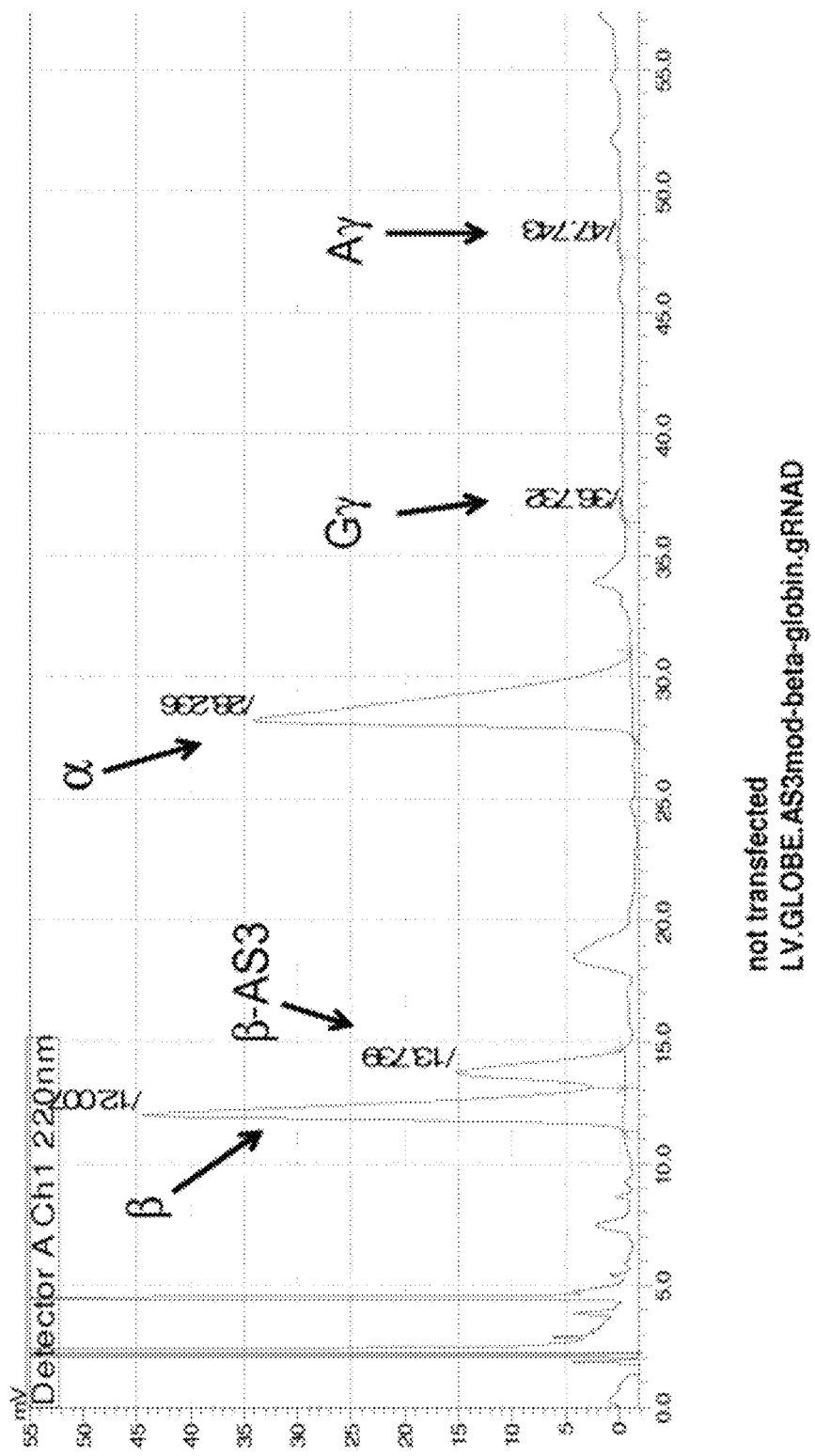
Figure 16:
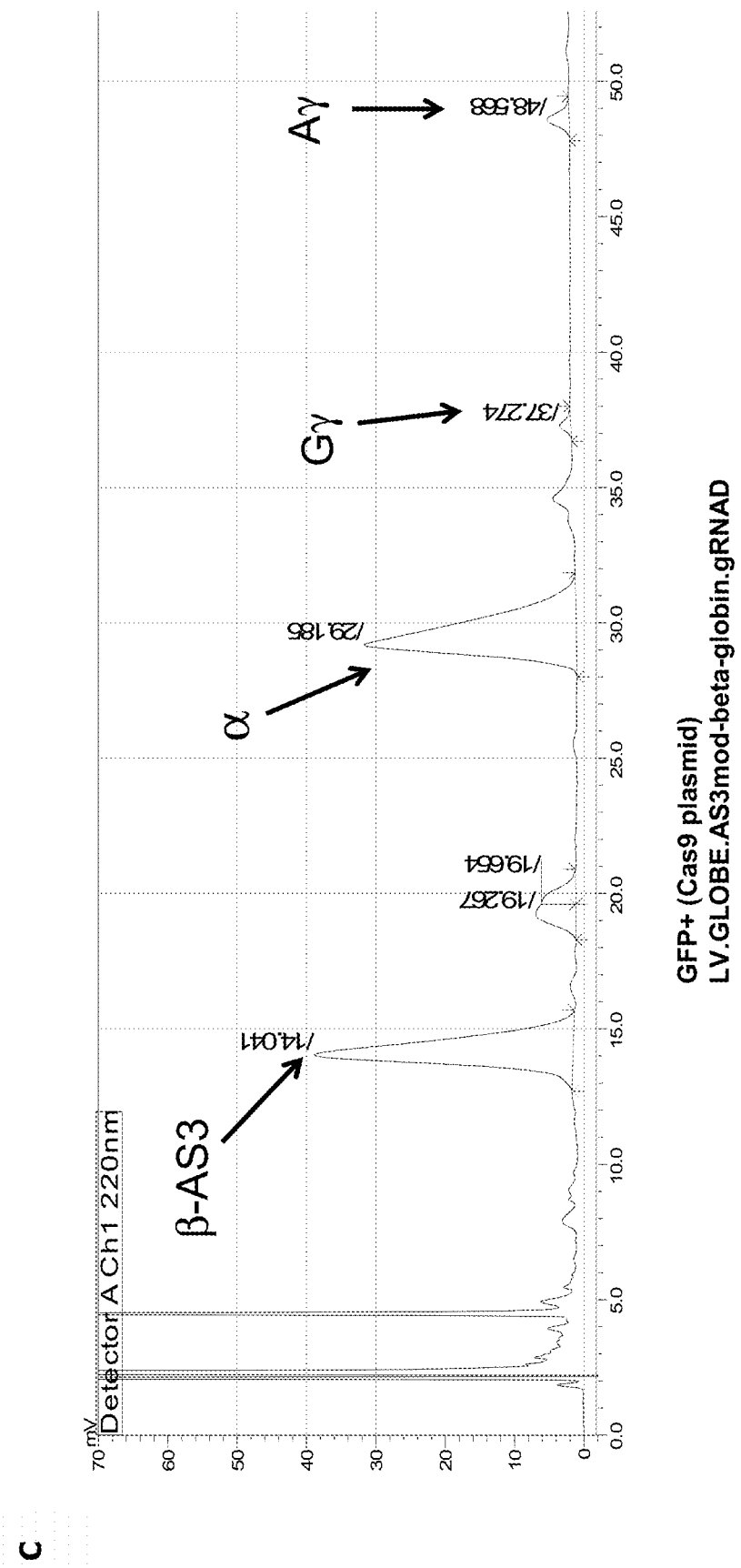
Figure 18:
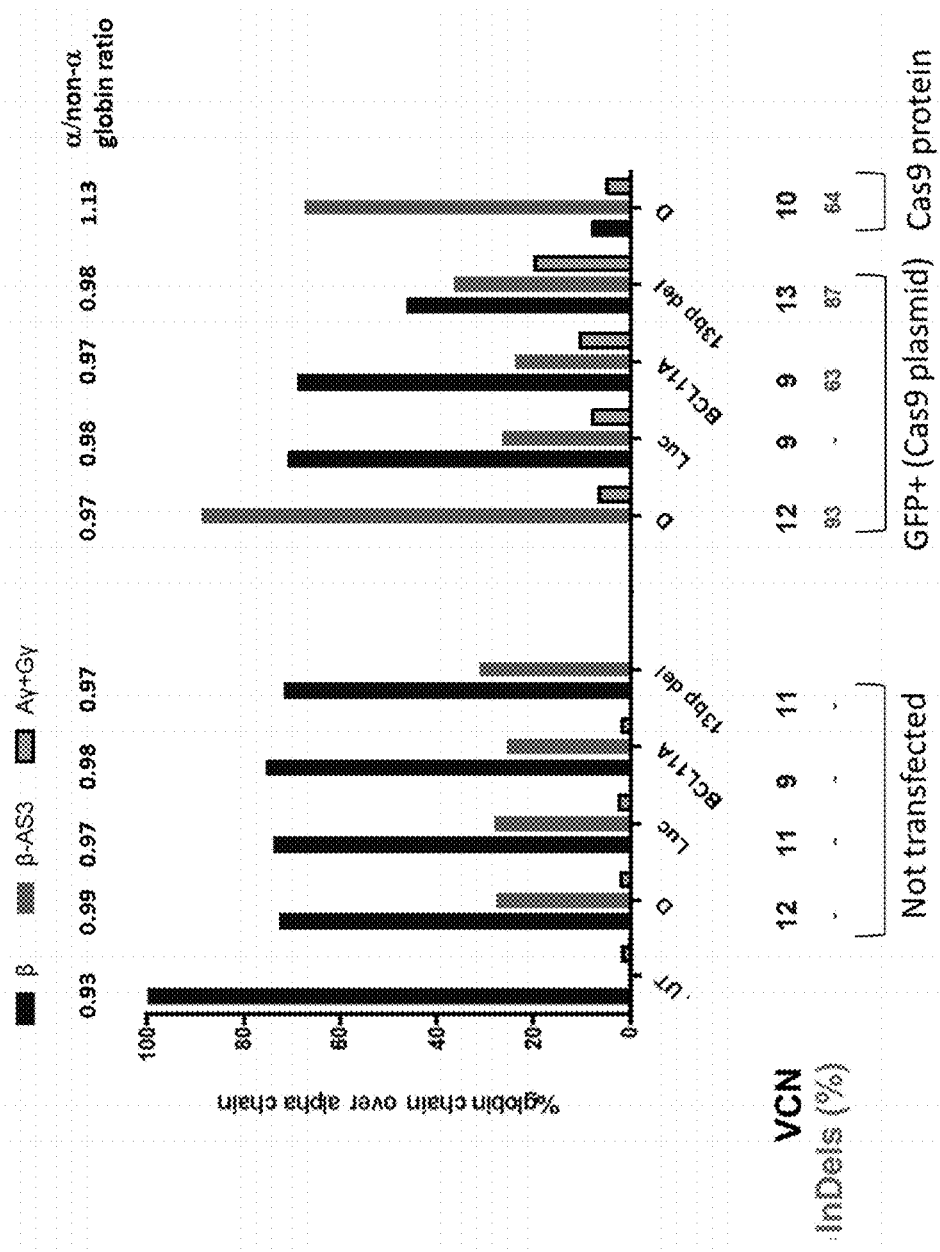
FIG. 18: Reverse phase HPLC analysis of single globin chains in mature erythroblasts (day 9 of differentiation) derived from control and genetically modified HUDEP-2 cell lines. UT: mature erythroblasts derived from non-transduced and non-transfected HUDEP-2 cells: "normal" level of globin β, δ and γ globin (negative control); VCN: «vector copy number»; Not transfected: mature erythroblasts derived from non-transfected HUDEP-2 cells; GFP+ (Cas9 plasmid): mature erythroblasts derived from HUDEP-2 cells expressing Cas9-GFP fusion protein, selected by FACS upon transfection with GFP-Cas9 plasmid; Cas9 protein: mature erythroblasts derived from HUDEP-2 cells transfected with Cas9-GFP protein without using selection-based strategies; when transduced, cells were treated with a lentiviral vector expressing AS3mod beta-globin transgene and a gRNA selected from: "D" lentiviral vector encoding optimized gRNA D, "luc" lentiviral vector encoding an optimized gRNA targeting the luciferase gene (negative control), "BCL11A" lentiviral vector encoding an optimized gRNA targeting the intronic erythroid-specific enhancer of BCL11A gene, "13bpdel" lentiviral vector encoding a gRNA designed to reproduce the 13 bp small HPFH deletion within the promoters of HBG1 and HBG2 genes; β: endogenous beta-globin chain; β-AS3: AS3 beta-globin chain; Aγ+Gγ: gamma-globin chains; δ: delta-globin chain

Globin chain profiles obtained using reverse phase HPLC in mature erythroblasts derived from control or genetically modified HUDEP cells (day 9 of differentiation) are presented in FIG. 16. Quantification of beta-like globin protein levels normalized to alpha-globin levels are shown in FIG. 18.

Briefly, reverse phase HPLC (RP-HPLC) analysis of globin chains was performed using a NexeraX2 SIL-30AC chromatograph (Shimadzu) and the LC Solution software. Globin chains from in vitro differentiated mature erythroblasts were separated by HPLC using a 250×4.6 mm, 3.6 μm Aeris Widepore column (Phenomenex). Samples were eluted with a gradient mixture of solution A (water/acetonitrile/trifluoroacetic acid, 95:5:0.1) and solution B (water/acetonitrile/trifluoroacetic acid, 5:95:0.1). The absorbance was measured at 220 nm.

Figure 19:
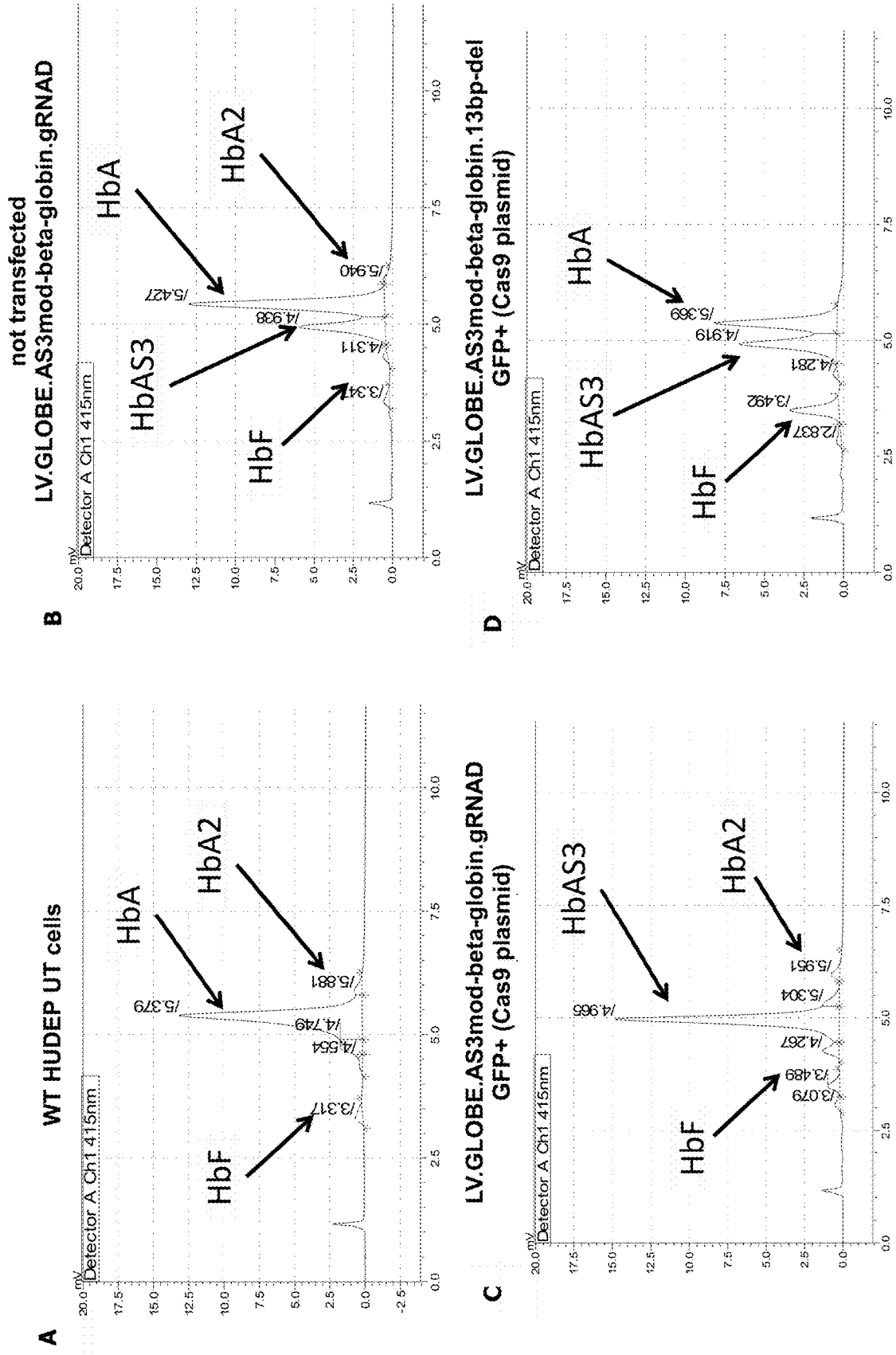
FIG. 19: Cation-exchange HPLC profile of hemoglobin tetramers in mature erythroblasts (day 9 of differentiation) derived from control and genetically modified HUDEP-2 cell line (A) WT (wild-type) HUDEP-2 UT cells: mature erythroblasts derived from non-transduced and non-transfected HUDEP-2 cells: "normal" level of globin HbA (hemoglobin tetramer containing the endogenous beta-globin chain), HbA2 (hemoglobin tetramer containing the endogenous delta-globin chain) and HbF (hemoglobin tetramer containing the endogenous gamma-globin chain) (negative control); mature erythroblasts derived from HUDEP-2 cells transduced with LV.GLOBE.AS3mod-beta-globin.gRNA D (lentiviral GLOBE vector encoding the AS3modified beta-globin and the optimized gRNA D) but not transfected with Cas9-GFP plasmid: cells express the Hb tetramer containing the AS3modified beta-globin transgene (HbAS3) and HbA containing the endogenous beta-globin chain (no modification of the endogenous HBB gene); (C) mature erythroblasts derived from HUDEP-2 cells transduced with the LV.GLOBE.AS3mod-beta-globin.gRNA D (lentiviral GLOBE vector encoding the AS3modified beta-globin and the optimized gRNA D) and transfected with the GFP-Cas9 plasmid: cells express HbAS3 but not HbA because of the high rate of genome editing in the exon 1 of the endogenous HBB gene; (D) mature erythroblasts derived from HUDEP-2 cells transduced cells with the LV.GLOBE.AS3mod-beta-globin.gRNA 13 bp-del (lentiviral GLOBE vector encoding the AS3modified beta-globin and the optimized gRNA "13bpdel" encoding a gRNA designed to reproduce the 13 bp small HPFH deletion within the promoters of HBG1 and HBG2 genes) and transfected with the GFP-Cas9 plasmid: cells express the HbAS3, HbA and high levels of HbF upon genome editing of the promoters of HBG1 and HBG2 genes. HbA: $\alpha_2\beta_2$ tetramers; HbAS3: $\alpha_2\beta$-AS3$_2$ tetramers; HbA2: $\alpha_2\delta_2$ tetramers; HbF: $\alpha_2\gamma_2$ tetramers.
Figure 20:
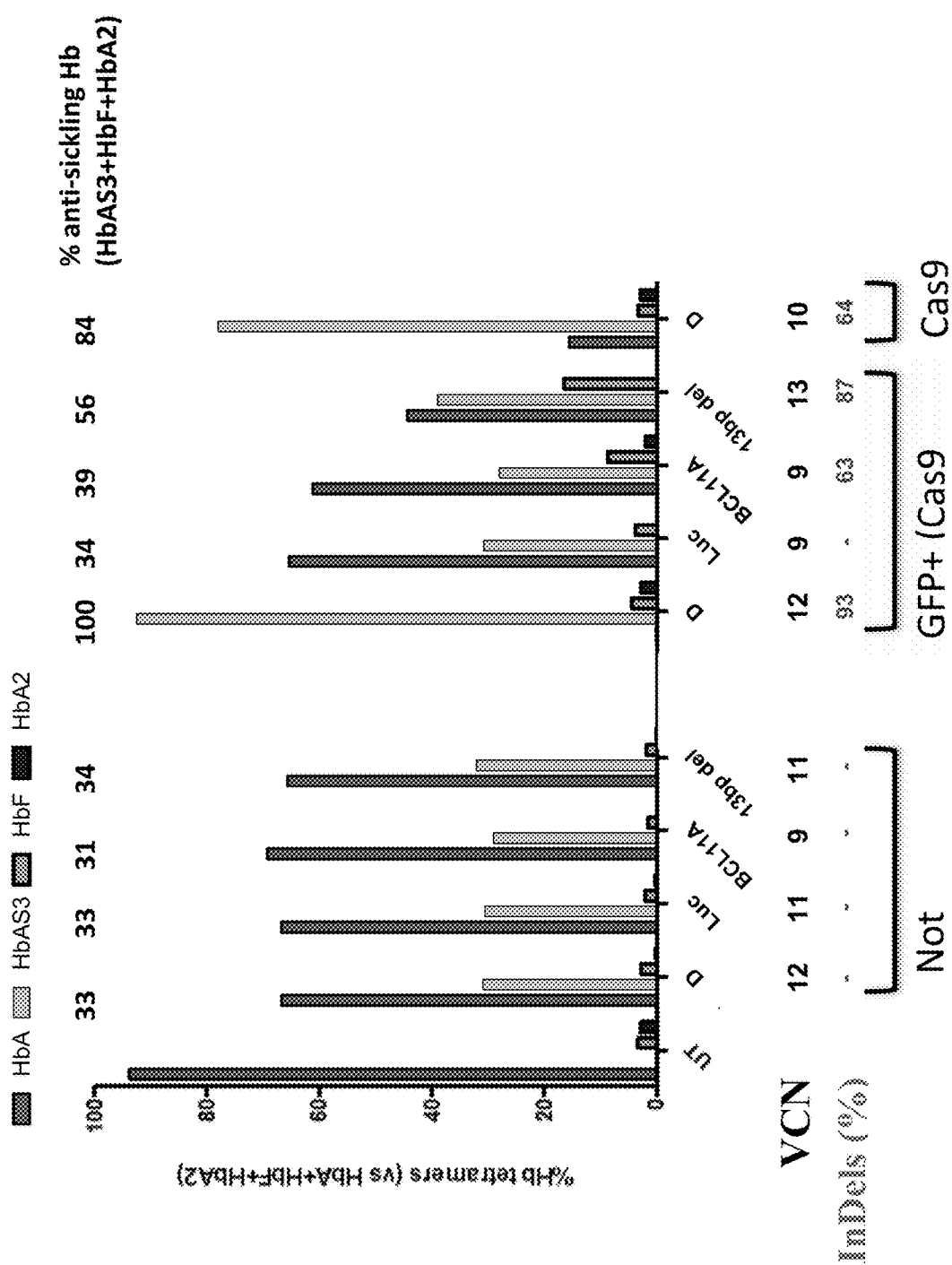
FIG. 20: Quantification of hemoglobin tetramers by HPLC, as in FIG. 19, in mature erythroblasts (day 9 of differentiation) from control and genetically modified HUDEP-2 cell line. UT: mature erythroblasts derived from non-transduced and non-transfected HUDEP-2 cells: "normal" level of globin HbA, HbA2 and HbF (negative control); VCN: «vector copy number»; Not transfected: mature erythroblasts derived from HUDEP-2 cells non-transfected with GFP-Cas9 plasmid or Cas9-GFP protein; GFP+(Cas9 plasmid): mature erythroblasts derived from HUDEP-2 cells expressing Cas9-GFP fusion protein, selected by FACS upon transfection with GFP-Cas9; Cas9 protein: mature erythroblasts derived from HUDEP-2 cells transfected with Cas9-GFP protein without using selection-based strategies; when transduced, cells were treated with a lentiviral vector expressing beta-globin AS3mod transgene and a gRNA selected from: "D" lentiviral vector encoding optimized gRNA D, "luc" lentiviral vector encoding an optimized gRNA targeting the luciferase gene (negative control), "BCL11A" lentiviral vector encoding an optimized gRNA targeting the intronic erythroid-specific enhancer of BCL11A gene, "13bpdel" lentiviral vector encoding a gRNA designed to reproduce the 13 bp small HPFH deletion within the promoters of HBG1 and HBG2 genes. HbA: $\alpha_2\beta_2$ tetramers; HbAS3: $\alpha_2\beta$-AS3$_2$ tetramers; HbA2: $\alpha_2\delta_2$ tetramers; HbF: $\alpha_2\gamma_2$ tetramers.

Hemoglobin profiles obtained using cation-exchange HPLC in mature erythroblasts derived from unmodified or genetically modified HUDEP cells (day 9 of differentiation) are presented in FIG. 19. Results of the quantification of each hemoglobin tetramer (HbA, HbAS3, HbF and HbA2) were reported as percentage over the total amount of hemoglobin tetramers and are shown in FIG. 20.

Analysis of hemoglobin tetramers was performed by cation-exchange HPLC using a NexeraX2 SIL-30AC chromatograph (Shimadzu) and the LC Solution software. Hemoglobin tetramers from mature erythroblasts were separated using a 2 cation-exchange column (PolyCAT A, PolyLC, Columbia, MD). Samples were eluted with a gradient mixture of solution A (20 mM bis Tris, 2 mM KCN, pH=6.5) and solution B (20 mM bis Tris, 2 mM KCN, 250 mM NaCl, pH=6.8). The absorbance was measured at 415 nm.

Results:
A) Globin (FIG. 15) and BCL11A mRNA Expression (FIG. 17)
1) Cells not Transfected (not Transfected)

AS3mod (not shown in the figures): higher expression level of β-AS3 associated with the higher VCN compared to other samples.

"Luc" transduced cells: Similar expression level of endogenous HBB mRNA compared to controls (UT) and lower expression of AS3 beta-globin mRNA transgene compared to AS3mod due to lower VCN (FIG. 15).

"D" transduced cells: no inactivation of endogenous β-globin gene (i.e. HBB), due to the absence of Cas9 delivery. Similar expression level of endogenous HBB mRNA compared to controls (UT and "luc"). "D" also expresses AS3 beta-globin mRNA transgene at similar level compared to control ("luc") with similar VCN (FIG. 15).

"BCL11A" and "13 bp del" transduced cells: no inactivation of endogenous β-globin gene (i.e. HBB), because of the expression of gRNAs that do not target HBB. Similar expression level of endogenous HBB mRNA in the BCL11A and 13 bp del samples compared to controls (UT and "luc"). Similar levels of expression of AS3 beta-globin mRNA transgene for both BCL11A and 13 bp del samples in comparison with control ("luc") with similar VCN (FIG. 15).

Figure 17:
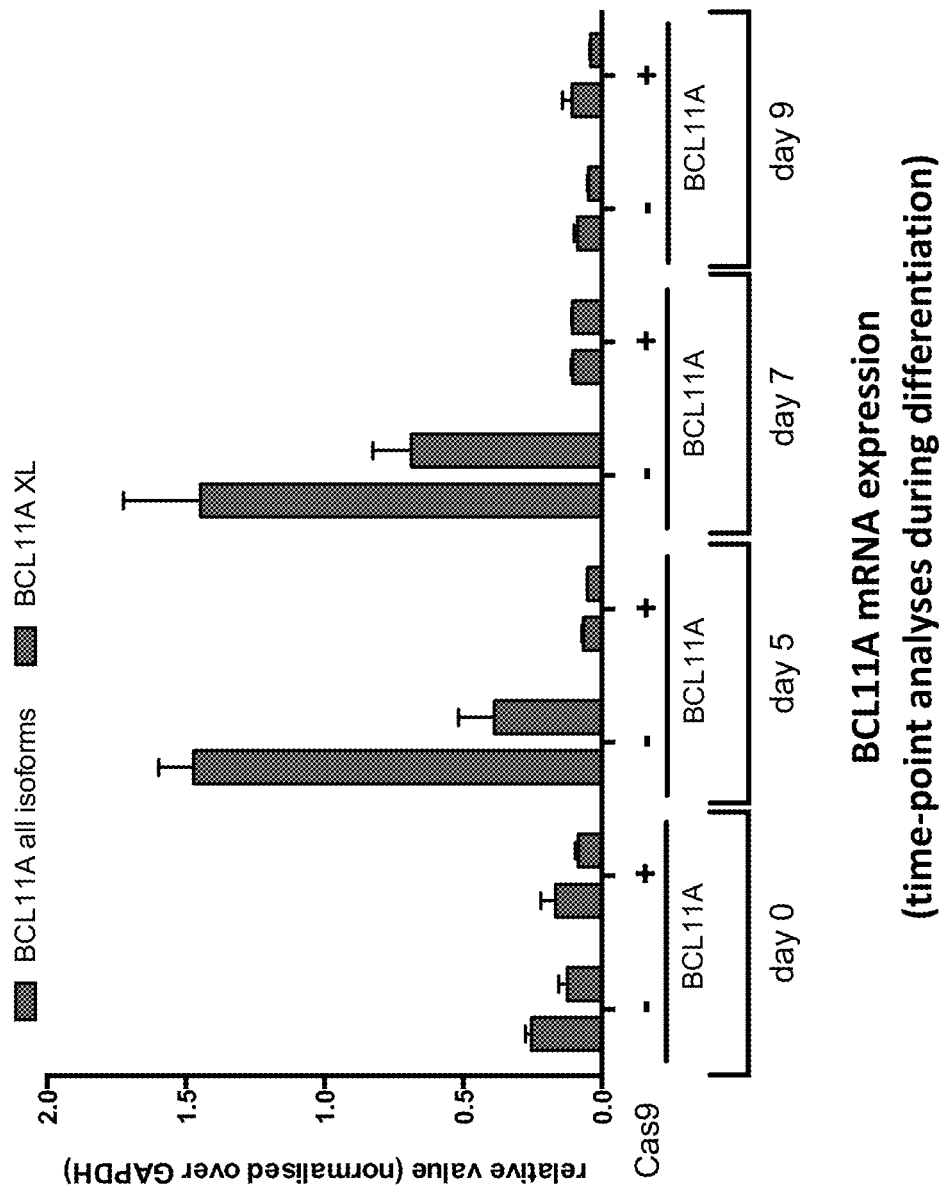
FIG. 17: Assessment of BCL11A mRNA expression (time-point analyses during differentiation) in HUDEP-2 cells transduced with a lentiviral vector encoding beta-globin AS3mod and a gRNA targeting the intronic erythroid-specific enhancer of BCL11A gene with ("+") or without ("−") transfection with Cas9-GFP plasmid.

Note that BCL11A/BCL11AXL mRNA expression levels are increased over-time with a peak at days 5 and 7 of differentiation in non-transfected BCL11A sample (used as control in FIG. 17).

2) Cells Transfected with GFP-Cas9 Plasmid (GFP+(Cas9 Plasmid)) or with Cas9-GFP Protein (Cas9 Protein)

AS3mod and Luc transduced cells: no genome editing in the exon 1 of endogenous HBB gene, as well as in the gamma-globin promoters or in the intronic enhancer of BCL11A gene, due to the absence of gRNAs in the LV vector (AS3mod) or the presence of a gRNA targeting the luciferase gene (Luc). Similar expression levels of endogenous beta-, AS3 beta-, gamma- and delta-globin chains compared to samples transduced with the same LV but «not transfected» with Cas9-GFP plasmid.

"D" transduced cells: down-regulation of endogenous β-globin gene expression in comparison with D «not transfected» sample and controls samples, due to the targeting of endogenous HBB gene by gRNA D and plasmid or protein delivery of Cas9. The expression of β-AS3 transgene and gamma-globin chains (Aγ+Gγ) tend to increase maybe as a consequence of HBB downregulation.

"BCL11A" and "13 bp del" transduced cells: an up-regulation of gamma-globin chains (Aγ+Gγ) expression is observed in comparison with "BCL11A" and "13 bp del" «not transfected» samples and controls, due to the disruption of the erythroid-specific BCL11A enhancer (BCL11A sample) or to the deletion of the 13-bp region in gamma-globin promoters (13 bp del sample) as a consequence of gRNA expression and plasmid delivery of Cas9. Indeed, the treatment with Cas9 strongly downregulated the expression of BCL11A, including XL isoform, in mature erythroblasts derived from Cas9-GFP+ BCL11A sample demonstrating that gRNA targeting the BCL11A enhancer is effective in decreasing BCL11A expression in erythroid cells and consequently implying a deregulation of γ-globin gene expression (see for example FIG. 15 or protein expression levels below). The 13 bp del sample showed reduced expression of the endogenous beta-globin gene. Similar expression levels of β-AS3- and delta-globin chains compared to samples transduced with the same LVs but «not transfected» with Cas9-GFP plasmid.

B) Protein Expression

HPLC analyses showed a dramatic down-regulation of endogenous beta-globin expression ("β") and HbA tetramers (FIGS. 18 and 20) and increased amounts of exogenous β-AS3-globin and HbAS3 tetramers (FIGS. 18 and 20) in mature erythroblasts derived from HUDEP-2 cells transduced with LV.AS3-beta-globin.gRNAD and transfected with Cas9-GFP plasmid or Cas9 protein (FIG. 16 panel C and FIGS. 18 and 20), when compared LV.AS3-beta-globin.gRNAD transduced but non-transfected cells (FIG. 16 panel B and FIGS. 18 and 20).

In particular mature erythroblasts derived from HUDEP-2 cells transduced with LV.AS3-beta-globin.gRNA-D and transfected with Cas9-GFP plasmid or Cas9 protein showed almost a complete knock-down of endogenous beta-globin chain expression ("β") and HbA tetramers compensated by the expression of exogenous β-AS3-globin expression and HbAS3 tetramers as demonstrated by the alpha/not-alpha ratio that is similar in control samples (FIGS. 18 and 20). Genome editing at HBB target site and, as a consequence, the reduction in endogenous beta-globin chain/HbA and the increase in beta-globin AS3/HbAS3 is VCN-dependent (not shown) but significant even at low VCN (VCN=3).

Figure 21:
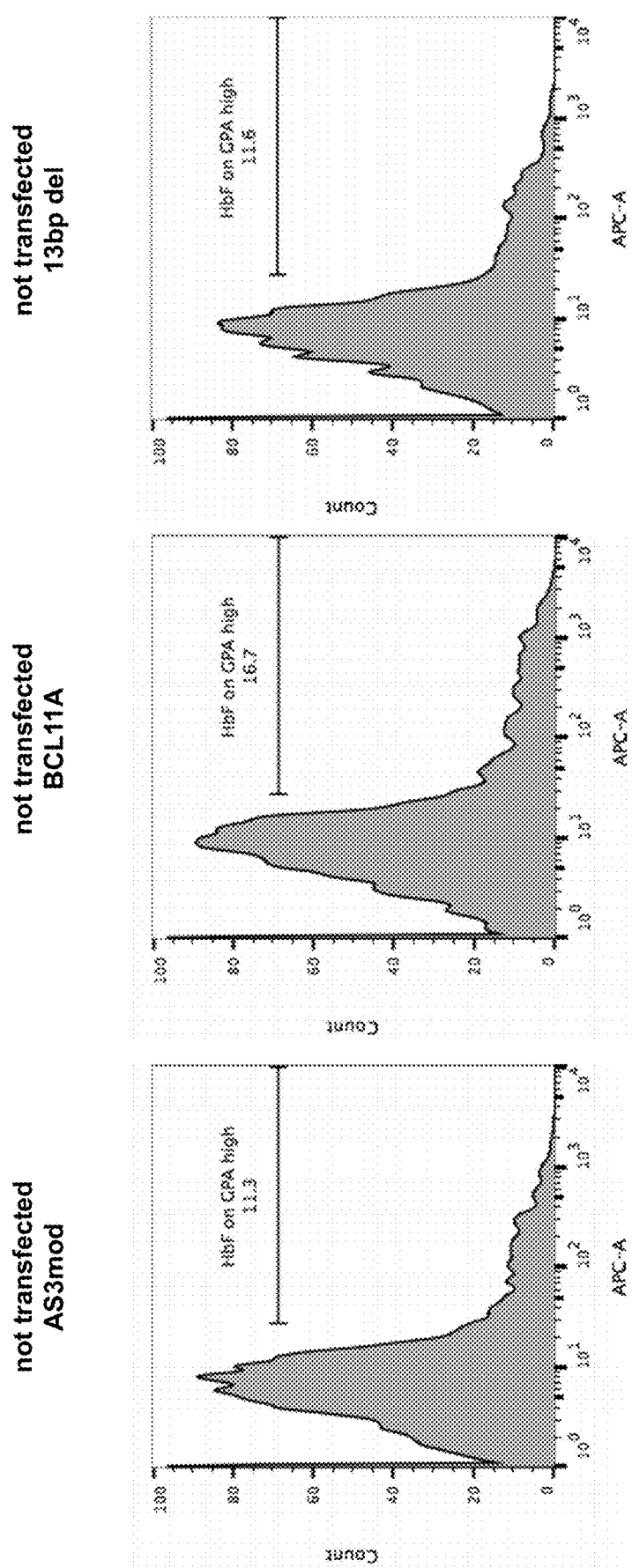
FIG. 21: HbF expression in mature erythroblasts (flow cytometry analysis on GPA(glycophorinA)$^{high}$ populations) derived from control and genetically modified HUDEP-2 cells (day 9 of differentiation)
Figure 21:
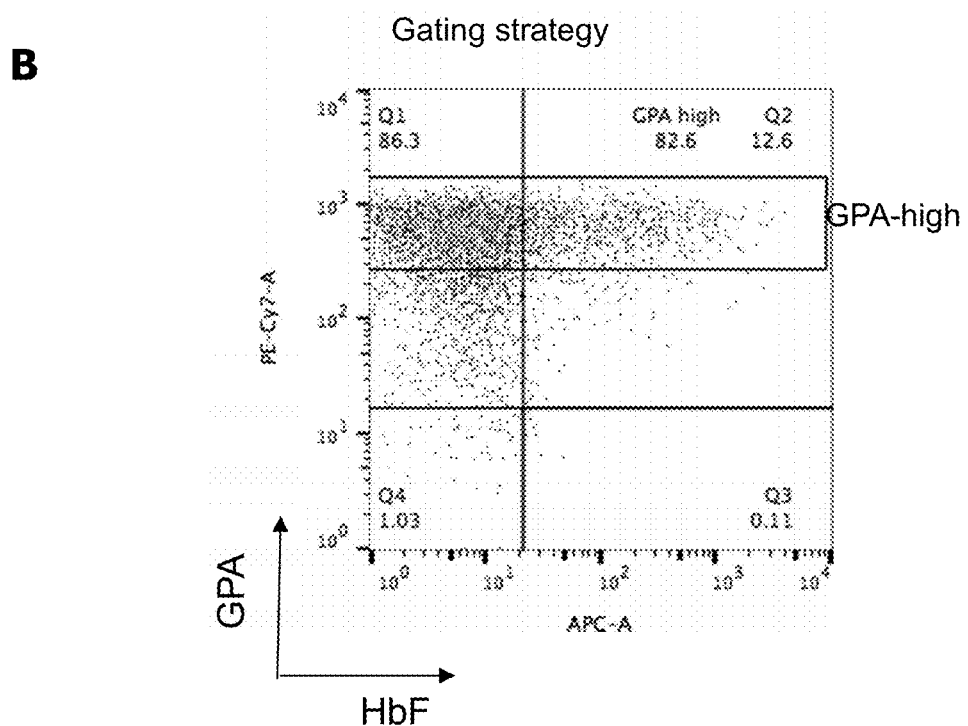

In mature erythroblasts derived from HUDEP-2 cells transduced with LV.AS3-beta-globin.gRNA-BCL11Aenhancer or LV.AS3-beta-globin.gRNA-13bpdel and transfected with Cas9-GFP plasmid, gamma-globin expression and HbF levels were significantly increased (FIGS. 18 and 20) compared to control samples and HbF expression pattern is close to be pan-cellular reaching 61% and 74% of F+(HbF+) cells in mature erythroblasts derived from Cas9-expressing BCL11A and 13bpdel HUDEP-2, respectively (FIG. 21).

Conclusions

Transgene expression at mRNA and protein levels (FIGS. 18 and 20) are correlated and are not impaired by gRNA expression and Cas9 delivery. Transgene expression is correlated with VCN at both mRNA (FIG. 15) and protein levels (FIGS. 18 and 20).

In Cas9-GFP+D samples the knock-down of endogenous β-globin gene at mRNA level (FIG. 15) results in complete knock-out of endogenous β-globin protein expression (FIGS. 16 and 18) and absence of HbA tetramers (FIGS. 19 and 20). Hence a majority of anti-sickling tetramers (HbAS3) are observed in these cells.

The ratio between the expression of alpha-globin and non-alpha-globins (alpha/non-alpha ratio) is similar between all samples. The concomitant increase of anti-sickling globin expression (FIGS. 15-16), mainly AS3-β-globin (+60% in comparison with not-transfected D sample; FIGS. 16 and 19), compensates the observed robust endogenous β-globin downregulation. Hence, no modification in the balance between α- and other globin chain synthesis (FIGS. 18-19) is observed thereby avoiding generation of α-globin precipitates (FIGS. 19-20) which might be seen as a risk in the case of this therapeutic strategy.

Cas9 protein-mediated genome editing in "D" samples resulted in a clinically relevant switching between endogenous HbA tetramer (16%) and anti-sickling tetramers (HbAS3, HbF and HbA2; 84%) (FIGS. 19-20).

In mature erythroblasts derived from Cas9-GFP+13bpdel and BCL11A samples, a robust increase in γ-globin expression at both mRNA (FIG. 15) and protein (Z5 and Z10 fold increase for 13bpdel and BCL11A, respectively; (FIG. 18)) levels in comparison with not-transfected 13bpdel and BCL11A samples was observed. Compared to matched non-transfected controls, in both 13bpdel and BCL11A samples an increased production of anti-sickling tetramers (+9% and +22% in 13bpdel and BCL11A, respectively; (FIGS. 19-20)) was observed, mainly associated with an enhanced generation of HbF tetramers. This finally resulted in ≈50% of HbA and ≈50% of HbAS3+HbF in 13bpdel sample, a condition resembling healthy heterozygous SCD carriers.

Relative amounts of HbA, HbA2, HbF and HbAS3 tetramers are shown in FIG. 20. Individuals with a level of of anti-sickling Hb above 50% are considered healthy (i.e. HbAS3+HbF+HbA2), which is the case for erythroblasts derived from HUDEP-2 cells transduced with D or 13bpdel and transfected with Cas9.

All together these results showed the effectiveness of the integrative system as set up by the inventors in:
  inactivating mutant beta-globin gene involved in SCD pathophysiology when gRNA D is used; and
  expressing HbAS3 and, when gRNA BCL11A or gRNA 13bpdel are used instead of gRNAD, increasing expression of γ-globin chains, resulting in the production of an amount of antisickling hemoglobin tetramers sufficient to correct sickle cell disease and avoid alpha-globin precipitations.

SEQUENCE LISTING

<160> NUMBER OF SEQ ID NOS: 99

<210> SEQ ID NO 1
<211> LENGTH: 830

<212> TYPE: DNA
<213> ORGANISM: Artificial Sequence
<220> FEATURE:
<223> OTHER INFORMATION: Beta AS1 (T87Q) (not modified)

<400> SEQUENCE: 1

```
ttagtgatac ttgtgggcca gggcattagc cacaccagcc accactttct gataggcagc      60
ctgcactggt ggggtgaatt ctttgccaaa gtgatgggcc agcacacaga ccagcacgtt     120
gcccaggagc tgtgggagga agataagagg tatgaacatg attagcaaaa gggcctagct     180
tggactcaga ataatccagc cttatcccaa ccataaaata aaagcagaat ggtagctgga     240
ttgtagctgc tattagcaat atgaaacctc ttacatcagt tacaatttat atgcagaaat     300
accctgttac ttctccccct cctatgacat gaacttaacc atagaaaaga aggggaaaga     360
aaacatcaag ggtcccatag actcaccctg aagttctcag gatccacgtg cagcttgtca     420
cagtgcagct cactcagctg ggcaaaggtg cccttgaggt tgtccaggtg agccaggca      480
tcactaaagg caccgagcac tttcttgcca tgagccttca ccttagggtt gcccataaca     540
gcatcaggag tggacagatc cccaaaggac tcaaagaacc tctgggtcca agggtagacc     600
accagcagcc taagggtggg aaaatagacc aataggcaga gagagtcagt gcctatcaga     660
aacccaagag tcttctctgt ctccacatgc ccagtttcta ttggtctcct taaacctgtc     720
ttgtaacctt gataccaacc tgcccagggc ctcaccacca acttcatcca cgttcacctt     780
gccccacagg gcagtaacgg cagacttctc ctcaggagtc aggtgcacca                830
```

<210> SEQ ID NO 2
<211> LENGTH: 831
<212> TYPE: DNA
<213> ORGANISM: Artificial Sequence
<220> FEATURE:
<223> OTHER INFORMATION: Beta AS3 (not modified)

<400> SEQUENCE: 2

```
ttagtgatac ttgtgggcca gggcattagc cacaccagcc accactttct gataggcagc      60
ctgcactggt ggggtgaatt ctttgccaaa gtgatgggcc agcacacaga ccagcacgtt     120
gcccaggagc tgtgggagga agataagagg tatgaacatg attagcaaaa gggcctagct     180
tggactcaga ataatccagc cttatcccaa ccataaaata aaagcagaat ggtagctgga     240
ttgtagctgc tattagcaat atgaaacctc ttacatcagt tacaatttat atgcagaaat     300
accctgttac ttctccccct cctatgacat gaacttaacc atagaaaaga aggggaaaga     360
aaacatcaag ggtcccatag actcaccctg aagttctcag gatccacgtg cagcttgtca     420
cagtgcagct cactcagctg ggcaaaggtg cccttgaggt tgtccaggtg agccaggca      480
tcactaaagg caccgagcac tttcttgcca tgagccttca ccttagggtt gcccataaca     540
gcatcaggag tggacagatc cccaaaggac tcaaagaacc tctgggtcca agggtagacc     600
accagcagcc taagggtggg aaaatagacc aataggcaga gagagtcagt gcctatcaga     660
aacccaagag tcttctctgt ctccacatgc ccagtttcta ttggtctcct taaacctgtc     720
ttgtaacctt gataccaacc tgcccagggc ctcaccacca acggcatcca cgttcacctt     780
gtcccacagg gcagtaacgg cagacttctc ctcaggagtc aggtgcacca t              831
```

<210> SEQ ID NO 3
<211> LENGTH: 848
<212> TYPE: DNA
<213> ORGANISM: Artificial Sequence
<220> FEATURE:

<223> OTHER INFORMATION: Gamma-beta hybrid

<400> SEQUENCE: 3

```
tcagtggtat ctggaggaca gggcactggc cactgcagtc accatcttct gccaggaagc    60
ctgcacctca ggggtgaatt ctttgccgaa atggattgcc aaaacggtca ccagcacatt   120
tcccaggagc tgtgggagga agataagagg tatgaacatg attagcaaaa gggcctagct   180
tggactcaga ataatccagc cttatcccaa ccataaaata aaagcagaat ggtagctgga   240
ttgtagctgc tattagcaat atgaaacctc ttacatcagt tacaatttat atgcagaaat   300
accctgttac ttctcccctt cctatgacat gaacttaacc atagaaaaga aggggaaaga   360
aaacatcaag ggtcccatag actcacgggt cccatagact caccttgaag ttctcaggat   420
ccacatgcag cttgtcacag tgcagttcac tcagctgggc aaaggtgccc ttgagatcat   480
ccaggtgctt tgtggcatct cccaaggaag tcagcacctt cttgccatgt gccttgactt   540
tggggttgcc catgatggca gaggcagagg acaggttgcc aaagctgtca agaacctct    600
gggtccatgg gtagacaacc aggagcctaa gggtgggaaa atagaccaat aggcagagag   660
agtcagtgcc tatcagaaac ccaagagtct tctctgtctc cacatgccca gtttctattg   720
gtctccttaa acctgtcttg taaccttgat accaaccttc cagggtttc tcctccagca    780
tcttccacat tcaccttgcc ccacaggctt gtgatagtag ccttgtcctc ctctgtgaaa   840
tgacccat                                                            848
```

<210> SEQ ID NO 4
<211> LENGTH: 848
<212> TYPE: DNA
<213> ORGANISM: Artificial Sequence
<220> FEATURE:
<223> OTHER INFORMATION: Gamma-beta hybrid AS2 (G16D and D22A)

<400> SEQUENCE: 4

```
tcagtggtat ctggaggaca gggcactggc cactgcagtc accatcttct gccaggaagc    60
ctgcacctca ggggtgaatt ctttgccgaa atggattgcc aaaacggtca ccagcacatt   120
tcccaggagc tgtgggagga agataagagg tatgaacatg attagcaaaa gggcctagct   180
tggactcaga ataatccagc cttatcccaa ccataaaata aaagcagaat ggtagctgga   240
ttgtagctgc tattagcaat atgaaacctc ttacatcagt tacaatttat atgcagaaat   300
accctgttac ttctcccctt cctatgacat gaacttaacc atagaaaaga aggggaaaga   360
aaacatcaag ggtcccatag actcacgggt cccatagact caccttgaag ttctcaggat   420
ccacatgcag cttgtcacag tgcagttcac tcagctgggc aaaggtgccc ttgagatcat   480
ccaggtgctt tgtggcatct cccaaggaag tcagcacctt cttgccatgt gccttgactt   540
tggggttgcc catgatggca gaggcagagg acaggttgcc aaagctgtca agaacctct    600
gggtccatgg gtagacaacc aggagcctaa gggtgggaaa atagaccaat aggcagagag   660
agtcagtgcc tatcagaaac ccaagagtct tctctgtctc cacatgccca gtttctattg   720
gtctccttaa acctgtcttg taaccttgat accaaccttc cagggtttc tcctccagcg    780
gcttccacat tcaccttgtc ccacaggctt gtgatagtag ccttgtcctc ctctgtgaaa   840
tgacccat                                                            848
```

<210> SEQ ID NO 5
<211> LENGTH: 831
<212> TYPE: DNA
<213> ORGANISM: Artificial Sequence

```
<220> FEATURE:
<223> OTHER INFORMATION: Delta-beta hybrid

<400> SEQUENCE: 5
tcaatggtac ttgtgagcca gggcattagc cacaccagcc accaccttct gataggcagc      60
ctgcatttgt ggggtgaatt ccttgccaaa gttgcgggcc agcacacaca ccagcacatt     120
gcccaagagc tgtgggagga agataagagg tatgaacatg attagcaaaa gggcctagct     180
tggactcaga ataatccagc cttatcccaa ccataaaata aaagcagaat ggtagctgga     240
ttgtagctgc tattagcaat atgaaacctc ttacatcagt tacaatttat atgcagaaat     300
accctgttac ttctcccctt cctatgacat gaacttaacc atagaaaaga aggggaaaga     360
aaacatcaag ggtcccatag actcaccctg aagttctcag gatccacgtg cagcttgtca     420
cagtgcagct cactcagctg agaaaaagtg cccttgaggt tgtccaggtg agccaggcca     480
tcactaaagg cacctagcac cttcttgcca tgagccttca ccttagggtt gcccataaca     540
gcatcaggag aggacagatc cccaaaggac tcaaagaacc tctgggtcca agggtagacc     600
accagtaatc taagggtggg aaaatagacc aataggcaga gagagtcagt gcctatcaga     660
aacccaagag tcttctctgt ctccacatgc ccagtttcta ttggtctcct taaacctgtc     720
ttgtaacctt gataccaacc tgcccagggc ctcaccacca actgcatcca cgttcacttt     780
gccccacagg gcattgacag cagtcttctc ctcaggagtc agatgcacca t                 831

<210> SEQ ID NO 6
<211> LENGTH: 848
<212> TYPE: DNA
<213> ORGANISM: Artificial Sequence
<220> FEATURE:
<223> OTHER INFORMATION: Delta-beta hybrid AS1 (G16D)

<400> SEQUENCE: 6
tcaatggtac ttgtgagcca gggcattagc cacaccagcc accaccttct gataggcagc      60
ctgcatttgt ggggtgaatt ccttgccaaa gttgcgggcc agcacacaca ccagcacatt     120
gcccaagagc tgtgggagga agataagagg tatgaacatg attagcaaaa gggcctagct     180
tggactcaga ataatccagc cttatcccaa ccataaaata aaagcagaat ggtagctgga     240
ttgtagctgc tattagcaat atgaaacctc ttacatcagt tacaatttat atgcagaaat     300
accctgttac ttctcccctt cctatgacat gaacttaacc atagaaaaga aggggaaaga     360
aaacatcaag ggtcccatag actcacgggt cccatagact caccctgaag ttctcaggat     420
ccacgtgcag cttgtcacag tgcagctcac tcagctgaga aaaagtgccc ttgaggttgt     480
ccaggtgagc caggccatca ctaaaggcac ctagcacctt cttgccatga gccttcacct     540
tagggttgcc cataacagca tcaggagagg acagatcccc aaaggactca agaacctct     600 gggtccaagg gtagaccacc agtaatctaa gggtgggaaa ataccaat aggcagagag     660 agtcagtgcc tatcagaaac ccaagagtct tctctgtctc cacatgccca gtttctattg     720
gtctccttaa acctgtcttg taaccttgat accaacctgc ccagggcctc accaccaact     780
gcatccacgt tcactttgtc ccacagggca ttgacagcag tcttctcctc aggagtcaga     840
tgcaccat                                                             848

<210> SEQ ID NO 7
<211> LENGTH: 831
<212> TYPE: DNA
<213> ORGANISM: Artificial Sequence
<220> FEATURE:
```

<223> OTHER INFORMATION: Beta AS1 (T87Q) (modified to avoid targeting by gRNA D)

<400> SEQUENCE: 7

```
ttagtgatac ttgtgggcca gggcattagc cacaccagcc accactttct gataggcagc    60
ctgcactggt ggggtgaatt ctttgccaaa gtgatgggcc agcacacaga ccagcacgtt   120
gcccaggagc tgtgggagga agataagagg tatgaacatg attagcaaaa gggcctagct   180
tggactcaga ataatccagc cttatcccaa ccataaaata aaagcagaat ggtagctgga   240
ttgtagctgc tattagcaat atgaaacctc ttacatcagt tacaatttat atgcagaaat   300
accctgttac ttctccccct tcctatgacat gaacttaacc atagaaaaga aggggaaaga  360
aaacatcaag ggtcccatag actcaccctg aagttctcag gatccacgtg cagcttgtca   420
cagtgcagct cactcagctg ggcaaaggtg cccttgaggt tgtccaggtg agccaggcca   480
tcactaaagg caccgagcac tttcttgcca tgagccttca ccttagggtt gcccataaca   540
gcatcaggag tggacagatc cccaaaggac tcaaagaacc tctgggtcca agggtagacc   600
accagcagcc taagggtggg aaaatagacc aataggcaga gagagtcagt gcctatcaga   660
aacccaagag tcttctctgt ctccacatgc ccagtttcta ttggtctcct taaacctgtc   720
ttgtaacctt gataccaacc tgcccagggc ctcaccacca acttcatcca cgttcacctt   780
gccccagaga gcggtcacag cggacttctc ctcaggagtc aggtgcacca t            831
```

<210> SEQ ID NO 8
<211> LENGTH: 831
<212> TYPE: DNA
<213> ORGANISM: Artificial Sequence
<220> FEATURE:
<223> OTHER INFORMATION: Beta AS3 (modified to avoid targeting by gRNA D)

<400> SEQUENCE: 8

```
ttagtgatac ttgtgggcca gggcattagc cacaccagcc accactttct gataggcagc    60
ctgcactggt ggggtgaatt ctttgccaaa gtgatgggcc agcacacaga ccagcacgtt   120
gcccaggagc tgtgggagga agataagagg tatgaacatg attagcaaaa gggcctagct   180
tggactcaga ataatccagc cttatcccaa ccataaaata aaagcagaat ggtagctgga   240
ttgtagctgc tattagcaat atgaaacctc ttacatcagt tacaatttat atgcagaaat   300
accctgttac ttctccccct tcctatgacat gaacttaacc atagaaaaga aggggaaaga  360
aaacatcaag ggtcccatag actcaccctg aagttctcag gatccacgtg cagcttgtca   420
cagtgcagct cactcagctg ggcaaaggtg cccttgaggt tgtccaggtg agccaggcca   480
tcactaaagg caccgagcac tttcttgcca tgagccttca ccttagggtt gcccataaca   540
gcatcaggag tggacagatc cccaaaggac tcaaagaacc tctgggtcca agggtagacc   600
accagcagcc taagggtggg aaaatagacc aataggcaga gagagtcagt gcctatcaga   660
aacccaagag tcttctctgt ctccacatgc ccagtttcta ttggtctcct taaacctgtc   720
ttgtaacctt gataccaacc tgcccagggc ctcaccacca acggcatcca cgttcacctt   780
gtcccagaga gcggtcacag cggacttctc ctcaggagtc aggtgcacca t            831
```

<210> SEQ ID NO 9
<211> LENGTH: 20
<212> TYPE: DNA
<213> ORGANISM: Artificial Sequence
<220> FEATURE:
<223> OTHER INFORMATION: Primer HBBex1 F -continued

```
<400> SEQUENCE: 9
cagcatcagg agtggacaga                                                    20

<210> SEQ ID NO 10
<211> LENGTH: 20
<212> TYPE: DNA
<213> ORGANISM: Artificial Sequence
<220> FEATURE:
<223> OTHER INFORMATION: Primer HBBex1 R

<400> SEQUENCE: 10
agtcagggca gagccatcta                                                    20

<210> SEQ ID NO 11
<211> LENGTH: 22
<212> TYPE: DNA
<213> ORGANISM: Artificial Sequence
<220> FEATURE:
<223> OTHER INFORMATION: Primer HBB F

<400> SEQUENCE: 11
gcaaggtgaa cgtggatgaa gt                                                 22

<210> SEQ ID NO 12
<211> LENGTH: 23
<212> TYPE: DNA
<213> ORGANISM: Artificial Sequence
<220> FEATURE:
<223> OTHER INFORMATION: Primer HBB R

<400> SEQUENCE: 12
taacagcatc aggagtggac aga                                                23

<210> SEQ ID NO 13
<211> LENGTH: 21
<212> TYPE: DNA
<213> ORGANISM: Artificial Sequence
<220> FEATURE:
<223> OTHER INFORMATION: Primer HBA1 F

<400> SEQUENCE: 13
cggtcaactt caagctccta a                                                  21

<210> SEQ ID NO 14
<211> LENGTH: 20
<212> TYPE: DNA
<213> ORGANISM: Artificial Sequence
<220> FEATURE:
<223> OTHER INFORMATION: Primer HBA1 R

<400> SEQUENCE: 14
acagaagcca ggaacttgtc                                                    20

<210> SEQ ID NO 15
<211> LENGTH: 24
<212> TYPE: DNA
<213> ORGANISM: Artificial Sequence
<220> FEATURE:
<223> OTHER INFORMATION: Oligo FOR-Opt_gRNA B

<400> SEQUENCE: 15
caccgtaacg gcagacttct cctc                                               24

<210> SEQ ID NO 16
```

-continued

```
<211> LENGTH: 24
<212> TYPE: DNA
<213> ORGANISM: Artificial Sequence
<220> FEATURE:
<223> OTHER INFORMATION: Oligo REV-Opt_gRNA B

<400> SEQUENCE: 16
aaacgaggag aagtctgccg ttac                                              24

<210> SEQ ID NO 17
<211> LENGTH: 24
<212> TYPE: DNA
<213> ORGANISM: Artificial Sequence
<220> FEATURE:
<223> OTHER INFORMATION: Oligo FOR-Opt_gRNA D

<400> SEQUENCE: 17
caccgtctgc cgttactgcc ctgt                                              24

<210> SEQ ID NO 18
<211> LENGTH: 24
<212> TYPE: DNA
<213> ORGANISM: Artificial Sequence
<220> FEATURE:
<223> OTHER INFORMATION: Oligo REV-Opt_gRNA D

<400> SEQUENCE: 18
aaacacaggg cagtaacggc agac                                              24

<210> SEQ ID NO 19
<211> LENGTH: 25
<212> TYPE: DNA
<213> ORGANISM: Artificial Sequence
<220> FEATURE:
<223> OTHER INFORMATION: Oligo FOR-Opt_gRNA E

<400> SEQUENCE: 19
caccgaaggt gaacgtggat gaagt                                             25

<210> SEQ ID NO 20
<211> LENGTH: 25
<212> TYPE: DNA
<213> ORGANISM: Artificial Sequence
<220> FEATURE:
<223> OTHER INFORMATION: Oligo REV-Opt_gRNA E

<400> SEQUENCE: 20
aaacacttca tccacgttca ccttc                                             25

<210> SEQ ID NO 21
<211> LENGTH: 18
<212> TYPE: DNA
<213> ORGANISM: Artificial Sequence
<220> FEATURE:
<223> OTHER INFORMATION: Primer HBB-AS3 F

<400> SEQUENCE: 21
aagggcacct ttgcccag                                                     18

<210> SEQ ID NO 22
<211> LENGTH: 22
<212> TYPE: DNA
<213> ORGANISM: Artificial Sequence
<220> FEATURE:
<223> OTHER INFORMATION: Primer HBB-AS3 R

<400> SEQUENCE: 22
```
gccaccactt tctgataggc ag                                              22

<210> SEQ ID NO 23
<211> LENGTH: 20
<212> TYPE: DNA
<213> ORGANISM: Artificial Sequence
<220> FEATURE:
<223> OTHER INFORMATION: gRNA A spacer

<400> SEQUENCE: 23
cttgccccac agggcagtaa                                                 20

<210> SEQ ID NO 24
<211> LENGTH: 20
<212> TYPE: DNA
<213> ORGANISM: Artificial Sequence
<220> FEATURE:
<223> OTHER INFORMATION: gRNA B spacer

<400> SEQUENCE: 24
gtaacggcag acttctcctc                                                 20

<210> SEQ ID NO 25
<211> LENGTH: 19
<212> TYPE: DNA
<213> ORGANISM: Artificial Sequence
<220> FEATURE:
<223> OTHER INFORMATION: gRNA D spacer

<400> SEQUENCE: 25
tctgccgtta ctgccctgt                                                  19

<210> SEQ ID NO 26
<211> LENGTH: 20
<212> TYPE: DNA
<213> ORGANISM: Artificial Sequence
<220> FEATURE:
<223> OTHER INFORMATION: gRNA E spacer

<400> SEQUENCE: 26
aaggtgaacg tggatgaagt                                                 20

<210> SEQ ID NO 27
<211> LENGTH: 20
<212> TYPE: DNA
<213> ORGANISM: Artificial Sequence
<220> FEATURE:
<223> OTHER INFORMATION: gRNA F spacer

<400> SEQUENCE: 27
gtgtggcaaa ggtgcccttg                                                 20

<210> SEQ ID NO 28
<211> LENGTH: 20
<212> TYPE: DNA
<213> ORGANISM: Artificial Sequence
<220> FEATURE:
<223> OTHER INFORMATION: gRNA G spacer

<400> SEQUENCE: 28
acagtgcagc tcactcagtg                                                 20

<210> SEQ ID NO 29
<211> LENGTH: 20
<212> TYPE: DNA

```
<213> ORGANISM: Artificial Sequence
<220> FEATURE:
<223> OTHER INFORMATION: gRNA H spacer

<400> SEQUENCE: 29
tctgccgtta ctgccctgtg                                                    20

<210> SEQ ID NO 30
<211> LENGTH: 20
<212> TYPE: DNA
<213> ORGANISM: Artificial Sequence
<220> FEATURE:
<223> OTHER INFORMATION: gRNA I spacer

<400> SEQUENCE: 30
cgttactgcc ctgtggggca                                                    20

<210> SEQ ID NO 31
<211> LENGTH: 20
<212> TYPE: DNA
<213> ORGANISM: Artificial Sequence
<220> FEATURE:
<223> OTHER INFORMATION: gRNA J spacer

<400> SEQUENCE: 31
gtctgccgtt actgccctgt                                                    20

<210> SEQ ID NO 32
<211> LENGTH: 20
<212> TYPE: DNA
<213> ORGANISM: Artificial Sequence
<220> FEATURE:
<223> OTHER INFORMATION: gRNA K spacer

<400> SEQUENCE: 32
cagctcactc agtgtggcaa                                                    20

<210> SEQ ID NO 33
<211> LENGTH: 20
<212> TYPE: DNA
<213> ORGANISM: Artificial Sequence
<220> FEATURE:
<223> OTHER INFORMATION: gRNA L spacer

<400> SEQUENCE: 33 tcccacccctt aggctgctgg                                                   20

<210> SEQ ID NO 34
<211> LENGTH: 20
<212> TYPE: DNA
<213> ORGANISM: Artificial Sequence
<220> FEATURE:
<223> OTHER INFORMATION: gRNA M spacer

<400> SEQUENCE: 34
ggctgctggt ggtctaccct                                                    20

<210> SEQ ID NO 35
<211> LENGTH: 20
<212> TYPE: DNA
<213> ORGANISM: Artificial Sequence
<220> FEATURE:
<223> OTHER INFORMATION: gRNA N spacer

<400> SEQUENCE: 35
ccccacaggg cagtaacggc                                                    20
```

<210> SEQ ID NO 36
<211> LENGTH: 20
<212> TYPE: DNA
<213> ORGANISM: Artificial Sequence
<220> FEATURE:
<223> OTHER INFORMATION: gRNA O spacer

<400> SEQUENCE: 36
taacggcaga cttctccaca                                          20

<210> SEQ ID NO 37
<211> LENGTH: 27
<212> TYPE: DNA
<213> ORGANISM: Artificial Sequence
<220> FEATURE:
<223> OTHER INFORMATION: Oligo FOR-gRNA A

<400> SEQUENCE: 37
acaccgcttg ccccacaggg cagtaag                                  27

<210> SEQ ID NO 38
<211> LENGTH: 27
<212> TYPE: DNA
<213> ORGANISM: Artificial Sequence
<220> FEATURE:
<223> OTHER INFORMATION: Oligo REV-gRNA A

<400> SEQUENCE: 38
aaaacttact gccctgtggg gcaagcg                                  27

<210> SEQ ID NO 39
<211> LENGTH: 26
<212> TYPE: DNA
<213> ORGANISM: Artificial Sequence
<220> FEATURE:
<223> OTHER INFORMATION: Oligo FOR-gRNA B

<400> SEQUENCE: 39
acaccgtaac ggcagacttc tcctcg                                   26

<210> SEQ ID NO 40
<211> LENGTH: 26
<212> TYPE: DNA
<213> ORGANISM: Artificial Sequence
<220> FEATURE:
<223> OTHER INFORMATION: Oligo REV-gRNA B

<400> SEQUENCE: 40
aaaacgagga gaagtctgcc gttacg                                   26

<210> SEQ ID NO 41
<211> LENGTH: 26
<212> TYPE: DNA
<213> ORGANISM: Artificial Sequence
<220> FEATURE:
<223> OTHER INFORMATION: Oligo FOR-gRNA D

<400> SEQUENCE: 41
acaccgtctg ccgttactgc cctgtg                                   26

<210> SEQ ID NO 42
<211> LENGTH: 26
<212> TYPE: DNA
<213> ORGANISM: Artificial Sequence
<220> FEATURE:

<223> OTHER INFORMATION: Oligo REV-gRNA D

<400> SEQUENCE: 42
aaaacacagg gcagtaacgg cagacg                                          26

<210> SEQ ID NO 43
<211> LENGTH: 27
<212> TYPE: DNA
<213> ORGANISM: Artificial Sequence
<220> FEATURE:
<223> OTHER INFORMATION: Oligo FOR-gRNA E

<400> SEQUENCE: 43
acaccgaagg tgaacgtgga tgaagtg                                         27

<210> SEQ ID NO 44
<211> LENGTH: 27
<212> TYPE: DNA
<213> ORGANISM: Artificial Sequence
<220> FEATURE:
<223> OTHER INFORMATION: Oligo REV-gRNA E

<400> SEQUENCE: 44
aaaacacttc atccacgttc accttcg                                         27

<210> SEQ ID NO 45
<211> LENGTH: 10195
<212> TYPE: DNA
<213> ORGANISM: Artificial Sequence
<220> FEATURE:
<223> OTHER INFORMATION: LV.GLOBE.betaAS3-GLOBIN

<400> SEQUENCE: 45
ccattgcata cgttgtatcc atatcataat atgtacattt atattggctc atgtccaaca      60
ttaccgccat gttgacattg attattgact agttattaat agtaatcaat tacggggtca    120
ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca gtacgcccc ctattgacgt caatgacggt     360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccacccat tgacgtcaat     540 gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc ggggtctctc tggttagacc agatctgagc ctgggagctc tctggctaac    720
tagggaaccc actgcttaag cctcaataaa gcttgccttg agtgcttcaa gtagtgtgtg    780
cccgtctgtt gtgtgactct ggtaactaga gatccctcag accctttag tcagtgtgga     840 aaatctctag cagtggcgcc cgaacaggga cttgaaagcg aaagggaaac cagaggagct    900
ctctcgacgc aggactcggc ttgctgaagc gcgcacggca agaggcgagg ggcggcgact    960
ggtgagtacg ccaaaaattt tgactagcgg aggctagaag gagagagatg ggtgcgagag   1020
cgtcagtatt aagcgggga gaattagatc gcgatgggaa aaaattcggt taaggccagg    1080
gggaaagaaa aaatataaat taaaacatat agtatgggca agcagggagc tagaacgatt    1140
cgcagttaat cctggcctgt tagaaacatc agaaggctgt agacaaatac tgggacagct    1200

```
acaaccatcc cttcagacag gatcagaaga acttagatca ttatataata cagtagcaac    1260
cctctattgt gtgcatcaaa ggatagagat aaaagacacc aaggaagctt tagacaagat    1320
agaggaagag caaaacaaaa gtaagaccac cgcacagcaa gcggccgctg atcttcagac    1380
ctggaggagg agatatgagg gacaattgga gaagtgaatt atataaatat aaagtagtaa    1440
aaattgaacc attaggagta gcacccacca aggcaaagag aagagtggtg cagagagaaa    1500
aaagagcagt gggaatagga gctttgttcc ttgggttctt gggagcagca ggaagcacta    1560
tgggcgcagc gtcaatgacg ctgacggtac aggccagaca attattgtct ggtatagtgc    1620
agcagcagaa caatttgctg agggctattg aggcgcaaca gcatctgttg caactcacag    1680
tctggggcat caagcagctc caggcaagaa tcctggctgt ggaaagatac ctaaaggatc    1740
aacagctcct ggggatttgg ggttgctctg gaaaactcat ttgcaccact gctgtgcctt    1800
ggaatgctag ttggagtaat aaatctctgg aacagatttg gaatcacacg acctggatgg    1860
agtgggacag agaaattaac aattacacaa gcttaataca ctccttaatt gaagaatcgc    1920
aaaaccagca agaaaagaat gaacaagaat tattggaatt agataaatgg gcaagtttgt    1980
ggaattggtt taacataaca aattggctgt ggtatataaa attattcata atgatagtag    2040
gaggcttggt aggtttaaga atagtttttg ctgtactttc tatagtgaat agagttaggc    2100
agggatattc accattatcg tttcagaccc acctcccaac cccgagggga cccgacaggc    2160
ccgaaggaat agaagaagaa ggtggagaga gagacagaga cagatccatt cgattagtga    2220
acggatctcg acggtatcgg ttaacttta aagaaaagg ggggattggg gggtacagtg    2280
caggggaaag aatagtagac ataatagcaa cagacataca aactaaagaa ttacaaaaac    2340
aaattacaaa attcaaaatt ttatcggtac gtaccatgag gacagctaaa acaataagta    2400
atgtaaaata cagcatagca aactttaac ctccaaatca agcctctact tgaatccttt    2460
tctgagggat gaataaggca taggcatcag gggctgttgc caatgtgcat tagctgtttg    2520
cagcctcacc ttctttcatg gagtttaaga tatagtgtat tttcccaagg tttgaactag    2580
ctcttcattt ctttatgttt taaatgcact gacctcccac attcccttttt tagtaaaata    2640 ttcagaaata atttaaatac atcattgcaa tgaaaataaa tgtttttttat taggcagaat    2700 ccagatgctc aaggcccttc ataatatccc ccagtttagt agttggactt agggaacaaa    2760 ggaacctta atagaaattg gacagcaaga aagcgagctt agtgatactt gtgggccagg    2820
gcattagcca caccagccac cactttctga taggcagcct gcactggtgg ggtgaattct    2880
ttgccaaagt gatgggccag cacacagacc agcacgttgc ccaggagctg tgggaggaag    2940
ataagaggta tgaacatgat tagcaaaagg gcctagcttg gactcagaat aatccagcct    3000
tatcccaacc ataaaataaa agcagaatgg tagctggatt gtagctgcta ttagcaatat    3060
gaaacctctt acatcagtta caatttatat gcagaaatac cctgttactt ctccccttcc    3120
tatgacatga acttaaccat agaaaagaag gggaaagaaa acatcaaggg tcccatagac    3180
tcaccctgaa gttctcagga tccacgtgca gcttgtcaca gtgcagctca ctcagctggg    3240
caaaggtgcc cttgaggttg tccaggtgag ccaggccatc actaaaggca ccgagcactt    3300
tcttgccatg agccttcacc ttagggttgc ccataacagc atcaggagtg gacagatccc    3360
caaaggactc aaagaacctc tgggtccaag ggtagaccac cagcagccta agggtgggaa    3420
aatagaccaa taggcagaga gagtcagtgc ctatcagaaa cccaagagtc ttctctgtct    3480
ccacatgccc agtttctatt ggtctcctta aacctgtctt gtaaccttga taccaacctg    3540
```

```
cccagggcct caccaccaac ggcatccacg ttcaccttgt cccagagagc ggtcacagcg    3600
gacttctcct caggagtcag gtgcaccatg gtgtctgttt gaggttgcta gtgaacacag    3660
ttgtgtcaga agcaaatgta agcaatagat ggctctgccc tgacttttat gcccagccct    3720
ggctcctgcc ctccctgctc ctgggagtag attggccaac cctagggtgt ggctccacag    3780
ggtgaggtct aagtgatgac agccgtacct gtccttggct cttctggcac tggcttagga    3840
gttggacttc aaaccctcag ccctccctct aagatatatc tcttggcccc ataccatcag    3900
tacaaattgc tactaaaaac atcctccttt gcaagtgtat ttacacggta tcgataagct    3960
tgatatcgaa ttcctgcagc ccccttttgc cacctagctg tccaggggtg ccttaaaatg    4020
gcaaacaagg tttgttttct tttcctgttt tcatgccttc ctcttccata tccttgtttc    4080
atattaatac atgtgtatag atcctaaaaa tctatacaca tgtattaata aagcctgatt    4140
ctgccgcttc taggtataga ggccacctgc aagataaata tttgattcac ataactaat    4200 cattctatgg caattgataa caacaaatat atatatatat atatatacgt atatgtgtat    4260
atatatatat atatattcag gaaataatat attctagaat atgtcacatt ctgtctcagg    4320
catccatttt ctttatgatg ccgtttgagg tggagtttta gtcaggtggt cagcttctcc    4380 tttttttttgc catctgccct gtaagcatcc tgctggggac ccagatagga gtcatcactc    4440
taggctgaga acatctgggc acacacccta agcctcagca tgactcatca tgactcagca    4500
ttgctgtgct tgagccagaa ggtttgctta gaaggttaca cagaaccaga aggcgggggt    4560
ggggcactga ccccgacagg ggcctggcca gaactgctca tgcttggact atgggaggtc    4620
actaatggag acacacagaa atgtaacagg aactaaggaa aaactgaagc ttatttaatc    4680
agagatgagg atgctggaag ggatagaggg agctgagctt gtaaaaagta tagtaatcat    4740
tcagcaaatg gttttgaagc acctgctgga tgctaaacac tattttcagt gcttgaatca    4800
taaataagaa taaaacatgt atcttattcc ccacaagagt ccaagtaaaa ataacagtt    4860 aattataatg tgctctgtcc cccaggctgg agtgcagtgg cacgatctca gctcactgca    4920
acctccgcct cccgggttca agcaattctc ctgcctcagc caccctaata gctgggatta    4980
caggtgcaca ccaccatgcc aggctaattt ttgtactttt tgtagaggca gggtatcacc    5040
atgttgtcca agatggtctt gaactcctga gctccaagca gtccaccac ctcagcctcc    5100 caaagtgctg ggattacagg tgtgagacac catgcccaga ttttccatat ttaatagagg    5160
tatttatggg atgggggaaa agaatgtttc tctcactgtg gattatttta gagagtggag    5220
aatggtcaag atttttttaa aaattaagaa aacataagtt ggaccttgag aaatgaaaat    5280 ttatttttttt gttggaggat acccattctc tatctcccat cagggcaagc tgtaaggaac    5340
tggctaagac acagtgagac agagtgactt agtcttagag gccccactgg tacgacggtc    5400
accaagcttt cattaaaaaa agtctaacca gctgcattcg actttgactg cagcagctgg    5460
ttagaaggtt ctactggagg agggtcccag cccattgcta aattaacatc aggctctgag    5520
actggcagta tatctctaac agtggttgat gctatcttct ggaacttgcc tgctacattg    5580
agaccactga cccatacata ggaagcccat agctctgtcc tgaactgtta ggccactggt    5640
ccagagagtg tgcatctcct ttgatcctca taataaccct atgagataga cacaattatt    5700
actcttactt tatagatgat gatcctgaaa acataggagt caaggcactt gcccctagct    5760
gggggtatag gggagcagtc ccatgtagta gtagaatgaa aaatgctgct atgctgtgcc    5820 tccccccacct ttcccatgtc tgccctctac tcatggtcta tctctcctgg ctcctgggag    5880
tcatggactc cacccagcac caccaacctg acctaaccac ctatctgagc ctgccagcct    5940
```

```
ataacccatc tgggccctga tagctggtgg ccagccctga ccccacccca ccctccctgg      6000
aacctctgat agacacatct ggcacaccag ctcgcaaagt caccgtgagg gtcttgtgtt      6060
tgctgagtca aaattccttg aaatccaagt ccttagagac tcctgctccc aaatttacag     6120
tcatagactt cttcatggct gtctccttta tccacagaat gattcctttg cttcattgcc     6180
ccatccatct gatcctcctc atcagtgcag cacagggccc atgagcagta gctgcagagt     6240
ctcacatagg tctggcactg cctctgacat gtccgacctt aggcaaatgc ttgactcttc     6300
tgagctcagt cttgtcatgg caaaataaag ataataatag tgttttttta tggagttagc     6360
gtgaggatgg aaaacaatag caaaattgat tagactataa aaggtctcaa caaatagtag     6420
tagattttat catccattaa tccttccctc tcctctctta ctcatcccat cacgtatgcc     6480
tcttaatttt cccttaccta taataagagt tattcctctt attatattct tcttatagtg     6540
attctggata ttaaagtggg aatgaggggc aggccactaa cgaagaagat gtttctcaaa     6600 gaagcgggggg atccactagt tctagagcgg ccaaatggcg gccgtacctt taagaccaat     6660
gacttacaag gcagctgtag atcttagcca ctttttaaaa gaaaaggggg gactggaagg     6720
gctaattcac tcccaacgaa gacaagatct gcttttttgct tgtactgggt ctctctggtt     6780
agaccagatc tgagcctggg agctctctgg ctaactaggg aacccactgc ttaagcctca     6840
ataaagcttg ccttgagtgc ttcaagtagt gtgtgcccgt ctgttgtgtg actctggtaa     6900
ctagagatcc ctcagaccct tttagtcagt gtggaaaatc tctagcagta gtagttcatg     6960
tcatcttatt attcagtatt tataacttgc aaagaaatga atatcagaga gtgagaggaa     7020
cttgtttatt gcagcttata atggttacaa ataaagcaat agcatcacaa atttcacaaa     7080
taaagcattt ttttcactgc attctagttg tggtttgtcc aaactcatca atgtatctta     7140
tcatgtctgg ctctagctat cccgccccta actccgccca tcccgcccct aactccgccc     7200
agttccgccc attctccgcc ccatggctga ctaatttttt ttatttatgc agaggccgag     7260
gccgcctcgg cctctgagct attccagaag tagtgaggag gcttttttgg aggcctaggg     7320
acgtacccaa ttcgccctat agtgagtcgt attacgcgcg ctcactggcc gtcgttttac     7380
aacgtcgtga ctgggaaaac cctggcgtta cccaacttaa tcgccttgca gcacatcccc     7440
ctttcgccag ctggcgtaat agcgaagagg cccgcaccga tcgcccttcc caacagttgc     7500
gcagcctgaa tggcgaatgg gacgcgccct gtagcggcgc attaagcgcg gcgggtgtgg     7560
tggttacgcg cagcgtgacc gctacacttg ccagcgccct agcgcccgct cctttcgctt     7620
tcttcccttc ctttctcgcc acgttcgccg gctttccccg tcaagctcta aatcgggggc     7680
tccctttagg gttccgattt agtgctttac ggcacctcga ccccaaaaaa cttgattagg     7740
gtgatggttc acgtagtggg ccatcgccct gatagacggt ttttcgccct ttgacgttgg     7800
agtccacgtt ctttaatagt ggactcttgt tccaaactgg aacaacactc aaccctatct     7860
cggtctattc ttttgattta agggattt gccgatttc ggcctattgg ttaaaaaatg     7920
agctgattta caaaaattt aacgcgaatt ttaacaaaat attaacgctt acaatttagg     7980
tggcactttt cggggaaatg tgcgcggaac ccctatttgt ttatttttct aaatacattc     8040
aaatatgtat ccgctcatga gacaataacc ctgataaatg cttcaataat attgaaaaag     8100
gaagagtatg agtattcaac atttccgtgt cgcccttatt cccttttttg cggcattttg     8160
ccttcctgtt tttgctcacc cagaaacgct ggtgaaagta aaagatgctg aagatcagtt     8220
gggtgcacga gtgggttaca tcgaactgga tctcaacagc ggtaagatcc ttgagagttt     8280
```

```
tcgccccgaa gaacgttttc caatgatgag cacttttaaa gttctgctat gtggcgcggt    8340
attatcccgt attgacgccg ggcaagagca actcggtcgc cgcatacact attctcagaa    8400
tgacttggtt gagtactcac cagtcacaga aaagcatctt acggatggca tgacagtaag    8460
agaattatgc agtgctgcca taaccatgag tgataacact gcggccaact tacttctgac    8520
aacgatcgga ggaccgaagg agctaaccgc ttttttgcac aacatggggg atcatgtaac    8580
tcgccttgat cgttgggaac cggagctgaa tgaagccata ccaaacgacg agcgtgacac    8640
cacgatgcct gtagcaatgg caacaacgtt gcgcaaacta ttaactggcg aactacttac    8700
tctagcttcc cggcaacaat taatagactg gatggaggcg gataaagttg caggaccact    8760
tctgcgctcg gcccttccgg ctggctggtt tattgctgat aaatctggag ccggtgagcg    8820
tgggtctcgc ggtatcattg cagcactggg gccagatggt aagccctccc gtatcgtagt    8880
tatctacacg acggggagtc aggcaactat ggatgaacga atagacaga tcgctgagat    8940 aggtgcctca ctgattaagc attggtaact gtcagaccaa gtttactcat atatacttta    9000
gattgattta aaacttcatt tttaatttaa aaggatctag gtgaagatcc ttttttgataa    9060 tctcatgacc aaaatccctt aacgtgagtt ttcgttccac tgagcgtcag accccgtaga    9120
aaagatcaaa ggatcttctt gagatccttt ttttctgcgc gtaatctgct gcttgcaaac    9180
aaaaaaacca ccgctaccag cggtggtttg tttgccggat caagagctac caactctttt    9240
tccgaaggta actggcttca gcagagcgca gataccaaat actgttcttc tagtgtagcc    9300
gtagttaggc caccacttca agaactctgt agcaccgcct acatacctcg ctctgctaat    9360
cctgttacca gtggctgctg ccagtggcga taagtcgtgt cttaccgggt tggactcaag    9420
acgatagtta ccggataagg cgcagcggtc gggctgaacg gggggttcgt gcacacagcc    9480
cagcttggag cgaacgacct acaccgaact gagatacta cagcgtgagc tatgagaaag    9540
cgccacgctt cccgaaggga gaaaggcgga caggtatccg gtaagcggca gggtcggaac    9600
aggagagcgc acgagggagc ttccaggggg aaacgcctgg tatctttata gtcctgtcgg    9660
gtttcgccac ctctgacttg agcgtcgatt tttgtgatgc tcgtcagggg ggcggagcct    9720
atggaaaaac gccagcaacg cggccttttt acggttcctg gccttttgct ggccttttgc    9780
tcacatgttc tttcctgcgt tatcccctga ttctgtggat aaccgtatta ccgcctttga    9840
gtgagctgat accgctcgcc gcagccgaac gaccgagcgc agcgagtcag tgagcgagga    9900
agcggaagag cgcccaatac gcaaaccgcc tctccccgcg cgttggccga ttcattaatg    9960
cagctggcac gacaggtttc ccgactggaa agcgggcagt gagcgcaacg caattaatgt    10020
gagttagctc actcattagg caccccaggc tttacacttt atgcttccgg ctcgtatgtt    10080
gtgtggaatt gtgagcggat aacaatttca cacaggaaac agctatgacc atgattacgc    10140
caagcgcgca attaaccctc actaaaggga acaaaagctg gagctgcaag cttgg          10195
```

<210> SEQ ID NO 46
<211> LENGTH: 10195
<212> TYPE: DNA
<213> ORGANISM: Artificial Sequence
<220> FEATURE:
<223> OTHER INFORMATION: LV.GLOBE.betaAS3-GLOBIN Sal1 (with restriction site for Sal1)

<400> SEQUENCE: 46

```
ccattgcata cgttgtatcc atatcataat atgtacattt atattggctc atgtccaaca    60
ttaccgccat gttgacattg attattgact agttattaat agtaatcaat tacggggtca    120
```

-continued

| | |
|---|---|
| ttagttcata gcccatatat ggagttccgc gttacataac ttacggtaaa tggcccgcct | 180 |
| ggctgaccgc ccaacgaccc ccgcccattg acgtcaataa tgacgtatgt tcccatagta | 240 |
| acgccaatag ggactttcca ttgacgtcaa tgggtggagt atttacggta aactgcccac | 300 |
| ttggcagtac atcaagtgta tcatatgcca agtacgcccc ctattgacgt caatgacggt | 360 |
| aaatggcccg cctggcatta tgcccagtac atgaccttat gggactttcc tacttggcag | 420 |
| tacatctacg tattagtcat cgctattacc atggtgatgc ggttttggca gtacatcaat | 480 |
| gggcgtggat agcggtttga ctcacgggga tttccaagtc tccaccccat tgacgtcaat | 540 |
| gggagtttgt tttggcacca aaatcaacgg gactttccaa aatgtcgtaa caactccgcc | 600 |
| ccattgacgc aaatgggcgg taggcgtgta cggtgggagg tctatataag cagagctcgt | 660 |
| ttagtgaacc ggggtctctc tggttagacc agatctgagc ctgggagctc tctggctaac | 720 |
| tagggaaccc actgcttaag cctcaataaa gcttgccttg agtgcttcaa gtagtgtgtg | 780 |
| cccgtctgtt gtgtgactct ggtaactaga tccctcag acccttttag tcagtgtgga | 840 |
| aaatctctag cagtggcgcc cgaacaggga cttgaaagcg aaagggaaac cagaggagct | 900 |
| ctctcgacgc aggactcggc ttgctgaagc gcgcacggca agaggcgagg ggcggcgact | 960 |
| ggtgagtacg ccaaaaattt tgactagcgg aggctagaag gagagagatg ggtgcgagag | 1020 |
| cgtcagtatt aagcggggga gaattagatc gcgatgggaa aaaattcggt taaggccagg | 1080 |
| gggaagaaa aaatataaat taaaacatat agtatgggca agcagggagc tagaacgatt | 1140 |
| cgcagttaat cctggcctgt tagaaacatc agaaggctgt agacaaatac tgggacagct | 1200 |
| acaaccatcc cttcagacag gatcagaaga acttagatca ttatataata cagtagcaac | 1260 |
| cctctattgt gtgcatcaaa ggatagagat aaaagacacc aaggaagctt tagacaagat | 1320 |
| agaggaagag caaaacaaaa gtaagaccac cgcacagcaa gcggccgctg atcttcagac | 1380 |
| ctggaggagg agatatgagg gacaattgga gaagtgaatt atataaatat aaagtagtaa | 1440 |
| aaattgaacc attaggagta gcacccacca aggcaaagag aagagtggtg cagagagaaa | 1500 |
| aaagagcagt gggaatagga gctttgttcc ttgggttctt gggagcagca ggaagcacta | 1560 |
| tgggcgcagc gtcaatgacg ctgacggtac aggccagaca attattgtct ggtatagtgc | 1620 |
| agcagcagaa caatttgctg agggctattg aggcgcaaca gcatctgttg caactcacag | 1680 |
| tctggggcat caagcagctc caggcaagaa tcctggctgt ggaaagatac ctaaaggatc | 1740 |
| aacagctcct ggggatttgg ggttgctctg gaaaactcat ttgcaccact gctgtgcctt | 1800 |
| ggaatgctag ttggagtaat aaatctctgg aacagatttg gaatcacacg acctggatgg | 1860 |
| agtgggacag agaaattaac aattacacaa gcttaataca ctccttaatt gaagaatcgc | 1920 |
| aaaaccagca agaaaagaat gaacaagaat tattggaatt agataaatgg gcaagtttgt | 1980 |
| ggaattggtt taacataaca aattggctgt ggtatataaa attattcata atgatagtag | 2040 |
| gaggcttggt aggtttaaga atagtttttg ctgtactttc tatagtgaat agagttaggc | 2100 |
| agggatattc accattatcg tttcagaccc acctcccaac cccgagggga cccgacaggc | 2160 |
| ccgaaggaat agaagaagaa ggtggagaga gagacagaga cagatccatt cgattagtga | 2220 |
| acggatctcg acggtatcgg ttaacttta aagaaaagg ggggattggg gggtacagtg | 2280 |
| caggggaaag aatagtagac ataatagcaa cagacataca aactaaagaa ttacaaaaac | 2340 |
| aaattacaaa attcaaaatt ttatcggtac gtaccatgag gacagctaaa acaataagta | 2400 |
| atgtaaaata cagcatagca aaactttaac ctccaaatca agcctctact tgaatccttt | 2460 |
| tctgagggat gaataaggca taggcatcag gggctgttgc caatgtgcat tagctgtttg | 2520 |

```
cagcctcacc ttctttcatg gagtttaaga tatagtgtat tttcccaagg tttgaactag   2580
ctcttcattt ctttatgttt taaatgcact gacctcccac attcccttt tagtaaaata   2640 ttcagaaata atttaaatac atcattgcaa tgaaaataaa tgttttttat taggcagaat   2700
ccagatgctc aaggcccttc ataatatccc ccagtttagt agttggactt agggaacaaa   2760 ggaacccttta atagaaattg gacagcaaga aagcgagctt agtgatactt gtgggccagg   2820
gcattagcca caccagccac cactttctga taggcagcct gcactggtgg ggtgaattct   2880
ttgccaaagt gatgggccag cacacagacc agcacgttgc ccaggagctg tgggaggaag   2940
ataagaggta tgaacatgat tagcaaaagg gcctagcttg gactcagaat aatccagcct   3000
tatcccaacc ataaaataaa agcagaatgg tagctggatt gtagctgcta ttagcaatat   3060
gaaacctctt acatcagtta caatttatat gcagaaatac cctgttactt ctcccctttcc  3120 tatgacatga acttaaccat agaaagaag gggaagaaa acatcaaggg tcccatagac   3180
tcaccctgaa gttctcagga tccacgtgca gcttgtcaca gtgcagctca ctcagctggg   3240
caaaggtgcc cttgaggttg tccaggtgag ccaggccatc actaaaggca ccgagcactt   3300
tcttgccatg agccttcacc ttaggggttgc ccataacagc atcaggagtg gacagatccc   3360
caaaggactc aaagaacctc tgggtccaag ggtagaccac cagcagccta agggtgggaa   3420
aatagaccaa taggcagaga gagtcagtgc ctatcagaaa cccaagagtc ttctctgtct   3480
ccacatgccc agtttctatt ggtctcctta aacctgtctt gtaaccttga taccaacctg   3540
cccagggcct caccaccaac ggcatccacg ttcaccttgt cccagagagc ggtcacagcg   3600
gacttctcct caggagtcag gtgcaccatg gtgtctgttt gaggttgcta gtgaacacag   3660
ttgtgtcaga agcaaatgta agcaatagat ggctctgccc tgactttat gcccagccct   3720 ggctcctgcc ctccctgctc ctgggagtag attggccaac cctagggtgt ggctccacag   3780
ggtgaggtct aagtgatgac agccgtacct gtccttggct cttctggcac tggcttagga   3840
gttggacttc aaaccctcag ccctccctct aagatatatc tcttggcccc ataccatcag   3900
tacaaattgc tactaaaaac atcctccttt gcaagtgtat ttacacggta tcgataagct   3960
tgatatcgaa ttcctgcagc cccttttgc cacctagctg tccaggggtg ccttaaaatg   4020
gcaaacaagg tttgttttct tttcctgttt tcatgccttc ctcttccata tccttgtttc   4080
atattaatac atgtgtatag atcctaaaaa tctatacaca tgtattaata aagcctgatt   4140
ctgccgcttc taggtataga ggccacctgc aagataaata tttgattcac aataactaat   4200
cattctatgg caattgataa caacaaatat atatatatat atatatacgt atatgtgtat   4260
atatatatat atatattcag gaaataatat attctagaat atgtcacatt ctgtctcagg   4320
catccatttt ctttatgatg ccgtttgagg tggagtttta tcaggtggt cagcttctcc   4380 ttttttttgc catctgccct gtaagcatcc tgctgggac ccagatagga gtcatcactc   4440
taggctgaga acatctgggc acacacccta agcctcagca tgactcatca tgactcagca   4500
ttgctgtgct tgagccagaa ggtttgctta gaaggttaca cagaaccaga aggcggggt   4560 ggggcactga ccccgacagg ggcctggcca gaactgctca tgcttggact atgggaggtc   4620
actaatggag acacacagaa atgtaacagg aactaaggaa aaactgaagc ttatttaatc   4680
agagatgagg atgctggaag ggatagaggg agctgagctt gtaaaaagta tagtaatcat   4740
tcagcaaatg gttttgaagc acctgctgga tgctaaacac tattttcagt gcttgaatca   4800
taaataagaa taaaacatgt atcttattcc ccacaagagt ccaagtaaaa aataacagtt   4860
```

```
aattataatg tgctctgtcc cccaggctgg agtgcagtgg cacgatctca gctcactgca    4920
acctccgcct cccgggttca agcaattctc ctgcctcagc caccctaata gctgggatta    4980
caggtgcaca ccaccatgcc aggctaattt ttgtactttt tgtagaggca gggtatcacc    5040
atgttgtcca agatggtctt gaactcctga gctccaagca gtccaccac ctcagcctcc     5100
caaagtgctg ggattacagg tgtgagacac catgcccaga ttttccatat ttaatagagg    5160
tatttatggg atgggggaaa agaatgtttc tctcactgtg gattatttta gagagtggag    5220
aatggtcaag attttttttaa aaattaagaa aacataagtt ggaccttgag aaatgaaaat   5280
ttatttttt gttggaggat acccattctc tatctcccat cagggcaagc tgtaaggaac     5340
tggctaagac acagtgagac agagtgactt agtcttagag gccccactgg tacgacggtc    5400
accaagcttt cattaaaaaa agtctaacca gctgcattcg actttgactg cagcagctgg    5460
ttagaaggtt ctactggagg agggtcccag cccattgcta aattaacatc aggctctgag    5520
actggcagta tatctctaac agtggttgat gctatcttct ggaacttgcc tgctacattg    5580
agaccactga cccatacata ggaagcccat agctctgtcc tgaactgtta ggccactggt    5640
ccagagagtg tgcatctcct ttgatcctca taataaccct atgagataga cacaattatt    5700
actcttactt tatagatgat gatcctgaaa acataggagt caaggcactt gcccctagct    5760
gggggtatag gggagcagtc ccatgtagta gtagaatgaa aaatgctgct atgctgtgcc    5820
tccccccacct ttcccatgtc tgccctctac tcatggtcta tctctcctgg ctcctgggag   5880
tcatggactc cacccagcac caccaacctg acctaaccac ctatctgagc ctgccagcct    5940
ataacccatc tgggccctga tagctggtgg ccagccctga ccccacccca ccctccctgg    6000
aacctctgat agacacatct ggcacaccag ctcgcaaagt caccgtgagg gtcttgtgtt    6060
tgctgagtca aaattccttg aaatccaagt ccttagagac tcctgctccc aaatttacag    6120
tcatagactt cttcatggct gtctccttta tccacagaat gattcctttg cttcattgcc    6180
ccatccatct gatcctcctc atcagtgcag cacagggccc atgagcagta gctgcagagt    6240
ctcacatagg tctggcactg cctctgacat gtccgacctt aggcaaatgc ttgactcttc    6300
tgagctcagt cttgtcatgg caaaataaag ataataatag tgttttttta tggagttagc    6360
gtgaggatgg aaaacaatag caaaattgat tagactataa aaggtctcaa caaatagtag    6420
tagattttat catccattaa tccttccctc tcctctctta ctcatcccat cacgtatgcc    6480
tcttaatttt cccttaccta taataagagt tattcctctt attatattct tcttatagtg    6540
attctggata ttaaagtggg aatgaggggc aggccactaa cgaagaagat gtttctcaaa    6600
gaagcggggg atccactagt tctagagcgg ccaaatggcg gccgtacctt taagaccaat    6660
gacttacaag gcagctgtcg accttagcca cttttttaaaa gaaaaggggg gactggaagg    6720
gctaattcac tcccaacgaa gacaagatct gcttttgct tgtactgggt ctctctggtt     6780
agaccagatc tgagcctggg agctctctgg ctaactaggg aacccactgc ttaagcctca    6840
ataaagcttg ccttgagtgc ttcaagtagt gtgtgcccgt ctgttgtgtg actctggtaa    6900
ctagagatcc ctcagaccct tttagtcagt gtggaaaatc tctagcagta gtagttcatg    6960
tcatcttatt attcagtatt tataacttgc aaagaaatga atatcagaga gtgagaggaa    7020
cttgtttatt gcagcttata atggttacaa ataaagcaat agcatcacaa atttcacaaa    7080
taaagcattt ttttcactgc attctagttg tggtttgtcc aaactcatca atgtatctta    7140
tcatgtctgg ctctagctat cccgcccta actccgccca tccgcccct aactccgccc      7200
agttccgccc attctccgcc ccatggctga ctaattttt ttatttatgc agaggccgag     7260
```

```
gccgcctcgg cctctgagct attccagaag tagtgaggag gcttttttgg aggcctaggg      7320
acgtacccaa ttcgccctat agtgagtcgt attacgcgcg ctcactggcc gtcgttttac      7380
aacgtcgtga ctgggaaaac cctggcgtta cccaacttaa tcgccttgca gcacatcccc      7440
ctttcgccag ctggcgtaat agcgaagagg cccgcaccga tcgcccttcc caacagttgc      7500
gcagcctgaa tggcgaatgg gacgcgccct gtagcggcgc attaagcgcg gcgggtgtgg      7560
tggttacgcg cagcgtgacc gctacacttg ccagcgccct agcgcccgct cctttcgctt      7620
tcttcccttc ctttctcgcc acgttcgccg gctttccccg tcaagctcta atcgggggc       7680 tccctttagg gttccgattt agtgctttac ggcacctcga ccccaaaaaa cttgattagg      7740
gtgatggttc acgtagtggg ccatcgccct gatagacggt ttttcgccct tgacgttgg       7800 agtccacgtt ctttaatagt ggactcttgt tccaaactgg aacaacactc aaccctatct      7860
cggtctattc ttttgattta aagggattt tgccgatttc ggcctattgg ttaaaaaatg       7920
agctgattta caaaaatttt aacgcgaatt ttaacaaaat attaacgctt acaatttagg      7980
tggcactttt cggggaaatg tgcgcggaac ccctatttgt ttatttttct aaatacattc      8040
aaatatgtat ccgctcatga caataaccc tgataaatg cttcaataat attgaaaaag        8100
gaagagtatg agtattcaac atttccgtgt cgcccttatt ccctttttg cggcattttg       8160 ccttcctgtt tttgctcacc cagaaacgct ggtgaaagta aaagatgctg aagatcagtt      8220
gggtgcacga gtgggttaca tcgaactgga tctcaacagc ggtaagatcc ttgagagttt      8280
tcgccccgaa gaacgttttc caatgatgag cacttttaaa gttctgctat gtggcgcggt      8340
attatcccgt attgacgccg ggcaagagca actcggtcgc cgcatacact attctcagaa      8400
tgacttggtt gagtactcac cagtcacaga aaagcatctt acggatggca tgacagtaag      8460
agaattatgc agtgctgcca taaccatgag tgataacact gcggccaact tacttctgac      8520
aacgatcgga ggaccgaagg agctaaccgc ttttttgcac aacatggggg atcatgtaac      8580
tcgccttgat cgttgggaac cggagctgaa tgaagccata ccaaacgacg agcgtgacac      8640
cacgatgcct gtagcaatgg caacaacgtt gcgcaaacta ttaactggcg aactacttac      8700
tctagcttcc cggcaacaat taatagactg gatggaggcg gataaagttg caggaccact      8760
tctgcgctcg gcccttccgg ctggctggtt tattgctgat aaatctggag ccggtgagcg      8820
tgggtctcgc ggtatcattg cagcactggg gccagatggt aagccctccc gtatcgtagt      8880
tatctacacg acggggagtc aggcaactat ggatgaacga aatagacaga tcgctgagat      8940
aggtgcctca ctgattaagc attggtaact gtcagaccaa gtttactcat atatacttta      9000
gattgattta aaacttcatt tttaatttaa aaggatctag gtgaagatcc tttttgataa      9060
tctcatgacc aaaatccctt aacgtgagtt ttcgttccac tgagcgtcag accccgtaga      9120
aaagatcaaa ggatcttctt gagatccttt ttttctgcgc gtaatctgct gcttgcaaac      9180
aaaaaaacca ccgctaccag cggtggtttg tttgccggat caagagctac caactctttt      9240
tccgaaggta actggcttca gcagagcgca gataccaaat actgttcttc tagtgtagcc      9300
gtagttaggc caccacttca agaactctgt agcaccgcct acatacctcg ctctgctaat      9360
cctgttacca gtggctgctg ccagtggcga taagtcgtgt cttaccgggt tggactcaag      9420
acgatagtta ccggataagg cgcagcggtc gggctgaacg gggggttcgt gcacacagcc      9480
cagcttggag cgaacgacct acaccgaact gagatacta cagcgtgagc tatgagaaag      9540
cgccacgctt cccgaaggga gaaaggcgga caggtatccg gtaagcggca gggtcggaac      9600
```

| | |
|---|---|
| aggagagcgc acgagggagc ttccaggggg aaacgcctgg tatctttata gtcctgtcgg | 9660 |
| gtttcgccac ctctgacttg agcgtcgatt tttgtgatgc tcgtcagggg ggcggagcct | 9720 |
| atggaaaaac gccagcaacg cggcctttt acggttcctg gccttttgct ggccttttgc | 9780 |
| tcacatgttc tttcctgcgt tatcccctga ttctgtggat aaccgtatta ccgcctttga | 9840 |
| gtgagctgat accgctcgcc gcagccgaac gaccgagcgc agcgagtcag tgagcgagga | 9900 |
| agcggaagag cgcccaatac gcaaaccgcc tctccccgcg cgttggccga ttcattaatg | 9960 |
| cagctggcac gacaggtttc ccgactggaa agcgggcagt gagcgcaacg caattaatgt | 10020 |
| gagttagctc actcattagg caccccaggc tttacacttt atgcttccgg ctcgtatgtt | 10080 |
| gtgtggaatt gtgagcggat aacaatttca cacaggaaac agctatgacc atgattacgc | 10140 |
| caagcgcgca attacccctc actaaaggga acaaaagctg agctgcaag cttgg | 10195 |

<210> SEQ ID NO 47
<211> LENGTH: 10578
<212> TYPE: DNA
<213> ORGANISM: Artificial Sequence
<220> FEATURE:
<223> OTHER INFORMATION: LV.GLOBE.betaAS3-GLOBIN.gRNAD-OPTIMIZED
(harboring the expression cassette for grna D - dang scaffold - U6
promoter)

<400> SEQUENCE: 47

| | |
|---|---|
| ccattgcata cgttgtatcc atatcataat atgtacattt atattggctc atgtccaaca | 60 |
| ttaccgccat gttgacattg attattgact agttattaat agtaatcaat tacggggtca | 120 |
| ttagttcata gcccatatat ggagttccgc gttacataac ttacggtaaa tggcccgcct | 180 |
| ggctgaccgc ccaacgaccc ccgcccattg acgtcaataa tgacgtatgt tcccatagta | 240 |
| acgccaatag ggactttcca ttgacgtcaa tgggtggagt atttacggta aactgcccac | 300 |
| ttggcagtac atcaagtgta tcatatgcca gtacgcccc ctattgacgt caatgacggt | 360 |
| aaatggcccg cctggcatta tgcccagtac atgaccttat gggactttcc tacttggcag | 420 |
| tacatctacg tattagtcat cgctattacc atggtgatgc ggttttggca gtacatcaat | 480 |
| gggcgtggat agcggtttga ctcacgggga tttccaagtc tccacccat tgacgtcaat | 540 |
| gggagtttgt tttggcacca aaatcaacgg gactttccaa aatgtcgtaa caactccgcc | 600 |
| ccattgacgc aaatgggcgg taggcgtgta cggtgggagg tctatataag cagagctcgt | 660 |
| ttagtgaacc ggggtctctc tggttagacc agatctgagc ctgggagctc tctggctaac | 720 |
| tagggaaccc actgcttaag cctcaataaa gcttgccttg agtgcttcaa gtagtgtgtg | 780 |
| cccgtctgtt gtgtgactct ggtaactaga tccctcag accctttag tcagtgtgga | 840 |
| aaatctctag cagtggcgcc cgaacaggga cttgaaagcg aaagggaaac cagaggagct | 900 |
| ctctcgacgc aggactcggc ttgctgaagc gcgcacggca agaggcgagg ggcggcgact | 960 |
| ggtgagtacg ccaaaaattt tgactagcgg aggctagaag gagagagatg ggtgcgagag | 1020 |
| cgtcagtatt aagcggggga gaattagatc gcgatggaa aaaattcggt taaggccagg | 1080 |
| gggaaagaaa aaatataaat taaaacatat agtatgggca agcagggagc tagaacgatt | 1140 |
| cgcagttaat cctggcctgt tagaaacatc agaaggctgt agacaaatac tgggacagct | 1200 |
| acaaccatcc cttcagacag gatcagaaga acttagatca ttatataata cagtagcaac | 1260 |
| cctctattgt gtgcatcaaa ggatagagat aaaagacacc aaggaagctt tagacaagat | 1320 |
| agaggaagag caaaacaaaa gtaagaccac cgcacagcaa gcggccgctg atcttcagac | 1380 |
| ctggaggagg agatatgagg gacaattgga gaagtgaatt atataaatat aaagtagtaa | 1440 |

```
aaattgaacc attaggagta gcacccacca aggcaaagag aagagtggtg cagagagaaa    1500
aaagagcagt gggaatagga gctttgttcc ttgggttctt gggagcagca ggaagcacta    1560
tgggcgcagc gtcaatgacg ctgacggtac aggccagaca attattgtct ggtatagtgc    1620
agcagcagaa caatttgctg agggctattg aggcgcaaca gcatctgttg caactcacag    1680
tctggggcat caagcagctc caggcaagaa tcctggctgt ggaaagatac ctaaaggatc    1740
aacagctcct ggggatttgg ggttgctctg gaaaactcat ttgcaccact gctgtgcctt    1800
ggaatgctag ttggagtaat aaatctctgg aacagatttg gaatcacacg acctggatgg    1860
agtgggacag agaaattaac aattacacaa gcttaataca ctccttaatt gaagaatcgc    1920
aaaaccagca agaaaagaat gaacaagaat tattggaatt agataaatgg gcaagtttgt    1980
ggaattggtt taacataaca aattggctgt ggtatataaa attattcata atgatagtag    2040
gaggcttggt aggtttaaga atagttttg ctgtactttc tatagtgaat agagttaggc    2100
agggatattc accattatcg tttcagaccc acctcccaac cccgagggga cccgacaggc    2160
ccgaaggaat agaagaagaa ggtggagaga gagacagaga cagatccatt cgattagtga    2220
acggatctcg acggtatcgg ttaacttta aagaaaagg ggggattggg gggtacagtg    2280
caggggaaag aatagtagac ataatagcaa cagacataca aactaaagaa ttacaaaaac    2340
aaattacaaa attcaaaatt ttatcggtac gtaccatgag gacagctaaa acaataagta    2400
atgtaaaata cagcatagca aactttaac ctccaaatca agcctctact tgaatccttt    2460
tctgagggat gaataaggca taggcatcag gggctgttgc caatgtgcat tagctgtttg    2520
cagcctcacc ttctttcatg gagtttaaga tatagtgtat tttcccaagg tttgaactag    2580
ctcttcattt ctttatgttt taaatgcact gacctcccac attcccttt tagtaaaata    2640 ttcagaaata atttaaatac atcattgcaa tgaaaataaa tgttttttat taggcagaat    2700
ccagatgctc aaggcccttc ataatatccc ccagtttagt agttggactt agggaacaaa    2760
ggaaccttta atagaaattg gacagcaaga aagcgagctt agtgatactt gtgggccagg    2820
gcattagcca caccagccac cactttctga taggcagcct gcactggtgg ggtgaattct    2880
ttgccaaagt gatgggccag cacacagacc agcacgttgc ccaggagctg tgggaggaag    2940
ataagaggta tgaacatgat tagcaaaagg gcctagcttg gactcagaat aatccagcct    3000
tatcccaacc ataaaataaa agcagaatgg tagctgggatt gtagctgcta ttagcaatat    3060
gaaacctctt acatcagtta caatttatat gcagaaatac cctgttactt ctcccctcc    3120 tatgacatga acttaaccat agaaaagaag gggaaagaaa acatcaaggg tcccatagac    3180
tcaccctgaa gttctcagga tccacgtgca gcttgtcaca gtgcagctca ctcagctggg    3240
caaaggtgcc cttgaggttg tccaggtgag ccaggccatc actaaaggca ccgagcactt    3300
tcttgccatg agccttcacc ttagggttgc ccataacagc atcaggagtg gacagatccc    3360
caaaggactc aaagaaacctc tgggtccaag ggtagaccac cagcagccta agggtgggaa    3420
aatagaccaa taggcagaga gagtcagtgc ctatcagaaa cccaagagtc ttctctgtct    3480
ccacatgccc agtttctatt ggtctcctta aacctgtctt gtaaccttga taccaacctg    3540
cccagggcct caccaccaac ggcatccacg ttcaccttgt cccagagagc ggtcacagcg    3600
gacttctcct caggagtcag gtgcaccatg tgtctgtttt gaggttgcta gtgaacacag    3660
ttgtgtcaga agcaaatgta agcaatagat ggctctgccc tgacttttat gcccagccct    3720
ggctcctgcc ctccctgctc ctgggagtag attggccaac cctagggtgt ggctccacag    3780
```

```
ggtgaggtct aagtgatgac agccgtacct gtccttggct cttctggcac tggcttagga    3840
gttggacttc aaaccctcag ccctccctct aagatatatc tcttggcccc ataccatcag    3900
tacaaattgc tactaaaaac atcctccttt gcaagtgtat ttacacggta tcgataagct    3960
tgatatcgaa ttcctgcagc ccccttttgc cacctagctg tccaggggtg ccttaaaatg    4020
gcaaacaagg tttgttttct tttcctgttt tcatgccttc ctcttccata tccttgtttc    4080
atattaatac atgtgtatag atcctaaaaa tctatacaca tgtattaata aagcctgatt    4140
ctgccgcttc taggtataga ggccacctgc aagataaata tttgattcac ataactaat    4200
cattctatgg caattgataa caacaaatat atatatatat atatatacgt atatgtgtat    4260
atatatatat atatattcag gaaataatat attctagaat atgtcacatt ctgtctcagg    4320
catccatttt ctttatgatg ccgtttgagg tggagtttta gtcaggtggt cagcttctcc    4380
tttttttgc catctgccct gtaagcatcc tgctggggac ccagatagga gtcatcactc     4440
taggctgaga acatctgggc acacacccta agcctcagca tgactcatca tgactcagca    4500
ttgctgtgct tgagccagaa ggtttgctta gaaggttaca cagaaccaga aggcggggt    4560
ggggcactga ccccgacagg ggcctggcca gaactgctca tgcttggact atgggaggtc    4620
actaatggag acacacagaa atgtaacagg aactaaggaa aaactgaagc ttatttaatc    4680
agagatgagg atgctggaag ggatagaggg agctgagctt gtaaaaagta tagtaatcat    4740
tcagcaaatg gttttgaagc acctgctgga tgctaaacac tattttcagt gcttgaatca    4800
taaataagaa taaaacatgt atcttattcc ccacaagagt ccaagtaaaa aataacagtt    4860
aattataatg tgctctgtcc cccaggctgg agtgcagtgg cacgatctca gctcactgca    4920
acctccgcct cccgggttca agcaattctc ctgcctcagc caccctaata gctgggatta    4980
caggtgcaca ccaccatgcc aggctaattt ttgtacttt tgtagaggca gggtatcacc      5040
atgttgtcca agatggtctt gaactcctga gctccaagca gtccaccac ctcagcctcc     5100
caaagtgctg ggattacagg tgtgagacac catgcccaga ttttccatat ttaatagagg    5160
tatttatggg atgggggaaa agaatgtttc tctcactgtg gattatttta gagagtggag    5220
aatggtcaag attttttttaa aaattaagaa aacataagtt ggaccttgag aaatgaaaat    5280
ttatttttt gttggaggat acccattctc tatctcccat cagggcaagc tgtaaggaac      5340
tggctaagac acagtgagac agagtgactt agtcttagag gccccactgg tacgacggtc    5400
accaagcttt cattaaaaaa agtctaacca gctgcattcg actttgactg cagcagctgg    5460
ttagaaggtt ctactggagg agggtcccag cccattgcta aattaacatc aggctctgag    5520
actggcagta tatctctaac agtggttgat gctatcttct ggaacttgcc tgctacattg    5580
agaccactga cccatacata ggaagcccat agctctgtcc tgaactgtta ggccactggt    5640
ccagagagtg tgcatctcct ttgatcctca taataaccct atgagataga cacaattatt    5700
actcttactt tatagatgat gatcctgaaa acataggagt caaggcactt gcccctagct    5760
gggggtatag gggagcagtc ccatgtagta gtagaatgaa aaatgctgct atgctgtgcc    5820
tccccacct ttcccatgtc tgccctctac tcatggtcta tctctcctgg ctcctgggag     5880
tcatggactc cacccagcac caccaacctg acctaaccac ctatctgagc ctgccagcct    5940
ataacccatc tgggccctga tagctggtgg ccagccctga ccccaccccca cctccctgg   6000
aacctctgat agacacatct ggcacaccag ctcgcaaagt caccgtgagg gtcttgtgtt    6060
tgctgagtca aaattccttg aaatccaagt ccttagagac tcctgctccc aaatttacag    6120
tcatagactt cttcatggct gtctcctttta tccacagaat gattcctttg cttcattgcc   6180
```

```
ccatccatct gatcctcctc atcagtgcag cacagggccc atgagcagta gctgcagagt    6240
ctcacatagg tctggcactg cctctgacat gtccgacctt aggcaaatgc ttgactcttc    6300
tgagctcagt cttgtcatgg caaaataaag ataataatag tgttttttta tggagttagc    6360
gtgaggatgg aaaacaatag caaaattgat tagactataa aaggtctcaa caaatagtag    6420
tagattttat catccattaa tccttccctc tcctctctta ctcatcccat cacgtatgcc    6480
tcttaatttt cccttaccta taataagagt tattcctctt attatattct tcttatagtg    6540
attctggata ttaaagtggg aatgagggc aggccactaa cgaagaagat gtttctcaaa    6600
gaagcggggg atccactagt tctagagcgg ccaaatggcg gccgtacctt aagaccaat    6660 gacttacaag gcagctgtcg acaggtcggg caggaagagg gcctatttcc catgattcct    6720
tcatatttgc atatacgata caaggctgtt agagagataa ttagaattaa tttgactgta    6780
aacacaaaga tattagtaca aaatacgtga cgtagaaagt aataaatttct tgggtagttt    6840 gcagttttaa aattatgttt taaaatggac tatcatatgc ttaccgtaac ttgaaagtat    6900
ttcgatttct tggctttata tatcttgtgg aaaggacgaa acaccgtctg ccgttactgc    6960
cctgtggttt cagagctatg ctggaaacag catagcaagt gaaataagg ctagtccgtt    7020 atcaacttga aaaagtggca ccgagtcggt gcttttttg tcgaccttag ccactttta    7080 aaagaaaagg ggggactgga agggctaatt cactcccaac gaagacaaga tctgcttttt    7140
gcttgtactg ggtctctctg gttagaccag atctgagcct gggagctctc tggctaacta    7200
gggaacccac tgcttaagcc tcaataaagc ttgccttgag tgcttcaagt agtgtgtgcc    7260
cgtctgttgt gtgactctgg taactagaga tccctcagac ccttttagtc agtgtggaaa    7320
atctctagca gtagtagttc atgtcatctt attattcagt atttataact tgcaaagaaa    7380
tgaatatcag agagtgagag gaacttgttt attgcagctt ataatggtta caaataaagc    7440
aatagcatca caaatttcac aaataaagca ttttttcac tgcattctag ttgtggtttg    7500
tccaaactca tcaatgtatc ttatcatgtc tggctctagc tatcccgccc ctaactccgc    7560
ccatcccgcc cctaactccg cccagttccg cccattctcc gccccatggc tgactaattt    7620 tttttatta tgcagaggcc gaggccgcct cggcctctga gctattccag aagtagtgag    7680
gaggcttttt tggaggccta gggacgtacc caattcgccc tatagtgagt cgtattacgc    7740
gcgctcactg gccgtcgttt tacaacgtcg tgactgggaa aacctggcg ttacccaact    7800 taatcgcctt gcagcacatc cccctttcgc cagctggcgt aatagcgaag aggcccgcac    7860
cgatcgccct tcccaacagt tgcgcagcct gaatggcgaa tgggacgcgc cctgtagcgg    7920
cgcattaagc gcggcgggtg tggtggttac gcgcagcgtg accgctacac ttgccagcgc    7980
cctagcgccc gctcctttcg ctttcttccc ttcctttctc gccacgttcg ccggctttcc    8040
ccgtcaagct ctaaatcggg ggctccctt agggttccga tttagtgctt tacggcacct    8100
cgaccccaaa aaacttgatt agggtgatgg ttcacgtagt gggccatcgc cctgatagac    8160 ggttttttcgc cctttgacgt tggagtccac gttctttaat agtggactct tgttccaaac    8220
tggaacaaca ctcaacccta tctcggtcta ttcttttgat ttataaggga ttttgccgat    8280
ttcggcctat tggttaaaaa atgagctgat ttaacaaaaa tttaacgcga attttaacaa    8340
aatattaacg cttacaattt aggtggcact tttcggggaa atgtgcgcgg aacccctatt    8400
tgtttatttt tctaaataca ttcaaatatg tatccgctca tgagacaata accctgataa    8460
atgcttcaat aatattgaaa aaggaagagt atgagtattc aacatttccg tgtcgccctt    8520
```

| | |
|---|---|
| attcccttttt ttgcggcatt ttgccttcct gttttttgctc acccagaaac gctggtgaaa | 8580 |
| gtaaaagatg ctgaagatca gttgggtgca cgagtgggtt acatcgaact ggatctcaac | 8640 |
| agcggtaaga tccttgagag ttttcgcccc gaagaacgtt ttccaatgat gagcacttttt | 8700 |
| aaagttctgc tatgtggcgc ggtattatcc cgtattgacg ccgggcaaga gcaactcggt | 8760 |
| cgccgcatac actattctca gaatgacttg gttgagtact caccagtcac agaaaagcat | 8820 |
| cttacggatg gcatgacagt aagagaatta tgcagtgctg ccataaccat gagtgataac | 8880 |
| actgcggcca acttacttct gacaacgatc ggaggaccga aggagctaac cgcttttttg | 8940 |
| cacaacatgg gggatcatgt aactcgcctt gatcgttggg aaccgagct gaatgaagcc | 9000 |
| ataccaaacg acgagcgtga caccacgatg cctgtagcaa tggcaacaac gttgcgcaaa | 9060 |
| ctattaactg gcgaactact tactctagct tcccggcaac aattaataga ctggatggag | 9120 |
| gcggataaag ttgcaggacc acttctgcgc tcggcccttc cggctggctg gtttattgct | 9180 |
| gataaatctg gagccggtga gcgtgggtct cgcggtatca ttgcagcact ggggccagat | 9240 |
| ggtaagccct cccgtatcgt agttatctac acgacgggga gtcaggcaac tatggatgaa | 9300 |
| cgaaatagac agatcgctga gataggtgcc tcactgatta gcattggta actgtcagac | 9360 |
| caagtttact catatatact ttagattgat ttaaaacttc atttttaatt taaaaggatc | 9420 |
| taggtgaaga tcctttttga taatctcatg accaaaatcc cttaacgtga gttttcgttc | 9480 |
| cactgagcgt cagaccccgt agaaaagatc aaaggatctt cttgagatcc ttttttctg | 9540 |
| cgcgtaatct gctgcttgca acaaaaaaa ccaccgctac cagcggtggt ttgtttgccg | 9600 |
| gatcaagagc taccaactct ttttccgaag gtaactggct tcagcagagc gcagatacca | 9660 |
| aatactgttc ttctagtgta gccgtagtta ggccaccact tcaagaactc tgtagcaccg | 9720 |
| cctacatacc tcgctctgct aatcctgtta ccagtggctg ctgccagtgg cgataagtcg | 9780 |
| tgtcttaccg ggttggactc aagacgatag ttaccggata aggcgcagcg gtcgggctga | 9840 |
| acggggggtt cgtgcacaca gcccagcttg gagcgaacga cctacaccga actgagatac | 9900 |
| ctacagcgtg agctatgaga aagcgccacg cttcccgaag ggagaaaggc ggacaggtat | 9960 |
| ccggtaagcg gcagggtcgg aacaggagag cgcacgaggg agcttccagg gggaaacgcc | 10020 |
| tggtatcttt atagtcctgt cgggtttcgc cacctctgac ttgagcgtcg attttttgtga | 10080 |
| tgctcgtcag gggggcggag cctatggaaa aacgccagca acgcggcctt tttacggttc | 10140 |
| ctggccttttt gctggccttt tgctcacatg ttctttcctg cgttatcccc tgattctgtg | 10200 |
| gataaccgta ttaccgcctt tgagtgagct gataccgctc gccgcagccg aacgaccgag | 10260 |
| cgcagcgagt cagtgagcga ggaagcggaa gagcgcccaa tacgcaaacc gcctctcccc | 10320 |
| gcgcgttggc cgattcatta atgcagctgg cacgacaggt ttcccgactg gaaagcgggc | 10380 |
| agtgagcgca acgcaattaa tgtgagttag ctcactcatt aggcacccca ggctttacac | 10440 |
| tttatgcttc cggctcgtat gttgtgtgga attgtgagcg gataacaatt tcacacagga | 10500 |
| aacagctatg accatgatta cgccaagcgc gcaattaacc ctcactaaag ggaacaaaag | 10560 |
| ctggagctgc aagcttgg | 10578 |

<210> SEQ ID NO 48
<211> LENGTH: 18
<212> TYPE: DNA
<213> ORGANISM: Artificial Sequence
<220> FEATURE:
<223> OTHER INFORMATION: gRNA against gamma-delta intergenic region

<400> SEQUENCE: 48
ggtgctctat acttccta                                                18

<210> SEQ ID NO 49
<211> LENGTH: 20
<212> TYPE: DNA
<213> ORGANISM: Artificial Sequence
<220> FEATURE:
<223> OTHER INFORMATION: gRNA A spacer inverted sequence

<400> SEQUENCE: 49
gaacggggtg tcccgtcatt                                              20

<210> SEQ ID NO 50
<211> LENGTH: 20
<212> TYPE: DNA
<213> ORGANISM: Artificial Sequence
<220> FEATURE:
<223> OTHER INFORMATION: HBG genes inverted sequence OFF-TARGET gRNA A

<400> SEQUENCE: 50
gaacggggtg tccgaacact                                              20

<210> SEQ ID NO 51
<211> LENGTH: 20
<212> TYPE: DNA
<213> ORGANISM: Artificial Sequence
<220> FEATURE:
<223> OTHER INFORMATION: HBD gene inverted sequence OFF-TARGET gRNA A

<400> SEQUENCE: 51
aaacggggtg tcccgtaact                                              20

<210> SEQ ID NO 52
<211> LENGTH: 20
<212> TYPE: DNA
<213> ORGANISM: Artificial Sequence
<220> FEATURE:
<223> OTHER INFORMATION: gRNA B spacer inverted sequence

<400> SEQUENCE: 52
cattgccgtc tgaagaggag                                              20

<210> SEQ ID NO 53
<211> LENGTH: 20
<212> TYPE: DNA
<213> ORGANISM: Artificial Sequence
<220> FEATURE:
<223> OTHER INFORMATION: HBG genes inverted sequence OFF-TARGET gRNA B

<400> SEQUENCE: 53
tatcatcgga acaggaggag                                              20

<210> SEQ ID NO 54
<211> LENGTH: 20
<212> TYPE: DNA
<213> ORGANISM: Artificial Sequence
<220> FEATURE:
<223> OTHER INFORMATION: HBD gene inverted sequence OFF-TARGET gRNA B

<400> SEQUENCE: 54
aactgtcgtc agaagaggag                                              20

<210> SEQ ID NO 55
<211> LENGTH: 19
<212> TYPE: DNA

```
<213> ORGANISM: Artificial Sequence
<220> FEATURE:
<223> OTHER INFORMATION: gRNA D spacer inverted sequence

<400> SEQUENCE: 55
agacggcaat gacgggaca                                                    19

<210> SEQ ID NO 56
<211> LENGTH: 19
<212> TYPE: DNA
<213> ORGANISM: Artificial Sequence
<220> FEATURE:
<223> OTHER INFORMATION: HBG genes inverted sequence OFF-TARGET gRNA D

<400> SEQUENCE: 56
cgatgatagt gttcggaca                                                    19

<210> SEQ ID NO 57
<211> LENGTH: 19
<212> TYPE: DNA
<213> ORGANISM: Artificial Sequence
<220> FEATURE:
<223> OTHER INFORMATION: HBD gene inverted sequence OFF-TARGET gRNA D

<400> SEQUENCE: 57
tgacgacagt tacgggaca                                                    19

<210> SEQ ID NO 58
<211> LENGTH: 20
<212> TYPE: DNA
<213> ORGANISM: Artificial Sequence
<220> FEATURE:
<223> OTHER INFORMATION: gRNA E spacer inverted sequence

<400> SEQUENCE: 58
ttccacttgc acctacttca                                                   20

<210> SEQ ID NO 59
<211> LENGTH: 20
<212> TYPE: DNA
<213> ORGANISM: Artificial Sequence
<220> FEATURE:
<223> OTHER INFORMATION: HBG genes inverted sequence OFF-TARGET gRNA E

<400> SEQUENCE: 59
ttccacttac accttctacg                                                   20

<210> SEQ ID NO 60
<211> LENGTH: 20
<212> TYPE: DNA
<213> ORGANISM: Artificial Sequence
<220> FEATURE:
<223> OTHER INFORMATION: HBD gene inverted sequence OFF-TARGET gRNA E

<400> SEQUENCE: 60
tttcacttgc acctacgtca                                                   20

<210> SEQ ID NO 61
<211> LENGTH: 101
<212> TYPE: RNA
<213> ORGANISM: Artificial Sequence
<220> FEATURE:
<223> OTHER INFORMATION: ORIGINAL gRNA SCAFFOLD sequence
<220> FEATURE:
<221> NAME/KEY: misc_feature
<222> LOCATION: (1)..(20)
<223> OTHER INFORMATION: n is a, c, g, or u
```

<400> SEQUENCE: 61
nnnnnnnnnn nnnnnnnnnn guuuuagagc uagaaauagc aaguuaaaau aaggcuaguc    60
cguuaucaac uugaaaaagu ggcaccgagu cggugcuuuu u                       101

<210> SEQ ID NO 62
<211> LENGTH: 112
<212> TYPE: RNA
<213> ORGANISM: Artificial Sequence
<220> FEATURE:
<223> OTHER INFORMATION: OPTIMIZED gRNA SCAFFOLD sequence
<220> FEATURE:
<221> NAME/KEY: misc_feature
<222> LOCATION: (1)..(20)
<223> OTHER INFORMATION: n is a, c, g, or u

<400> SEQUENCE: 62
nnnnnnnnnn nnnnnnnnnn guuucagagc uaugcuggaa acagcauagc aaguugaaau    60
aaggcuaguc cguuaucaac uugaaaaagu ggcaccgagu cggugcuuuu uu           112

<210> SEQ ID NO 63
<211> LENGTH: 101
<212> TYPE: RNA
<213> ORGANISM: Artificial Sequence
<220> FEATURE:
<223> OTHER INFORMATION: ORIGINAL SCAFFOLD gRNA B sequence

<400> SEQUENCE: 63
guaacggcag acuucuccuc guuuuagagc uagaaauagc aaguuaaaau aaggcuaguc    60
cguuaucaac uugaaaaagu ggcaccgagu cggugcuuuu u                       101

<210> SEQ ID NO 64
<211> LENGTH: 100
<212> TYPE: RNA
<213> ORGANISM: Artificial Sequence
<220> FEATURE:
<223> OTHER INFORMATION: ORIGINAL SCAFFOLD gRNA D sequence

<400> SEQUENCE: 64
ucugccguua cugcccugug uuuuagagcu agaaauagca aguuaaaaua aggcuaguccc   60 guuaucaacu ugaaaaagug gcaccgaguc ggugcuuuuu                        100

<210> SEQ ID NO 65
<211> LENGTH: 101
<212> TYPE: RNA
<213> ORGANISM: Artificial Sequence
<220> FEATURE:
<223> OTHER INFORMATION: ORIGINAL SCAFFOLD gRNA E sequence

<400> SEQUENCE: 65
aaggugaacg uggaugaagu guuuuagagc uagaaauagc aaguuaaaau aaggcuaguc    60
cguuaucaac uugaaaaagu ggcaccgagu cggugcuuuu u                       101

<210> SEQ ID NO 66
<211> LENGTH: 113
<212> TYPE: RNA
<213> ORGANISM: Artificial Sequence
<220> FEATURE:
<223> OTHER INFORMATION: OPTIMIZED SCAFFOLD gRNA B sequence

<400> SEQUENCE: 66
guaacggcag acuucuccuc gguuucagag cuaugcugga aacagcauag caaguugaaa    60
uaaggcuagu ccguuaucaa cuugaaaaag uggcaccgag ucggugcuuu uuu        113

<210> SEQ ID NO 67
<211> LENGTH: 112
<212> TYPE: RNA
<213> ORGANISM: Artificial Sequence
<220> FEATURE:
<223> OTHER INFORMATION: OPTIMIZED SCAFFOLD gRNA D sequence

<400> SEQUENCE: 67
ucugccguua cugcccugug guuucagagc uaugcuggaa acagcauagc aaguugaaau        60
aaggcuaguc cguuaucaac uugaaaaagu ggcaccgagu cggugcuuuu uu              112

<210> SEQ ID NO 68
<211> LENGTH: 114
<212> TYPE: RNA
<213> ORGANISM: Artificial Sequence
<220> FEATURE:
<223> OTHER INFORMATION: OPTIMIZED SCAFFOLD gRNA E sequence

<400> SEQUENCE: 68
gaaggugaac guggaugaag ugguuucaga gcuaugcugg aaacagcaua gcaaguugaa        60
auaaggcuag uccguuauca acuugaaaaa guggcaccga gucggugcuu uuuu            114

<210> SEQ ID NO 69
<211> LENGTH: 34
<212> TYPE: DNA
<213> ORGANISM: Artificial Sequence
<220> FEATURE:
<223> OTHER INFORMATION: HBB gene SCD sequence

<400> SEQUENCE: 69
cctgtggaga agtctgccgt tactgccctg tggg                                    34

<210> SEQ ID NO 70
<211> LENGTH: 11
<212> TYPE: PRT
<213> ORGANISM: Artificial Sequence
<220> FEATURE:
<223> OTHER INFORMATION: Beta-S globin protein sequence

<400> SEQUENCE: 70

Pro Val Glu Lys Ser Ala Val Thr Ala Leu Trp
1               5                   10

<210> SEQ ID NO 71
<211> LENGTH: 34
<212> TYPE: DNA
<213> ORGANISM: Artificial Sequence
<220> FEATURE:
<223> OTHER INFORMATION: HBB-AS3 modified sequence

<400> SEQUENCE: 71
cctgaggaga agtccgctgt gaccgctctc tggg                                    34

<210> SEQ ID NO 72
<211> LENGTH: 11
<212> TYPE: PRT
<213> ORGANISM: Artificial Sequence
<220> FEATURE:
<223> OTHER INFORMATION: Beta-AS3 globin sequence

<400> SEQUENCE: 72

Pro Glu Glu Lys Ser Ala Val Thr Ala Leu Trp
1               5                   10

```
<210> SEQ ID NO 73
<211> LENGTH: 20
<212> TYPE: DNA
<213> ORGANISM: Artificial Sequence
<220> FEATURE:
<223> OTHER INFORMATION: gRNA 13bp-del spacer

<400> SEQUENCE: 73
cttgtcaagg ctattggtca                                                  20

<210> SEQ ID NO 74
<211> LENGTH: 20
<212> TYPE: DNA
<213> ORGANISM: Artificial Sequence
<220> FEATURE:
<223> OTHER INFORMATION: gRNA BCL11A spacer

<400> SEQUENCE: 74
cacaggctcc aggaagggtt                                                  20

<210> SEQ ID NO 75
<211> LENGTH: 10584
<212> TYPE: DNA
<213> ORGANISM: Artificial Sequence
<220> FEATURE:
<223> OTHER INFORMATION: LV.GLOBE-AS3modified.gRNA-BCL11Aenhancer

<400> SEQUENCE: 75
ccattgcata cgttgtatcc atatcataat atgtacattt atattggctc atgtccaaca        60
ttaccgccat gttgacattg attattgact agttattaat agtaatcaat tacggggtca       120
ttagttcata gcccatatat ggagttccgc gttacataac ttacggtaaa tggcccgcct       180
ggctgaccgc ccaacgaccc ccgcccattg acgtcaataa tgacgtatgt tcccatagta       240
acgccaatag ggactttcca ttgacgtcaa tgggtggagt atttacggta aactgcccac       300
ttggcagtac atcaagtgta tcatatgcca agtacgcccc ctattgacgt caatgacggt       360
aaatggcccg cctggcatta tgcccagtac atgaccttat gggactttcc tacttggcag       420
tacatctacg tattagtcat cgctattacc atggtgatgc ggttttggca gtacatcaat       480
gggcgtggat agcggtttga ctcacgggga tttccaagtc tccaccccat tgacgtcaat       540
gggagtttgt tttggcacca aaatcaacgg gactttccaa aatgtcgtaa caactccgcc       600
ccattgacgc aaatgggcgg taggcgtgta cggtgggagg tctatataag cagagctcgt       660
ttagtgaacc ggggtctctc tggttagacc agatctgagc ctgggagctc tctggctaac       720
tagggaaccc actgcttaag cctcaataaa gcttgccttg agtgcttcaa gtagtgtgtg       780
cccgtctgtt gtgtgactct ggtaactaga gatccctcag acccttttag tcagtgtgga       840
aaatctctag cagtggcgcc cgaacaggga cttgaaagcg aaagggaaac cagaggagct       900
ctctcgacgc aggactcggc ttgctgaagc gcgcacggca agaggcgagg ggcggcgact       960
ggtgagtacg ccaaaaattt tgactagcgg aggctagaag gagagagatg ggtgcgagag      1020
cgtcagtatt aagcggggga gaattagatc gcgatgggaa aaaattcggt taaggccagg      1080
gggaaagaaa aaatataaat taaaacatat agtatgggca agcagggagc tagaacgatt      1140
cgcagttaat cctggcctgt tagaaacatc agaaggctgt agacaaatac tgggacagct      1200
acaaccatcc cttcagacag gatcagaaga acttagatca ttatataata cagtagcaac      1260
cctctattgt gtgcatcaaa ggatagagat aaaagacacc aaggaagctt tagacaagat      1320
```

```
agaggaagag caaaacaaaa gtaagaccac cgcacagcaa gcggccgctg atcttcagac    1380
ctggaggagg agatatgagg gacaattgga gaagtgaatt atataaatat aaagtagtaa    1440
aaattgaacc attaggagta gcacccacca aggcaaagag aagagtggtg cagagagaaa    1500
aaagagcagt gggaatagga gctttgttcc ttgggttctt gggagcagca ggaagcacta    1560
tgggcgcagc gtcaatgacg ctgacggtac aggccagaca attattgtct ggtatagtgc    1620
agcagcagaa caatttgctg agggctattg aggcgcaaca gcatctgttg caactcacag    1680 tctgggcat caagcagctc caggcaagaa tcctggctgt ggaaagatac ctaaaggatc     1740
aacagctcct ggggatttgg ggttgctctg gaaaactcat ttgcaccact gctgtgcctt    1800
ggaatgctag ttggagtaat aaatctctgg aacagatttg gaatcacacg acctggatgg    1860
agtgggacag agaaattaac aattacacaa gcttaataca ctccttaatt gaagaatcgc    1920
aaaaccagca agaaaagaat gaacaagaat tattggaatt agataaatgg gcaagtttgt    1980
ggaattggtt taacataaca aattggctgt ggtatataaa attattcata atgatagtag    2040
gaggcttggt aggtttaaga atagttttg ctgtactttc tatagtgaat agagttaggc     2100
agggatattc accattatcg tttcagaccc acctcccaac cccgagggga cccgacaggc    2160
ccgaaggaat agaagaagaa ggtggagaga gagacagaga cagatccatt cgattagtga    2220
acggatctcg acggtatcgg ttaacttta aagaaaagg ggggattggg gggtacagtg      2280
caggggaaag aatagtagac ataatagcaa cagacataca aactaaagaa ttacaaaaac    2340
aaattacaaa attcaaaatt ttatcggtac gtaccatgag gacagctaaa acaataagta    2400
atgtaaaata cagcatagca aaactttaac ctccaaatca agcctctact tgaatccttt    2460
tctgagggat gaataaggca taggcatcag gggctgttgc caatgtgcat agctgtttg    2520 cagcctcacc ttctttcatg gagtttaaga tatagtgtat tttcccaagg tttgaactag    2580
ctcttcattt ctttatgttt taaatgcact gacctcccac attccttttt tagtaaaata    2640
ttcagaaata atttaaatac atcattgcaa tgaaaataaa tgttttttat taggcagaat    2700
ccagatgctc aaggcccttc ataatatccc ccagtttagt agttggactt agggaacaaa    2760
ggaaccttta atagaaattg gacagcaaga aagcgagctt agtgatactt gtgggccagg    2820
gcattagcca caccagccac cactttctga taggcagcct gcactggtgg ggtgaattct    2880
ttgccaaagt gatgggccag cacacagacc agcacgttgc ccaggagctg tgggaggaag    2940
ataagaggta tgaacatgat tagcaaaagg gcctagcttg gactcagaat aatccagcct    3000
tatcccaacc ataaaataaa agcagaatgg tagctggatt gtagctgcta ttagcaatat    3060
gaaacctctt acatcagtta caatttatat gcagaaatac cctgttactt ctccccttcc    3120
tatgacatga acttaaccat agaaaagaag gggaaagaaa acatcaaggg tcccatagac    3180
tcaccctgaa gttctcagga tccacgtgca gcttgtcaca gtgcagctca ctcagctggg    3240
caaaggtgcc cttgaggttg tccaggtgag ccaggccatc actaaaggca ccgagcactt    3300
tcttgccatg agccttcacc ttagggttgc ccataacagc atcaggagtg acagatccc    3360 caaaggactc aaagaaccct ctgggtccaag ggtagaccac cagcagccta agggtgggaa    3420
aatagaccaa taggcagaga gagtcagtgc ctatcagaaa cccaagagtc ttctctgtct    3480
ccacatgccc agtttctatt ggtctcctta aacctgtctt gtaaccttga taccaacctg    3540
cccagggcct caccaccaac ggcatccacg ttcaccttgt cccagagagc ggtcacagcg    3600
gacttctcct caggagtcag gtgcaccatg gtgtctgttt gaggttgcta gtgaacacag    3660
ttgtgtcaga agcaaatgta agcaatagat ggctctgccc tgacttttat gcccagccct    3720
```

```
ggctcctgcc ctccctgctc ctgggagtag attggccaac cctagggtgt ggctccacag      3780
ggtgaggtct aagtgatgac agccgtacct gtccttggct cttctggcac tggcttagga      3840
gttggacttc aaaccctcag ccctccctct aagatatatc tcttggcccc ataccatcag      3900
tacaaattgc tactaaaaac atcctccttt gcaagtgtat ttacacggta tcgataagct      3960
tgatatcgaa ttcctgcagc cccctttggc cacctagctg tccaggggtg ccttaaaatg      4020
gcaaacaagg tttgttttct tttcctgttt tcatgccttc ctcttccata tccttgtttc      4080
atattaatac atgtgtatag atcctaaaaa tctatacaca tgtattaata aagcctgatt      4140
ctgccgcttc taggtataga ggccacctgc aagataaata tttgattcac aataactaat      4200
cattctatgg caattgataa caacaaatat atatatatat atatatacgt atatgtgtat      4260
atatatatat atatattcag gaaataatat attctagaat atgtcacatt ctgtctcagg      4320
catccatttt ctttatgatg ccgtttgagg tggagtttta gtcaggtggt cagcttctcc      4380
ttttttttgc catctgccct gtaagcatcc tgctggggac ccagatagga gtcatcactc      4440
taggctgaga acatctgggc acacacccta agcctcagca tgactcatca tgactcagca      4500
ttgctgtgct tgagccagaa ggtttgctta gaaggttaca cagaaccaga aggcggggt       4560 ggggcactga ccccgacagg ggcctggcca gaactgctca tgcttggact atgggaggtc      4620
actaatggag acacacagaa atgtaacagg aactaaggaa aaactgaagc ttatttaatc      4680
agagatgagg atgctggaag ggatagaggg agctgagctt gtaaaaagta tagtaatcat      4740
tcagcaaatg gttttgaagc acctgctgga tgctaaacac tattttcagt gcttgaatca      4800
taaataagaa taaaacatgt atcttattcc ccacaagagt ccaagtaaaa aataacagtt      4860
aattataatg tgctctgtcc cccaggctgg agtgcagtgg cacgatctca gctcactgca      4920
acctccgcct cccgggttca agcaattctc ctgcctcagc caccctaata gctgggatta      4980
caggtgcaca ccaccatgcc aggctaattt ttgtactttt tgtagaggca gggtatcacc      5040
atgttgtcca agatggtctt gaactcctga gctccaagca gtccacccac ctcagcctcc      5100
caaagtgctg ggattacagg tgtgagacac catgcccaga ttttccatat ttaatagagg      5160
tatttatggg atggggaaa agaatgtttc tctcactgtg gattattta gagagtggag        5220 aatggtcaag attttttttaa aaattaagaa aacataagtt ggaccttgag aaatgaaaat      5280 ttatttttttt gttggaggat acccattctc tatctcccat cagggcaagc tgtaaggaac      5340
tggctaagac acagtgagac agagtgactt agtcttagag gccccactgg tacgacggtc      5400
accaagcttt cattaaaaaa agtctaacca gctgcattcg actttgactg cagcagctgg      5460
ttagaaggtt ctactggagg agggtcccag cccattgcta aattaacatc aggctctgag      5520
actggcagta tatctctaac agtggttgat gctatcttct ggaacttgcc tgctacattg      5580
agaccactga cccatacata ggaagcccat agctctgtcc tgaactgtta ggccactggt      5640
ccagagagtg tgcatctcct ttgatcctca taataaccct atgagataga cacaattatt      5700
actcttactt tatagatgat gatcctgaaa acataggagt caaggcactt gcccctagct      5760
gggggtatag gggagcagtc ccatgtagta gtagaatgaa aaatgctgct atgctgtgcc      5820
tcccccacct ttcccatgtc tgccctctac tcatggtcta tctctcctgg ctcctgggag      5880
tcatggactc cacccagcac caccaacctg acctaaccac ctatctgagc ctgccagcct      5940
ataacccatc tgggccctga tagctggtgg ccagccctga ccccacccca ccctccctgg      6000
aacctctgat agacacatct ggcacaccag ctcgcaaagt caccgtgagg gtcttgtgtt      6060
```

```
tgctgagtca aaattccttg aaatccaagt ccttagagac tcctgctccc aaatttacag   6120
tcatagactt cttcatggct gtctccttta tccacagaat gattcctttg cttcattgcc   6180
ccatccatct gatcctcctc atcagtgcag cacagggccc atgagcagta gctgcagagt   6240
ctcacatagg tctggcactg cctctgacat gtccgacctt aggcaaatgc ttgactcttc   6300
tgagctcagt cttgtcatgg caaaataaag ataataatag tgttttttta tggagttagc   6360
gtgaggatgg aaaacaatag caaaattgat tagactataa aaggtctcaa caaatagtag   6420
tagattttat catccattaa tccttccctc tcctctctta ctcatcccat cacgtatgcc   6480
tcttaatttt cccttaccta taataagagt tattcctctt attatattct tcttatagtg   6540
attctggata ttaaagtggg aatgaggggc aggccactaa cgaagaagat gtttctcaaa   6600
gaagcggggg atccgtcgac aggtcgggca ggaagagggc ctatttccca tgattccttc   6660
atatttgcat atacgataca aggctgttag agagataatt agaattaatt tgactgtaaa   6720
cacaagata ttagtacaaa atacgtgacg tagaaagtaa taatttcttg ggtagtttgc    6780
agttttaaaa ttatgtttta aaatggacta tcatatgctt accgtaactt gaaagtattt   6840
cgatttcttg ctttatata tcttgtggaa aggacgaaac accgcacagg ctccaggaag    6900
ggttgtttca gagctatgct ggaaacagca tagcaagttg aaataaggct agtccgttat   6960
caacttgaaa aagtggcacc gagtcggtgc ttttttttgtc gacactagtt ctagagcggc   7020
caaatggcgg ccgtaccttt aagaccaatg acttacaagg cagctgtaga tcttagccac   7080
ttttttaaaag aaaagggggg actggaaggg ctaattcact cccaacgaag acaagatctg   7140
cttttttgctt gtactgggtc tctctggtta gaccagatct gagcctggga gctctctggc   7200
taactaggga acccactgct taagcctcaa taaagcttgc cttgagtgct tcaagtagtg   7260
tgtgcccgtc tgttgtgtga ctctggtaac tagagatccc tcagaccctt ttagtcagtg   7320
tggaaaatct ctagcagtag tagttcatgt catcttatta ttcagtattt ataacttgca   7380
aagaaatgaa tatcagagag tgagaggaac ttgtttattg cagcttataa tggttacaaa   7440
taaagcaata gcatcacaaa tttcacaaat aaagcatttt tttcactgca ttctagttgt   7500
ggtttgtcca aactcatcaa tgtatcttat catgtctggc tctagctatc ccgcccctaa   7560
ctccgcccat cccgccccta actccgccca gttccgccca ttctccgccc catggctgac   7620
taatttttt tatttatgca gaggccgagg ccgcctcggc ctctgagcta ttccagaagt   7680
agtgaggagg ctttttttgga ggcctaggga cgtacccaat cgccctata gtgagtcgta   7740
ttacgcgcgc tcactggccg tcgttttaca acgtcgtgac tgggaaaacc ctggcgttac   7800
ccaacttaat cgccttgcag cacatccccc tttcgccagc tggcgtaata gcgaagaggc   7860
ccgcaccgat cgcccttccc aacagttgcg cagcctgaat ggcgaatggg acgcgcctg    7920
tagcggcgca ttaagcgcgg cgggtgtggt ggttacgcgc agcgtgaccg ctacacttgc   7980
cagcgcccta gcgcccgctc ctttcgcttt cttcccttcc tttctcgcca cgttcgccgg   8040
ctttccccgt caagctctaa atcggggggct cccttaggg ttccgattta gtgctttacg    8100
gcacctcgac cccaaaaaac ttgattaggg tgatggttca cgtagtgggc catcgccctg   8160
atagacggtt tttcgccctt tgacgttgga gtccacgttc tttaatagtg gactcttgtt   8220
ccaaactgga acaacactca accctatctc ggtctattct tttgatttat aagggatttt   8280
gccgatttcg gcctattggt taaaaaatga gctgatttaa caaaaattta acgcgaattt   8340
taacaaaata ttaacgctta caatttaggt ggcacttttc ggggaaatgt gcgcggaacc   8400
cctatttgtt tatttttcta aatacattca aatatgtatc cgctcatgag acaataaccc   8460
```

```
tgataaatgc ttcaataata ttgaaaaagg aagagtatga gtattcaaca tttccgtgtc    8520
gcccttattc ccttttttgc ggcattttgc cttcctgttt ttgctcaccc agaaacgctg    8580
gtgaaagtaa aagatgctga agatcagttg ggtgcacgag tgggttacat cgaactggat    8640
ctcaacagcg gtaagatcct tgagagtttt cgccccgaag aacgttttcc aatgatgagc    8700
acttttaaag ttctgctatg tggcgcggta ttatcccgta ttgacgccgg gcaagagcaa    8760
ctcggtcgcc gcatacacta ttctcagaat gacttggttg agtactcacc agtcacagaa    8820
aagcatctta cggatggcat gacagtaaga gaattatgca gtgctgccat aaccatgagt    8880
gataacactg cggccaactt acttctgaca acgatcggag gaccgaagga gctaaccgct    8940
tttttgcaca acatggggga tcatgtaact cgccttgatc gttgggaacc ggagctgaat    9000
gaagccatac caaacgacga gcgtgacacc acgatgcctg tagcaatggc aacaacgttg    9060
cgcaaactat taactggcga actacttact ctagcttccc ggcaacaatt aatagactgg    9120
atggaggcgg ataaagttgc aggaccactt ctgcgctcgg cccttccggc tggctggttt    9180
attgctgata atctggagcc ggtgagcgt gggtctcgcg gtatcattgc agcactgggg    9240
ccagatggta agccctcccg tatcgtagtt atctacacga cggggagtca ggcaactatg    9300
gatgaacgaa atagacagat cgctgagata ggtgcctcac tgattaagca ttggtaactg    9360
tcagaccaag tttactcata tatactttag attgatttaa aacttcattt ttaatttaaa    9420
aggatctagg tgaagatcct ttttgataat ctcatgacca aaatccctta acgtgagttt    9480
tcgttccact gagcgtcaga ccccgtagaa aagatcaaag gatcttcttg agatcctttt    9540
tttctgcgcg taatctgctg cttgcaaaca aaaaaaccac cgctaccagc ggtggtttgt    9600
ttgccggatc aagagctacc aactcttttt ccgaaggtaa ctggcttcag cagagcgcag    9660
ataccaaata ctgttcttct agtgtagccg tagttaggcc accacttcaa gaactctgta    9720
gcaccgccta catacctcgc tctgctaatc ctgttaccag tggctgctgc cagtggcgat    9780
aagtcgtgtc ttaccgggtt ggactcaaga cgatagttac cggataaggc gcagcggtcg    9840
ggctgaacgg ggggttcgtg cacacagccc agcttggagc gaacgaccta caccgaactg    9900
agatacctac agcgtgagct atgagaaagc gccacgcttc ccgaagggag aaaggcggac    9960
aggtatccgg taagcggcag ggtcggaaca ggagagcgca cgagggagct tccaggggga   10020
aacgcctggt atctttatag tcctgtcggg tttcgccacc tctgacttga gcgtcgattt   10080
ttgtgatgct cgtcaggggg gcggagccta tggaaaaacg ccagcaacgc ggccttttta   10140
cggttcctgg ccttttgctg gccttttgct cacatgttct ttcctgcgtt atcccctgat   10200
tctgtggata accgtattac cgcctttgag tgagctgata ccgctcgccg cagccgaacg   10260
accgagcgca gcgagtcagt gagcgaggaa gcggaagagc gcccaatacg caaaccgcct   10320
ctccccgcgc gttggccgat tcattaatgc agctggcacg acaggtttcc cgactggaaa   10380
gcgggcagtg agcgcaacgc aattaatgtg agttagctca ctcattaggc acccccaggct   10440 ttacacttta tgcttccggc tcgtatgttg tgtggaattg tgagcggata acaatttcac   10500
acaggaaaca gctatgacca tgattacgcc aagcgcgcaa ttaaccctca ctaaagggaa   10560
caaaagctgg agctgcaagc ttgg                                          10584
```

<210> SEQ ID NO 76
<211> LENGTH: 10584
<212> TYPE: DNA
<213> ORGANISM: Artificial Sequence
<220> FEATURE:

<223> OTHER INFORMATION: LV.GLOBE-AS3modified.gRNA-13bp-del

<400> SEQUENCE: 76

```
ccattgcata cgttgtatcc atatcataat atgtacattt atattggctc atgtccaaca      60
ttaccgccat gttgacattg attattgact agtattaat agtaatcaat tacggggtca     120
ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc ggggtctctc tggttagacc agatctgagc ctgggagctc tctggctaac    720
tagggaaccc actgcttaag cctcaataaa gcttgccttg agtgcttcaa gtagtgtgtg    780
cccgtctgtt gtgtgactct ggtaactaga gatccctcag accctttag tcagtgtgga     840
aaatctctag cagtggcgcc cgaacaggga cttgaaagcg aaaggaaac cagaggagct      900
ctctcgacgc aggactcggc ttgctgaagc gcgcacggca agaggcgagg ggcggcgact    960
ggtgagtacg ccaaaaattt tgactagcgg aggctagaag gagagagatg ggtgcgagag   1020
cgtcagtatt aagcggggga gaattagatc gcgatgggaa aaaattcggt taaggccagg   1080
gggaaagaaa aaatataat taaaacatat agtatgggca agcagggagc tagaacgatt    1140
cgcagttaat cctggcctgt tagaaacatc agaaggctgt agacaaatac tgggacagct   1200
acaaccatcc cttcagacag gatcagaaga acttagatca ttatataata cagtagcaac   1260
cctctattgt gtgcatcaaa ggatagagat aaaagacacc aaggaagctt tagacaagat   1320
agaggaagag caaaacaaaa gtaagaccac cgcacagcaa gcggccgctg atcttcagac   1380
ctggaggagg agatatgagg gacaattgga gaagtgaatt atataaatat aaagtagtaa   1440
aaattgaacc attaggagta gcacccacca aggcaaagag aagagtggtg cagagagaaa   1500
aaagagcagt gggaatagga gctttgttcc ttgggttctt gggagcagca ggaagcacta   1560
tgggcgcagc gtcaatgacg ctgacggtac aggccagaca attattgtct ggtatagtgc   1620
agcagcagaa caatttgctg agggctattg aggcgcaaca gcatctgttg caactcacag   1680
tctgggcat caagcagctc caggcaagaa tcctggctgt ggaaagatac ctaaaggatc    1740
aacagctcct ggggatttgg ggttgctctg gaaaactcat ttgcaccact gctgtgcctt   1800
ggaatgctag ttggagtaat aaatctctgg aacagatttg gaatcacacg acctggatgg   1860
agtgggacag agaaattaac aattacacaa gcttaataca ctccttaatt gaagaatcgc   1920
aaaaccagca agaaaagaat gaacaagaat tattggaatt agataaatgg gcaagtttgt   1980
ggaattggtt taacataaca aattggctgt ggtatataaa attattcata atgatagtag   2040
gaggcttggt aggtttaaga atagtttttg ctgtactttc tatagtgaat agagttaggc   2100
agggatattc accattatcg tttcagaccc acctcccaac cccgagggga cccgacaggc   2160
ccgaaggaat agaagaagaa ggtggagaga gagacagaga cagatccatt cgattagtga   2220
acggatctcg acggtatcgg ttaacttta aagaaaagg ggggattggg gggtacagtg     2280
```

```
caggggaaag aatagtagac ataatagcaa cagacataca aactaaagaa ttacaaaaac    2340
aaattacaaa attcaaaatt ttatcggtac gtaccatgag gacagctaaa acaataagta    2400
atgtaaaata cagcatagca aaactttaac ctccaaatca agcctctact tgaatccttt    2460
tctgagggat gaataaggca taggcatcag gggctgttgc caatgtgcat tagctgtttg    2520
cagcctcacc ttctttcatg gagtttaaga tatagtgtat tttcccaagg tttgaactag    2580
ctcttcattt ctttatgttt taaatgcact gacctcccac attccctttt tagtaaaata    2640
ttcagaaata atttaaatac atcattgcaa tgaaaataaa tgttttttat taggcagaat    2700
ccagatgctc aaggcccttc ataatatccc ccagtttagt agttggactt agggaacaaa    2760 ggaacccttta atagaaattg gacagcaaga aagcgagctt agtgatactt gtgggccagg    2820
gcattagcca caccagccac cactttctga taggcagcct gcactggtgg ggtgaattct    2880
ttgccaaagt gatgggccag cacacagacc agcacgttgc ccaggagctg tgggaggaag    2940
ataagaggta tgaacatgat tagcaaaagg gcctagcttg gactcagaat aatccagcct    3000
tatcccaacc ataaaataaa agcagaatgg tagctggatt gtagctgcta ttagcaatat    3060
gaaacctctt acatcagtta caatttatat gcagaaatac cctgttactt ctccccttcc    3120
tatgacatga acttaaccat agaaaagaag gggaaagaaa acatcaaggg tcccatagac    3180
tcaccctgaa gttctcagga tccacgtgca gcttgtcaca gtgcagctca ctcagctggg    3240
caaaggtgcc cttgaggttg tccaggtgag ccaggccatc actaaaggca ccgagcactt    3300
tcttgccatg agccttcacc ttaggggttgc ccataacagc atcaggagtg gacagatccc    3360
caaaggactc aaagaacctc tgggtccaag ggtagaccac cagcagccta agggtgggaa    3420
aatagaccaa taggcagaga gagtcagtgc ctatcagaaa cccaagagtc ttctctgtct    3480
ccacatgccc agtttctatt ggtctcctta aacctgtctt gtaaccttga taccaacctg    3540
cccagggcct caccaccaac ggcatccacg ttcaccttgt cccagagagc ggtcacagcg    3600
gacttctcct caggagtcag gtgcaccatg gtgtctgttt gaggttgcta gtgaacacag    3660
ttgtgtcaga agcaaatgta agcaatagat ggctctgccc tgacttttat gcccagccct    3720
ggctcctgcc ctccctgctc ctgggagtag attggccaac ctagggtgt ggctccacag    3780 ggtgaggtct aagtgatgac agccgtacct gtccttggct cttctggcac tggcttagga    3840
gttggacttc aaaccctcag ccctccctct aagatatatc tcttggcccc ataccatcag    3900
tacaaattgc tactaaaaac atcctccttt gcaagtgtat ttacacggta tcgataagct    3960
tgatatcgaa ttcctgcagc ccccttttgc cacctagctg tccaggggtg ccttaaaatg    4020
gcaaacaagg tttgttttct tttcctgttt tcatgccttc ctcttccata tccttgtttc    4080
atattaatac atgtgtatag atcctaaaaa tctatacaca tgtattaata aagcctgatt    4140
ctgccgcttc taggtataga ggccacctgc aagataaata tttgattcac aataactaat    4200
cattctatgg caattgataa caacaaatat atatatatat atatatacgt atatgtgtat    4260
atatatatat atatattcag gaaataatat attctagaat atgtcacatt ctgtctcagg    4320
catccatttt ctttatgatg ccgtttgagg tggagtttta gtcaggtggt cagcttctcc    4380
ttttttttgc catctgccct gtaagcatcc tgctggggac ccagatagga gtcatcactc    4440
taggctgaga acatctgggc acacacccta agcctcagca tgactcatca tgactcagca    4500
ttgctgtgct tgagccagaa ggtttgctta gaaggttaca cagaaccaga aggcgggggt    4560
ggggcactga ccccgacagg ggcctggcca gaactgctca tgcttggact atgggaggtc    4620
```

```
actaatggag acacacagaa atgtaacagg aactaaggaa aaactgaagc ttatttaatc    4680
agagatgagg atgctggaag ggatagaggg agctgagctt gtaaaaagta tagtaatcat    4740
tcagcaaatg gttttgaagc acctgctgga tgctaaacac tattttcagt gcttgaatca    4800
taaataagaa taaacatgt atcttattcc ccacagagt ccaagtaaaa aataacagtt      4860
aattataatg tgctctgtcc cccaggctgg agtgcagtgg cacgatctca gctcactgca    4920
acctccgcct cccgggttca gcaattctc ctgcctcagc caccctaata gctgggatta    4980
caggtgcaca ccaccatgcc aggctaattt ttgtactttt tgtagaggca gggtatcacc    5040
atgttgtcca agatggtctt gaactcctga gctccaagca gtccacccac ctcagcctcc    5100
caaagtgctg ggattacagg tgtgagacac catgcccaga ttttccatat ttaatagagg    5160
tatttatggg atgggggaaa agaatgtttc tctcactgtg gattatttta gagagtggag    5220
aatggtcaag atttttttaa aaattaagaa aacataagtt ggaccttgag aaatgaaaat    5280
ttattttttt gttggaggat acccattctc tatctcccat cagggcaagc tgtaaggaac    5340
tggctaagac acagtgagac agagtgactt agtcttagag gccccactgg tacgacggtc    5400
accaagcttt cattaaaaaa agtctaacca gctgcattcg actttgactg cagcagctgg    5460
ttagaaggtt ctactggagg agggtcccag cccattgcta aattaacatc aggctctgag    5520
actggcagta tatctctaac agtggttgat gctatcttct ggaacttgcc tgctacattg    5580
agaccactga cccatacata ggaagcccat agctctgtcc tgaactgtta ggccactggt    5640
ccagagagtg tgcatctcct ttgatcctca taataaccct atgagataga cacaattatt    5700
actcttactt tatagatgat gatcctgaaa acataggagt caaggcactt gcccctagct    5760
gggggtatag gggagcagtc ccatgtagta gtagaatgaa aaatgctgct atgctgtgcc    5820
tcccccacct ttcccatgtc tgccctctac tcatggtcta tctctcctgg ctcctgggag    5880
tcatggactc cacccagcac caccaacctg acctaaccac ctatctgagc ctgccagcct    5940
ataacccatc tgggccctga tagctggtgg ccagccctga ccccacccca ccctccctgg    6000
aacctctgat agacacatct ggcacaccag ctcgcaaagt caccgtgagg gtcttgtgtt    6060
tgctgagtca aaattccttg aaatccaagt ccttagagac tcctgctccc aaatttacag    6120
tcatagactt cttcatggct gtctccttta tccacagaat gattcctttg cttcattgcc    6180
ccatccatct gatcctcctc atcagtgcag cacagggccc atgagcagta gctgcagagt    6240
ctcacatagg tctggcactg cctctgacat gtccgacctt aggcaaatgc ttgactcttc    6300
tgagctcagt cttgtcatgg caaaataaag ataataatag tgttttttta tggagttagc    6360
gtgaggatgg aaaacaatag caaaattgat tagactataa aaggtctcaa caaatagtag    6420
tagattttat catccattaa tccttccctc tcctctctta ctcatcccat cacgtatgcc    6480
tcttaatttt cccttaccta taataagagt tattcctctt attatattct tcttatagtg    6540
attctggata ttaaagtggg aatgaggggc aggccactaa cgaagaagat gtttctcaaa    6600
gaagcggggg atccgtcgac aggtcgggca ggaagagggc ctatttccca tgattccttc    6660
atatttgcat atacgataca aggctgttag agagataatt agaattaatt tgactgtaaa    6720
cacaaagata ttagtacaaa atacgtacg tagaaagtaa taatttcttg ggtagtttgc     6780
agttttaaaa ttatgttttta aaatggacta tcatatgctt accgtaactt gaaagtattt    6840
cgatttcttg gctttatata tcttgtggaa aggacgaaac accgcttgtc aaggctattg    6900
gtcagtttca gagctatgct ggaaacagca tagcaagttg aaataaggct agtccgttat    6960
caacttgaaa aagtggcacc gagtcggtgc ttttttgtc gacactagtt ctagagcggc     7020
```

-continued

```
caaatggcgg ccgtacccttt aagaccaatg acttacaagg cagctgtaga tcttagccac    7080 ttttttaaaag aaaagggggg actggaaggg ctaattcact cccaacgaag acaagatctg    7140 cttttttgctt gtactgggtc tctctggtta gaccagatct gagcctggga gctctctggc    7200
taactaggga acccactgct taagcctcaa taaagcttgc cttgagtgct tcaagtagtg    7260
tgtgcccgtc tgttgtgtga ctctggtaac tagagatccc tcagaccctt ttagtcagtg    7320
tggaaaatct ctagcagtag tagttcatgt catcttatta ttcagtattt ataacttgca    7380
aagaaatgaa tatcagagag tgagaggaac ttgtttattg cagcttataa tggttacaaa    7440
taaagcaata gcatcacaaa tttcacaaat aaagcatttt tttcactgca ttctagttgt    7500
ggtttgtcca aactcatcaa tgtatcttat catgtctggc tctagctatc ccgcccctaa    7560
ctccgcccat cccgcccta actccgccca gttccgccca ttctccgccc catggctgac    7620
taattttttt tatttatgca gaggccgagg ccgcctcggc ctctgagcta ttccagaagt    7680
agtgaggagg cttttttgga ggcctaggga cgtacccaat tcgccctata gtgagtcgta    7740
ttacgcgcgc tcactggccg tcgttttaca acgtcgtgac tgggaaaacc ctggcgttac    7800
ccaacttaat cgccttgcag cacatccccc tttcgccagc tggcgtaata gcgaagaggc    7860
ccgcaccgat cgcccttccc aacagttgcg cagcctgaat ggcgaatggg acgcgccctg    7920
tagcggcgca ttaagcgcgg cgggtgtggt ggttacgcgc agcgtgaccg ctacacttgc    7980
cagcgcccta gcgcccgctc ctttcgcttt cttcccttcc tttctcgcca cgttcgccgg    8040
ctttccccgt caagctctaa atcggggggct ccctttaggg ttccgattta gtgctttacg    8100
gcacctcgac cccaaaaaac ttgattaggg tgatggttca cgtagtgggc catcgccctg    8160
atagacggtt tttcgccctt tgacgttgga gtccacgttc tttaatagtg gactcttgtt    8220
ccaaactgga acaacactca accctatctc ggtctattct tttgatttat aagggatttt    8280
gccgatttcg gcctattggt taaaaaatga gctgatttaa caaaaattta acgcgaattt    8340
taacaaaata ttaacgctta caatttaggt ggcacttttc ggggaaatgt gcgcggaacc    8400
cctatttgtt tatttttcta aatacattca aatatgtatc cgctcatgag acaataaccc    8460
tgataaatgc ttcaataata ttgaaaaagg aagagtatga gtattcaaca tttccgtgtc    8520
gcccttattc cctttttgc ggcatttttgc cttcctgttt ttgctcaccc agaaacgctg    8580
gtgaaagtaa aagatgctga agatcagttg ggtgcacgag tgggttacat cgaactggat    8640
ctcaacagcg gtaagatcct tgagagtttt cgccccgaag aacgttttcc aatgatgagc    8700
acttttaaag ttctgctatg tggcgcggta ttatcccgta ttgacgccgg gcaagagcaa    8760
ctcggtcgcc gcatacacta ttctcagaat gacttggttg agtactcacc agtcacagaa    8820
aagcatctta cggatggcat gacagtaaga gaattatgca gtgctgccat aaccatgagt    8880
gataacactg cggccaactt acttctgaca acgatcggag gaccgaagga gctaaccgct    8940
tttttgcaca acatggggga tcatgtaact cgccttgatc gttgggaacc ggagctgaat    9000
gaagccatac caaacgacga gcgtgacacc acgatgcctg tagcaatggc aacaacgttg    9060
cgcaaactat taactggcga actacttact ctagcttccc ggcaacaatt aatagactgg    9120
atggaggcgg ataaagttgc aggaccactt ctgcgctcgg cccttccggc tggctggttt    9180
attgctgata aatctggagc cggtgagcgt gggtctcgcg gtatcattgc agcactgggg    9240
ccagatggta agccctcccg tatcgtagtt atctacacga cggggagtca ggcaactatg    9300
gatgaacgaa atagacagat cgctgagata ggtgcctcac tgattaagca ttggtaactg    9360
```

-continued

```
tcagaccaag tttactcata tatactttag attgatttaa aacttcattt ttaatttaaa    9420
aggatctagg tgaagatcct ttttgataat ctcatgacca aaatcccctta acgtgagttt    9480 tcgttccact gagcgtcaga ccccgtagaa aagatcaaag gatcttcttg agatcctttt    9540
tttctgcgcg taatctgctg cttgcaaaca aaaaaccac cgctaccagc ggtggtttgt    9600
ttgccggatc aagagctacc aactctttt ccgaaggtaa ctggcttcag cagagcgcag    9660
ataccaaata ctgttcttct agtgtagccg tagttaggcc accttcaa gaactctgta    9720 gcaccgccta catacctcgc tctgctaatc ctgttaccag tggctgctgc cagtggcgat    9780
aagtcgtgtc ttaccgggtt ggactcaaga cgatagttac cggataaggc gcagcggtcg    9840
ggctgaacgg ggggttcgtg cacacagccc agcttggagc gaacgaccta caccgaactg    9900
agatacctac agcgtgagct atgagaaagc gccacgcttc ccgaagggag aaaggcggac    9960
aggtatccgg taagcggcag ggtcggaaca ggagagcgca cgagggagct tccaggggga   10020
aacgcctggt atctttatag tcctgtcggg tttcgccacc tctgacttga gcgtcgattt   10080
ttgtgatgct cgtcagggggg gcggagccta tggaaaaacg ccagcaacgc ggccttttta   10140
cggttcctgg ccttttgctg gccttttgct cacatgttct ttcctgcgtt atcccctgat   10200
tctgtggata accgtattac cgcctttgag tgagctgata ccgctcgccg cagccgaacg   10260
accgagcgca gcgagtcagt gagcgaggaa gcggaagagc gcccaatacg caaaccgcct   10320
ctccccgcgc gttggccgat tcattaatgc agctggcacg acaggtttcc cgactggaaa   10380
gcgggcagtg agcgcaacgc aattaatgtg agttagctca ctcattaggc accccaggct   10440
ttacacttta tgcttccggc tcgtatgttg tgtggaattg tgagcggata acaatttcac   10500
acaggaaaca gctatgacca tgattacgcc aagcgcgcaa ttaaccctca ctaaagggaa   10560
caaaagctgg agctgcaagc ttgg                                        10584
```

```
<210> SEQ ID NO 77
<211> LENGTH: 20
<212> TYPE: DNA
<213> ORGANISM: Artificial Sequence
<220> FEATURE:
<223> OTHER INFORMATION: BCL11A-TIDE FORWARD

<400> SEQUENCE: 77
tggacagccc gacagatgaa                                              20

<210> SEQ ID NO 78
<211> LENGTH: 20
<212> TYPE: DNA
<213> ORGANISM: Artificial Sequence
<220> FEATURE:
<223> OTHER INFORMATION: BCL11A-TIDE REVERSE

<400> SEQUENCE: 78
aaaagcgata cagggctggc                                              20

<210> SEQ ID NO 79
<211> LENGTH: 30
<212> TYPE: DNA
<213> ORGANISM: Artificial Sequence
<220> FEATURE:
<223> OTHER INFORMATION: 13bp-del-TIDE FORWARD

<400> SEQUENCE: 79
aaaaacggct gacaaaagaa gtcctggtat                                   30
```

```
<210> SEQ ID NO 80
<211> LENGTH: 30
<212> TYPE: DNA
<213> ORGANISM: Artificial Sequence
<220> FEATURE:
<223> OTHER INFORMATION: 13bp-del-TIDE REVERSE

<400> SEQUENCE: 80
ataacctcag acgttccaga agcgagtgtg                                           30

<210> SEQ ID NO 81
<211> LENGTH: 19
<212> TYPE: DNA
<213> ORGANISM: Artificial Sequence
<220> FEATURE:
<223> OTHER INFORMATION: HBG1 + HBG2   FORWARD

<400> SEQUENCE: 81
cctgtcctct gcctctgcc                                                       19

<210> SEQ ID NO 82
<211> LENGTH: 19
<212> TYPE: DNA
<213> ORGANISM: Artificial Sequence
<220> FEATURE:
<223> OTHER INFORMATION: HBG1 + HBG2 REVERSE

<400> SEQUENCE: 82
ggattgccaa aacggtcac                                                       19

<210> SEQ ID NO 83
<211> LENGTH: 18
<212> TYPE: DNA
<213> ORGANISM: Artificial Sequence
<220> FEATURE:
<223> OTHER INFORMATION: HBB FORWARD

<400> SEQUENCE: 83
aagggcacct ttgccaca                                                        18

<210> SEQ ID NO 84
<211> LENGTH: 22
<212> TYPE: DNA
<213> ORGANISM: Artificial Sequence
<220> FEATURE:
<223> OTHER INFORMATION: HBB REVERSE

<400> SEQUENCE: 84
gccaccactt tctgataggc ag                                                   22

<210> SEQ ID NO 85
<211> LENGTH: 19
<212> TYPE: DNA
<213> ORGANISM: Artificial Sequence
<220> FEATURE:
<223> OTHER INFORMATION: HBD FORWARD

<400> SEQUENCE: 85
caagggcact ttttctcag                                                       19

<210> SEQ ID NO 86
<211> LENGTH: 19
<212> TYPE: DNA
<213> ORGANISM: Artificial Sequence
<220> FEATURE:
<223> OTHER INFORMATION: HBD REVERSE
```

<400> SEQUENCE: 86
aattccttgc caaagttgc                                                    19

<210> SEQ ID NO 87
<211> LENGTH: 20
<212> TYPE: DNA
<213> ORGANISM: Artificial Sequence
<220> FEATURE:
<223> OTHER INFORMATION: BCL11A FORWARD

<400> SEQUENCE: 87
aaccccagca cttaagcaaa                                                   20

<210> SEQ ID NO 88
<211> LENGTH: 20
<212> TYPE: DNA
<213> ORGANISM: Artificial Sequence
<220> FEATURE:
<223> OTHER INFORMATION: BCL11A REVERSE

<400> SEQUENCE: 88
ggaggtcatg atcccttct                                                    20

<210> SEQ ID NO 89
<211> LENGTH: 20
<212> TYPE: DNA
<213> ORGANISM: Artificial Sequence
<220> FEATURE:
<223> OTHER INFORMATION: BCL11AXL FORWARD

<400> SEQUENCE: 89
atgcgagctg tgcaactatg                                                   20

<210> SEQ ID NO 90
<211> LENGTH: 20
<212> TYPE: DNA
<213> ORGANISM: Artificial Sequence
<220> FEATURE:
<223> OTHER INFORMATION: BCL11AXL REVERSE

<400> SEQUENCE: 90
gtaaacgtcc ttccccacct                                                   20

<210> SEQ ID NO 91
<211> LENGTH: 26
<212> TYPE: DNA
<213> ORGANISM: Artificial Sequence
<220> FEATURE:
<223> OTHER INFORMATION: GAPDH FORWARD

<400> SEQUENCE: 91
cttcattgac ctcaactaca tggttt                                            26

<210> SEQ ID NO 92
<211> LENGTH: 22
<212> TYPE: DNA
<213> ORGANISM: Artificial Sequence
<220> FEATURE:
<223> OTHER INFORMATION: GAPDH REVERSE

<400> SEQUENCE: 92
tgggatttcc attgatgaca ag                                                22

<210> SEQ ID NO 93
<211> LENGTH: 10584

```
<212> TYPE: DNA
<213> ORGANISM: Artificial Sequence
<220> FEATURE:
<223> OTHER INFORMATION: LV.GLOBE-AS3modified.gRNA-luciferase

<400> SEQUENCE: 93
ccattgcata cgttgtatcc atatcataat atgtacattt atattggctc atgtccaaca      60
ttaccgccat gttgacattg attattgact agttattaat agtaatcaat acggggtca     120
ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccacccat tgacgtcaat     540
gggagtttgt tttggcacca aaatcaacgg gactttccaa aatgtcgtaa caactccgcc    600
ccattgacga aaatgggcgg taggcgtgta cggtgggagg tctatataag cagagctcgt    660
ttagtgaacc ggggtctctc tggttagacc agatctgagc ctgggagctc tctggctaac    720
tagggaaccc actgcttaag cctcaataaa gcttgccttg agtgcttcaa gtagtgtgtg    780
cccgtctgtt gtgtgactct ggtaactaga gatccctcag acccttttag tcagtgtgga    840
aaatctctag cagtggcgcc cgaacaggga cttgaaagcg aaagggaaac cagaggagct    900
ctctcgacgc aggactcggc ttgctgaagc gcgcacggca agaggcgagg ggcggcgact    960
ggtgagtacg ccaaaaattt tgactagcgg aggctagaag gagagagatg ggtgcgagag   1020
cgtcagtatt aagcggggga gaattagatc gcgatgggaa aaaattcggt taaggccagg   1080
gggaaagaaa aaatataaat taaaacatat agtatgggca agcagggagc tagaacgatt   1140
cgcagttaat cctggcctgt tagaaacatc agaaggctgt agacaaatac tgggacagct   1200
acaaccatcc cttcagacag gatcagaaga acttagatca ttatataata cagtagcaac   1260
cctctattgt gtgcatcaaa ggatagagat aaaagacacc aaggaagctt tagacaagat   1320
agaggaagag caaaacaaaa gtaagaccac cgcacagcaa gcggccgctg atcttcagac   1380
ctggaggagg agatatgagg gacaattgga gaagtgaatt atataaatat aaagtagtaa   1440
aaattgaacc attaggagta gcacccacca aggcaaagag aagagtggtg cagagagaaa   1500
aaagagcagt gggaatagga gctttgttcc ttgggttctt gggagcagca ggaagcacta   1560
tgggcgcagc gtcaatgacg ctgacggtac aggccagaca attattgtct ggtatagtgc   1620
agcagcagaa caatttgctg agggctattg aggcgcaaca gcatctgttg caactcacag   1680
tctggggcat caagcagctc caggcaagaa tcctggctgt ggaaagatac ctaaaggatc   1740
aacagctcct ggggatttgg ggttgctctg gaaaactcat ttgcaccact gctgtgcctt   1800
ggaatgctag ttggagtaat aaatctctgg aacagatttg gaatcacacg acctggatgg   1860
agtgggacag agaaattaac aattacacaa gcttaataca ctccttaatt gaagaatcgc   1920
aaaaccagca agaaaagaat gaacaagaat tattggaatt agataaatgg gcaagtttgt   1980
ggaattggtt taacataaca aattggctgt ggtatataaa attattcata atgatagtag   2040
gaggcttggt aggtttaaga atagtttttg ctgtactttc tatagtgaat agagttaggc   2100
agggatattc accattatcg tttcagaccc acctcccaac cccgagggga cccgacaggc   2160
```

```
ccgaaggaat agaagaagaa ggtggagaga gagacagaga cagatccatt cgattagtga    2220
acggatctcg acggtatcgg ttaactttta aaagaaaagg ggggattggg gggtacagtg    2280
caggggaaag aatagtagac ataatagcaa cagacataca aactaaagaa ttacaaaaac    2340
aaattacaaa attcaaaatt ttatcggtac gtaccatgag acagctaaa acaataagta    2400
atgtaaaata cagcatagca aaactttaac ctccaaatca agcctctact tgaatccttt    2460
tctgagggat gaataaggca taggcatcag gggctgttgc caatgtgcat tagctgtttg    2520
cagcctcacc ttctttcatg gagtttaaga tatagtgtat tttcccaagg tttgaactag    2580
ctcttcattt ctttatgttt taaatgcact gacctcccac attccctttt tagtaaaata    2640
ttcagaaata atttaaatac atcattgcaa tgaaaataaa tgtttttat taggcagaat     2700
ccagatgctc aaggcccttc ataatatccc ccagtttagt agttggactt agggaacaaa    2760
ggaacccttta atagaaattg gacagcaaga aagcgagctt agtgatactt gtgggccagg   2820
gcattagcca caccagccac cacttttctga taggcagcct gcactggtgg ggtgaattct   2880
ttgccaaagt gatgggccag cacacagacc agcacgttgc ccaggagctg tgggaggaag   2940
ataagaggta tgaacatgat tagcaaaagg gcctagcttg gactcagaat aatccagcct    3000
tatcccaacc ataaaataaa agcagaatgg tagctggatt gtagctgcta ttagcaatat    3060
gaaacctctt acatcagtta caatttatat gcagaaatac cctgttactt ctccccttcc    3120
tatgacatga acttaaccat agaaaagaag gggaaagaaa acatcaaggg tcccatagac    3180
tcaccctgaa gttctcagga tccacgtgca gcttgtcaca gtgcagctca ctcagctggg    3240
caaaggtgcc cttgaggttg tccaggtgag ccaggccatc actaaaggca ccgagcactt    3300
tcttgccatg agccttcacc ttagggttgc ccataacagc atcaggagtg acagatccc    3360
caaaggactc aaagaacctc tgggtccaag ggtagaccac cagcagccta agggtgggaa   3420
aatagaccaa taggcagaga gagtcagtgc ctatcagaaa cccaagagtc ttctctgtct    3480
ccacatgccc agtttctatt ggtctcctta aacctgtctt gtaacttga taccaacctg    3540
cccagggcct caccaccaac ggcatccacg ttcaccttgt cccagagagc ggtcacagcg   3600
gacttctcct caggagtcag gtgcaccatg gtgtctgttt gaggttgcta gtgaacacag   3660
ttgtgtcaga agcaaatgta agcaatagat ggctctgccc tgacttttat gcccagccct   3720
ggctcctgcc ctccctgctc ctgggagtag attggccaac cctagggtgt ggctccacag    3780
ggtgaggtct aagtgatgac agccgtacct gtccttggct cttctggcac tggcttagga    3840
gttggacttc aaaccctcag ccctccctct aagatatatc tcttggcccc ataccatcag    3900
tacaaattgc tactaaaaac atcctccttt gcaagtgtat ttacacggta tcgataagct   3960
tgatatcgaa ttcctgcagc ccccttttgc cacctagctg tccaggggtg ccttaaaatg    4020
gcaaacaagg tttgttttct tttcctgttt tcatgccttc ctcttccata tccttgtttc    4080
atattaatac atgtgtatag atcctaaaaa tctatacaca tgtattaata aagcctgatt    4140
ctgccgcttc taggtataga ggccacctgc aagataaata tttgattcac aataactaat    4200
cattctatgg caattgataa caacaaatat atatatatat atatatacgt atatgtgtat    4260
atatatatat atatattcag gaaataatat attctagaat atgtcacatt ctgtctcagg    4320
catccatttt ctttatgatg ccgtttgagg tggagtttta gtcaggtggt cagcttctcc    4380
ttttttttgc catctgccct gtaagcatcc tgctggggac ccagatagga gtcatcactc    4440
taggctgaga acatctgggc acacacccta agcctcagca tgactcatca tgactcagca    4500
ttgctgtgct tgagccagaa ggtttgctta gaaggttaca cagaaccaga aggcgggggt    4560
```

```
ggggcactga ccccgacagg ggcctggcca gaactgctca tgcttggact atgggaggtc      4620
actaatggag acacacagaa atgtaacagg aactaaggaa aaactgaagc ttatttaatc      4680
agagatgagg atgctggaag ggatagaggg agctgagctt gtaaaaagta tagtaatcat      4740
tcagcaaatg gttttgaagc acctgctgga tgctaaacac tattttcagt gcttgaatca      4800
taaataagaa taaacatgt atcttattcc ccacaagagt ccaagtaaaa aataacagtt       4860
aattataatg tgctctgtcc cccaggctgg agtgcagtgg cacgatctca gctcactgca      4920
acctccgcct cccgggttca agcaattctc ctgcctcagc caccctaata gctgggatta     4980
caggtgcaca ccaccatgcc aggctaattt ttgtactttt tgtagaggca gggtatcacc      5040
atgttgtcca agatggtctt gaactcctga gctccaagca gtccacccac ctcagcctcc      5100
caaagtgctg ggattacagg tgtgagacac catgcccaga ttttccatat ttaatagagg      5160
tatttatggg atggggaaaa agaatgtttc tctcactgtg gattatttta gagagtggag      5220
aatggtcaag attttttttaa aaattaagaa aacataagtt ggaccttgag aaatgaaaat     5280
ttattttttt gttggaggat acccattctc tatctcccat cagggcaagc tgtaaggaac      5340
tggctaagac acagtgagac agagtgactt agtcttagag gccccactgg tacgacggtc      5400
accaagcttt cattaaaaaa agtctaacca gctgcattcg actttgactg cagcagctgg      5460
ttagaaggtt ctactggagg agggtcccag cccattgcta aattaacatc aggctctgag      5520
actggcagta tatctctaac agtggttgat gctatcttct ggaacttgcc tgctacattg      5580
agaccactga cccatacata ggaagcccat agctctgtcc tgaactgtta ggccactggt      5640
ccagagagtg tgcatctcct ttgatcctca taataaccct atgagataga cacaattatt      5700
actcttactt tatagatgat gatcctgaaa acataggagt caaggcactt gccctagct      5760 gggggtatag gggagcagtc ccatgtagta gtagaatgaa aaatgctgct atgctgtgcc      5820 tccccacct ttcccatgtc tgccctctac tcatggtcta tctctcctgg ctcctgggag       5880
tcatggactc cacccagcac caccaacctg acctaaccac ctatctgagc ctgccagcct      5940
ataacccatc tgggccctga tagctggtgg ccagccctga ccccacccca ccctccctgg      6000
aacctctgat agacacatct ggcacaccag ctcgcaaagt caccgtgagg gtcttgtgtt      6060
tgctgagtca aaattccttg aaatccaagt ccttagagac tcctgctccc aaatttacag      6120
tcatagactt cttcatggct gtctcctta tccacagaat gattcctttg cttcattgcc       6180
ccatccatct gatcctcctc atcagtgcag cacagggccc atgagcagta gctgcagagt      6240
ctcacatagg tctggcactg cctctgacat gtccgacctt aggcaaatgc ttgactcttc      6300
tgagctcagt cttgtcatgg caaaataaag ataataatag tgttttttta tggagttagc      6360
gtgaggatgg aaaacaatag caaaattgat tagactataa aaggtctcaa caaatagtag      6420
tagattttat catccattaa tccttccctc tcctctctta ctcatcccat cacgtatgcc      6480
tcttaatttt cccttaccta taataagagt tattcctctt attatattct tcttatagtg      6540
attctggata ttaaagtggg aatgagggc aggccactaa cgaagaagat gtttctcaaa       6600
gaagcggggg atccgtcgac aggtcgggca ggaagagggc ctatttccca tgattccttc      6660
atatttgcat atacgataca aggctgttag agagataatt agaattaatt tgactgtaaa      6720
cacaaagata ttagtacaaa atacgtgacg tagaaagtaa taatttcttg ggtagtttgc      6780
agttttaaaa ttatgtttta aaatggacta tcatatgctt accgtaactt gaaagtattt      6840
cgatttcttg gctttatata tcttgtggaa aggacgaaac accgcttcga aatgtccgtt      6900
```

```
cggtgtttca gagctatgct ggaaacagca tagcaagttg aaataaggct agtccgttat    6960
caacttgaaa aagtggcacc gagtcggtgc ttttttttgtc gacactagtt ctagagcggc    7020
caaatggcgg ccgtaccttt aagaccaatg acttacaagg cagctgtaga tcttagccac    7080 ttttttaaaag aaaaggggggg actggaaggg ctaattcact cccaacgaag acaagatctg    7140 cttttttgctt gtactgggtc tctctggtta gaccagatct gagcctggga gctctctggc    7200
taactaggga acccactgct taagcctcaa taaagcttgc cttgagtgct tcaagtagtg    7260
tgtgcccgtc tgttgtgtga ctctggtaac tagagatccc tcagaccctt ttagtcagtg    7320
tggaaaatct ctagcagtag tagttcatgt catcttatta ttcagtattt ataacttgca    7380
aagaaatgaa tatcagagag tgagaggaac ttgtttattg cagcttataa tggttacaaa    7440
taaagcaata gcatcacaaa tttcacaaat aaagcatttt tttcactgca ttctagttgt    7500
ggtttgtcca aactcatcaa tgtatcttat catgtctggc tctagctatc ccgcccctaa    7560
ctccgcccat cccgcccta actccgccca gttccgccca ttctccgccc catggctgac    7620 taatttttttt tatttatgca gaggccgagg ccgcctcggc ctctgagcta ttccagaagt    7680
agtgaggagg cttttttgga ggcctaggga cgtacccaat cgccctata gtgagtcgta    7740 ttacgcgcgc tcactggccg tcgttttaca acgtcgtgac tgggaaaacc ctggcgttac    7800
ccaacttaat cgccttgcag cacatccccc tttcgccagc tggcgtaata gcgaagaggc    7860
ccgcaccgat cgcccttccc aacagttgcg cagcctgaat ggcgaatggg acgcgccctg    7920
tagcggcgca ttaagcgcgg cgggtgtggt ggttacgcgc agcgtgaccg ctacacttgc    7980
cagcgcccta gcgcccgctc ctttcgcttt cttcccttcc tttctcgcca cgttcgccgg    8040
ctttccccgt caagctctaa atcgggggct ccctttaggg ttccgattta gtgctttacg    8100
gcacctcgac cccaaaaaac ttgattaggg tgatggttca cgtagtgggc catcgccctg    8160
atagacggtt tttcgccctt tgacgttgga gtccacgttc tttaatagtg gactcttgtt    8220
ccaaactgga acaacactca accctatctc ggtctattct tttgatttat aagggatttt    8280
gccgatttcg gcctattggt taaaaaatga ctgatttaa caaaaattta acgcgaattt    8340
taacaaaata ttaacgctta caatttaggt ggcacttttc ggggaaatgt gcgcggaacc    8400
cctatttgtt tatttttcta aatacattca aatatgtatc cgctcatgag acaataaccc    8460
tgataaatgc ttcaataata ttgaaaaagg aagagtatga gtattcaaca tttccgtgtc    8520
gcccttattc ccttttttgc ggcattttgc cttcctgttt ttgctcaccc agaaacgctg    8580
gtgaaagtaa aagatgctga agatcagttg ggtgcacgag tgggttacat cgaactggat    8640
ctcaacagcg gtaagatcct tgagagtttt cgccccgaag aacgttttcc aatgatgagc    8700
acttttaaag ttctgctatg tggcgcggta ttatcccgta ttgacgccgg caagagcaa    8760 ctcggtcgcc gcatacacta ttctcagaat gacttggttg agtactcacc agtcacagaa    8820
aagcatctta cggatggcat gacagtaaga gaattatgca gtgctgccat aaccatgagt    8880
gataacactg cggccaactt acttctgaca acgatcggag gaccgaagga gctaaccgct    8940
tttttgcaca acatggggga tcatgtaact cgccttgatc gttgggaacc ggagctgaat    9000
gaagccatac caaacgacga gcgtgacacc acgatgcctg tagcaatggc aacaacgttg    9060
cgcaaactat taactggcga actacttact ctagcttccc ggcaacaatt aatagactgg    9120
atggaggcgg ataaagttgc aggaccactt ctgcgctcgg cccttccggc tggctggttt    9180
attgctgata aatctggagc cggtgagcgt gggtctcgcg gtatcattgc agcactgggg    9240
ccagatggta agccctcccg tatcgtagtt atctacacga cggggagtca ggcaactatg    9300
```

```
gatgaacgaa atagacagat cgctgagata ggtgcctcac tgattaagca ttggtaactg    9360
tcagaccaag tttactcata tatactttag attgatttaa aacttcattt ttaatttaaa    9420
aggatctagg tgaagatcct ttttgataat ctcatgacca aaatccctta acgtgagttt    9480
tcgttccact gagcgtcaga ccccgtagaa aagatcaaag gatcttcttg agatcctttt    9540
tttctgcgcg taatctgctg cttgcaaaca aaaaaccac cgctaccagc ggtggtttgt     9600
ttgccggatc aagagctacc aactcttttt ccgaaggtaa ctggcttcag cagagcgcag    9660
ataccaaata ctgttcttct agtgtagccg tagttaggcc accacttcaa gaactctgta    9720
gcaccgccta catacctcgc tctgctaatc ctgttaccag tggctgctgc cagtggcgat    9780
aagtcgtgtc ttaccgggtt ggactcaaga cgatagttac cggataaggc gcagcggtcg    9840
ggctgaacgg ggggttcgtg cacacagccc agcttggagc gaacgaccta caccgaactg    9900
agatacctac agcgtgagct atgagaaagc gccacgcttc ccgaagggag aaaggcggac    9960
aggtatccgg taagcggcag ggtcggaaca ggagagcgca cgagggagct tccaggggga    10020
aacgcctggt atctttatag tcctgtcggg tttcgccacc tctgacttga gcgtcgattt    10080
ttgtgatgct cgtcaggggg gcggagccta tggaaaaacg ccagcaacgc ggcctttttta   10140
cggttcctgg ccttttgctg gccttttgct cacatgttct ttcctgcgtt atcccctgat    10200
tctgtggata accgtattac cgcctttgag tgagctgata ccgctcgccg cagccgaacg    10260
accgagcgca gcgagtcagt gagcgaggaa gcggaagagc gcccaatacg caaaccgcct    10320
ctccccgcgc gttggccgat tcattaatgc agctggcacg acaggtttcc cgactggaaa    10380
gcgggcagtg agcgcaacgc aattaatgtg agttagctca ctcattaggc accccaggct    10440
ttacacttta tgcttccggc tcgtatgttg tgtggaattg tgagcggata acaatttcac    10500
acaggaaaca gctatgacca tgattacgcc aagcgcgcaa ttaaccctca ctaaagggaa    10560
caaaagctgg agctgcaagc ttgg                                           10584
```

<210> SEQ ID NO 94
<211> LENGTH: 10583
<212> TYPE: DNA
<213> ORGANISM: Artificial Sequence
<220> FEATURE:
<223> OTHER INFORMATION: LV.GLOBE-AS3modified.gRNAD

<400> SEQUENCE: 94

```
ccattgcata cgttgtatcc atatcataat atgtacattt atattggctc atgtccaaca      60
ttaccgccat gttgacattg attattgact agttattaat agtaatcaat tacgggtca      120
ttagttcata gcccatatat ggagttccgc gttacataac ttacggtaaa tggcccgcct     180
ggctgaccgc ccaacgaccc ccgcccattg acgtcaataa tgacgtatgt tcccatagta     240
acgccaatag ggactttcca ttgacgtcaa tgggtggagt atttacggta aactgcccac     300
ttggcagtac atcaagtgta tcatatgcca agtacgcccc ctattgacgt caatgacggt     360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
ccattgacga aatgggcgg taggcgtgta cggtgggagg tctatataag cagagctcgt     660
ttagtgaacc ggggtctctc tggttagacc agatctgagc ctgggagctc tctggctaac    720
```

```
tagggaaccc actgcttaag cctcaataaa gcttgccttg agtgcttcaa gtagtgtgtg        780
cccgtctgtt gtgtgactct ggtaactaga gatccctcag acccttttag tcagtgtgga        840
aaatctctag cagtggcgcc cgaacaggga cttgaaagcg aaagggaaac cagaggagct        900
ctctcgacgc aggactcggc ttgctgaagc gcgcacggca agaggcgagg ggcggcgact        960
ggtgagtacg ccaaaaattt tgactagcgg aggctagaag gagagagatg ggtgcgagag       1020
cgtcagtatt aagcggggga gaattagatc gcgatgggaa aaaattcggt taaggccagg       1080
gggaaagaaa aaatataaat taaaacatat agtatgggca agcagggagc tagaacgatt       1140
cgcagttaat cctggcctgt tagaaacatc agaaggctgt agacaaatac tgggacagct       1200
acaaccatcc cttcagacag gatcagaaga acttagatca ttatataata cagtagcaac       1260
cctctattgt gtgcatcaaa ggatagagat aaaagacacc aaggaagctt tagacaagat       1320
agaggaagag caaaacaaaa gtaagaccac cgcacagcaa gcggccgctg atcttcagac       1380
ctggaggagg agatatgagg gacaattgga gaagtgaatt atataaatat aaagtagtaa       1440
aaattgaacc attaggagta gcacccacca aggcaaagag aagagtggtg cagagagaaa       1500
aaagagcagt gggaatagga gctttgttcc ttgggttctt gggagcagca ggaagcacta       1560
tgggcgcagc gtcaatgacg ctgacggtac aggccagaca attattgtct ggtatagtgc       1620
agcagcagaa caatttgctg agggctattg aggcgcaaca gcatctgttg caactcacag       1680
tctgggggcat caagcagctc caggcaagaa tcctggctgt ggaaagatac ctaaaggatc       1740
aacagctcct ggggatttgg ggttgctctg gaaaactcat ttgcaccact gctgtgcctt       1800
ggaatgctag ttggagtaat aaatctctgg aacagatttg gaatcacacg acctggatgg       1860
agtgggacag agaaattaac aattacacaa gcttaataca ctccttaatt gaagaatcgc       1920
aaaaccagca agaaaagaat gaacaagaat tattggaatt agataaatgg gcaagtttgt       1980
ggaattggtt taacataaca aattggctgt ggtatataaa attattcata atgatagtag       2040
gaggcttggt aggtttaaga atagttttg ctgtactttc tatagtgaat agagttaggc       2100
agggatattc accattatcg tttcagaccc acctcccaac cccgagggga cccgacaggc       2160
ccgaaggaat agaagaagaa ggtggagaga gagacagaga cagatccatt cgattagtga       2220
acggatctcg acggtatcgg ttaacttttta aaagaaaagg ggggattggg gggtacagtg       2280
caggggaaag aatagtagac ataatagcaa cagacataca aactaaagaa ttacaaaaac       2340
aaattacaaa attcaaaatt ttatcggtac gtaccatgag gacagctaaa acaataagta       2400
atgtaaaata cagcatagca aaactttaac ctccaaatca agcctctact tgaatccttt       2460
tctgagggat gaataaggca taggcatcag gggctgttgc caatgtgcat tagctgtttg       2520
cagcctcacc ttctttcatg gagtttaaga tatagtgtat tttcccaagg tttgaactag       2580
ctcttcattt ctttatgttt taaatgcact gacctcccac attccttttt tagtaaaata       2640
ttcagaaata atttaaatac atcattgcaa tgaaaataaa tgttttttat taggcagaat       2700
ccagatgctc aaggcccttc ataatatccc ccagtttagt agttggactt agggaacaaa       2760
ggaacctttta atagaaattg gacagcaaga aagcgagctt agtgatactt gtgggccagg       2820
gcattagcca caccagccac cactttctga taggcagcct gcactggtgg ggtgaattct       2880
ttgccaaagt gatgggccag cacacagacc agcacgttgc ccaggagctg tgggaggaag       2940
ataagaggta tgaacatgat tagcaaaagg gcctagcttg gactcagaat aatccagcct       3000
tatcccaacc ataaaataaa agcagaatgg tagctggatt gtagctgcta ttagcaatat       3060
gaaacctctt acatcagtta caatttatat gcagaaatac cctgttactt ctccccttcc       3120
```

| | |
|---|---|
| tatgacatga acttaaccat agaaaagaag gggaagaaa acatcaaggg tcccatagac | 3180 |
| tcaccctgaa gttctcagga tccacgtgca gcttgtcaca gtgcagctca ctcagctggg | 3240 |
| caaaggtgcc cttgaggttg tccaggtgag ccaggccatc actaaaggca ccgagcactt | 3300 |
| tcttgccatg agccttcacc ttaggggttgc ccataacagc atcaggagtg acagatccc | 3360 |
| caaaggactc aaagaacctc tgggtccaag ggtagaccac cagcagccta agggtgggaa | 3420 |
| aatagaccaa taggcagaga gagtcagtgc ctatcagaaa cccaagagtc ttctctgtct | 3480 |
| ccacatgccc agtttctatt ggtctcctta aacctgtctt gtaaccttga taccaacctg | 3540 |
| cccagggcct caccaccaac ggcatccacg ttcaccttgt cccagagagc ggtcacagcg | 3600 |
| gacttctcct caggagtcag gtgcaccatg gtgtctgttt gaggttgcta gtgaacacag | 3660 |
| ttgtgtcaga agcaaatgta agcaatagat ggctctgccc tgactttat gcccagccct | 3720 |
| ggctcctgcc ctccctgctc ctgggagtag attggccaac cctagggtgt ggctccacag | 3780 |
| ggtgaggtct aagtgatgac agccgtacct gtccttggct cttctggcac tggcttagga | 3840 |
| gttggacttc aaaccctcag ccctccctct aagatatatc tcttggcccc ataccatcag | 3900 |
| tacaaattgc tactaaaaac atcctccttt gcaagtgtat ttacacggta tcgataagct | 3960 |
| tgatatcgaa ttcctgcagc cccttttgc cacctagctg tccaggggtg ccttaaaatg | 4020 |
| gcaaacaagg tttgttttct tttcctgttt tcatgccttc ctcttccata tccttgtttc | 4080 |
| atattaatac atgtgtatag atcctaaaaa tctatacaca tgtattaata aagcctgatt | 4140 |
| ctgccgcttc taggtataga ggccacctgc aagataaata tttgattcac ataactaat | 4200 |
| cattctatgg caattgataa caacaaatat atatatatat atatatacgt atatgtgtat | 4260 |
| atatatatat atatattcag gaaataatat attctagaat atgtcacatt ctgtctcagg | 4320 |
| catccatttt ctttatgatg ccgtttgagg tggagttta gtcaggtggt cagcttctcc | 4380 |
| ttttttttgc catctgccct gtaagcatcc tgctggggac ccagatagga gtcatcactc | 4440 |
| taggctgaga acatctgggc acacaccta agcctcagca tgactcatca tgactcagca | 4500 |
| ttgctgtgct tgagccagaa ggtttgctta gaaggttaca cagaaccaga aggcggggt | 4560 |
| ggggcactga ccccgacagg ggcctggcca gaactgctca tgcttggact atgggaggtc | 4620 |
| actaatggag acacagaa atgtaacagg aactaaggaa aaactgaagc ttatttaatc | 4680 |
| agagatgagg atgctggaag ggatagaggg agctgagctt gtaaaaagta tagtaatcat | 4740 |
| tcagcaaatg gttttgaagc acctgctgga tgctaaacac tattttcagt gcttgaatca | 4800 |
| taaataagaa taaaacatgt atcttattcc ccacaagagt ccaagtaaaa aataacagtt | 4860 |
| aattataatg tgctctgtcc cccaggctgg agtgcagtgg cacgatctca gctcactgca | 4920 |
| acctccgcct cccgggttca gcaattctc ctgcctcagc cacctaata gctgggatta | 4980 |
| caggtgcaca ccaccatgcc aggctaattt ttgtactttt tgtagaggca gggtatcacc | 5040 |
| atgttgtcca agatggtctt gaactcctga gctccaagca gtccaccac ctcagcctcc | 5100 |
| caaagtgctg ggattacagg tgtgagacac catgcccaga ttttccatat ttaatagagg | 5160 |
| tatttatggg atgggggaaa agaatgtttc tctcactgtg gattattta gagagtggag | 5220 |
| aatggtcaag attttttttaa aaattaagaa aacataagtt ggaccttgag aaatgaaaat | 5280 |
| ttatttttt gttggaggat acccattctc tatctcccat cagggcaagc tgtaaggaac | 5340 |
| tggctaagac acagtgagac agagtgactt agtcttagag gccccactgg tacgacggtc | 5400 |
| accaagcttt cattaaaaaa agtctaacca gctgcattcg actttgactg cagcagctgg | 5460 |

```
ttagaaggtt ctactggagg agggtcccag cccattgcta aattaacatc aggctctgag    5520
actggcagta tatctctaac agtggttgat gctatcttct ggaacttgcc tgctacattg    5580
agaccactga cccatacata ggaagcccat agctctgtcc tgaactgtta ggccactggt    5640
ccagagagtg tgcatctcct ttgatcctca taataaccct atgagataga cacaattatt    5700
actcttactt tatagatgat gatcctgaaa acataggagt caaggcactt gcccctagct    5760
gggggtatag gggagcagtc ccatgtagta gtagaatgaa aaatgctgct atgctgtgcc    5820
tcccccacct ttcccatgtc tgccctctac tcatggtcta tctctcctgg ctcctgggag    5880
tcatggactc cacccagcac caccaacctg acctaaccac ctatctgagc ctgccagcct    5940
ataacccatc tgggccctga tagctggtgg ccagccctga ccccacccca ccctccctgg    6000
aacctctgat agacacatct ggcacaccag ctcgcaaagt caccgtgagg gtcttgtgtt    6060
tgctgagtca aaattccttg aaatccaagt ccttagagac tcctgctccc aaatttacag    6120
tcatagactt cttcatggct gtctccttta tccacagaat gattcctttg cttcattgcc    6180
ccatccatct gatcctcctc atcagtgcag cacagggccc atgagcagta gctgcagagt    6240
ctcacatagg tctggcactg cctctgacat gtccgacctt aggcaaatgc ttgactcttc    6300
tgagctcagt cttgtcatgg caaaataaag ataataaatg tgttttttta tggagttagc    6360
gtgaggatgg aaaacaatag caaaattgat tagactataa aaggtctcaa caaatagtag    6420
tagattttat catccattaa tccttccctc tcctctctta ctcatcccat cacgtatgcc    6480
tcttaatttt cccttaccta taataagagt tattcctctt attatattct tcttatagtg    6540
attctggata ttaaagtggg aatgaggggc aggccactaa cgaagaagat gtttctcaaa    6600
gaagcggggg atccgtcgac aggtcgggca ggaagagggc ctatttccca tgattccttc    6660
atatttgcat atacgataca aggctgttag agagataatt agaattaatt tgactgtaaa    6720
cacaaagata ttagtacaaa atacgtgacg tagaaagtaa taatttcttg ggtagtttgc    6780
agttttaaaa ttatgtttta aaatggacta tcatatgctt accgtaactt gaaagtattt    6840
cgatttcttg gctttatata tcttgtggaa aggacgaaac accgtctgcc gttactgccc    6900
tgtgtttcag agctatgctg gaaacagcat agcaagttga aataaggcta gtccgttatc    6960
aacttgaaaa agtggcaccg agtcggtgct ttttttgtcg acactagttc tagagcggcc    7020
aaatggcggc cgtaccttta agaccaatga cttacaaggc agctgtagat cttagccact    7080
ttttaaaaga aaaggggggga ctggaagggc taattcactc ccaacgaaga caagatctgc    7140
tttttgcttg tactgggtct ctctggttag accagatctg agcctgggag ctctctggct    7200
aactagggaa cccactgctt aagcctcaat aaagcttgcc ttgagtgctt caagtagtgt    7260
gtgcccgtct gttgtgtgac tctggtaact agagatccct cagaccctt tagtcagtgt    7320
ggaaaatctc tagcagtagt agttcatgtc atcttattat tcagtattta aacttgcaa    7380
agaaatgaat atcagagagt gagaggaact tgtttattgc agcttataat ggttacaaat    7440
aaagcaatag catcacaaat ttcacaaata aagcattttt tcactgcat tctagttgtg    7500
gtttgtccaa actcatcaat gtatcttatc atgtctggct ctagctatcc cgcccctaac    7560
tccgcccatc ccgcccctaa ctccgcccag ttccgcccat tctccgcccc atggctgact    7620
aatttttttt atttatgcag aggccgaggc cgcctcggcc tctgagctat tccagaagta    7680
gtgaggaggc tttttttggag gcctaggact gtacccaatt cgccctatag tgagtcgtat    7740
tacgcgcgct cactggccgt cgttttacaa cgtcgtgact gggaaaaccc tggcgttacc    7800
caacttaatc gccttgcagc acatccccct ttcgccagct ggcgtaatag cgaagaggcc    7860
```

-continued

```
cgcaccgatc gcccttccca acagttgcgc agcctgaatg gcgaatggga cgcgccctgt    7920
agcggcgcat taagcgcggc gggtgtggtg gttacgcgca gcgtgaccgc tacacttgcc    7980
agcgccctag cgcccgctcc tttcgctttc ttcccttcct ttctcgccac gttcgccggc    8040
tttccccgtc aagctctaaa tcggggctc cctttagggt tccgatttag tgctttacgg     8100
cacctcgacc ccaaaaaact tgattagggt gatggttcac gtagtgggcc atcgccctga    8160
tagacggttt ttcgcccttt gacgttggag tccacgttct ttaatagtgg actcttgttc    8220
caaactggaa caacactcaa ccctatctcg gtctattctt ttgatttata agggattttg    8280
ccgatttcgg cctattggtt aaaaaatgag ctgatttaac aaaaatttaa cgcgaatttt    8340
aacaaaatat taacgcttac aatttaggtg cacttttcg gggaaatgtg cgcggaaccc     8400
ctatttgttt attttctaa atacattcaa atatgtatcc gctcatgaga caataaccct     8460
gataaatgct tcaataatat tgaaaaagga agagtatgag tattcaacat ttccgtgtcg    8520
cccttattcc cttttttgcg cattttgcc ttcctgtttt tgctcaccca gaaacgctgg     8580
tgaaagtaaa agatgctgaa gatcagttgg gtgcacgagt gggttacatc gaactggatc    8640
tcaacagcgg taagatcctt gagagttttc gccccgaaga acgttttcca atgatgagca    8700
cttttaaagt tctgctatgt ggcgcggtat tatcccgtat tgacgccggg caagagcaac    8760
tcggtcgccg catacactat tctcagaatg acttggttga gtactcacca gtcacagaaa    8820
agcatcttac ggatggcatg acagtaagag aattatgcag tgctgccata accatgagtg    8880
ataacactgc ggccaactta cttctgacaa cgatcgagg accgaaggag ctaaccgctt     8940
ttttgcacaa catgggggat catgtaactc gccttgatcg ttgggaaccg gagctgaatg    9000
aagccatacc aaacgacgag cgtgacacca cgatgcctgt agcaatggca acaacgttgc    9060
gcaaactatt aactggcgaa ctacttactc tagcttcccg gcaacaatta atagactgga    9120
tggaggcgga taaagttgca ggaccacttc tgcgctcggc ccttccggct ggctggttta    9180
ttgctgataa atctggagcc ggtgagcgtg ggtctcgcgg tatcattgca gcactggggc    9240
cagatggtaa gccctcccgt atcgtagtta tctacacgac ggggagtcag gcaactatgg    9300
atgaacgaaa tagacagatc gctgagatag gtgcctcact gattaagcat tggtaactgt    9360
cagaccaagt ttactcatat atactttaga ttgatttaaa acttcatttt taatttaaaa    9420
ggatctaggt gaagatcctt tttgataatc tcatgaccaa aatcccttaa cgtgagtttt    9480
cgttccactg agcgtcagac cccgtagaaa agatcaaagg atcttcttga tccttttt     9540
ttctgcgcgt aatctgctgc ttgcaaacaa aaaaaccacc gctaccagcg gtggtttgtt    9600
tgccggatca gagctacca actctttttc cgaaggtaac tggcttcagc agagcgcaga    9660
taccaaatac tgttcttcta gtgtagccgt agttaggcca ccacttcaag aactctgtag    9720
caccgcctac atacctcgct ctgctaatcc tgttaccagt ggctgctgcc agtggcgata    9780
agtcgtgtct taccgggttg gactcaagac gatagttacc ggataaggcg cagcggtcgg    9840
gctgaacggg gggttcgtgc acacagccca gcttggagcg aacgacctac accgaactga    9900
gatacctaca gcgtgagcta tgagaaagcg ccacgcttcc cgaagggaga aaggcggaca    9960
ggtatccggt aagcggcagg gtcggaacag gagagcgcac gagggagctt ccaggggaa    10020
acgcctggta tctttatagt cctgtcgggt ttcgccacct ctgacttgag cgtcgatttt    10080
tgtgatgctc gtcaggggg cggagccat ggaaaaacgc cagcaacgcg gcctttttac     10140
ggttcctggc cttttgctgg ccttttgctc acatgttctt tcctgcgtta tccctgatt    10200
```

```
ctgtggataa ccgtattacc gcctttgagt gagctgatac cgctcgccgc agccgaacga    10260
ccgagcgcag cgagtcagtg agcgaggaag cggaagagcg cccaatacgc aaaccgcctc    10320
tccccgcgcg ttggccgatt cattaatgca gctggcacga caggtttccc gactggaaag    10380
cgggcagtga gcgcaacgca attaatgtga gttagctcac tcattaggca ccccaggctt    10440
tacactttat gcttccggct cgtatgttgt gtggaattgt gagcggataa caatttcaca    10500
caggaaacag ctatgaccat gattacgcca agcgcgcaat taaccctcac taaagggaac    10560
aaaagctgga gctgcaagct tgg                                            10583
```

```
<210> SEQ ID NO 95
<211> LENGTH: 31
<212> TYPE: PRT
<213> ORGANISM: Homo sapiens

<400> SEQUENCE: 95

Arg Gly Leu Ala Glu Gly Gly Val Glu Asp Val Asn Val Lys Gly Trp
1               5                   10                  15

Leu Ala Thr Val Ala Ser Lys Glu Glu Pro Thr Leu His Val Met
            20                  25                  30
```

```
<210> SEQ ID NO 96
<211> LENGTH: 93
<212> TYPE: DNA
<213> ORGANISM: Homo sapiens

<400> SEQUENCE: 96
ggacgggtcc cggagtggtg gttgaagtag gtgcaagtgg aacgggtgtc ccgtcattgc    60
cgtctgaaga ggagtcctca gtctacgtgg tac                                 93
```

```
<210> SEQ ID NO 97
<211> LENGTH: 94
<212> TYPE: DNA
<213> ORGANISM: Homo sapiens

<400> SEQUENCE: 97
cctgcccagg gcctcaccac caacttcatc cacgttcacc ttgccccaca gggcagtaac    60
ggcagacttc tcctcaggag tcagatgcac catg                                94
```

Figure 4:
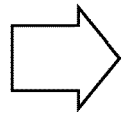
FIG. 4: Selection of gRNAs targeting the beta-globin gene: design of novel gRNAs The sequences depicted in step A are set forth as SEQ ID NO: 95 (amino acid) and SEQ ID NO: 96 (nucleotide). The sequence depicted in step C is set forth as SEQ ID NO: 97. The primer sequences depicted in step D are set forth as SEQ ID NOS: 98 and 99.

```
<210> SEQ ID NO 98
<211> LENGTH: 23
<212> TYPE: DNA
<213> ORGANISM: Artificial Sequence
<220> FEATURE:
<223> OTHER INFORMATION: Figure 4 primer at position/strand 76/fw

<400> SEQUENCE: 98
gtaacggcag acttctcctc agg                                            23
```

```
<210> SEQ ID NO 99
<211> LENGTH: 23
<212> TYPE: DNA
<213> ORGANISM: Artificial Sequence
<220> FEATURE:
<223> OTHER INFORMATION: Figure 4 primer at postion/strand 45/rev

<400> SEQUENCE: 99
gtctgccgtt actgccctgt ggg                                            23
```

The invention claimed is:

1. A recombinant lentiviral vector comprising in its genome:
   (i) a nucleotide sequence encoding a protein that has a therapeutic effect, said protein being selected from the group consisting of delta-globin and gamma globin; and
   (ii) a nucleotide sequence encoding a guide RNA (gRNA) that comprises a spacer adapted to bind to a target nucleotide sequence, said target nucleotide sequence being:
      a. within the coding sequence or within a transcribed non-coding sequence of a target gene, said target gene being selected from beta-globin gene and BCL11A gene, or
      b. within the promoter region of a target gene, wherein said target gene is a gamma-globin gene when the nucleotide sequence (i) encoding the protein that has the therapeutic effect is delta-globin.

2. The recombinant lentiviral vector according to claim 1, wherein the protein that has a therapeutic effect is selected from the group consisting of human delta-globin and human gamma-globin.

3. A recombinant lentiviral vector comprising in its genome:
   (i) a nucleotide sequence encoding a protein that has a therapeutic effect, said protein being human beta AS3 globin; and
   (ii) a nucleotide sequence encoding a guide RNA (gRNA) that comprises a spacer adapted to bind to a target nucleotide sequence, said target nucleotide sequence being:
      a. within the coding sequence or within a transcribed non-coding sequence of a target gene, said target gene being BCL11A gene, or
      b. within the promoter region of a target gene, said target gene being gamma-globin gene.

4. The recombinant lentiviral vector according to claim 1, wherein the beta-globin gene, gamma-globin gene or BCL11A gene is human.

5. A composition comprising the recombinant lentiviral vector according to claim 1 or a plurality of said recombinant lentiviral vectors.

6. A kit comprising:
   the recombinant lentiviral vector according to claim 1; and
      a catalytically active Cas9 or Cpf1 protein or a nucleotide sequence encoding a catalytically active Cas9 or Cpf1 protein.

7. The recombinant lentiviral vector according to claim 1 for introducing into a hematopoietic stem/progenitor cell (HSPC)
   (i) the nucleotide sequence encoding a protein that has a therapeutic effect, said protein being selected from the group consisting of delta-globin and gamma globin, and
   (ii) the nucleotide sequence encoding a guide RNA (gRNA) that comprises a spacer adapted to bind to a target nucleotide sequence, said target nucleotide sequence is:
      a. within the coding sequence or within a transcribed non-coding sequence of a target gene, said target gene is selected from beta-globin gene and BCL11A gene, or
      b. within the promoter region of a target gene, wherein said target gene is a gamma-globin gene when the nucleotide sequence (i) encoding the protein that has the therapeutic effect is delta-globin.

8. A method for modifying the genome of a hematopoietic stem/progenitor cell (HSPC), in vitro or ex vivo, comprising the steps of:
   a) contacting a HSPC with a recombinant lentiviral vector of claim 1 to obtain a transduced HSPC, wherein the lentiviral vector is integrated into the genome of said HSPC; and
   b) introducing into the transduced HSPC a catalytically active Cas9 or Cpf1 protein or a nucleotide sequence encoding a catalytically active Cas9 or Cpf1 protein, said catalytically active Cas9 or Cpf1 protein disrupts the expression and/or the function of the target gene when introduced or expressed into the transduced HSPC.

9. A method for preparing a genetically modified hematopoietic stem/progenitor cell (HSPC), in vitro or ex vivo, comprising the steps of:
   a) contacting a HSPC with a recombinant lentiviral vector of claim 1 to obtain a transduced HSPC, wherein the lentiviral vector is integrated into the genome of said HSPC; and
   b) introducing into the transduced HSPC a catalytically active Cas9 or Cpf1 protein or a nucleotide sequence encoding a catalytically active Cas9 or Cpf1 protein, said catalytically active Cas9 or Cpf1 protein disrupts the expression and/or the function of the target gene when introduced or expressed into the transduced HSPC.

10. A kit comprising:
    a composition according to claim 5; and
    a catalytically active Cas9 or Cpf1 protein or a nucleotide sequence encoding a catalytically active Cas9 or Cpf1 protein.

11. The composition according to claim 5 for introducing into a hematopoietic stem/progenitor cell (HSPC)
    (i) the nucleotide sequence encoding a protein that has a therapeutic effect, said protein being selected from the group consisting of delta-globin and gamma globin, and
    (ii) the nucleotide sequence encoding a guide RNA (gRNA) that comprises a spacer adapted to bind to a target nucleotide sequence, said target nucleotide sequence is:
       a. within the coding sequence or within a transcribed non-coding sequence of a target gene, said target gene being selected from beta-globin gene and BCL11A gene, or
       b. within the promoter region of a target gene, wherein said target gene is a gamma-globin gene when the nucleotide sequence (i) encoding the protein that has the therapeutic effect is delta-globin.

12. The kit according to claim 6 for use in introducing into a hematopoietic stem/progenitor cell (HSPC)
    (i) the nucleotide sequence encoding a protein that has a therapeutic effect, said protein being selected from the group consisting of delta-globin and gamma globin, and
    (ii) the nucleotide sequence encoding a guide RNA (gRNA) that comprises a spacer adapted to bind to a target nucleotide sequence, said target nucleotide sequence is:
       a. within the coding sequence or within a transcribed non-coding sequence of a target gene, said target gene being selected from beta-globin gene and BCL11A gene, or b. within the promoter region of a target gene, wherein said target gene is a gamma-globin gene when the nucleotide sequence (i) encoding the protein that has the therapeutic effect is delta-globin.

13. A method for modifying the genome of a hematopoietic stem/progenitor cell (HSPC), in vitro or ex vivo, comprising the steps of:
   a) contacting a HSPC with a composition according to claim 5 to obtain a transduced HSPC, wherein the lentiviral vector is integrated into the genome of said HSPC; and
   b) introducing into the transduced HSPC a catalytically active Cas9 or Cpf1 protein or a nucleotide sequence encoding a catalytically active Cas9 or Cpf1 protein, wherein said catalytically active Cas9 or Cpf1 protein disrupts the expression and/or the function of the target gene when introduced or expressed into the transduced HSPC.

14. A method for preparing a genetically modified hematopoietic stem/progenitor cell (HSPC), in vitro or ex vivo, comprising the steps of:
   a) contacting a HSPC with a composition according to claim 5 to obtain a transduced HSPC, wherein the lentiviral vector is integrated into the genome of said HSPC; and
   b) introducing into the transduced HSPC a catalytically active Cas9 or Cpf1 protein or a nucleotide sequence encoding a catalytically active Cas9 or Cpf1 protein, wherein said catalytically active Cas9 or Cpf1 protein disrupts the expression and/or the function of the target gene when introduced or expressed into the transduced HSPC.

15. A composition comprising a recombinant lentiviral vector according to claim 3 or a plurality of said recombinant lentiviral vectors.

16. A kit comprising: the recombinant lentiviral vector according to claim 3; and
   a catalytically active Cas9 or Cpf1 protein or a nucleotide sequence encoding a catalytically active Cas9 or Cpf1 protein.

17. A recombinant lentiviral vector comprising in its genome:
   (i) a nucleotide sequence encoding a protein that has a therapeutic effect, said protein being selected from the group consisting of beta-globin, gamma-globin, and delta-globin; and
   (ii) a nucleotide sequence encoding a guide RNA (gRNA) that comprises a spacer adapted to bind to a target nucleotide sequence, said target nucleotide sequence being:
      a. within the coding sequence or within a transcribed non-coding sequence of a target gene, said target gene being BCL11A gene, or
      b. within the promoter region of a target gene, wherein said target gene is a gamma-globin gene when the nucleotide sequence (i) encoding the protein that has the therapeutic effect is selected from the group consisting of delta-globin and beta-globin.

18. A composition comprising a recombinant lentiviral vector according to claim 17 or a plurality of said recombinant lentiviral vectors.

19. A kit comprising the recombinant lentiviral vector according to claim 17; and
   a catalytically active Cas9 or Cpf1 protein or a nucleotide sequence encoding a catalytically active Cas9 or Cpf1 protein.

20. A recombinant lentiviral integrative vector comprising in its genome:
   (i) a nucleotide sequence encoding a protein that has a therapeutic effect, said protein being selected from the group consisting of beta-globin, gamma-globin, and delta-globin; and
   (ii) a nucleotide sequence encoding a guide RNA (gRNA) that comprises a spacer adapted to bind to a target nucleotide sequence, said target nucleotide sequence is:
      (a) within the coding sequence or within a transcribed non-coding sequence of a target gene, said target gene being selected from beta-globin gene and BCL11A gene, or
      (b) within the promoter region of a target gene, wherein said target gene is a gamma-globin gene when the nucleotide sequence (i) encoding the protein that has the therapeutic effect is selected from the group consisting of delta-globin and beta-globin.

21. A composition comprising a recombinant lentiviral vector according to claim 20 or a plurality of said recombinant lentiviral vectors.

22. A kit comprising:
   the recombinant lentiviral integrative vector according to claim 20; and
   a catalytically active Cas9 or Cpf1 protein or a nucleotide sequence encoding a catalytically active Cas9 or Cpf1 protein.

* * * * *